(12) United States Patent
Grundfest et al.

(10) Patent No.: US 10,939,844 B2
(45) Date of Patent: Mar. 9, 2021

(54) THZ SENSING OF CORNEAL TISSUE WATER CONTENT

(71) Applicant: The Regents of the University of California, Oakland, CA (US)

(72) Inventors: Warren S. Grundfest, Los Angeles, CA (US); Zachary Taylor, Oakland, CA (US); James Garritano, Los Angeles, CA (US); Bryan Nowroozi, Oakland, CA (US); Neha Bajwa, Oakland, CA (US); Shijun Sung, Elk Grove, CA (US)

(73) Assignee: The Regents of the University of California, Oakland, CA (US)

( * ) Notice: Subject to any disclaimer, the term of this patent is extended or adjusted under 35 U.S.C. 154(b) by 130 days.

(21) Appl. No.: 16/093,953

(22) PCT Filed: Apr. 17, 2017

(86) PCT No.: PCT/US2017/028006
§ 371 (c)(1),
(2) Date: Oct. 15, 2018

(87) PCT Pub. No.: WO2017/181201
PCT Pub. Date: Oct. 19, 2017

(65) Prior Publication Data
US 2019/0117109 A1 Apr. 25, 2019

Related U.S. Application Data

(60) Provisional application No. 62/323,455, filed on Apr. 15, 2016.

(51) Int. Cl.
*A61B 3/10* (2006.01)
*A61B 3/14* (2006.01)
(Continued)

(52) U.S. Cl.
CPC .......... *A61B 5/0507* (2013.01); *A61B 3/0025* (2013.01); *A61B 3/101* (2013.01);
(Continued)

(58) Field of Classification Search
CPC ......... A61B 3/1015; A61B 1/103; A61B 3/14; A61B 3/113; A61B 3/1208; A61B 3/1225; A61B 3/024; A61B 3/18
(Continued)

(56) References Cited

U.S. PATENT DOCUMENTS 4,021,031 A 5/1977 Meihofer et al.
5,317,389 A 5/1994 Hochberg et al.
(Continued)

FOREIGN PATENT DOCUMENTS

EP 3265863 A1 1/2018
EP 3442398 A1 2/2019
(Continued)

OTHER PUBLICATIONS

Dougherty et al., "Excimer Laser Ablation Rate and Corneal Hydration", American Journal of Ophthalmology, vol. 118, No. 2, Aug. 1994, pp. 169-176.
(Continued)

*Primary Examiner* — Dawayne Pinkney
(74) *Attorney, Agent, or Firm* — KPPB LLP

(57) ABSTRACT

Methods and apparatus for corneal imaging and sensing are provided. Apparatus capable of utilizing single or multiple frequency emissions at terahertz (THz) wavelengths to create reflectivity maps of the cornea in either a contact or non-contact modes are also provided. Methods of obtaining data from THz imaging and sensing apparatus about the corneal tissue-aqueous humor system, including information about the corneal tissue water content (CTWC) and/or the central corneal thickness (CCT) are likewise provided.
(Continued)

Methodologies may use multiple transfer functions (frequencies) in obtaining simultaneous data about CTWC and CCT. Methods using frequency sweeping to allow for determination of CTWC and CCT may also be utilized. Methods may also be used to assess CTWC using multiple bandwidths at the same frequency, or multiple frequencies at the same bandwidth. Methods may use data from CTWC measurements to aid in the diagnosis of various corneal and brain disorders.

25 Claims, 56 Drawing Sheets

(51) Int. Cl.
  A61B 3/02 (2006.01)
  A61B 3/00 (2006.01)
  A61B 5/0507 (2021.01)
  A61B 5/00 (2006.01)
  G01B 11/24 (2006.01)
  A61B 8/10 (2006.01)
(52) U.S. Cl.
  CPC .............. *A61B 3/1025* (2013.01); *A61B 3/14* (2013.01); *A61B 5/4875* (2013.01); *G01B 11/24* (2013.01); *A61B 8/10* (2013.01)
(58) Field of Classification Search
  USPC ........ 351/246, 200, 205–206, 209–210, 218, 351/221–222
  See application file for complete search history.

(56) References Cited

U.S. PATENT DOCUMENTS

| | | |
|---|---|---|
| 10,517,477 B2 | 12/2019 | Grundfest et al. |
| 2001/0000978 A1 | 5/2001 | Hitzenberger et al. |
| 2003/0130579 A1 | 7/2003 | McClane et al. |
| 2006/0036181 A1 | 2/2006 | Treado et al. |
| 2007/0114419 A1 | 5/2007 | Bastiaans et al. |
| 2009/0048510 A1 | 2/2009 | Miller et al. |
| 2010/0195048 A1 | 8/2010 | Hammer et al. |
| 2011/0005932 A1 | 1/2011 | Jovanovich et al. |
| 2012/0198912 A1 | 8/2012 | Ewing et al. |
| 2013/0070234 A1 | 3/2013 | Li et al. |
| 2013/0162949 A1 | 6/2013 | Culjat et al. |
| 2013/0190594 A1 | 7/2013 | Oraevsky et al. |
| 2014/0103215 A1 | 4/2014 | Rahman et al. |
| 2015/0090881 A1 | 4/2015 | King et al. |
| 2015/0164327 A1 | 6/2015 | Yaroslaysky et al. |
| 2015/0316511 A1 | 11/2015 | Guo |
| 2018/0020913 A1 | 1/2018 | Grundfest et al. |
| 2018/0303347 A1 | 10/2018 | Grundfest et al. |
| 2019/0082998 A1 | 3/2019 | Nowroozi et al. |

FOREIGN PATENT DOCUMENTS

| | | |
|---|---|---|
| HK | 1248826 A | 10/2018 |
| WO | 1989002718 A1 | 4/1989 |
| WO | 2000078217 A1 | 12/2000 |
| WO | 2003023383 A2 | 3/2003 |
| WO | 2012083206 A1 | 6/2012 |
| WO | 2015195975 A1 | 12/2015 |
| WO | 2016131047 A1 | 8/2016 |
| WO | 2017181200 A1 | 10/2017 |
| WO | 2017181201 A1 | 10/2017 |

OTHER PUBLICATIONS

Doughty et al., "Human Corneal Thickness and Its Impact on Intraocular Pressure Measures: A Review and Meta-analysis Approach", Survey of Ophthalmology, vol. 44, No. 5, Mar.-Apr. 2000, pp. 367-408.

Ehlers et al., "Central Thickness in Corneal Disorders", Acta Ophthalmologica, vol. 56, No. 3, Jun. 1978, pp. 412-416.
Ehlers et al., "Corneal thickness: measurement and implications", Experimental Eye Research, vol. 78, No. 3, Mar. 2004, pp. 543-548.
Epstein et al., "Cutaneous Wound Healing", New England Journal of Medicine, vol. 341, Sep. 2, 1999, pp. 738-746.
Evans et al., "Chemical imaging of tissue in vivo with video-rate coherent anti-Stokes Raman Scattering microscopy", PNAS, Nov. 15, 2005, vol. 102, No. 46, pp. 16807-16812.
Federici, "Review of Moisture and Liquid Detection and Mapping using Terahertz Imaging", Journal of Infrared, Millimeter, and Terahertz Waves, Feb. 1, 2012 (Feb. 1, 2012), vol. 33, pp. 97-126. entire document.
Ferguson et al., "Materials for terahertz science and technology", Nature Materials, vol. 1, No. 1, Sep. 1, 2002, pp. 26-33.
Fisher et al., "Assessment of Transient Changes in Corneal Hydration Using Confocal Raman Spectroscopy", Cornea, vol. 22, No. 4, May 2003, pp. 363-370.
Fitzgerald et al., "Terahertz Pulsed Imaging of Human Breast Tumors", Radiology, vol. 239, No. 2, May 2006, Electronic Publication: Mar. 16, 2006, pp. 533-540.
Frankel et al., "High-Voltage Picosecond Photoconductor Switch Based on Low-Temperature-Grown GaAs", IEEE Transactions on Electron Devices, vol. 37, No. 12, Dec. 1990, pp. 2493-2498.
Glass et al., "A Viscoelastic Biomechanical Model of the Cornea Describing the Effect of Viscosity and Elasticity on Hysteresis", Investigative Ophthalmology & Visual Science, vol. 49, No. 9, Sep. 2008, pp. 3919-3926.
Gromacki et al., "Central and Peripheral Corneal Thickness in Keratoconus and Normal Patient Groups", Optometry and Vision Science, vol. 71, No. 7, Jul. 1994, pp. 437-441.
Hesler et al., "NEP and Responsivity of THz Zero-Bias Schottky Diode Detectors", Proceedings of the Joint 32nd International Conference on Infrared and Millimeter Waves and the 15th International Conference on Terahertz Electronics, Cardiff, United Kingdom, Sep. 2-9, 2007, 2 pgs.
Hinton et al., "A Fast Learning Algorithm for Deep Belief Nets", Neural Computation, vol. 18, 2006, pp. 1527-1554.
Hitzenberger et al., "Measurement of Corneal Thickness by Loser Doppler Interferometry", Investigative Ophthalmology & Visual Science, vol. 33, No. 1, Jan. 1992, pp. 98-103.
Hoshina et al., "Terahertz pulsed imaging of frozen biological tissues", Applied Physics Letters, vol. 94, No. 12, Mar. 23, 2009, 3 pgs.
Hu et al., "Terahertz Radiation Induced by Subband-Gap Femtosecond Optical Excitation of GaAs", Physical Review Letters, vol. 67, No. 19, Nov. 4, 1991, pp. 2709-2712.
Huang et al., "Optical Coherence Tomography", Science, vol. 254, No. 5035, Nov. 22, 1991, pp. 1178-1181.
Izatt et al., "Micrometer-Scale Resolution Imaging of the Anterior Eye In Vivo Wth Optical Coherence Tomography", Archives of Ophthalmology, vol. 112, No. 12, Dec. 1994, pp. 1584-1589.
Jaskille et al., "Critical Review of Burn Depth Assessment Techniques: Part I. Historical Review", Journal of Burn Care & Research, vol. 30, No. 6, Nov. 1, 2009, pp. 937-947.
Jaskille et al., "Critical Review of Burn Depth Assessment Techniques: Part II. Review of Laser Doppler Technology", Journal of Burn Care & Research, vol. 31, No. 1, Jan. 1, 2010, pp. 151-157.
Johnson et al., "Novel Corneal Hydration Imaging Technology Using Terahertz Illumination", Investigative Ophthalmology & Visual Science, Association for Research in Vision and Ophthalmology (ARVO) Annual Meeting Abstract, vol. 52, No. 14, Apr. 2011, pp. 4092.
Karkkainen et al., "Effective Permittivity of Mixtures: Numerical Validation by the FDTD Method", IEEE Transactions on Geoscience and Remote Sensing, vol. 38, No. 3, May 2000, pp. 1303-1308.
Ketchen et al., "Generation of subpicosecond electrical pulses on coplanar transmission lines", Applied Physics Letters, vol. 48, No. 12, 1986, pp. 751-753.
King-Smith et al., "Tear Film Interferometry and Corneal Surface Roughness", Investigative Ophthalmology & Visual Science, vol. 55, No. 4, Apr. 2014, pp. 2614-2618.

(56) References Cited

OTHER PUBLICATIONS

King-Smith et al., "The Thickness of the Human Precorneal Tear Film: Evidence from Reflection Spectra", Investigative Ophthalmology & Visual Science, vol. 41, No. 11, Oct. 2000, pp. 3348-3359.
Klintworth, "Corneal dystrophies", Orphanet Journal of Rare Diseases, vol. 4, No. 7, Feb. 23, 2009, 38 pgs.
Knabl et al., "Controlled partial skin thickness burns: an animal model for studies of burnwound progression", Burns, vol. 25, No. 3, May 1999, pp. 229-235.
Lackner et al., "Repeatability and Reproducibility of Central Corneal Thickness Measurement Wth Pentacam, Orbscan, and Ultrasound", Optometry and Vision Science, vol. 82, No. 10, Oct. 2005, pp. 892-899.
Lamb, "Miscellaneous data on materials for millimetre and submillimetre optics", International Journal of Infrared and Millimeter Waves, vol. 17, No. 12, Dec. 1996, pp. 1997-2034.
Landauer, "Electrical Conductivity in Inhomogeneous Media", AIP Conference Proceedings, vol. 40, No. 2, Mar. 1978, pp. 2-45.
Li et al., "Corneal Pachymetry Mapping with High-speed Optical Coherence Tomography", Ophthalmology, vol. 113, No. 5, May 2006, pp. 792-799.e2.
Li et al., "Differences in Healing of Skin Wounds Caused by Burn and Freeze Injuries", Annals of Surgery, vol. 191, No. 2, Feb. 1980, pp. 244-248.
Liebe et al., "A Model for the Complex Permittivity of Water at Frequencies Below 1 THz", International Journal of Infrared and Millimeter Waves, vol. 12, No. 7, Jul. 1991, pp. 659-675.
Liu et al., "Evaluation of corneal thickness and topography in normal eyes using the Orbscan corneal topography system", British Journal of Ophthalmology, vol. 83, No. 7, Jul. 1, 1999, pp. 774-778.
Maccabi et al., "Reflectivity Measurements of Water and Dioxane Mixtures using a 100 GHz Gunn Diode Source", Proceedings of SPIE BiOS Terahertz and Ultrashort Electromagnetic Pulses for Biomedical Applications, San Francisco, California, vol. 8585, 2013, 7 pgs.
Malik et al., "Corneal confocal microscopy: a non-invasive surrogate of nerve fibre damage and repair in diabetic patients", Diabetologia, vol. 46, No. 5, May 2003, pp. 683-688.
Malone et al., "Design of a thermal imaging diagnostic using 90-degree off-axis parabolic mirrors", Proceedings of the SPIE Optics + Photonics, San Diego, California, vol. 6288, Sep. 2006, 9 pgs.
Mandell et al., "Corneal Hydration Control in Fuchs' Dystrophy", Investigative Ophthalmology & Visual Science, vol. 30, No. 5, May 1989, pp. 845-852.
Manson et al., "The Role of Oxygen-free Radicals in Ischemic Tissue Injury in Island Skin Flaps", Annals of Surgery, vol. 198, No. 1, Jul. 1983, pp. 87-90.
Markelz et al., "Pulsed terahertz spectroscopy of DNA, bovine serum albumin and collagen between 0.1 and 2.0 THz", Chemical Physics Letters, vol. 320, No. 1-2, Mar. 31, 2000, pp. 42-48.
Martin, "Wound Healing—Aiming for Perfect Skin Regeneration", Science, vol. 276, No. 5309, Apr. 4, 1997, pp. 75-81.
McCrackin et al., "Measurement of the Thickness and Refractive Index of Very Thin Films and the Optical Properties of Surfaces by Ellipsometry", Journal of Research of the National Bureau of Standards—A Physics and Chemistry, vol. 67A, No. 4, Jul.-Aug. 1963, pp. 363-377.
McDonnell et al., "Corneal Thickness Changes After High-Risk Penetrating Keratoplasty", Archives of Ophthalmology, vol. 111, No. 10, Oct. 1993, pp. 1374-1381.
Meissner et al., "The Complex Dielectric Constant of Pure and Sea Water From Microwave Satellite Observations", IEEE Transactions on Geoscience and Remote Sensing, vol. 42, No. 9, Sep. 2004, pp. 1836-1849.
Meyer et al., "A standard burn model using rats", Acta Cirurgica Brasileira, vol. 14, No. 4, Oct./Dec. 1999, 8 pgs.
Ney et al., "Modeling of reflectometric and ellipsometric spectra from the skin in the terahertz and submillimeter waves region", Journal of Biomedical Optics, vol. 16, No. 6, Jun. 2011, pp. 067006-1-067006-15.
Niklasson et al., "Effective medium models for the optical properties of inhomogeneous materials", Applied Optics, vol. 20, No. 1, Jan. 1981, pp. 26-30.
Orfanidis, Sophocles J., "Electromagnetic Waves and Antennas", Rutgers University, Jun. 1, 2014, retrieved from http://www.ece.rutgers.edu/~orfanidi/ewa/, 610 pages.
Extended European Search Report for European Application No. 16750060.2, Search completed Nov. 12, 2018, dated Nov. 22, 2018, 7 Pgs.
Extended European Search Report for European Application No. 17783377.9, Search completed Oct. 30, 2019, dated Nov. 11, 2019, 09 Pgs.
International Preliminary Report on Patentability for International Application PCT/US2017/028006, Report dated Oct. 16, 2018, dated Oct. 25, 2018, 10 Pgs.
International Preliminary Report on Patentability for International Application PCT/US2017/028003, Report dated Oct. 16, 2018, dated Oct. 25, 2016, 10 Pgs.
International Preliminary Report on Patentability for International Application PCT/US2015/036518, Report dated Dec. 20, 2016, dated Dec. 29, 2016, 7 Pgs.
International Preliminary Report on Patentability for International Application PCT/US2016/017998, Report dated Aug. 15, 2017, dated Aug. 24, 2017, 8 Pgs.
International Search Report and Written Opinion for International Application No. PCT/US2016/017998, Search completed May 26, 2016, dated May 26, 2016, 10 Pgs.
International Search Report and Written Opinion for International Application No. PCT/US2017/028003, Search completed Jun. 7, 2017, dated Jul. 17, 2017, 14 Pgs.
International Search Report and Written Opinion for International Application No. PCT/US2017/028006, Search completed Jun. 7, 201,7 dated Jul. 17, 2017, 14 Pgs.
International Search Report and Written Opinion for International Application PCT/US2015/036518, Report Completed Sep. 15, 2015, dated Sep. 15, 2015, 10 pgs.
"American National Standard for Safe Use of Lasers", American National Standards Institute, Inc., ANSI Z136.1, Mar. 16, 2007, 22 pgs.
"Gunn Oscillators", SpaceKLabs: MM-Wave Technology ISO 9001:2008 Certified, Retrieved from http://spaceklabs.com/cm/Products/Frequency_Sources/Gunn%20Oscillators.html on Sep. 12, 2015, 2 pgs.
"THz Detectors", gentec-eo, Retrieved from https://www.gentec-eo.com/products/thz-detectors on Nov. 28, 2012, 2 pgs.
Adamis et al., "Fuchs' Endothelial Dystrophy of the Cornea", Survey of Ophthalmology, vol. 38, Issue 2, Sep.-Oct. 1993, pp. 149-168.
Alemdaroglu et al., "An investigation on burn wound healing in rats with chitosan gel formulation containing epidermal growth factor", Burns, vol. 32, No. 3, May 2006, pp. 319-327.
Applegate et al., "Noninvasive Measurement of Corneal Topography", IEEE Engineering in Medicine and Biology Magazine, vol. 14, No. 1, Jan.-Feb. 1995, pp. 30-42.
Arbab et al., "Characterization of burn injuries using terahertz time-domain spectroscopy", Proceedings of the Advanced Biomedical and Clinical Diagnostic Systems IX, vol. 7890, Feb. 21, 2011, 7 pgs.
Arbab et al., "Terahertz reflectometry of burn wounds in a rat model", Biomedical Optics Express, vol. 2, No. 8, Jul. 21, 2011, pp. 2339-2347.
Arbab et al., "Terahertz spectroscopy for the assessment of burn injuries in vivo", Journal of Biomedical Optics, vol. 18, No. 7, Jul. 2013, pp. 077004-1077004-7.
Azartash et al., "Pre-corneal tear film thickness in humans measured with a novel technique", Molecular Vision, vol. 17, Mar. 22, 2011, pp. 756-767.
Bajwa et al., "Reflective Terahertz (THz) Imaging: System Calibration Using Hydration Phantoms", Proceedings of SPIE Terahertz

(56) References Cited

OTHER PUBLICATIONS and Ultrashort Electromagnetic Pulses for Biomedical Applications, San Francisco, California, vol. 8585, 2013, 10 pgs.

Bajwa et al., "Reflective THz and MR imaging of burn wounds: A Potential Clinical Validation of THz Contrast Mechanisms", Proceedings of SPIE Terahertz Emitters, Receivers, and Applications III, San Diego, California, vol. 8496, 2012, 7 pgs.

Bauer et al.,"In Vivo Confocal Raman Spectroscopy of the Human Cornea", Cornea, vol. 18, No. 4, Jul. 1999, pp. 483-488.

Bauer et al., "Noninvasive Assessment of the Hydration Gradient across the Cornea Using Confocal Raman Spectroscopy", Investigative Ophthalmology & Visual Science, vol. 39, No. 5, Apr. 1998, pp. 831-835.

Bechmann et al., "Central Corneal Thickness Measurement with a Retinal Optical Coherence Tomography Device Versus Standard Ultrasonic Pachymetry", Cornea, vol. 20, No. 1, Jan. 2001, pp. 50-54.

Bennett et al., "Assessment of corneal hydration sensing in the terahertz band: in vivo results at 100 GHz", Journal of Biomedical Optics, vol. 17, No. 9, Sep. 2012, pp. 097008.1-097008.7.

Bennett et al., "Stratified Media Model for Terahertz Reflectometry of the Skin", IEEE Sensors Journal, vol. 11, No. 5, May 2011, pp. 1253-1262.

Bennett et al., "Terahertz Sensing in Corneal Tissues", Journal of Biomedical Optics, vol. 16, No. 5, May 2011, pp. 057003.1-057003.8.

Bennett et al., "Terahertz Time-Lapse Imaging of Hydration in Physiological Tissues", Proc. SPIE 7938, Terahertz Technology and Applications IV, Article 793808, Feb. 24, 2011, 10 pages.; doi: 10.1117/12.882962.

Bittoun et al., "Advances in MR imaging of the skin", NMR in Biomedicine, vol. 19, No. 7, Oct. 31, 2006, pp. 723-730.

Borderie et al., "Outcome of Graft Central Thickness After Penetrating Keratoplasty", Ophthalmology, vol. 112, No. 4, Apr. 2005, pp. 626-633.

Brugin et al., "Central Corneal Thickness: Z-Ring Corneal Confocal Microscopy Versus Ultrasound Pachymetry", Cornea, vol. 26, No. 3, Apr. 2007, pp. 303-307.

Chakrabarti et al., "Comparison of corneal thickness measurements using ultrasound and Orbscan slit-scanning topography in normal and post-LASIK eyes", Journal of Cataract & Refractive Surgery, vol. 27, No. 11, Nov. 2001, pp. 1823-1828.

Cheung et al., "Excitation of Coherent Phonon Polaritons with Femtosecond Optical Pulses", Physical Review Letters, vol. 55, No. 20, Nov. 11, 1985, pp. 2152-2155.

Crane et al., "Raman spectroscopic evidence for octacalcium phosphate and other transient mineral species deposited during intramembranous mineralization", Bone, 2006, vol. 39, pp. 434-442.

Cutting et al., "Wound infection, dressings and pain, is there a relationship in the chronic wound?", International Wound Journal, vol. 10, No. 1, Feb. 2013, Electronic Publication: May 28, 2012, 10 pgs.

De Souza et al., "Influence of Temperature and Humidity on Laser in situ Keratomileusis Outcomes", Journal of Refractive Surgery, vol. 17, No. 2, Mar.-Apr. 2001, pp. S202-S204.

Devgan et al., "Modalities for the Assessment of Burn Wound Depth", Journal of Burns and Wounds, vol. 5, Feb. 15, 2006, pp. 7-15.

Di Sieno et al., "Time-domain diffuse optical tomography using silicon photomultipliers: feasibility study", Journal of Biomedical Optics, vol. 21, No. 11, Nov. 2016, pp. 116002-1-116002-9.

Dong et al., "Measurement of central corneal thickness and precorneal tear film thickness of rabbits using the Scheimpflug system", International Journal of Ophthalmology, vol. 6, No. 5, Oct. 18, 2013, pp. 584-587.

Panda et al., "Corneal Graft Rejection", Survey of Ophthalmology, vol. 52, Issue 4, Jul.-Aug. 2007, pp. 375-396.

Park et al., "In vivo burn depth determination by high-speed fiber-based polarization sensitive optical coherence tomography", Journal of Biomedical Optics, vol. 6, No. 4, Oct. 2001, pp. 474-479.

Pavlin et al., "Clinical Use of Ultrasound Biomicroscopy", Ophthalmology, vol. 98, No. 3, Mar. 1991, pp. 287-295.

Pavlin et al., "Subsurface Ultrasound Microscopic Imaging of the Intact Eye", Ophthalmology, vol. 97, No. 2, Feb. 1990, pp. 244-250.

Payette et al., "Assessment of Skin Flaps Using Optically Based Methods for Measuring Blood Flow and Oxygenation", Plastic and Reconstructive Surgery, vol. 115, No. 2, Feb. 2005, pp. 539-546.

Pfeffer et al., "Myocardial Infarct Size and Ventricular Function in Rats", Circulation Research, vol. 44, No. 4, Apr. 1979, pp. 503-512.

Pickwell et al., "In vivo study of human skin using pulsed terahertz radiation", Physics in Medicine & Biology, vol. 49, No. 9, Apr. 2004, pp. 1595-1607.

Pickwell et al., "Simulation of terahertz pulse propagation in biological systems", Applied Physics Letters, vol. 84, No. 12, Mar. 22, 2004, pp. 2190-2192.

Pierce et al., "Collagen denaturation can be quantified in burned human skin using polarization-sensitive optical coherence tomography", Burns, vol. 30, No. 6, Sep. 2004, pp. 511-517.

Raasch, "Corneal Topography and Irregular Astigmatism", Optometry and Vision Science, vol. 72, No. 11, Nov. 1995, pp. 809-815.

Riazuddin et al., "Missense Mutations in TCF8 Cause Late-Onset Fuchs Corneal Dystrophy and Interact with FCD4 on Chromosome 9p", The American Journal of Human Genetics, vol. 86, No. 1, Dec. 31, 2009, pp. 45-53.

Richard et al., "Characterization of the Skin In Vivo by High Resolution Magnetic Resonance Imaging: Water Behavior and Age-Related Effects", Journal of Investigative Dermatology, vol. 100, No. 5, May 1993, pp. 705-709.

Richard et al., "In Vivo Proton Relaxation Times Analysis of the Skin Layers by Magnetic Resonance Imaging", Journal of Investigative Dermatology, vol. 97, No. 1, Jul. 1991, pp. 120-125.

Rietschel, "A Method to Evaluate Skin Moisturizers in Vivo", Journal of Investigative Dermatology, vol. 70, No. 3, Mar. 1978, pp. 152-155.

Ruminski et al., "Thermal Parametric Imaging in the Evaluation of Skin Burn Depth", IEEE Transactions on Biomedical Engineering, vol. 54, No. 2, Feb. 2007, pp. 303-312.

Sajadi et al., "Terahertz-field-induced optical birefringence in common window and substrate materials", Optics Express, vol. 23, No. 22, Oct. 28, 2015, pp. 28985-28992.

Sharma, "Microimaging of hairless rat skin by magnetic resonance at 900 MHz", Magnetic Resonance Imaging, vol. 27, No. 2, Feb. 2009, pp. 240-255.

Singh et al., "Terahertz Sensing of Corneal Hydration", Annual International Conference of the IEEE Engineering in Medicine and Biology, Buenos Aires, Argentina, Aug. 31-Sep. 4, 2010, 4 pgs.

Singh et al., "THz Imaging of Skin Hydration: Motivation for the Frequency Band", Proceedings of SPIE Advanced Biomedical and Clinical Diagnostic Systems VIII, San Francisco, California, vol. 7555, 2010, 8 pgs.

Srinivas et al., "Determination of burn depth by polarization-sensitive optical coherence tomography", Journal of Biomedical Optics, vol. 9, No. 1, Jan./Feb. 2004, pp. 207-212.

Sung et al., "Preliminary results of non-contact THz imaging of cornea", Proc. SPIE 9362, Terahertz, RF, Millimeter, and Submillimeter-Wave Technology and Applications VIII, vol. 9362, Apr. 28, 2015, pp. 93620C-1-93620C-6. https://doi.org/10.1117/12.2086866.

Sung, "Terahertz Imaging and Remote Sensing Design for Applications in Medical Imaging", A thesis submitted in partial satisfaction of the requirements for the degree Master of Science in Electrical Engineering of University of California, 2013, see pp. 1-50 and figures 1-4 to 4-1(c).

Sung et al., "Fast-Scanning THz Medical Imaging System for Clinical Application", Proceedings of SPIE Terahertz Emitters, Receivers, and Applications III, San Diego, California, 2012, 7 pgs.

Sung et al., "Reflective measurement of Water Concentration Using Millimeter Wave Illumination", Proceedings of SPIE Health Monitoring of Structural and Biological Systems, San Diego, California, Apr. 18, 2011, 6 pgs.

(56) References Cited

OTHER PUBLICATIONS

Taylor, "Active THz Imaging for Medical Applications", Ph.D, Electrical and Computer Engineering, UC Santa Barbara, Santa Barbara, 2009, 201 pgs.

Taylor et al., "A Reflection Based, Pulsed THz Imaging System with 1 mm Spatial Resolution", IEEE/MTT-S International Microwave Symposium, Honolulu, Hawaii, Jun. 3-8, 2007, 4 pgs.

Taylor et al., "A scanned beam THz imaging system for medical applications", Proceedings of SPIE Terahertz Emitters, Receivers, and Applications II, San Diego, California, vol. 8119, 2011, 7 pgs.

Taylor et al., "Active THz Medical Imaging Using Broadband Direct Detection", Proceedings of SPIE Terahertz, RF, Millimeter, and Submillimeter-Wave Technology and Applications VI, San Francisco, California, vol. 8624, 2013, 10 pgs.

Taylor et al., "Analysis of Pulsed THz Imaging Using Optical Character Recognition", IEEE Sensors Journal, vol. 9, No. 1, Jan. 2009, pp. 3-8.

Taylor et al., "Pseudophakic Bullous Keratopathy", Ophthalmology, vol. 90, Issue 1, Jan. 1983, pp. 19-24.

Taylor et al., "THz and mm-Wave Sensing of Corneal Tissue Water Content: Electromagnetic Modeling and Analysis", IEEE Transactions on Terahertz Science and Technology, vol. 5, Issue 2, Mar. 2015, first published Feb. 18, 2015, pp. 170-183.

Taylor et al., "THz and mm-Wave Sensing of Corneal Tissue Water Content: In Vivo Sensing and Imaging Results", IEEE Transactions on Terahertz Science and Technology, vol. 5, Issue 2, Mar. 2015, first published Feb. 18, 2015, pp. 184-196.

Taylor et al., "THz imaging based on water-concentration contrast", Proceedings of SPIE Terahertz for Military and Security Applications VI, Orlando, Florida, vol. 6949, 2008, 8 pgs.

Taylor et al., "THz Medical Imaging", 6th ESA Workshop on Millimeter Wave Technology and Applications, 4th Global Symposium on Millimeter Waves, Helsinki, Finland, 2011, 6 pgs.

Taylor et al., "THz Medical Imaging: in vivo Hydration Sensing", IEEE Transactions on Terahertz Science and Technology, vol. 1, No. 1, Sep. 2011, pp. 201-219.

Tewari et al., "Advances in biomedical imaging using THz technology with applications to burn-wound assessment", Proceedings of SPIE Terahertz Technology and Applications V, San Francisco, California, vol. 8261, 2012, 8 pgs.

Tewari et al., "In vivo terahertz imaging of rat skin burns", Journal of Biomedical Optics, vol. 17, No. 4, Apr. 2012, pp. 040503-1-040503-3.

Thrane et al., "THz reflection spectroscopy of liquid water", Chemical Physics Letters, vol. 240, No. 4, Jun. 30, 1995, pp. 330-333.

Tonouchi, "Cutting-edge terahertz technology", Nature Photonics, vol. 1, No. 2, Feb. 2007, pp. 97-105.

Ucakhan et al., "Corneal thickness measurements in normal and keratoconic eyes: Pentacam comprehensive eye scanner versus noncontact specular microscopy and ultrasound pachymetry", Journal of Cataract & Refractive Surgery, vol. 32, No. 6, Jun. 2006, pp. 970-977.

Ung et al., "High-refractive-index composite materials for terahertz waveguides: trade-off between index contrast and absorption loss", Journal of the Optical Society of America B, vol. 28, No. 4, Apr. 2011, pp. 917-921.

Wallace et al., "Terahertz Pulsed Spectroscopy of Human Basal Cell Carcinoma", Applied Spectroscopy, vol. 60, No. 10, Oct. 2006, pp. 1127-1133.

Whitcher et al., "Corneal blindness: a global perspective", Bulletin of the World Health Organization, Special Theme—Blindness, vol. 79, No. 3, 2001, pp. 214-221.

Woodward et al., "Terahertz pulse imaging in reflection geometry of human skin cancer and skin tissue", Physics in Medicine and Biology, vol. 47, Oct. 17, 2002, pp. 3853-3863.

Xu et al., "0.15-3.72 THz absorption of aqueous salts and saline solutions", Applied Physics Letters, vol. 90, No. 3, Jan. 18, 2007, 3 pgs.

Yeh et al., "Electromagnetic propagation in periodic stratified media. I. General theory", Journal of the Optical Society of America, vol. 67, No. 4, Apr. 1977, pp. 423-438.

Ytteborg et al., "Corneal Edema and Intraocular Pressure: II. Clinical Results", Archives of Ophthalmology, vol. 74, No. 4, Oct. 1965, pp. 477-484.

Yue et al., "Histochemical studies of keratoconus", Current Eye Research, vol. 7, No. 1, 1988, pp. 81-86.

Bajwa et al., "In vivo Confirmation of Hydration Based Contrast Mechanisms for Terahertz Medical Imaging using MRI", Proceedings of SPIE Terahertz Emitters, Receivers, and Applications V, San Diego, California, vol. 9199, 2014, 8 pgs.

Broughton et al., "The Basic Science of Wound Healing", Plastic and Reconstructive Surgery, vol. 117, Jun. 2006, pp. 12S-34S.

Brown et al., "THz Imaging of Skin Tissue—Exploiting the Strong Reflectivity of Liquid Water", IEEE 35th International Conference on Infrared, Millimeter, and Terahertz Waves, Rome, Italy, Sep. 5-10, 2010, 2 pgs.

McFarlane et al., "The Design of a Pedicle Flap in the Rat to Study Necrosis and Its Prevention", Plastic and Reconstructive Surgery, vol. 35, Feb. 1965, pp. 177-182.

Taylor et al., "Reflective terahertz imaging of porcine skin burns", Optics Letters, vol. 33, No. 11, Jun. 1, 2008, pp. 1258-1260.

Wagner-Gentner et al., "Low Loss THz Window", Infrared Physics & Technology, vol. 48, No. 3, Aug. 2006, pp. 249-253.

THZ SENSING OF CORNEAL TISSUE WATER CONTENT

CROSS REFERENCE TO RELATED APPLICATIONS

This application is a national stage of PCT Patent Application No. PCT/US2017/028006, entitled "THz Sensing of Corneal Tissue Water Content" to Grundfest et al., filed Apr. 17, 2017, which claims priority to U.S. Provisional Application No. 62/323,455, entitled "THz Sensing of Corneal Tissue Water Content" to Grundfest et al., filed Apr. 15, 2016, the disclosures of which are incorporated by reference herein in their entirety.

STATEMENT OF FEDERAL FUNDING

This invention was made with Government support under Grant No. EY021590, awarded by the National Institutes of Health. The Government has certain rights in the invention.

FIELD OF THE INVENTION

The present invention is directed to apparatus and methods related to simultaneous corneal hydration thickness and hydration measurement through multi-spectral reflectometry.

BACKGROUND OF THE INVENTION

The cornea is the outermost structure of the eye and displays an average thickness in humans of ~580 μm. The normal water content of the cornea is closely related to its visible wavelength (400 nm-700 nm) transparency and refractive capabilities and typically contains 78% water by volume. It plays the leading role in collecting and focusing light on the retina, and provides 46 of the average 59 total diopters of refractive power in the eye.

The layered structure of the cornea is displayed in FIG. 1. The surface layer of the cornea (epithelium) is obscured by a thin layer of water called the tear film, which is replenished by blinking, reflex tearing, and a number of other mechanisms. The bottom layer of the cornea (endothelium) lies adjacent to a volume of water called the aqueous humor which is slightly more viscous than pure water but much less viscous than the vitreous humor. The function of the endothelium is to regulate the water content of the stroma using the aqueous humor as a reservoir. All the layers of the cornea are important for corneal health and visual acuity.

In ophthalmology, corneal disorders, such as Fuchs' endothelial dystrophy, keratoconus, pseudophakic bullous keratopathy and graft rejection, result in increased corneal tissue water content (CTWC) and subsequent swelling of the cornea, leading to chronic vision impairment and often requiring surgical intervention. (See, e.g., A. P. Adamis, et al., Survey of Ophthalmology, vol. 38, pp. 149468, Sep. 1, 1993; Y. S. Rabinowitz, Survey of Ophthalmology, vol. 42, pp. 297-319, November 1998; D. M. Taylor, et al., Ophthalmology, vol. 90, pp. 19-24, 1// 1983; and A. Panda, et al., Survey of Ophthalmology, vol. 52, pp. 375-396, 7// 2007, the disclosures of which are incorporated herein by reference.) Corneal disorders affect large populations worldwide especially that of elderly. It is believed that abnormal CTWC is a key clinical manifestation of endothelial malfunctions and corneal dystrophies. (See, e.g., J. P. Whitcher, M. Srinivasan, and M. P. Upadhyay, Bulletin of the World Health Organization, vol. 79, pp. 214-221, 2001; G. O. Waring, Ili, R. Stating, and D. Street, Archives of Ophthalmology, vol. 105, pp. 58-62, 1987; J. Ytteborg and C. H. Dohlman, Archives of Ophthalmology, vol. 74, pp. 477-484, 1965; G. O. Waring, M. M. Rodrigues, and P. R. Laibson, Survey of Ophthalmology, vol. 23, pp. 147-168, Nov. 1, 1978; M. M. Rodrigues, et al., Ophthalmology, vol. 93, pp. 789-796, Jun. 1, 1986; and J. H. Krachmer, et al., Archives of Ophthalmology, vol. 96, pp. 2036-2039, 1978, the disclosures of which are incorporated herein by reference.) Because abnormal CTWC is an important diagnostic target for assessing the extent of tissue damage in vivo, quantifying and tracking CTWC can (1) provide a better understanding of the formation, development, and progression of these disorders; and (2) become a clinically useful method for early diagnosis and assist in the choice and timing of interventions. However, accurate and non-invasive in vivo measurement of CTWC remains elusive.

SUMMARY OF THE INVENTION

Embodiments of the invention are directed generally to apparatus and methods for simultaneous corneal hydration thickness and hydration measurement through multi-spectral reflectometry.

Several embodiments are directed to a method for the THz imaging a cornea, which may involve generating a THz illumination beam having a frequency that is variable about at least one central wavelength greater than 0.1 THz; illuminating a cornea with the THz illumination beam at multiple frequencies to produce a plurality of reflected signals therefrom; detecting the plurality of reflected signals; and combining the plurality of reflected signals to obtain a plurality of reflectivity maps of the cornea, said reflectivity maps having a combined signal variation indicative of at least the corneal total water content.

In more embodiments, the illumination beam has a variable bandwidth configured such that both narrowband and broadband illumination beams may be generated.

In several more embodiments, one or both the frequency and bandwidth of the illumination beam may be varied during the illumination.

In even more embodiments, the frequency may be varied between 0.1 and 1 THz, and wherein the bandwidth of the illumination beam may have a Q of between about 5 and 50.

In several more embodiments, at least two illumination beams are generated, at least one millimeter wave illumination beam having a central frequency less 0.5 THz and at least one THz illumination beam having a central frequency greater than 0.5 THz, and wherein the at least one millimeter wave illumination beam generates a measurement of the central corneal thickness, and wherein the at least one THz millimeter wave illumination beam generates a reflectivity map of the corneal total water content.

In even more embodiments, the reflectivity maps are further correlated with a separately obtained spatially resolved thickness map.

In several more embodiments, the reflectivity map elucidates the nature of the tissue water content gradient of the cornea, and wherein the tissue water content gradient corresponds to a model tissue water content gradient selected from the group of pinned back, pinned front and global.

In even more embodiments, determining the tissue water content gradient is further used to diagnose at least one corneal disorder.

In several more embodiments, the disorder is selected from the group consisting of Fuchs' endothelial dystrophy, keratoconus, pseudophakic bullous keratopathy, graft rejection, and brain trauma.

In even more embodiments, the method generates simultaneous corneal total water content and central corneal thickness using parameters of the cornea determined a priori.

In several more embodiments, the cornea is field-flattened prior to illumination.

Many embodiments are directed to a THz cornea sensing apparatus comprising, which may include a THz emission source configured to generate a THz illumination beam having a frequency that is variable about at least one central wavelength greater than 0.1 THz; a detector configured to receive and record a THz signal; one or more transmission optics disposed in optical alignment between the THz emission source and a target cornea, and configured such that the transmission optics directs the THz illumination beam to impinge upon a target area on the surface of the cornea, and gathers a reflected THz signal from the target cornea and transmits the reflected THz signal to the detector; and an analyzer for using a plurality of reflected THz signals obtained at a plurality of illumination beam frequencies to produce a plurality of reflectivity maps of the cornea, said reflectivity maps having a combined signal variation indicative of at least the corneal total water content.

In more embodiments, the apparatus is configured to generate an illumination beam having a variable bandwidth configured such that both narrowband and broadband illumination beams may be generated.

In many more embodiments, one or both the frequency and bandwidth of the illumination beam may be varied.

In even more embodiments, the frequency may be varied between 0.1 and 1 THz, and wherein the bandwidth of the illumination beam may have a Q of between about 5 and 50.

In many more embodiments, the apparatus is configured to generate at least two illumination beams, at least one millimeter wave illumination beam having a central frequency less 0.5 THz and at least one THz illumination beam having a central frequency greater than 0.5 THz, and wherein the at least one millimeter wave illumination beam generates a measurement of the central corneal thickness, and wherein the at least one THz millimeter wave illumination beam generates a reflectivity map of the corneal total water content.

In even more embodiments, the analyzer is configured to correlate the reflectivity maps with a separately obtained spatially resolved thickness map.

In many more embodiments, the cornea is field-flattened prior to illumination using a dielectric window transparent to the illumination beam.

In even more embodiments, the transmission optics at least comprise at least two 90° off-axis parabolic mirrors arranged in an angled tip-to-tip geometry.

In many more embodiments, the illumination beam is collimated; the transmission optics includes at least one off-axis parabolic mirror, and at least one scanning mirror; wherein the center of curvature of the cornea is approximately coincident with the focal point of the off-axis parabolic mirror, and wherein the collimated illumination beam is reflected from off-axis parabolic mirror onto the cornea; wherein the reflected signal is recollimated by the off-axis parabolic mirror; and wherein the collimated illumination beam is reflected off the scanning mirror and onto the off-axis parabolic mirror, and wherein the scanning mirror is configured to alter the transverse location of the collimated illumination beam on the off-axis parabolic mirror, such that the target area of the surface of the cornea illuminated by the collimated illumination beam is concomitantly altered, and the reflectivity map of the cornea is obtained without field-flattening.

In even more embodiments, the scanning mirror maintains a parallel path of the collimated illumination beam relative to the clear normal of the off-axis parabolic mirror during alteration of the transverse location.

In many more embodiments, the apparatus may also include at least two scanning mirrors having axes that are mutually orthogonal, wherein a first scanning mirror controls the azimuthal location of the collimated illumination beam, and a second scanning mirror alters the elevation location of the collimated illumination beam.

In even more embodiments, the radius of the collimated illumination beam is varied dependent of the incident location of the beam on the off-axis parabolic mirror.

In many more embodiments, the apparatus may also include a second off-axis parabolic mirror disposed within a beam path of the collimated illumination beam in a symmetric tip to tip orientation; wherein the scanning mirror is configured to gimbal about a center point thereof; and wherein the scanning mirror directs the collimated illumination beam onto the second off-axis mirror, such that angular deflection of the scanning mirror causes transvers translation of the collimated illumination beam in the clear aperture plane of the first off-axis parabolic mirror.

In even more embodiments, the off-axis parabolic mirror is a low f/#off-axis parabolic mirror.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying data and figures, wherein.

DETAILED DISCLOSURE

Figure 1:
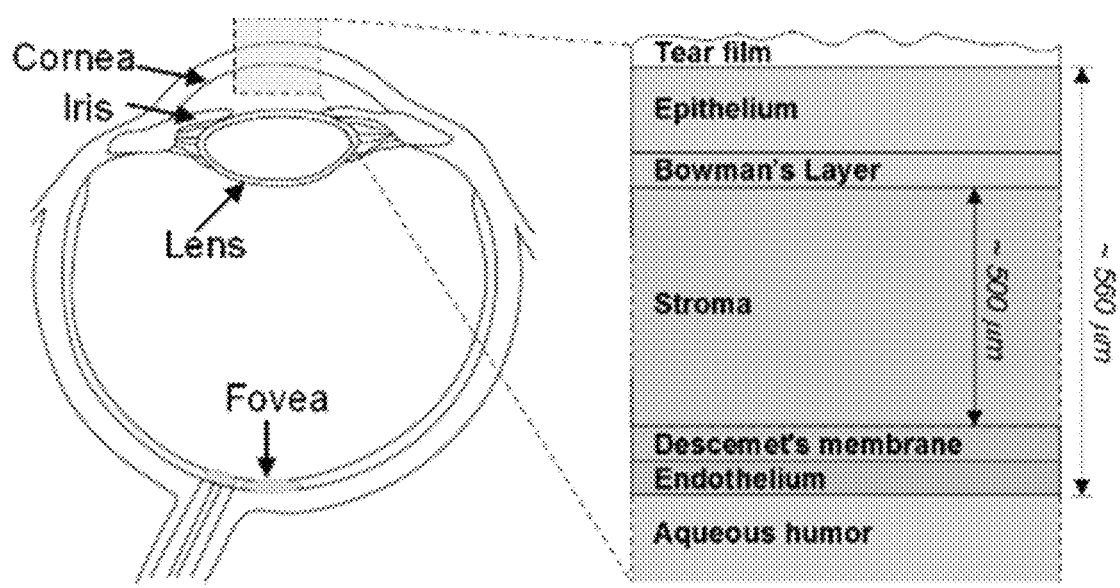
FIG. 1 provides a schematic of the physiology of the eye and the various layers of the cornea.

The embodiments of the invention described herein are not intended to be exhaustive or to limit the invention to precise forms disclosed. Rather, the embodiments selected for description have been chosen to enable one skilled in the art to practice the invention.

Turning now to the drawings, methods and apparatus for corneal imaging and sensing are provided. Various embodiments employ apparatus capable of utilizing single or multiple frequency emissions at terahertz (THz) wavelengths to create reflectivity maps of the cornea in either a contact or non-contact modes. Various embodiments are also directed to methods of obtaining data from THz imaging and sensing apparatus about the corneal tissue-aqueous humor system, including information about the corneal tissue water content (CTWC) and/or the central corneal thickness (CCT). In many such embodiments, methodologies may use multiple transfer functions (frequencies) in obtaining simultaneous data about CTWC and CCT. Some embodiments incorporate methods using frequency sweeping to allow for determination of CTWC and CCT. In other embodiments, systems and methods may assess CTWC using multiple bandwidths at the same frequency, or multiple frequencies at the same bandwidth. Still other embodiments are directed to methods for using data from CTWC measurements to aid in the diagnosis of various corneal and brain disorders.

Methods for Sensing Corneal Tissue Water Content

Many diseases of the eye measurably perturb corneal water content. Some, such as edema and corneal dystrophy, are diseases defined by the deterioration of the cornea's water-regulating process. (See, e.g., S. A. Riazuddin, et al., *The American Journal of Human Genetics*, vol. 86, pp. 45-53; and G. Klintworth, *Orphanet Journal of Rare Diseases*, vol. 4, p. 7, 2009, the disclosure of which is incorporated herein by reference.) Others, such as keratoconus, have poorly understood mechanics, yet have been observed to exhibit non-uniform changes in water concentration of the cornea. (See, e.g., B. Y. Yue, J. Sugar, and K. Schrode, *Curr Eye Res*, vol. 7, pp. 81-6, January 1988, the disclosure of which is incorporated herein by reference.) The water content of the cornea can also be perturbed by medical procedures, including Laser-Assisted in situ Keratomileusis (LASIK), Laser-Assisted Sub-Epithelial Keratectomy (LASEK), or corneal graft surgery. (See, e.g., V. M. Borderie, et al., *Ophthalmology*, vol. 112, pp. 626-633, 2005, the disclosure of which is incorporated herein by reference.) In photorefractive surgeries, such as LASIK and LASEK, tissue ablation rates are strongly linked to corneal water content and errors in the measurement of TWC can be responsible for surgical over-correction. (See, e.g., P. J. Dougherty, K. L. Wellish, and R. K. Maloney, *Am J. Ophthalmol*, vol. 118, pp. 169-76, Aug. 15, 1994; I. R. de Souza, et al., *J Refract Surg*, vol. 17, pp. S202-4, March- April 2001; B. T. B. S. Fisher, et al., *Cornea*, vol. 22, pp. 363-370, 2003; T. Bende, et al., Gracie's *Archive for Clinical and Experimental Ophthalmology*, vol. 226, 1988; and S. G. Farah and D. T. Azar, "Visual Outcomes After Primary LASIK," in LASIK: fundamentals, surgical techniques, and complications, D. T. Azar and D. D. Koch, Eds., ed New York: Marcel Dekker, 2003, pp. xiv, 506 p., the disclosures of which are incorporated herein by reference.) In corneal graft surgeries, immune rejection is preceded by the formation of edema and the reversibility of rejection events tends to diminish with abnormal increases in TWC. Furthermore, the survival rate of rejected grafts generally improves the earlier the formation of edema is detected. (See, e.g., J. Ytteborg and C. H. Dohlman, *Archives of Ophthalmology*, vol. 74, pp. 477-484, 1965, the disclosure of which is incorporated herein by reference.)

Currently available techniques limit the in vivo measurement of CTWC to extrapolation using central corneal thickness (CCT) measurements usually performed with ultrasound or optical coherence tomography (OCT) based pachymetry. (See, e.g., B. Lackner, et al., *Optom Vis Sci*, vol. 82, pp. 892-9, October 2005, the disclosure of which is incorporated herein by reference.) These techniques operate on the assumption of a monotonically increasing relationship between CCT and the average water content of the cornea, in accordance with:

$$H = \frac{m_{H2O}}{m_{H2O} + m_{dry}} = \frac{CCT - 0.091}{CCT + 0.051} \qquad \text{EQ. 1}$$

Figure 2:
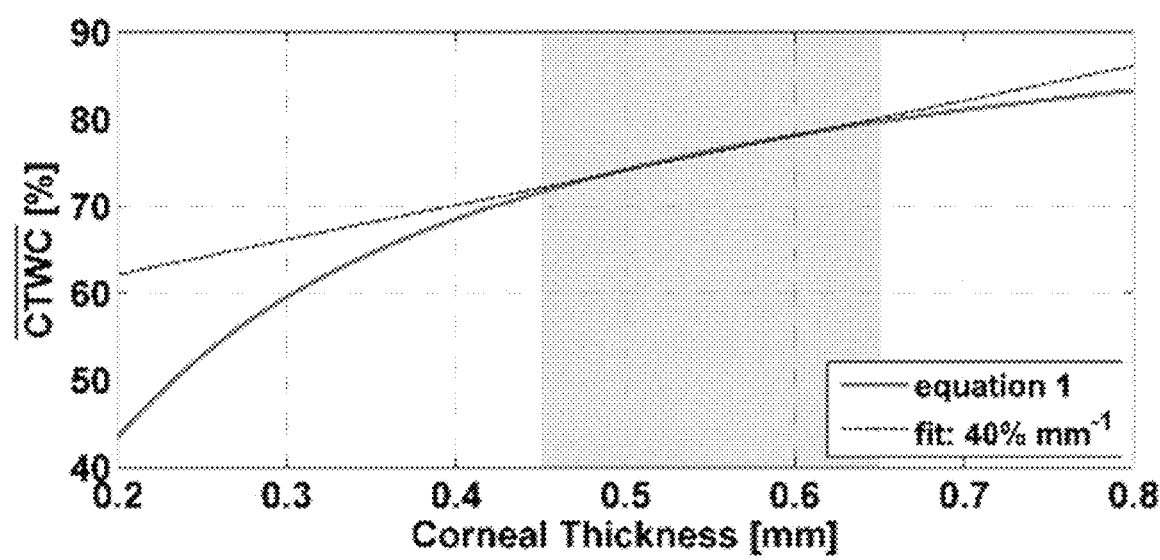
FIG. 2 provides a data plot of (EQ. 1) with physiologic relevant thickness denoted by the shaded region, and a linear fit to (EQ. 1) within the shaded region is represented by the dotted line.

This relationship was established in 1965 from the empirical fit of 11 healthy ex vivo human corneas from a cornea bank and deviations of 20% or greater are seen in the data. (See, e.g., J. Ytteborg and C. H. Dohlman, *Arch Ophthalmol*, vol. 74, pp. 477-484, Oct. 1, 1965, the disclosure of which is incorporated herein by reference.) Additionally, the model does not account for physiologic corneal thickness variation. (See, e.g., M. J. Doughty and M. L. Zaman, *Survey of Ophthalmology*, vol. 44, pp. 367-408, 3// 2000, the disclosure of which is incorporated herein by reference.) For example, healthy patients with corneas too thin to be considered candidates for photorefractive surgery (<450 µm) have predicted water content values of ~70%, a level not theoretically possible while the cornea is still attached to the eye. (See, e.g., M. A. Bamashmus, M. F. Saleh, and M. A. Awadalla, *Middle East Afri Ophthalmol*, vol. 17, pp. 349-53, October 2010, the disclosure of which is incorporated herein by reference.) Additional inaccuracies plague the utility of the linear fit, which predicts a dehydrated cornea thickness of ~127 µm where the generally accepted thickness is >200 µm. A plot of (EQ. 1) is displayed in FIG. 2 where the shaded area spans the physiologic range of thicknesses observed in healthy cornea and the dotted line is a linear fit to (EQ. 1) within the physiologically relevant range (shaded region) with an approximate slope of 40%/mm.

The small linearized slope of (EQ. 1) suggests that pachymetry is an insensitive measure of CTWC. Thus, while ultrasound or optical based pachymeters provide extremely accurate distance measurements (with axial resolution on the order of 10 microns) the mapping from thickness to water content is extremely inaccurate and severely limits the utility of the technique. Furthermore, pachymetry is a point measurement system, thus precluding the possibility of determining the spatial distribution of water in corneal tissue.

To further explore the uncertainty in CTWC diagnostics it is illustrative to compute the CTWC sensitivity required to detect specific diseases and pathologies. In previous work the following sensitivities were computed by referencing known data and (EQ. 1), these were computed as follows: graft rejection 2.7%, Keratoconus 1.6%, Fuchs dystrophy 1.0%, and Refractive surgery 2.0%. (See, e.g., D. Bennett, Z., et al., *Journal of Biomedical Optics*, vol. 17, pp. 097008-1, 2012; s. J. Gromacki and J. T. Barr, *Optometry & Vision Science*, vol. 71, pp. 437-441, 1994; P. J. McDonnell, C et al., *Arch Ophthalmol*, vol. 111, pp. 1374-81, October 1993; and R. B. Mandell, et al., *Invest Ophthalmol Vis Sci*, vol. 30, pp. 845-52, May 1989, the disclosures of each of which are incorporated herein by reference.) However, if statistically significant CCT values are taken from a different set of research the computed required sensitivity for these pathologies are: Keratoconus 4%, Fuchs dystrophy 1.0%, and refractive surgery 8.5%. (See, e.g., Ö. Ö. Uçakhan, et al., *Journal of Cataract & Refractive Surgery*, vol. 32, pp. 970-977, 6// 2006; R. B. Mandell, et al., *Investigative Ophthalmology & Visual Science*, vol. 30, pp. 845-52, May 1, 1989; and H. S. Chakrabarti, et al., *Journal of Cataract & Refractive Surgery*, vol. 27, pp. 1823-1828, 11// 2001, the disclosures of which are incorporated herein by reference.) Further, CCT measurements of in vivo healthy cornea suggest that average CTWC increases of <5% result in slight to no effect on the refractive, transparency, and mechanical functions of the cornea and diurnal percent increase in CTWC can occur during sleep. (See, e.g., N. Ehlers and T. Bramsen, *Acta Ophthaimologica*, vol. 56, pp. 412-416, 1978, the disclosure of which is incorporated herein by reference.) The stark disagreement and inconsistency between published CCT values and estimated CTWC demonstrate the poor understanding between the coupling of thickness and CTWC and indicate that CTWC measurement is both a clinical and a basic research problem.

Many optical techniques for corneal water content have been researched, including (OCT), near infrared reflectometry (laser Doppler), and confocal Raman spectroscopy. (See, e.g., M. Bechmann, et al., *Cornea*, vol. 20, pp. 50-54, 2001; C. K. Hitzenberger, et al., *Investigative Ophthalmology & Visual Science*, vol. 33, pp. 98-103, Jan. 1, 1992; and ANSI, "Z136.1—Safe Use of Lasers," ed, 2007, the disclosures of which are incorporated herein by reference.) Of these, only confocal Raman has provided an absolute measurement of corneal water content. (See, e.g., N. J. Bauer, et al., *Invest Ophthalmal Vis Sci*, vol. 39, pp. 831-5, April 1998, the disclosure of which is incorporated herein by reference.) However, the scattering cross section of water is so low that measurements must use clinically unacceptable integration times or unsafe fluence levels. (See, e.g., N. J. Bauer, F. Hendrikse, and W. F. March, *Cornea*, vol. 18, pp. 483-8, July 1999; and B. T. Fisher, et al., *Cornea*, vol. 22, pp. 363-70, May 2003, the disclosures of which are incorporated herein by reference.)

Numerous published studies explore the theoretical THz electromagnetic properties of tissue, primarily skin, through application of some forms of effective media theory 1D wave mechanics. While the utility of these studies as general case tools is manifest, they cannot be used to calculate the constituents of a specific tissue of interest due to the large physiologic variation of layer thickness, TWC axial distribution, scattering structure distribution, etc. leading to large intrapatient and interpatient variation. Accurate conversion of reflectometry data to axial/spatial distributions of tissue parameters requires a priori knowledge of constituent distribution which may be all but impossible, or at the very least impractical, to acquire in a clinical setting.

The significant role that CTWC plays in visual acuity coupled with the limitations of clinically accepted techniques and current research present a key opportunity for embodiments of methods based on THz reflectometry. Specifically, as previously discussed, the cornea is composed of water distributed throughout a protein matrix with a general increase in corneal tissue water content (CTWC) as a function of depth from the tissue surface. This blend of constituents and their large difference in dielectric function allows for high sensitivity measurement of temporal and/or spatial CTWC gradients. Proteins and other non-water constituents display refractive indices in the 1.5 to 1.9 range with low loss tangents and negligible frequency dependence. In contrast, the dielectric function of water has a large imaginary component (when referenced to protein) and a real part that decreases monotonically with increasing frequency. THz imaging systems, in accordance with embodiments, are very sensitive to changes in water based tissue constituents and very insensitive to changes in non-aqueous constituents. The cornea is essentially a smooth vessel of water in a nearly lossless homogenous matrix on the surface of the body with physiologic variation in thickness. In other words, with respect to THz frequencies, cornea is a lossy thin film lying on top of a lossy termination (aqueous humor).

As such, it is now suggested that the cornea is an ideal target for imaging and sensing using THz reflectometry. More specifically, in accordance with embodiments cornea can present spectrally varying information arising from tissue structure that can be utilized, along with a priori knowledge of tissue structure, to generate high sensitivity, high accuracy maps of CTWC in vivo. Further, due to the thin film properties, reflectivity measurements at multiple frequencies can be combined to deliver simultaneous corneal thickness measurements and thickness resolved CTWC measurements. This measurement capability is unprecedented in ophthalmology and has the potential to revolutionize the field through early detection of corneal pathology/disease/injury that are correlated with tissue edema.

Accordingly, many embodiments are directed to methods of implementing THz imaging and sensing systems to exploit the large differences in electromagnetic properties of protein and water in the THz regime, to measure deviations in water volume fractions characteristic of specific corneal pathologies with high accuracy. Given the tissue constituents, geometry, and location, using embodiments of a THz imaging method should provide CTWC measurements of higher accuracy than that of any other in vivo technique currently available. Furthermore, the required field of view (FOV) in accordance with embodiments is small (~1 cm diameter) and does not change based on the pathology, disease, or injury of interest, which will allow for fast acquisition speed and the possibility of one type of system design for all ophthalmologic applications.

Figure 3:
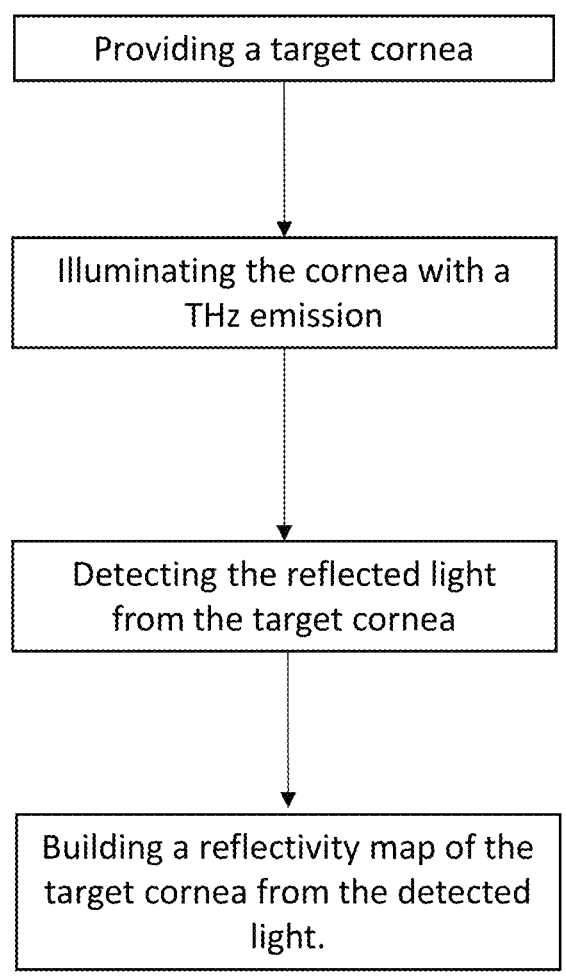
FIG. 3 provides a flowchart of methods of performing THz imaging/sensing in accordance with embodiments.

As summarized in the flow chart in FIG. 3, in many embodiments the method includes:
  illuminating a target cornea with a THz emission characterized by a wavelength between 0.1 and 1 THz, and
  detecting the reflected signal from said corneal target to build a reflectivity map of the illuminated portion of the cornea.

Although any suitable light source, detector, and optical scheme capable of directing a THz illumination onto the target cornea and detecting the reflected signal therefrom, including those systems described herein, may be used, in various embodiments the systems allows for the variation of the frequency and/or bandwidth of the THz emission used to illuminate the cornea. In various such embodiments, the frequency of the emission may be swept, or multiple bandwidths may be used at a single frequency, or multiple frequencies at a single bandwidth to obtain a multiplicity of corneal reflectivity maps in which CTWC and CCT signal variation are decoupled. In such embodiments, a transfer function may be implemented such that the information obtained from the target cornea is determined by the power spectral density function of the source and detector, rather than a particular central frequency, as described in greater detail below.

After having obtained reflectivity maps of the target cornea at multiple frequencies and/or bandwidths, these reflectivity maps may be used in conjunction with suitable analytic models of the cornea structure and/or spatially resolved thickness maps obtained via a suitable means (such as, for example, optical coherence tomography (OCT)) to determine either or both CTWC and CCT independently or simultaneously. For example, in various embodiments, the selection of the bandwidth and frequency of the THz emission is determined by the nature of the information needed of the corneal target.

As described in greater detail in Exemplary Embodiment 1, below, theoretical 1D wave model and simulation studies of the THz frequency properties of the cornea are presented that demonstrate that the properties of the lossy etalon effect that arises from the cornea lying in between the aqueous humor and the cornea, as described in relation to FIG. 1 above, presents to external radiation, and elucidates the THz electromagnetic properties under simultaneous perturbations of corneal tissue water content (CTWC) and central corneal thickness (CCT). Three candidate tissue water content (TWC) gradient types are elucidated by this simulation: (1) pinned back, where the CTWC changes occur primarily at the posterior surface, (2) pinned front, where the CTWC changes occur primarily at the anterior surface close to the aqueous humor, and (3) global where the CTWC modulation occurs evenly throughout the entire thickness of the cornea. Utilizing these models, it is possible, in accordance with embodiments to obtain a quantity $\overline{CTWC}$, which represents the CTWC averaged over the entire thickness of the cornea to allow for gradient types to be compared on a common axis.

In accordance with embodiments, and as described in Exemplary Embodiment 1, the expected reflectivities of these gradient types may be computed using spectral transfer functions with different center frequencies within the THz range (e.g., 100 GHz and 525 GHz), and at different bandwidths from narrowband (e.g., Q~50) to broadband (e.g., Q~5). The results confirm the thin film like behavior of cornea when probed THz frequency illumination, in accordance with embodiments, and the capability of THz imaging methods, in accordance with embodiments to provide simultaneous measurement of thickness and CTWC gradients through the acquisition of an ensemble of reflectivities at different THz emission frequencies. Furthermore, due to the low physiologic variation of the corneal structure, embodiments may utilize a strong set of a priori knowledge on corneal geometry that precludes the need for phase sensitive measurements and allows for depth resolved measurements of the axial CTWC distribution.

Specifically, the simulations presented in Exemplary Embodiment 1 (below), suggest that the cornea is unique among all other external human body structures. While the physiologic variation in thickness of the cornea (450

μm<$t_{cornea}$<650 μm) is quite large with respect to optical wavelengths (<1 μm) and high frequency ultrasonic wavelengths (<30 μm), it is extremely uniform with respect to THz wavelengths. (See, e.g., B. Lackner, G. et al., *Optometry & Vision Science*, vol. 82, pp. 892-899, 2005; D. Huang, et al., *Science*, vol. 254, pp. 1178-1181, Nov. 22, 1991; C. J. Pavlin, M. D. Sherar, and F. S. Foster, *Ophthalmology*, vol. 97, pp. 244-250, 2// 1990; and C. J. Pavlin, et al., *Ophthalmology*, vol. 98, pp. 287-295, 3// 1991, the disclosures of which are incorporated herein by reference.) Furthermore, these simulations show that the tissue structure of the cornea is very ordered and presents a lossy, homogenous medium to a THz frequency sensing system, in accordance with embodiments. These properties allow for THz methods and systems in accordance with embodiments to treat the cornea as a well-defined, curved etalon and support the use of spectrally resolved measurement techniques where specific spectral signatures arise from macroscopic structure and not material properties. In other words, using the THz imaging systems and methods, the cornea behaves like a curved thin film. (See, e.g., F. L. McCrackin, et al., *J. Res. Nat. Bur, Sect. A*, vol. 67, 1963, the disclosure of which is incorporated herein by reference.) These properties allow methods in accordance with embodiments to rely on the following physiologically relevant range of parameters a priori when making measurements:

Corneal thicknesses from 400 μm-700 μm;
Tissue water content from 75%-85%; and
Cornea bordered by air and a volume of water (aqueous humor. FIG. 1)

Embodiments are capable of leveraging these properties to perform simultaneous CTWC and thickness measurements by analyzing the lossy etalon formed by the cornea and underlying body of water (aqueous humor).

Accordingly, embodiments of THz imaging and millimeter-wave reflectometry may be used to generate spatially and temporally resolved reflectivity maps of cornea. In many such embodiments, reflectivity maps obtained from lower frequency (e.g., millimeter-wave) emissions may be used to obtain measurements of central corneal thickness (CCT). In various other embodiments, reflectivity maps obtained from higher frequency (e.g., THz frequency) may show weak correlation with CCT measurements, as the THz data shows both increases and decreases in THz reflectivity as the corneal thickness increased, such that CTWC measurements can be obtained that are decoupled from the CCT measurements. Exemplary Embodiment 2 (below) provides data from exemplary THz imaging systems and methods that show contrast generation in rabbit models, in vivo images of corneal tissue are presented, and a quantitative in vivo demonstration of the decoupled sensing of CTWC and CCT.

In accordance with embodiments, CTWC sensing and imaging methods may be implemented to obtain corneal reflectivity maps. Because of its location immediately below the cornea, the aqueous humor can present a stratified media target or a half space depending on operational parameters of such embodiments (e.g., frequency, angle of incidence, CTWC etc.), which can markedly change the computed CTWC due to the structural similarity with optical thin films. For this reason, many embodiments of CTWC sensing system architectures comprise one of the following:

1) Reflectivity maps obtained at multiple frequencies are acquired and correlated with spatially resolved thickness maps obtained with OCT; or
2) Reflectivity maps obtained at multiple frequencies are acquired and modeling is used to obtain both CTWC and thickness maps simultaneously.

Finally, although contact and non-contact imaging systems described in greater detail below) may be used with embodiments of such methods, contact between the imaging/sensing system and cornea may confounds the aggregate RF properties. Accordingly, some embodiments are directed to non-contact, spectrally resolved measurements using frequency swept transceivers and optical scanning architectures.

Although specific aspects of embodiments of THz imaging/sensing methods are described herein, it will be understood that additional modifications, permutations and aspects are elucidated in the Exemplary Embodiments (1 to 6) discussed in greater detail in the sections of the disclosure to follow. It will be understood, that aspects of these exemplary embodiments may be incorporated into the embodiments described here to improve and expand on the operation of said methods.

THz Mapping and Sensing Apparatus

Figure 4:
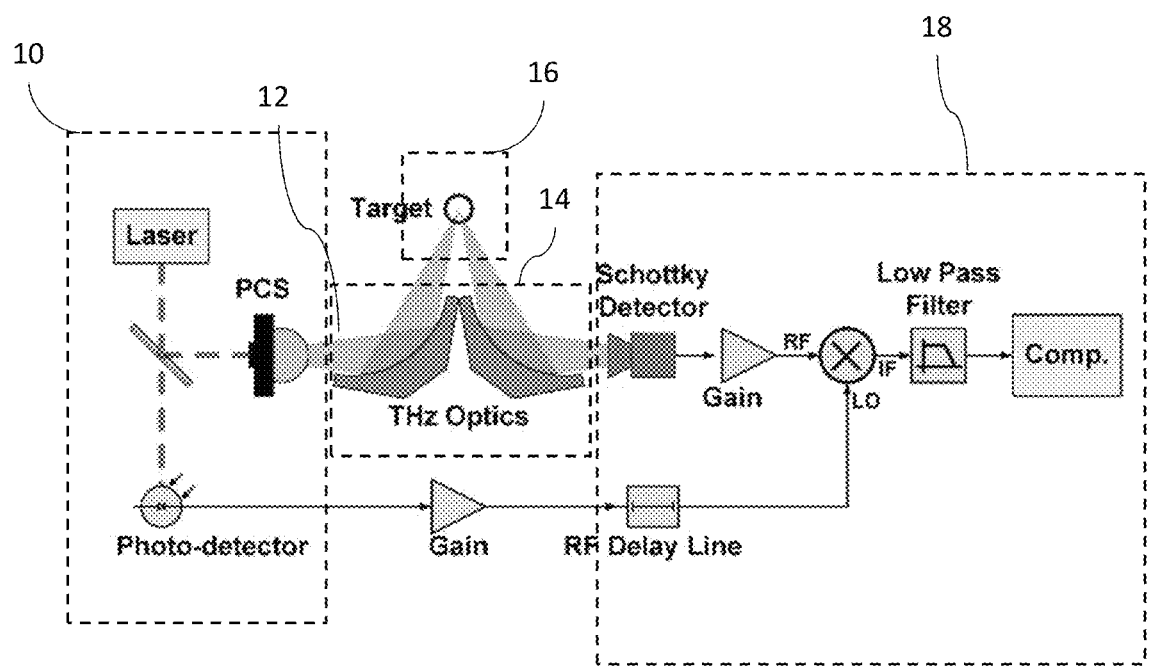
FIG. 4 provides a schematic of a THz imaging/sensing apparatus in accordance with embodiments.

Although methods of using THz imaging/sensing to determine cornea hydration have been described, it will be understood that embodiments are also directed to apparatus for performing reflectivity mapping using THz emission. Although specific embodiments of such systems are described in greater detail below, any such embodiments comprise at least and emissive source (10) capable of producing a THz emission (12), optics (14) capable of focusing the THz emission on a target cornea (16), and a detector (18) for detecting the reflected emission from the cornea. Although not shown, the apparatus may also include any suitable dedicated or software-based analyzer configured to generate a reflectivity map from the detected reflected emission from the cornea. (An example of one such set-up is provided, for example, in FIG. 4)

Specific emissive sources are described in greater detail in conjunction with the Exemplary Embodiments, however, it will be understood that the THz source may include one or more emissive sources capable of producing emission within the THz frequency range (e.g., from 0.1 THz and above). Exemplary embodiments of suitable emissive sources, include, for example, lasers, laser pumped photoconductive switch sources, Gunn diodes, etc. In various embodiments, the bandwidth and/or the wavelength of the emissive source(s) may be modified. In some such embodiments the emissive source(s) may produce wavelength ranging from the millimeter wave regime (e.g., less than 500 GHz) and the THz range (e.g., greater than 500 GHz), and may produce either narrow band (e.g., Q greater than 20) or broadband (e.g., Q less than 20) emissions. In many embodiments, the emissive source emits a broadband emission (e.g., Q less than 20, in some cases less than 10, and in still others less than 5) such that a spread of emissive wavelengths is produced around a central frequency. In various embodiments, such the central frequency may be in the millimeter wave or THz regimes.

Although a number of optical set-ups are described with respect to specific embodiments, it will be understood that any optical set-up capable of effectively focusing the emission from the emissive source on the target cornea and gathering the reflected light from said cornea and transmitting that reflected light onto a detector may be used. For example, in FIG. 4 a paired set (14) of lenses or mirrors are provided capable of focusing the emission from the THz source onto the cornea and collecting the reflected illumination from the cornea and focusing that onto the detector. It will be understood that the nature of the optics will depend on the specific bandwidth, wavelength and geometry of emission. For example, in a millimeter wave regime the optics may include, for example focal length plano-convex (PTFE) lenses. In a THz regime, the optics may comprise a pair of effective focal length (EFL) off-axis parabolic (OAP) mirrors. These optics may be configured to focus on a single region of the target cornea, or as will be described in greater detail, below, may be moved dynamically to obtain information across a greater curvature of the cornea.

The target cornea may be monitored in vivo or ex vivo, in a contact or non-contact mode. Although the non-contact mode is discussed in greater detail below, in the contact mode the front lens of the cornea may be flattened beneath a suitable substrate transparent to the THz emission. In many embodiments, the transparent substrate may be, for example a dielectric material (e.g., Mylar).

It will also be understood that any suitable combination of detector and detector/analyzer electronics may be used suitable for obtaining a signal from the reflected illumination produced by the THz emission impinging on the target cornea. Exemplary detectors and electronics include, for example, pyroelectric detector (either alone or in combination with suitable lock-in amplifiers), Schottky diode detectors, etc. The combination of optics, detector and electronics may be chosen to be advantageous for any specific parameter. For example, in some embodiments the sensitivity of the detector to the position of the target cornea may be lessened by employing dielectric lenses and large aperture detectors. It will be understood that specific combinations of light source, optics and detector/electronics may be derivable by those skilled in the art with reference to the specific THz imaging/sensing parameters developed in accordance with embodiments of this disclosure.

Although specific aspects of embodiments of THz imaging/sensing apparatus are described herein, it will be understood that additional modifications, permutations and aspects are elucidated in the Exemplary Embodiments (1 to 6) discussed in greater detail in the sections of the disclosure to follow. It will be understood, that aspects of these exemplary embodiments may be incorporated into the embodiments described here to improve and expand on the operation of said systems and apparatus.

Non-Contact THz Imaging/Sensing Apparatus

Several weaknesses exist in the field of THz imaging for CWTC diagnostics using current techniques. First, it has been shown that active imaging of the corneal surface can be difficult with simple x-y scanning techniques. The corneal surface is only ~10 mm in diameter en face and nearly spherical with a mean radius of curvature of ~8 mm (Z. Liu, A. J. Huang, and S. C. Pflugfelder, British Journal of Ophthalmology, 83:774-778, 1999, the disclosure of which is incorporated herein by reference). With conventional raster-scanning, only measurements at the central apex of the cornea can be acquired with sufficient SNR. Second, most, if not all, currently clinically accepted techniques of determining CTWC in viva are based on thickness measurements that extrapolate CTWC from CCT (Y. Li, R. Shekhar and D. Huang, Ophthalmology, 113:792-799.e2, 2006, the disclosure of which is incorporated herein by reference). Conversely, nearly all THz imaging modalities currently being applied to medical diagnostic research require contact through the application of a dielectric field-flattening window. Accordingly, in many embodiments THz imaging systems and methods capable of acquiring reflectivity maps of the cornea in viva without contact. The motivation for these systems/methods are encapsulated in the following summary points:

Corneal reflectivity is a coupled function of the illumination frequency, water content, and thickness and presents as a lossy etalon at THz frequencies. Application of a field-flattening window modifies the thickness and constrains the utilization of model based analysis. Additionally, contact adds a significant confounder to the acquired signal, making the establishment of statistical significance difficult.

(2) While CCT-based quantification of CTWC is fundamentally flawed, it is used as the reference standard to which THz imaging/sensing is compared. CCT measurements are the key diagnostic known to ophthalmologists and the development of THz imaging will be constrained if the necessity of contact with a dielectric window continues to confound CCT.

Accordingly, several embodiments address these needs by providing THz imaging/sensing systems capable of creating cornea images/reflectivity maps without contact. Multiple embodiments of the system architecture rely on the key observation that the cornea is nearly a perfect hypo hemisphere with respect to a THz wavelength. Additionally, the expected person to person (intra patient intra subject) variability of the morphological/geometric variation from an ideal sphere are also limited as a function of THz wavelength. Finally, many more embodiments take advantage of the fact that the hypo hemispherical diameter of the cornea (corneal extent) displays a quite limited variation when normalized by THz wavelengths. These three elements enable systems and methods to assume a curvature and field of view a priori with a high degree of confidence.

In Exemplary Embodiments 1 and 2 (discussed below), the utility of using THz and millimeter wave imaging and sensing to track changes in CTWC are described. During this time window, central corneal thickness (CCT) measurements were acquired with an ultrasound pachymeter (current clinical gold standard), and the corresponding RF reflectivities were acquired with a 100 GHz (narrowband) reflectometer and ~525 GHz (broadband) imaging system. The protocol included the application of a 12 µm thick Mylar window during imaging as it was necessary to gently flatten the cornea and provide a flat, specular surface for both systems. The experiment revealed a strong positive correlation between increasing CCT and increasing 100 GHz reflectivity, both consistent with the intended increase in CTWC. Model based analysis of the ensemble of measurements suggested that the protocol most likely modified the thickness of the cornea while leaving the aggregate CTWC relatively unperturbed thus resulting in a resolvable "etalon effect" at 100 GHz and an unresolvable (and hence apparent absence of) "etalon effect" at 525 GHz. It is also likely that the contact pressure of the window altered the natural and intended response of the cornea.

Accordingly, many embodiments are directed to THz optical apparatus and methods capable of performing non-contact THz imaging of cornea. Various embodiments incorporated beam scanning methodologies that perform angular, normal incidence sweeps of a focused beam while keeping the source, detector, and patient fixed. In many such embodiments, terahertz (THz) imaging systems and apparatus comprise a combination of plane and off axis parabolic (OAP) mirrors to scan a beam at normal incidence across the radial extent of the cornea while keeping the source, detector, and, most importantly, the patient stationary. In many embodiments, these systems, methods and apparatus acquire an image of a spherical surface with an arbitrary radius of curvature by an orthographic projection of the spherical surface to Cartesian coordinates. Embodiments result in non-contact imaging of corneal reflectivity and result in the elimination of temporal thickness variations.

Figure 5:
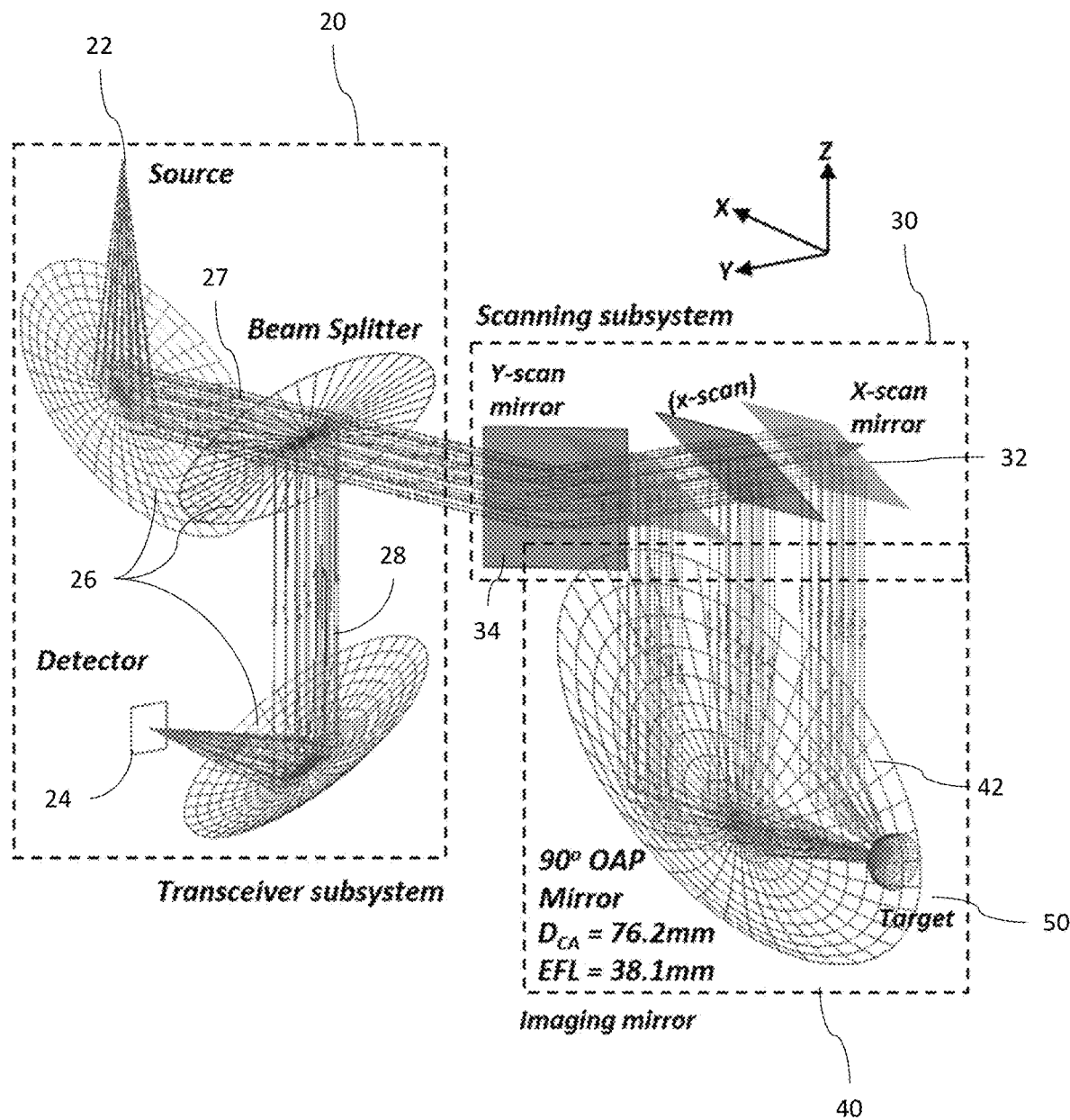
FIG. 5 provides a schematic of a non-contact THz imaging/sensing apparatus in accordance with embodiments.

In various embodiments of non-contact THz cornea imaging, a single OAP mirror-based rectilinear scanning system may be used, as shown schematically in FIG. 5. Many embodiments employ a system that may comprise a transceiver subsystem (20), a scanning subsystem (30), and an imaging mirror (40). In some such embodiments, the transceiver subsystem may comprise a source (22) (e.g., THz emissive source as discussed above), detector (24) (e.g., reflected light detector as discussed above), and suitable optics (26) (e.g., beam splitter, focus lenses/mirrors, etc.) to transmit a properly conditioned (e.g., collimated) illumination beam (27) and receive a reflected source of light (28). In some such embodiments the scanning subsystem (30) may comprise one or more movable scanning optics (32) (e.g., mirrors for example) capable of shifting the incident position of the transmitted illumination beam relative to the imaging mirror. It will be understood that any suitable electronic and/or mechanical means of scanning the mirror to provide for such incident illumination beam position shifting may be implemented. Specifically, it will be understood that systems and apparatus incorporating multiple scanning mirrors may be provided to decouple the azimuthal and elevation scan directions to separate planar mirrors (32 & 34) whose axes are mutually orthogonal. Still in some such embodiments, the imaging mirror (40) may comprise any suitable mirror capable of directing the incident illumination beam onto the target cornea and gathering the reflected light and transmitting that to the transceiver subsystem for detection. Exemplary embodiments of such a mirror may include a 90° off-axis parabolic mirror, although any optical mirror suitable for the specific target geometry may be implemented as will be understood by one of ordinary skill in the art.

During operation of such embodiments, active imaging of a spherical corneal surface, comprises positioning the center of curvature (CoC) of the target cornea (50) coincident with the focal point of the imaging mirror (e.g., OAP mirror)(40), and then transmitting a collimated illumination beam into the clear aperture of the mirror, parallel to the clear aperture (CA) normal (see, e.g., discussion in Exemplary Embodiment 3 and FIGS. 31A & 31B, below). Utilizing such embodiments, the focused illumination beam is provided at a normal incidence to the spherical surface and, in the limit of geometric optics, has a phase front curvature equal to the spherical surface radius of curvature (RoC). The reflected, diverging beam is then recollimated by the OAP mirror and arrives coincident with the transmitted beam path. In such embodiments, moving the transverse location of the collimated beam while maintaining a path parallel to the mirror's clear normal sweeps the location of the illumination spot on the spherical surface, and thus a complete image can be constructed. Although specific optical set-up are provided, it will be understood that the retrodirective nature of embodiments of such systems and apparatus is compatible with any transceiver design that can multiplex/demultiplex the input and output beams using, e.g., a wire grid, thin film, or polarizing beam splitter.

Although the above discussion has assumed a constant illumination emission, it will be recognized that for a fixed input beam radius, and optimal alignment, the signal from the lower region of the cornea will always be higher than the upper region of the cornea. Accordingly, in various embodiments the imaging field may be homogenized in terms of beam radius and coupling efficiency by varying the input beam radius as a function of mirror position. In various other embodiments the propagated beam can be decomposed to include higher-order Hermite-Gaussian or Laguerre-Gaussian modes, and an augmented ray-transfer method can be applied to beam propagation, thereby accounting for the asymmetric geometry of the mirror segment.

Figure 6:
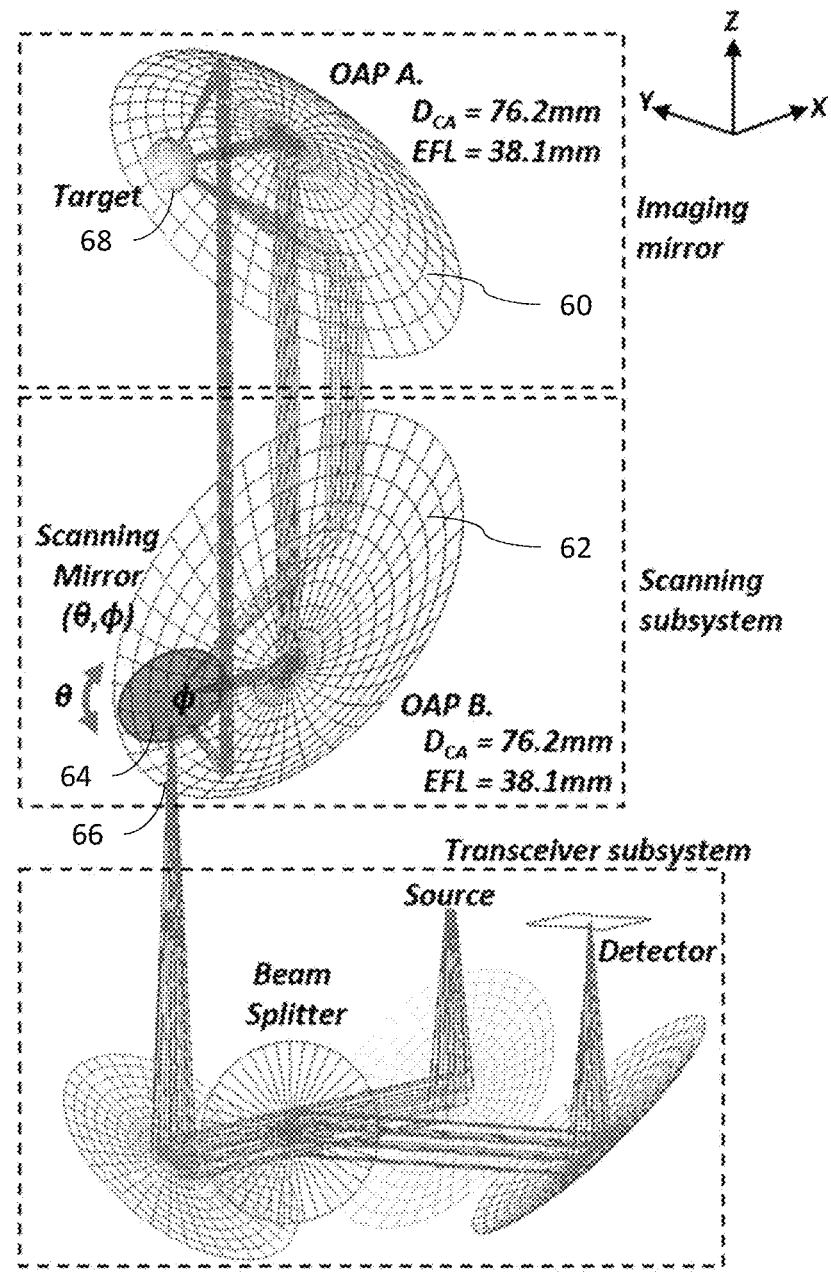
FIG. 6 provides a schematic of a dual-mirror non-contact THz imaging/sensing apparatus in accordance with embodiments.

Although the above discussion has been with reference to a single fixed OAP mirror designs, it will be understood that systems and apparatus incorporating multiple fixed OAP imaging mirrors (60 & 62) may be provided, as shown in FIG. 6. Specifically, due to the comparatively short Rayleigh lengths at the THz wavelengths, the angular scanning may be configured with a single gimbal-mirror-like optical translation where rotational motion is about the center point of the mirror surface (64), in accordance with many embodiments. This design allows for an overall shorter optical path compared to the rectilinear scanning design. In such embodiments transverse translation of a collimated beam (66) results in the angular scanning of a focused beam at the target plane (68). In this angular implementation, and in accordance with several embodiments, a second parabolic mirror (62), identical to the focusing objective, is added to the beam path in a symmetric "tip-to-tip" orientation. The THz beam (66) is focused onto the surface of the angular scanning mirror (64) and then the diverging beam is directed to varying sub-segments of the added parabolic reflector (60). This angular scan results in the transverse translation of a collimated beam in the clear aperture plane of the focusing OAP.

Although exemplary embodiments of non-contact THz imaging apparatus are provided here and in the Exemplary Embodiments (4 & 5) below, embodiments are also directed quasioptical methods for designing alternative in vivo non-contact corneal imaging systems in accordance with this disclosure. Specifically, regardless of the specific embodiment of the THz apparatus chosen, corneal imaging systems provided place the corneal CoC coincident with the focal point of a low f/#OAP mirror, and translation of a collimated beam in the clear aperture plane produces angular scanning of a focused beam along the surface of the cornea. Embodiments of quasioptic techniques are provided that segment parabolic mirrors into an ensemble of thin lenses where the effective focal length and free space beam paths are proportional to the distance between the parent focal point and mirror clear aperture centroid. The spot size on target, radius of curvature pre and post reflection, and coupling coefficient between transmit and received beams can then be simulated for a specified OAP reflector, and functional system parameters determined. Embodiments are also provided for computing the spot size on target and quasioptical coupling coefficient. As demonstrated in Exemplary Embodiments 4 & 5, the concurrence of the results strongly supports the use of quasioptical techniques as a design and analysis tool.

Although many embodiments are directed to the components described above, in various embodiments certain alignment tools and apparatus may be incorporated with THz imaging/sensing apparatus and methods. In various embodiments, for example, an ultrasound probe may be employed to target an interrogated area. In other embodiments, laser targeting, fiducial markers (transparent to THz illumination) on the Mylar window may be used to ensure repeatable probing location.

To confirm accurate placement of the probes and targets additional processing techniques may also be utilized to verify that the placement is in a desired location (e.g., at the apex of the cornea). In various embodiments, THz cornea images may be converted to binary masks using a threshold four times larger than the standard deviation of the pixels located in the corners of each field of view (FOV). The resulting masks may be morphologically closed using a disc-shaped structuring element. The centroids of the cornea masks may then be computed, and a circular mask with a radius corresponding to the probe radius placed at the centroid, creating a test mask. This result may then be compared to registered visible images of the fiducials markers against the cornea under test. The mean reflectivities and standard deviations in the probe mask and in the cornea mask may then be computed and confirmed to be statistically insignificant.

Diagnostic Methods Using THz Imaging

In ophthalmology, corneal disorders, such as Fuchs' endothelial dystrophy, keratoconus, pseudophakic bullous keratopathy and graft rejection, among others, result in increased corneal tissue water content (CTWC) and subsequent swelling of the cornea, leading to chronic vision impairment and often requiring surgical intervention. Corneal disorders affect large populations worldwide especially that of elderly. It is shown in accordance with embodiments that abnormal CTWC is a key clinical manifestation of endothelial malfunctions, corneal dystrophies, keratoconus, pseudophakic bullous keratopathy, graft rejection, and brain trauma. Because abnormal CTWC is an important diagnostic target for assessing the extent of tissue damage in vivo. Embodiments of THz imaging provide methods and systems for the spatiotemporal mapping of CTWC. Accordingly, many embodiments are directed to the use of THz imaging of corneal tissue water content (CTWC) as a method for the early and accurate detection and study of cornea related diseases.

EXEMPLARY EMBODIMENTS

The following sections set forth certain selected embodiments related to the above disclosure. It will be understood that the embodiments presented in this section are exemplary in nature and are provided to support and extend the broader disclosure, these embodiments are not meant to confine or otherwise limit the scope of the invention.

Example 1: THz Electromagnetic Modeling and Analysis

Exemplary embodiments exploring the THz spectral properties of human cornea as a function of CCT and corneal water content, and clinically useful models of THz based corneal water content sensing are provided.

The exemplary embodiment provides a 1D plane wave study of the electromagnetic properties of the cornea. Corneal tissue water content (CTWC) was modeled with a combination of Debye, Bruggeman, and stratified media theory. Reflectivities as a function of frequency, CTWC level, CTWC gradient type, and corneal thickness were computed and then the aggregate reflectivities of subsets of these spaces were explored with four different systems; two centered at 100 GHz and two centered at 525 GHz. Additionally each system was simulated broad band (Q=5) and narrow band (Q=50). The results elucidate the complex relationship between TWC, corneal thickness, and RF reflectivity, and demonstrate the utility of different frequency bands and bandwidths.

Embodiments of three CTWC perturbations, based on corneal physiology, and evidence of their effect on axial water distribution and total thickness are also provided. The THz frequency reflectivity properties of the three CTWC perturbations are simulated and explored with varying system center frequency and bandwidths (Q factors). The experiments demonstrate that at effective optical path lengths on the order of a wavelength the cornea presents a lossy etalon bordered by air at the anterior and the aqueous humor at the posterior. The simulated standing wave peak-to-valley ratio is pronounced at lower frequencies and its effect on acquired data can be modulated by adjusting the bandwidth of the sensing system, in accordance with embodiments. These observations are supplemented with experimental spectroscopic data.

The data presented in this exemplary embodiment provides evidence that there is a significant difference in THz reflectivity properties of cornea when the variation in CTWC is localized to the epithelial layer, endothelial layer, or is distributed evenly throughout the thickness dimension of the cornea. Such variation allows for a diagnostic determination of pathology based on the localization of CTWC and in vivo CTWC gradients as determined by reflectivity maps. The results from these exemplary studies indicate that a priori knowledge of corneal thickness can be utilized in accordance with embodiments for accurate assessment of corneal tissue water content and thus pathology.

Corneal Model

In vivo, the corneal matrix is ordered and displays birefringence at optical wavelengths. (See, e.g., N. J. Bauer et al., *Invest Ophthalmol Vis Sci*, vol. 39, pp. 831-5, April 1998, the disclosure of which is incorporated herein by reference.) However because optical anisotropy has not yet been demonstrated at THz wavelengths the cornea may be treated as a smooth, homogenous, isotropic medium whose dielectric constant is defined by axially varying tissue water content. Further collagen fibers, scars, vesicles, and other structures found in the cornea are very small (~50 µm) compared to the shortest wavelengths considered by this work ~500 µm) so their contributions to the THz electromagnetic properties of the cornea are considered negligible. Additionally, the surface of the cornea is optically smooth with respect to THz wavelengths with a root mean square (RMS) surface height standard deviation of ~0.129 µm. (See, e.g., P. E. King-Smith, S. H. Kimball, and J. J. Nichols, *Invest Ophthalmol Vis Sci*, vol. 55, pp. 2614-8, April 2014, the disclosure of which is incorporated herein by reference.)

Although curved with a radius close to that of the typical eye, the THz radiation is assumed to be focused to a spot size much less than either the radius or the corneal diameter. Then, the cornea's electromagnetic properties can be modeled with stratified media and effective media theories. (See, e.g., P. Yeh, A. Yariv, and C.-S. Hong, *Journal of the Optical Society of America*, vol. 67, pp. 423-438, 1977 Apr. 1 1977; and G. A. Niklasson, C. G. Granqvist, and O. Hunderi, *Appl. Opt.*, vol. 20, pp. 26-30, 1981, the disclosures of which are incorporated herein by reference.) This is accomplished, in accordance with embodiments by discretizing the cornea into adjacent slabs of material whose dielectric function is homogenous and water-content dependent. In various embodiments, the electric permittivity of each slab is then calculated using Bruggeman effective media theory (e.g., G. A. Niklasson, C. G. Granqvist, and O. Hunderi, *Appl. Opt.*, vol. 20, pp. 26-30, 1981; R. Landauer, *AIP Conference Proceedings*, vol. 40, pp. 2-45, 1978; and K. K. Karkkainen, A. H. Sihvola, and K. I. Nikoskinen, *Geoscience and Remote Sensing, IEEE Transactions* on, vol. 38, pp. 1303-1308, 2000, the disclosures of which are incorporated herein by reference) where the majority of the slabs represent the stroma due to its significant thickness as compared to all the other layers. Following computation of layer properties, the aggregate reflectivity may be computed in accordance with embodiments via the transfer-matrix method. (See, e.g., M. Born and E. Wolf, Principles of optics: electromagnetic theory of propagation, interference and diffraction of light: Cambridge University Press, 1980, the disclosure of which is incorporated herein by reference.)

Figure 7:
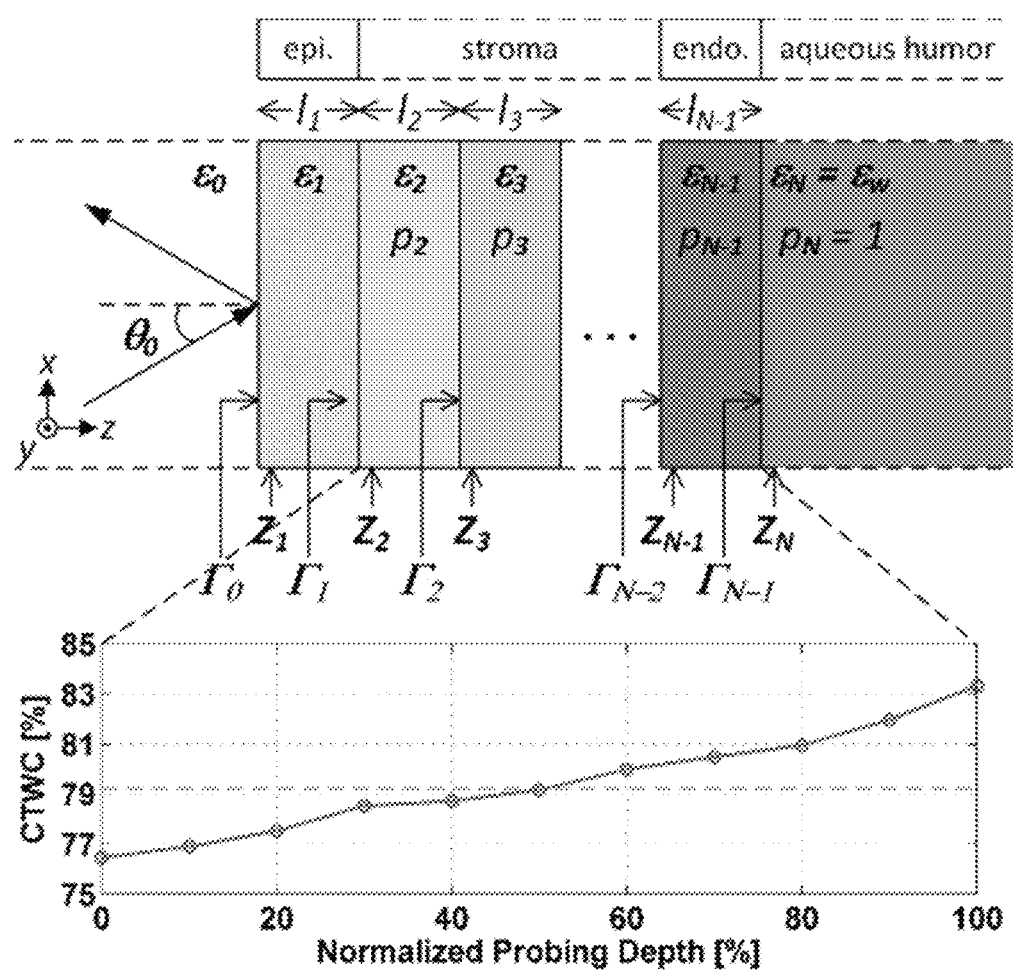
FIG. 7 provides a stratified media model of cornea combining effective media and stratified media theories, in accordance with embodiments.

Embodiments of such an approach are summarized in FIG. 7 where the first layer is occupied by the epithelium and the final layer is modeled as a half space of liquid water representing the aqueous humor (FIG. 1). Layers 1 through N+1 represent the discretized, axially dependent CTWC. The axially varying water content simulated via the stratified media model is adapted from N. J. Bauer, et al., 1998, previously cited. The data in N. J. Bauer, et al. was obtained from rabbit eyes (N=10) using confocal Raman spectroscopy. The trend is plotted in FIG. 4 as a function of normalized depth. The trend was generated by taking 11 evenly spaced points over the thickness of each cornea for 10 rabbits, converting their position to normalized thickness, and then averaging each point independently to produce the final presented trend.

An average tissue water content of the cornea of 79.4% was computed by averaging the trend along the normalized thickness axis. Note that this is higher than the accepted healthy cornea level of ~78%. In addition, note (discussed in greater detail below) the fluence level utilized to acquire these measurements most likely perturbed tissue properties in the cornea, which may have affected the overall accuracy of the measurement. However, this is the most complete in vivo dataset of CTWC that exists in the art.

The methodology for simulating the frequency dependent aggregate properties of tissue are now provided. First, the frequency dependent dielectric properties of water are captured by the double Debye model (EQ. 2) with the same constitutive parameters and relaxation frequencies (ε0, ε1, ε∞, f1, f2) that were presented previously.

$$\varepsilon_w(f) = \varepsilon_\infty + \frac{\varepsilon_s - \varepsilon_i}{1 - j2\pi f/f_s} + \frac{\varepsilon_i - \varepsilon_\infty}{1 - j2\pi f/f_s} \quad \text{EQ. 2}$$

The collagen and water of the cornea cannot be isolated volumetrically, which allows the implementation of the binary-mixture Bruggeman model (previously cited) (EQ. 3) where $\varepsilon_c$ is the frequency invariant dielectric constant of collagen, $\varepsilon_w$ is the frequency dependent dielectric function of water computed with (EQ. 2), $p_{w,i}$ is the water volume fraction, and $\hat{\varepsilon}_i$ is the effective permittivity of the layer that satisfies the effective media relation in (EQ. 3).

$$p_{w,i}\left(\frac{\hat{\varepsilon}_i - \varepsilon_w}{\varepsilon_w + 2\hat{\varepsilon}_i}\right) + (1 - p_{w,i})\left(\frac{\hat{\varepsilon}_i - \varepsilon_c}{\varepsilon_o + 2\hat{\varepsilon}_i}\right) = 0 \quad \text{EQ. 3}$$

$$\forall i \in [1, N]$$

The effective electrical length of the layer i is given in equation (EQ. 4) where $\hat{\varepsilon}_i$ is the complex, effective permittivity of layer i computed with (EQ. 3), $\theta_i$ is the complex angle of refraction computed with Snell's law, and h is the layer physical thickness.

$$\delta_i = \frac{2\pi}{\lambda} l_i \sqrt{\hat{\varepsilon}_i} \cos(\theta_i) \quad \text{EQ. 4}$$

$$\forall i \in [1, N]$$

For the simulations presented below the discretized layer thickness was set at ~10 μm where reflectivity simulation results with varying layer thicknesses converged to a differential less than $10^{-6}$. Thinner layers resulted in insignificant increases in precision at the expense of increases in computational complexity. The Fresnel reflection coefficient (elementary reflection coefficients arising from boundary conditions) from layer i−1 to layer i can be written as a function of the complex effective dielectric constants and the complex permittivities and electrical lengths (EQ. 5). (See, e.g., S. J. Orfanidis, Electromagnetic Waves and Antennas vol. 1: Rutgers Univ., 2014, the disclosure of which is incorporated herein by reference.)

$$\rho_i = \frac{\sqrt{\hat{\varepsilon}_{i-1}} \cos(\theta_{i-1}) - \sqrt{\hat{\varepsilon}_i} \cos(\theta_i)}{\sqrt{\hat{\varepsilon}_{i-1}} \cos(\theta_{i-1}) + \sqrt{\hat{\varepsilon}_i} \cos(\theta_i)} \quad \text{EQ. 5}$$

$$\forall i \in [1, N+1]$$

Note that the Fresnel coefficient has been written for TE polarization. This polarization has been shown to produce reflectivities and CTWC sensitivities larger than the TM polarization for any oblique incidence angle (Z. D. Taylor, et al., Terahertz Science and Technology, IEEE Transactions on, 1:201-19, 2011; D. B. Bennett, et al., IEEE Sensors Journal, 11:1530-437, 2010, the disclosures of which are incorporated herein by reference).

In accordance with numerous embodiments, the total aggregate electric field Γ recursive reflection coefficient from layer i to the stack consisting of layers i+1 to N+1 may thus be given by EQ. 6 where $\Gamma_{N+1}$ is defined as the Fresnel coefficient between the final layer of the cornea and the aqueous humor and $\Gamma_1$ is the total reflection of the cornea.

$$\Gamma_i = \frac{\rho_i + \Gamma_{i+1} e^{-j2\delta_i}}{1 + \rho_i \Gamma_{i+1} e^{-j2\delta_i}}, \Gamma_{N+1} = \rho_{N+1} \quad \text{EQ. 6}$$

$$\forall i \in [1, N+1]$$

One of the most quoted studies on biologically relevant proteins is by Markelz and Heilweil where a terahertz pulsed spectroscopic (TPS) system was used to assess the absorption coefficients of DNA, bovine serum albumin (BSA) and collagen, and the real index of DNA and BSA, between 0.1 and 2.0 THz (A. G. Markelz, A. Roitberg, and E. J. Heilweil, Chemical Physics Letters, 320:42-48, 2000, the disclosure of which is incorporated herein by reference). They measured a BSA refractive index of ~1.7 with negligible loss tangent, suggesting that the real part of the dielectric constant is ~2.9. In the absence of direct spectroscopic measurements of pure collagen, the properties of BSA have been deemed a good approximation.

In accordance with multiple embodiments, in EQ. 3, $\varepsilon_c$=2.9, and the absorption coefficient of the ith layer in the corneal tissue at any particular frequency can then be determined by EQ. 7, where $\hat{\varepsilon}_i{}'$ and $\hat{\varepsilon}_i{}''$ are the real and imaginary components respectively of the dielectric function of the ith layer.

$$\alpha_i = 2\pi f \left[\frac{\mu \hat{\varepsilon}_i'}{2}\left(\sqrt{1 + (\hat{\varepsilon}_i''/\hat{\varepsilon}_i')^2} - 1\right)\right]^{1/2} \quad \text{EQ. 7}$$

Figure 8:
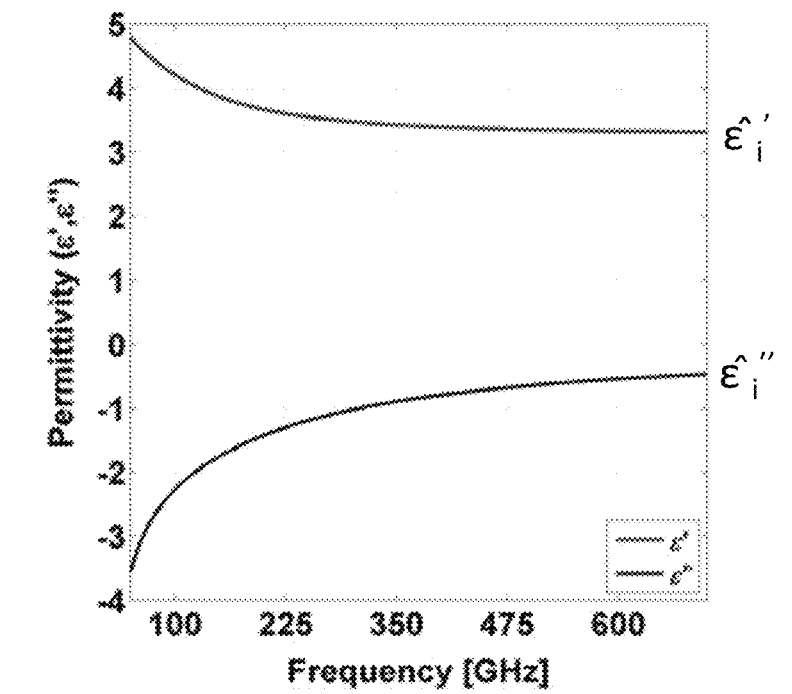
FIG. 8 provides a data plot of dielectric properties of the cornea, in accordance with embodiments.
Figure 8:
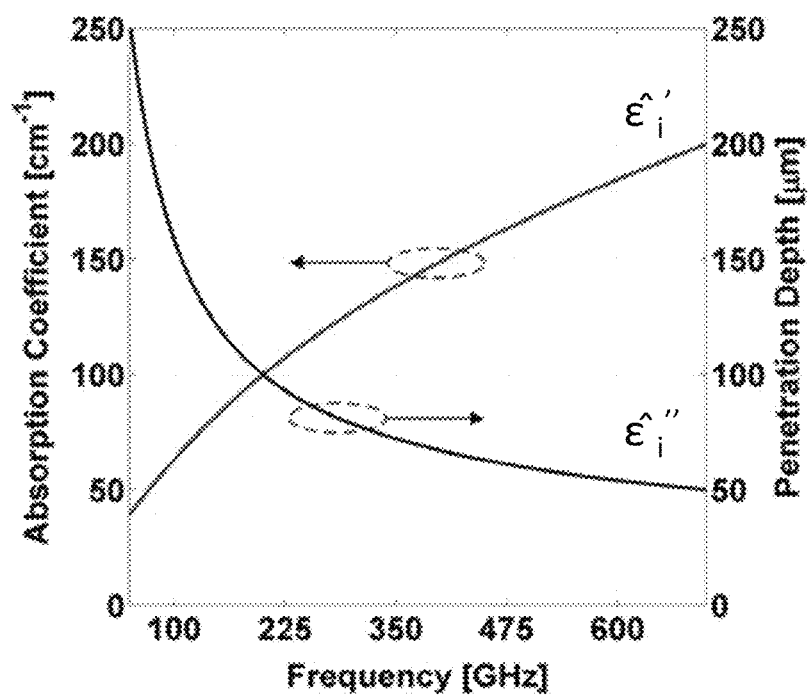

The aggregate dielectric function of corneal tissue, and the expected absorption coefficient and penetration depth are shown below in FIG. 8 over the frequency range utilized in simulation results described within.

CTWC Sensitivity Control Factors:

In accordance with many embodiments, the band normalized power reflectivity of the cornea may be described in EQ. 8, where $S_s(f)$ is the source power spectral density, $S_D(f)$ is the detector spectral responsivity, $p_w$ is the water fraction, d is central corneal thickness, f is the illumination frequency, and $\Omega_f$ is the system equivalent noise bandwidth (ENB). EQ. 8, in accordance with various embodiments, is interpreted as the weighted average of the corneal THz reflectivity where the weights are determined by the spectral response of the system.

$$\text{Power reflectivity} = R(p, d) = \frac{\int_{\Omega_f} S_s(f) S_D(f) |\Gamma_0(p_w, d, f)|^2 df}{\int_{\Omega_f} S_s(f) S_D(f) df} \quad \text{EQ. 8}$$

Note that EQ. 8 models a broadband measurement as an incoherent sum. In many embodiments, the intrinsic sensitivity of the cornea reflectometry system may also be computed as the gradient of EQ. 8 with respect to parameters of interest. For example, the CTWC sensitivity and corneal thickness sensitivity are given in EQ. 9 and EQ. 10, respectively.

$$\text{Hydration Sensitivity} = |\nabla_p H| = \left|\frac{\partial R(p_w, d)}{\partial p}\right| \quad \text{EQ. 9}$$

$$\text{Thickness Sensitivity} = |\nabla_d H| = \left|\frac{\partial R(p_w, d)}{\partial d}\right| \quad \text{EQ. 10}$$

Accordingly, it is possible with embodiments of a 1 Hz sensing system to maximize EQ. 9 and minimize EQ. 10, thus maximizing CTWC sensitivity while minimizing thickness sensitivity uncorrelated to CTWC. However, given the powerful a priori knowledge of corneal layer geometry many embodiments of various sensing systems may be provided that sensitive to both simultaneously, similar to what is done in ellipsometry (R. M. A. Azzam and N. M. Bashara, Ellipsometry and polarized light Elsevier Science Publishing Co., Inc., 1987, the disclosure of which is incorporated herein by reference). The CTWC sensitivity space described by EQ. 2-EQ. 10, and in accordance with embodiments of the systems and methods have a number of parameters that can be varied, including CTWC gradient, thickness, incidence angle, window properties, etc. to allow for control of the sensitivity of the system to either hydration or thickness.

Exemplary CTWC Gradient Models:

Water transport is regulated at the epithelium through water loss to the environment and moisture gain from tears and at the endothelium through the active exchange of water with the aqueous humor (See, FIG. 1). As previously discussed, many corneal diseases significantly perturb CTWC and the perturbation often originates locally in either the epithelium or endothelium. Accordingly, various embodiments analyze each of the following situations:

where CTWC of the stroma adjacent to the epithelium is fixed and the CTWC of the stroma adjacent to the endothelium is varied, and where CTWC of the stroma adjacent to the endothelium is fixed and the CTWC of the stroma adjacent to the epithelium is varied.

For purposes to ease discussion of these two concepts, these will be referred to as "Pinned Front" and "Pinned Back," respectively. As a comparison, a third model entitled "global" was also developed that modulates the CTWC of the entire stroma equally. Pachymetry treats changes in CTWC as occurring globally so the global model provides a benchmark against clinical results. To thoroughly explore corneal water content, these exemplary CTWC gradient models have been developed in accordance with embodiments that, to first order, capture CTWC gradient perturbations for all known corneal disease/pathology states.

These model embodiments are summarized in the following descriptions:

Pinned front CTWC: This embodiment simulates the expected change in CTWC gradient for diseases such as, for example, Fuch's Dystrophy where the endothelium (as shown in FIG. 1) fails and the cornea starts to hyperhydrate from the backside. ($H_1(x)$ in EQ. 12).

Pinned back CTWC: This embodiment simulates the expected change in CTWC gradient for dry eyes or perturbed front side CTWC from, for example, stromal ablation during LASIK/LASEK surgery. ($H_2(x)$ in EQ. 13). Note that this model embodiment is a good approximation of drying dynamics.

Global CTWC: This simulates the expected increase in corneal CTWC due to, for example, keratoconus where the entire volume of the cornea hyperhydrates. ($H_3(x)$ in EQ. 14).

Diffusion, which is thought to contribute to the overall distribution of TWC in the cornea (I. Fatt and T. K. Goldstick, Journal of Colloid Science, 20:962-89, 1965, the disclosure of which is incorporated herein by reference), suggests that in model gradient types 1 and 2 the deviation of CTWC from normal may be exponentially distributed. This behavior, as well as the global shifts, were modeled in accordance with several embodiments using the following equations:

$$g(x, \alpha) = \alpha(e^{x/\sigma} - 1), \sigma = \frac{100}{\ln(2)} \quad \text{EQ. 11}$$

$$H_{front}(x, \alpha) = p_w(x) + g(x, \alpha) = H_1(x, \alpha) \quad \text{EQ. 12}$$

$$H_{back}(x, \alpha) = p_w(x) + g(100 - x, \alpha) = H_2(x, \alpha) \quad \text{EQ. 13}$$

$$H_{global}(x, \alpha) = p_w(x) + \alpha\left[\frac{1}{\ln(2)} - 1\right] = H_3(x, \alpha) \quad \text{EQ. 14}$$

In EQs. 11-14, x represents the normalized depth [0%, 100%], $p_w(x)$ represents the experimental data displayed in FIG. 7, g(x) represents the exponential deviation from normal $p_w(x)$, a is defined such that the range of g(x) is bounded by $[0,\alpha]$ and a is the variable that modulates the CTWC and is defined such that the average CTWC, computed in accordance with many embodiments by taking the mean value of EQs. 12-14 are equal and satisfy the following equivalence relations:

$$\overline{H_N}(\alpha) = \frac{1}{100} \int_0^{100} H_N(x, \alpha)dx, \forall N = 1, 2, 3 \quad \text{EQ. 15}$$

$$\overline{H_1}(\alpha) = \overline{H_2}(\alpha) = \overline{H_3}(\alpha), \forall \alpha \in (-\infty, +\infty) \quad \text{EQ. 16}$$

Figure 9:
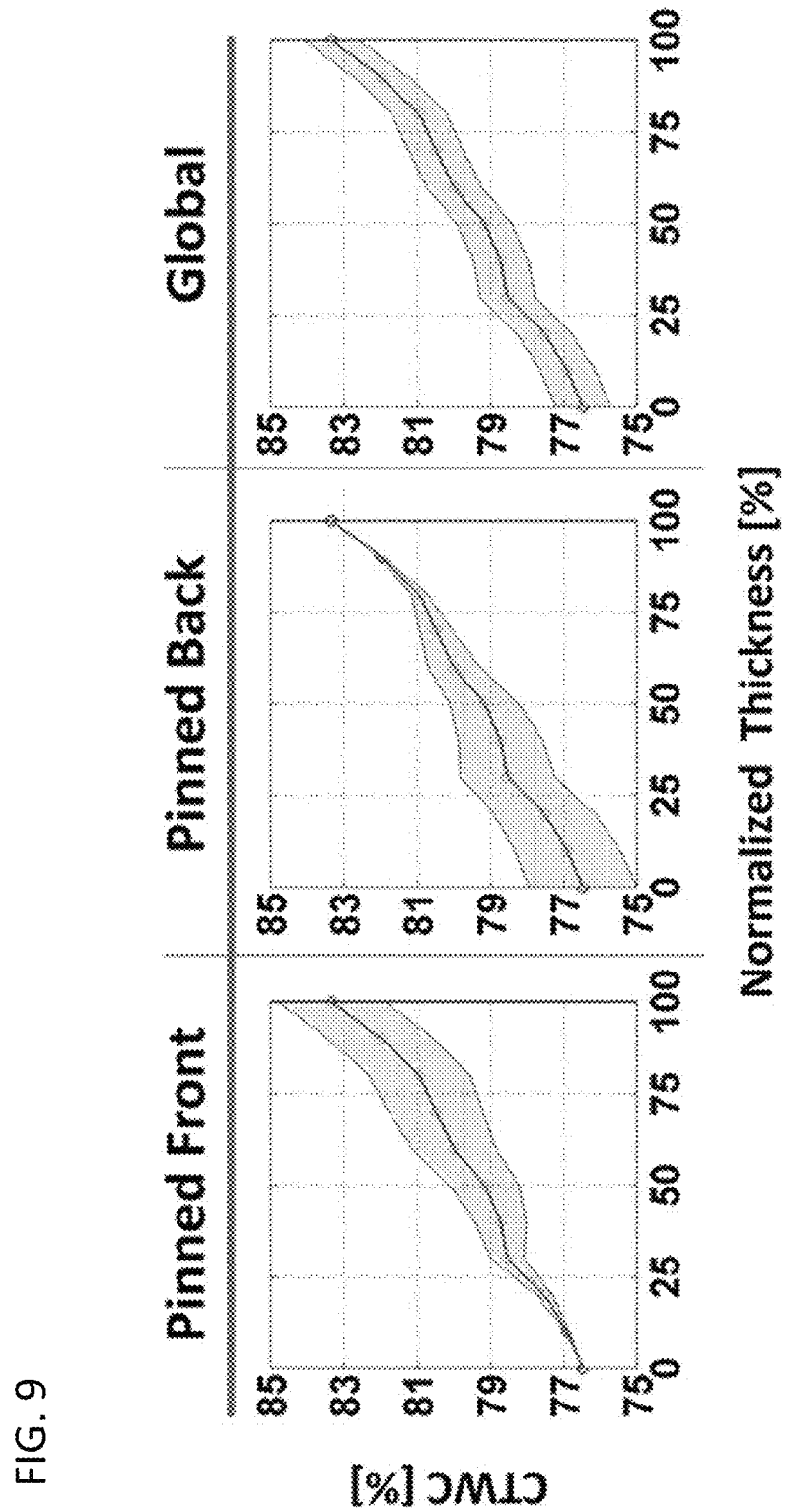
FIG. 9 provides candidate corneal tissue water content (CTWC) gradient model simulations for pinned front, pinned back, and global locations, in accordance with embodiments.

Equivalence relations EQ. 15 and EQ. 16 state that if the candidate CTWC gradients are perturbed with the variable a as described by EQ. 11-EQ 14, then, while the water content at any particular depth might be significantly different, the average water content, as computed along the axis (EQ. 15)), in accordance with several embodiments, will always be equal. Gradients 1, 2, and 3 are displayed in the left, middle, and right panels respectively of FIG. 9 where the line denotes axially varying CTWC and the shaded neighborhoods indicate the ranges explored in this simulation by varying the parameter α.

Note that while the equivalence relation in EQ. 16 holds for all a, the water content at any point along the axis must remain within the range [0%, 100%], limiting a to the domain [−p(0), 100−p(100)]=[−76.47, 16.66]. Also note that while a CTWC range of [0%, 100%) is theoretically realizable, physiology limits the range somewhere closer to [75%, 85%] while the cornea is attached to the eye.

In accordance with embodiments EQs. 11-16 enable a direct comparison of the expected THz properties of different pathologies through a shared, common, average CTWC, this value is denoted herein as $\overline{CTWC}$. Currently, corneal pachymetry does not discriminate between distributions but gives a corneal tissue water content that is assumed to be an average of the entire depth. In many embodiments, $\overline{CTWC}$ may be used as a basis of comparison of signals from different pathologies. For ease of understanding the specification, the following labeling is used throughout:

$$CTWC = H_N(x, \alpha), N=1,2,3 \quad \text{EQ. 17}$$

$$\overline{CTWC} = \overline{H_N}(\alpha) \forall \alpha, \forall N=1,2,3 \quad \text{EQ. 18}$$

Simulation Space Results

For ease of understanding various components and modes of various embodiments, the following exemplary analysis was limited to incoherent direct detection of pre-defined center frequency and bandwidths and focused on the performance of two different quality factor values (Q=5, 50) centered at 100 GHz and 525 GHz. These values were chosen to mimic the two systems that were used for the in vivo rabbit imaging trial, described in Exemplary Embodiment 2, below. It should be understood, that these values are exemplary and that other frequency and bandwidth values with similar properties could be used in various embodiments, as described throughout this disclosure.

Figure 10:
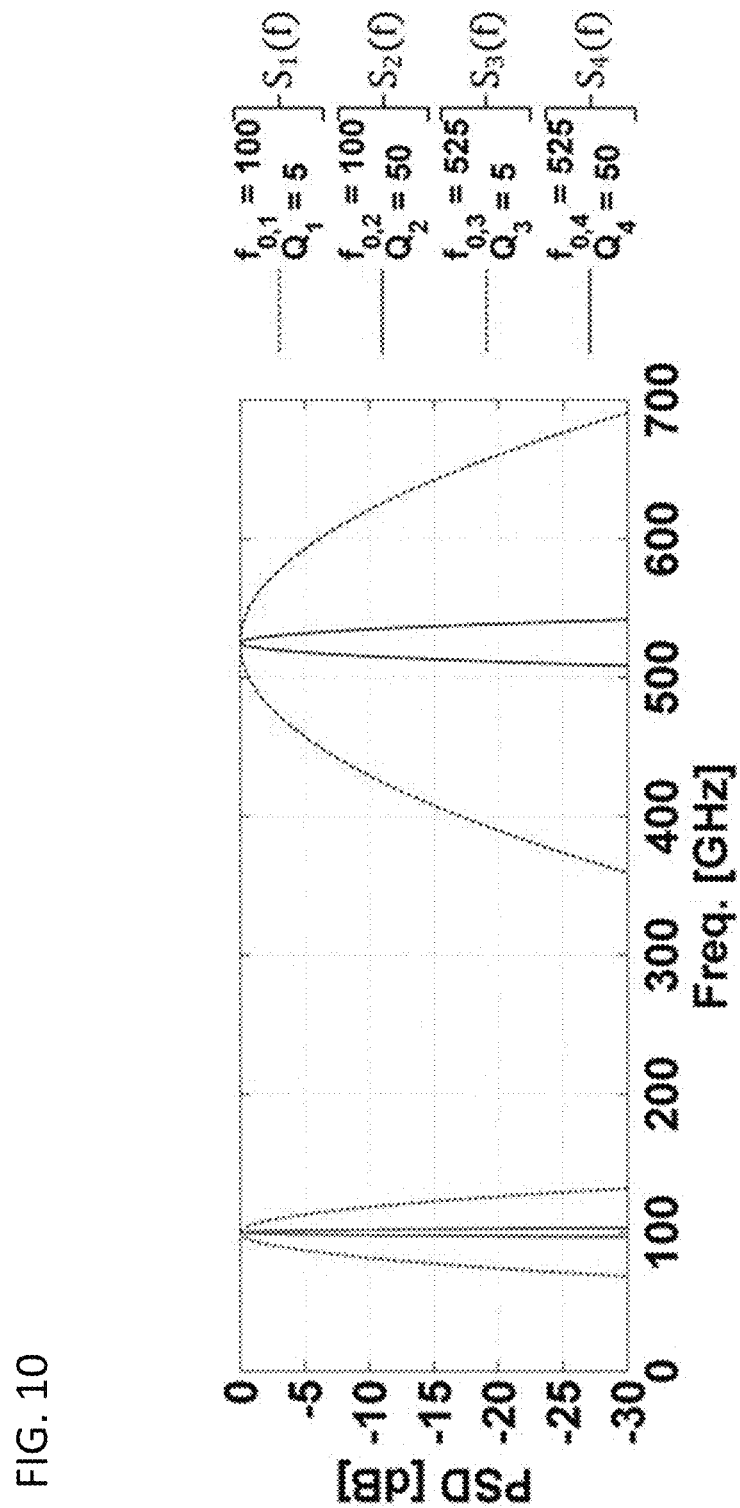
FIG. 10 provides a data plot of system power spectral densities at two center frequencies (100, 525 GHz) and two quality factors (Q=5, 50), generated in accordance with various embodiments.

The reflectivity of the whole space is calculated with a modified version of EQ. 8, given in EQ. 19, where the source and detector spectra have been combined into a single power spectral density $(PSD)S_n(f)$. A plot of the four spectral densities is displayed in FIG. 10. A general case Gaussian spectrum was utilized for the PSDs with functional forms described in EQ. 19-EQ. 21, where $f_{0,n}$ and $\Delta f_n$ are the center frequency and bandwidths respectively of $S_n(f)$ and $\sigma_n^2$ is defined (EQ. 21) such that $\Delta f_n$ is the full width at half maximum (FWHM) of $S_n(f)$.

$$\mathcal{R}_n(p, d) = \frac{\int_{\Omega_{f,n}} S_n(f)|\Gamma_0(p, d, f)|^2 df}{\int_{\Omega_{f,n}} S_n(f) df}, n = 1 \ldots 4 \quad \text{EQ. 19}$$

-continued $$S_n(f) = \exp\left(\frac{(f - f_{0,n})^2}{\sigma_n^2}\right), n = 1 \ldots 4 \quad \text{EQ. 20}$$

$$\Delta f_n = \frac{f_{0,n}}{Q_n}, \sigma_n^2 = \frac{\Delta f_n^2}{4 \ln(2)}, n = 1 \ldots 4 \quad \text{EQ. 21}$$

Note that while these Gaussian spectra are exemplary representations of the system spectra, they do not capture the asymmetry about the center frequency observed in the majority of THz imaging system implementations. For the following analysis, system PSDs $S_{1,2}(f)$ are referred to as millimeter wave spectra and PSDs $S_{3,4}(f)$ are referred to as THz spectra, however each fall within the broad definition of THz systems and methods in accordance with embodiments.

Millimeter Wave (0.1 THz) Reflectivity: The expected corneal reflectivity space (EQ. 8) for the band covered by the millimeter wave system are displayed in FIG. 11 for the three candidate CTWC gradient distributions and two system quality factors for a total of 6 unique pairs. The x-axis spans central corneal thickness (d in EQs. 8-10) values from 0.2 mm to 0.8 mm and the y-axis spans average CTWC volume fractions (CTWC) values (axial average of p in EQS. 8-10) from 75% to 85%. The pixel values are plotted in units of percent reflectivity as indicated by the color bar located on the right side of the figure, and all six figures are mapped using a shared color scale.

In addition to the space, the expected reflectivities of a human cornea with an average thickness (0.625 mm) were computed for discrete CTWCs of 75% to 85%, in increments of 1% for each of the three CTWC gradient generating functions (EQs. 12-16). Isoreflection lines corresponding to those reflectivities were superimposed on their respective thickness-$\overline{CTWC}$ spaces (one space per generating function). In many embodiments, each contour line in the level set represents all possible CTWC/thickness pairs, which yield the same reflectivity. Importantly, when the corneal thickness is unknown, in accordance with numerous embodiments, the contour's range of y values represents all possible $\overline{CTWC}$s mapping to a given reflectivity. The isoreflection lines also summarize the impact of thickness sensitivity on $(CTWC)^-$ sensing given sufficient system signal to noise ratio (SNR) as system sensitivity can be inferred from the contour line density. For the millimeter wave system under the Pinned Front case, in several embodiments, determining $\overline{CTWC}$ without a measurement of the cornea's thickness is impossible. In a Global Shift embodiment, the isoreflection lines span an interval of 1.5% (ml/ml), and in a Pinned Back embodiment, the isoreflection lines span an interval of 0.6% (ml/ml).

Three dotted lines are also superimposed on each thickness-$\overline{CTWC}$ contour map exploring three different variation profiles. The horizontal lines correspond to the expected corneal reflectivity when $\overline{CTWC}$ remains fixed at 79% and the thickness is varied. The vertical line explores the converse where the thickness is fixed at 0.625 mm and $\overline{CTWC}$ is varied from 75% to 85%. The curvilinear line indicates the thickness-$\overline{CTWC}$ profile described by EQ. 1, which predicts a coupled relationship between TWC and thickness.

Figure 11:
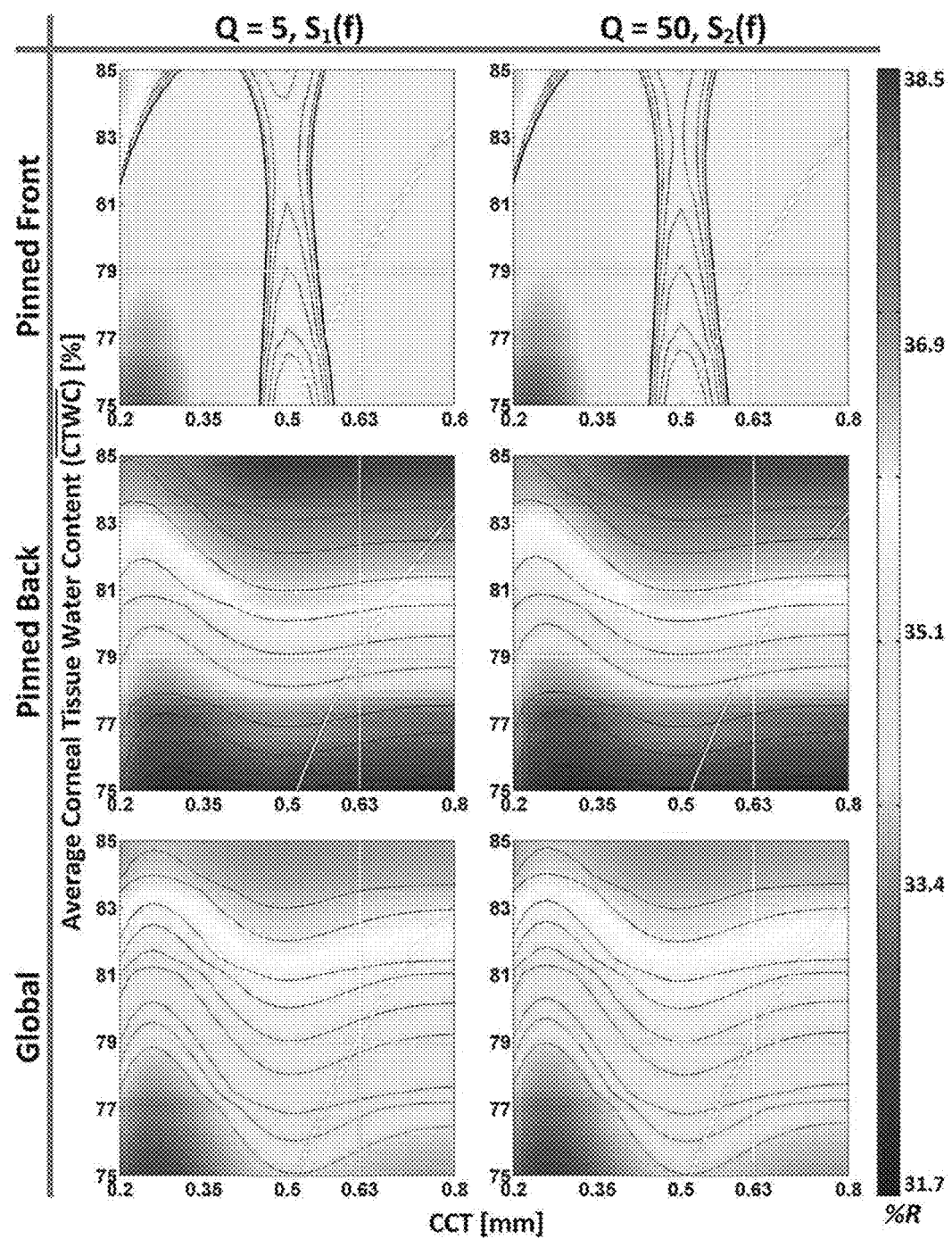
FIG. 11 provides the expected corneal reflectivity space for the band covered by the 100 GHz wave system in accordance with various embodiments.

As indicated by the color bar in FIG. 11, the exemplary reflectivity ranges from 31.7% to 38.5%. Further, while the entire reflectivity range is spanned by the pinned back gradient, the exemplary global gradient variation spans ~90% of the reflectivity range and the pinned front case spans ~80%. This result is consistent as the high absorptivity of water confines the majority of the millimeter wave-tissue interaction to the cornea's top surface. In accordance with many embodiments, these plots indicate that the modulation of the THz signal due to changes in top layers of the cornea is masking the contributions from the underlying layers. Consequently the presence of the aqueous humor is somewhat screened by the loss incurred from transmission through the upper layers.

Of interest is the apparent invariance of corneal reflectivity to system bandwidth. The exemplary thickness-$\overline{CTWC}$ maps for the Q=5 and Q=50 systems are nearly identical, and the discernable differences appear only upon study of the isoreflection lines in the pinned front case. This is due to the extremely thin geometry of the cornea with respect to the wavelength within the cornea: $n_{cornea}$~2.91− j1.45, $\lambda_{cornea}$(f=100 GHz)=$\lambda_{c,100}$~1.03 mm>$t_{cornea}$. At these frequencies m·$\lambda_{cornea}/2$>$t_{cornea}$ for all integers m>1, thus only one longitudinal mode is supported by the lossy cavity, and the difference between integrating over a larger bandwidth (Q=5) and smaller bandwidth (Q=50) does not change the number of accessed longitudinal modes.

Figure 12:
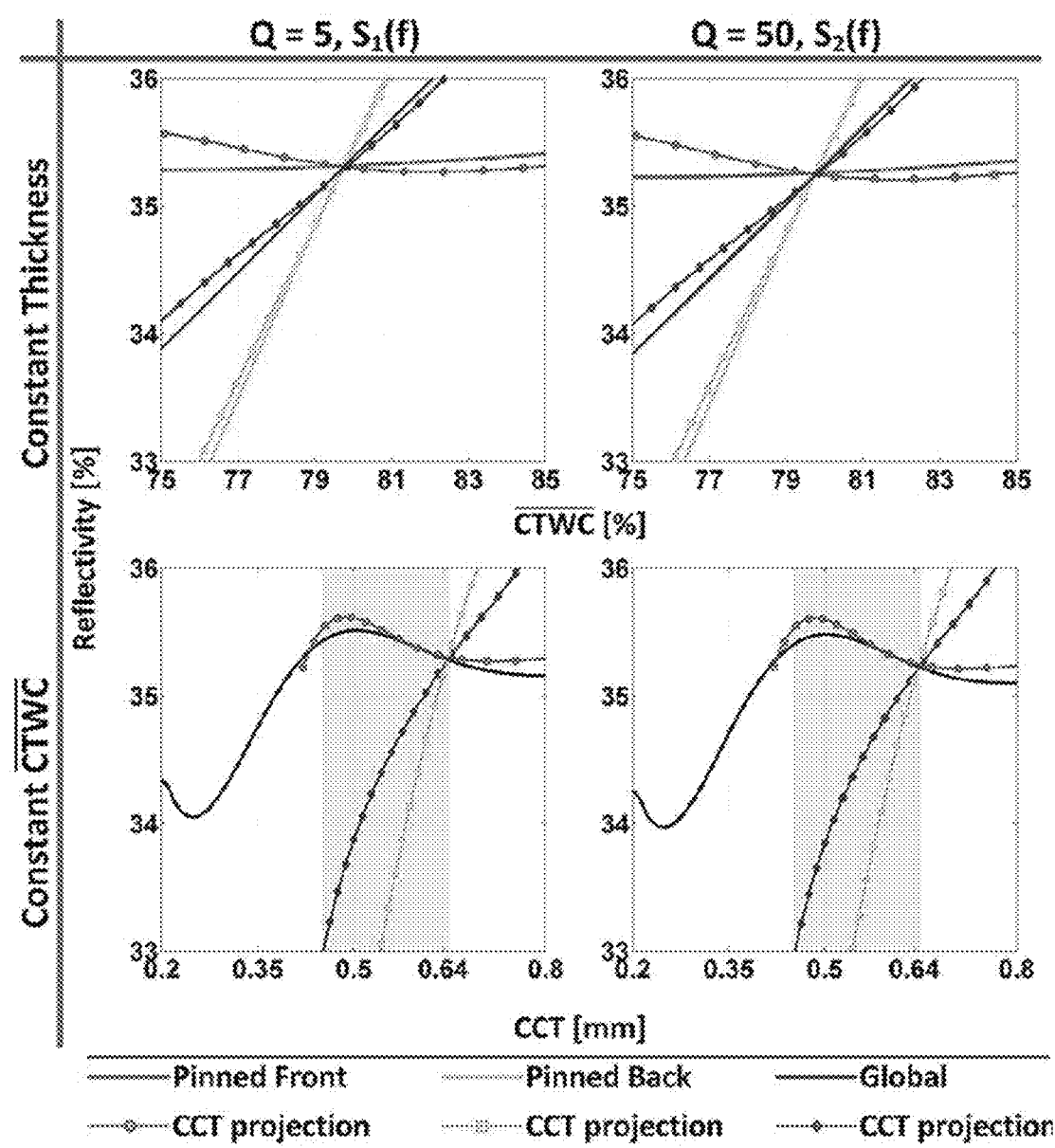
FIG. 12 provides 100 GHz-wave corneal reflectivity profiles in accordance with various embodiments.

This concept is further explored by analyzing pixel intensities along the white dotted lines in FIG. 11, which are displayed in FIG. 12. The constant thickness (0.625 mm), varying $\overline{CTWC}$ profiles are displayed in the top row and the constant $\overline{CTWC}$ (79.4%), varying thickness profiles are displayed in the bottom row for the pinned front (solid red), pinned back (solid green), and global (solid blue) CTWC variation cases. Further, the CCT projections for each CTWC gradient-system Q pair are plotted in a dotted line style with color corresponding to its associated CTWC gradient. These plots allow for a straightforward comparison between the one fixed parameter, one varied parameter behavior, and the coupled behavior predicted by EQ. 1. The shaded region in these plots indicates the average range of thicknesses observed in human patients.

The fixed thickness, varying $\overline{CTWC}$ curves all display monotonic, positive slope behavior, and the slope increases as the bulk of the change in CTWC gradient occurs closer to the front surface indicating, in accordance with multiple embodiments, that surface layers dominate the electromagnetic properties. The CCT projections closely follow the constant thickness-changing $\overline{CTWC}$ variation for both the global and pinned back cases but deviate somewhat in the pinned front case. The pinned front CCT projection displays both positive and negative slopes suggesting that diseases such as Fuch's dystrophy, for example, may in fact present a millimeter wave system with a decreasing signal for an increase in both thickness and $\overline{CTWC}$.

In accordance with numerous embodiments, the constant $\overline{CTWC}$, varying corneal thickness curves resemble that of a lossy etalon formed by the air/cornea and cornea/aqueous humor interfaces separated by a distance equal to the corneal thickness. This behavior is evidenced by the peak of each CTWC gradient case occurring at ~500 µm ($\lambda_{c,100}/2$). The three CTWC variation examples scale with corneal thickness variation and converge at the healthy CTWC percentage (79.4%) thus the three profiles are all represented by the same solid line (black) in FIG. 12. Note that the integer multiple of wavelength fraction relationships are approximate since any candidate percent CTWC is axially averaged. Due to the gradient, in accordance with many embodiments, the cornea index is lower in the posterior and greater in the anterior region. Furthermore, due to absorption the overall response is affected more by the posterior index.

Similar to previously discussed results, the CCT cuts demonstrate marked differences between the three CTWC cases. Again, pinned back and global gradients demonstrate monotonic, positive slopes while the pinned front case resembles a highly attenuated standing wave, albeit with a slight decrease in the distance that yields peak reflectivity.

These simulations confirm that using millimeter wave systems and methods in accordance with embodiments, it is possible to distinguish whether a corneal target best fits a pinned front or pinned back/global profile by monitoring whether the thickness of the cornea increases as the TWC is increased. Accordingly, several embodiments are directed to a millimeter wave system able to delineate between pinned front and the pinned back, global cases using millimeter reflectometry trends in CCT. Embodiments are also directed to methods of using such millimeter reflectometry trends and maps to diagnosis disorders associated with such gradient profiles, including, for example, Fuch's dystrophy and corneal graft rejection.

Figure 13:
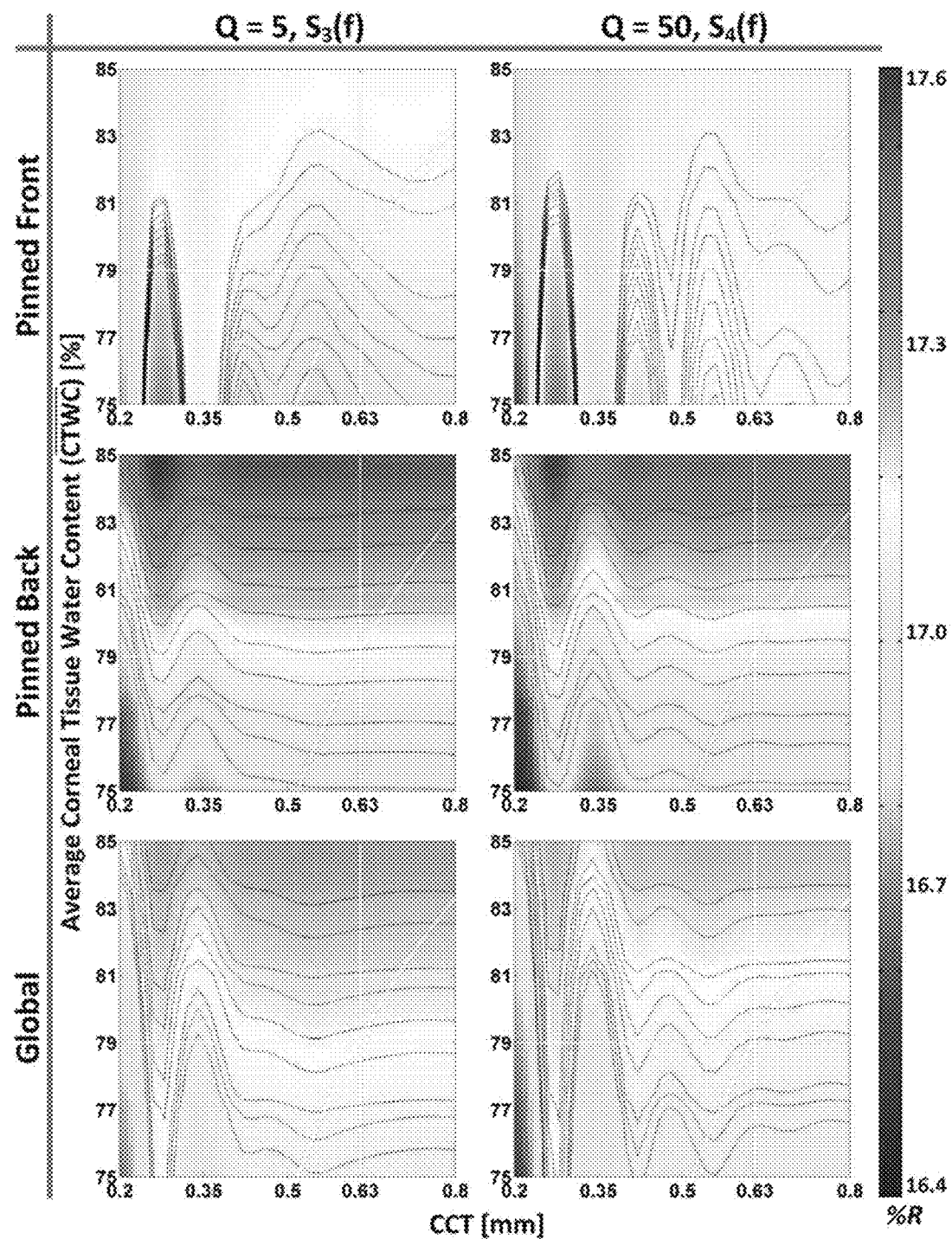
FIG. 13 provides the expected corneal reflectivity space for the band covered by the 525 GHz wave system in accordance with various embodiments.

Reflective THz imaging system: The expected corneal TWC-thickness reflectivity space (EQ. 8) for a THz system in accordance with embodiments (e.g., the band covered by a 525 GHz system) for the three candidate TWC distributions and two system quality factors are shown in FIG. 13. The spaces have the same x limits (0.2 mm to 0.8 mm) and y limits (75% to 85% 140 hydration) as used in the millimeter wave study shown in FIG. 12, and discussed above. Contour lines representing hydration-thickness sets with identical reflectivities were superimposed in the same manner as FIG. 11, as well as the pixel intensity paths exploring thickness variation, $\overline{CTWC}$ variation, and simultaneous $\overline{CTWC}$ and thickness variation. The exemplary plots in FIG. 13 are displayed with a shared color map and the reflectivity ranges from 16.4% to 17.6%. The plots in FIG. 13 are representative of data obtained using embodiments of a THz system/method display overall lower reflectivity and a smaller reflectivity range than that displayed in FIG. 11 for the millimeter wave system/method due to the significant decrease in water's permittivity and the intrinsic sensitivity (dR/dp) when comparing center frequencies 100 GHz and 525 GHz.

Similar to the millimeter wave system and in accordance with numerous embodiments, the entire reflectivity range is spanned by the pinned back case. In other embodiments, the pinned front case spans a larger reflectivity space than that of the global variation case, demonstrating 80% and 70% of the total range, respectively. There is also a noticeable difference in the thickness/CTWC maps between the Q=5 and Q=50 candidate systems. At 525 GHz, the approximate refractive index of the cornea is $n_{cornea}$~2.1−j0.45 resulting in a central illumination wavelength in the cornea of $\lambda_{cornea}$ (f=525 GHz)=$\lambda_{c,525}$~0.272 mm in numerous integer multiples of ~$\lambda_{c,525}/2$, a result that is supported by the lossy cornea cavity. This effect can be seen by comparing the spaces for the two quality factors at each CTWC gradient case where each Q=50 space displays a larger range than its Q=5 counterpart. This effect is also observed in the profiles of the contour lines that indicate the local extremum of the space.

Figure 14:
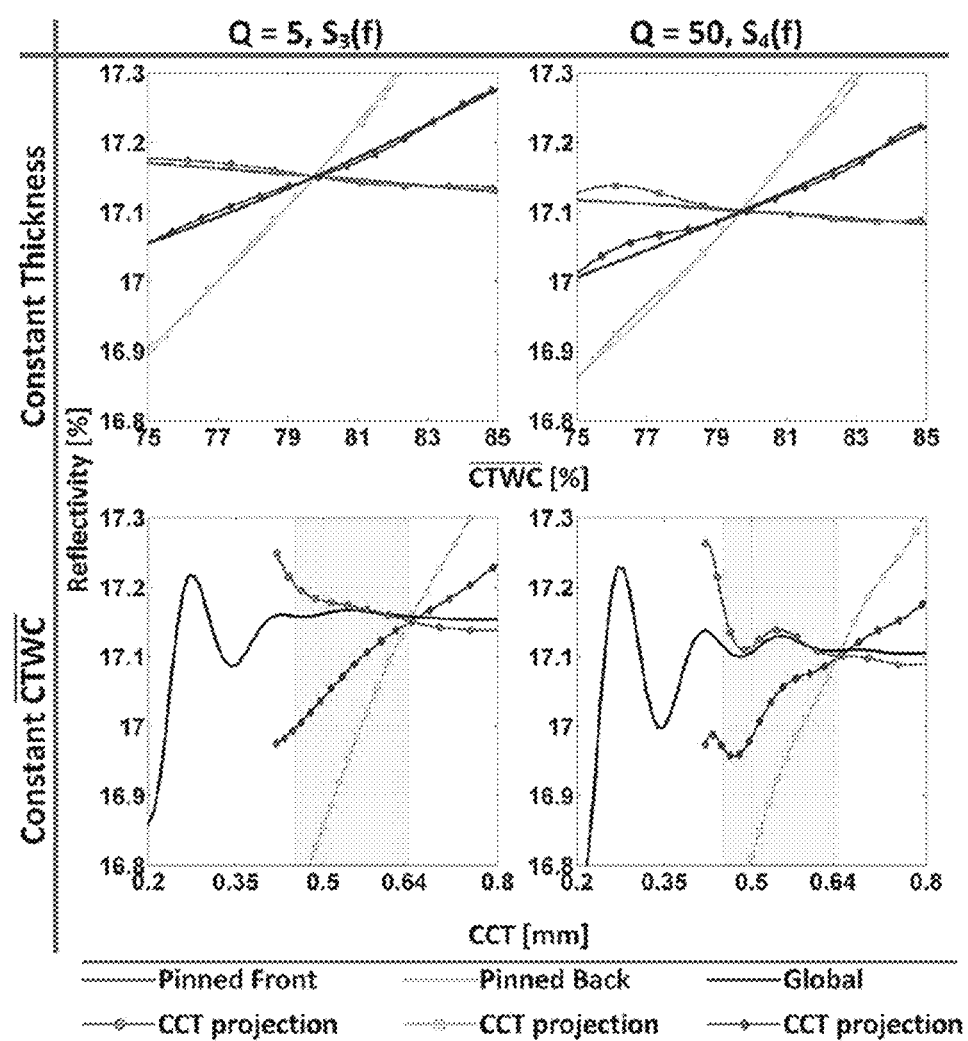
FIG. 14 provides 525 GHz-wave corneal reflectivity profiles in accordance with various embodiments.

Pixel intensities from the indicated profiles are shown in FIG. 14 with the same reference points (constant thickness=0.625 µm, constant CTWC=79%) and set of Qs (Q=5, Q=50) as the millimeter wave reflectometer and are displayed in the same arrangement as in FIG. 12. The broad band (Q=5) fixed thickness, varying $\overline{CTWC}$ shows monotonic increases in reflectivity as $\overline{CTWC}$ is increased for the pinned back and global variation cases and monotonic decreases in reflectivity for the pinned front case. Similar to the 100 GHz system, the CCT projections are aligned with the constant thickness, varying TWC profiles although the deviation is less, especially for the pinned front case. Increasing Q still results in little deviation between the constant thickness paths and the CCT projections, although an increase in path curvature is evident.

The exemplary fixed $\overline{CTWC}$, varying thickness paths show significant attenuated standing wave behavior with the first visible peak occurring at 0.276 mm (~2·1/2·$\lambda_{c,525}$); the approximate wavelength of illumination inside the cornea. The first valley is at ~5/4·$\lambda_{c,525}$ and there appears to be a second peak at ~3/2·$\lambda_{c,525}$ although the high absorption constant of water at these frequencies is overpowered the constructive interference arising from multiple passes within the cornea. Decreasing the bandwidth (Q=50), in accordance with many embodiments, leads to an amplification of standing wave effects as evidenced by the plot in the bottom right of FIG. 14. The extinction ratio is larger and local maxima are discernable at ~2·1/2·$\lambda_{c,525}$, ~3·1/2·$\lambda_{c,525}$, and ~4·1/2·$\lambda_{c,525}$.

The CCT projections are also markedly different from those observed with the millimeter wave system. In the Q=5 example, pinned back and global TWC distributions show monotonically increasing behavior while the pinned front shows monotonically decreasing behavior. In the narrow band example (Q=50), the pinned back case displays significant increases in reflectivity while both the global and pinned front cases show standing wave like behavior.

Like the millimeter wave system, the THz system cannot be used to determine CTWC in the pinned front scenario without a measurement of the cornea's thickness. However, in stark contrast to the 100 GHz system, in the global shift case, the THz systems' isoreflection lines span a diagnostically irrelevant interval of ~0.2% (ml/ml), and in the pinned back case, the isoreflection lines span an interval well below 0.1% (ml/ml). Accordingly, in many embodiments, the THz system and method may be used to sense CTWC for diagnostic applications in the Global Shift and Pinned Back cases without any accompanying thickness measurement.

Similar to FIG. 12, an etalon-like effect is observed in the constant CTWC plot of FIG. 14. In accordance with a number of embodiments, the reflectivity varies as the cornea-air interface and cornea-aqueous humor interfaces are moved apart due to interference effects that appear and disappear with the varying optical path length. However, in contrast to the millimeter wave corneal paths (FIG. 12), the Q=5, THz system has a minor variation in reflectivity due to thickness variation in the physiologically relevant thickness range. This behavior is due to both the differences in the cornea's skin depth and to the broadband nature of the Q=5, THz system. At 525 GHz, the skin depth of the cornea is significantly smaller than that at 100 GHz (0.58 mm and 1.1 mm, respectively), causing the front layers of the cornea to more strongly mask effects from the back layers of the cornea. This phenomena causes the interference effects formed by the cornea's thickness to be negligible relative to the cornea-air reflection, making the CTWC measurement for THz systems less sensitive to thickness variations than that acquired with the millimeter wave systems.

In view of these results, several embodiments are directed to a broadband THz system capable of reducing the etalon-like interference effect. These systems are advantageous because the sign of the interference effects is frequency dependent; optical path length varies with frequency, and the variations in the optical path length phase shift different frequencies by different amounts. As a result, systems that span multiple frequencies sum interference effects that oscillate in sign (which cancel one another), meaning that the interferences' relative contribution to the reflectivity decreases as the operating bandwidth grows. Accordingly, in many embodiments THz imaging systems and methods utilize broadband emissions (e.g., a Q<50, and preferably Q<10 or Q<5).

One interesting point that arises from this analysis is the differences between the predicted CTWC sensitivities calculated with each gradient type. This finding presents an excellent opportunity for THz corneal sensing as there are no one-to-one mappings between axial CTWC distributions and pachymetry measurements, and the simulations suggest that an ensemble of THz reflectivity measurements may allow one to ascertain this information. Accordingly, many embodiments are directed to systems and methods utilizing multiple frequencies and bandwidths of THz (e.g., 0.1 and higher emissions) to obtain complementary information concerning the cornea. In many of these embodiments, at least an emission greater than 0.5 THz and an emission less than 0.2 THz (millimeter wave) are used in a complementary manner to obtain simultaneous information about CCT and CTWC of a corneal target.

Spectroscopic Measurements

To explore the utility of the pinned front, pinned back, and global CTWC gradient types, in accordance with an exemplary embodiment, the expected change in reflectivity for a change in water content as a function of frequency was computed for each type and then compared to experimental data extracted from measurements of ex vivo corneas. These corneas were prepared by immersing them in polyethylene glycol (PEG) solutions of varying concentrations for 3 days to produce water concentrations (confirmed by dry weight to wet weight ratios) ranging from 78.8% to 91.5%. 78.8% was the lowest concentration achievable that still produced a smooth surface where surface roughness would not affect the measured reflectivity. 91.5% somewhat exceeds the physiologically relevant range, but the reflectivity curves are approximately linear over a broad range and additional data points improved the quality of fit.

In addition to the three CTWC gradient types, a half space model was generated using the Double Debye and Bruggeman described in EQs. 2-16 and compared to the gradient types. This model was generated for two reasons:

To determine if the perturbation of CTWC ex vivo through the use of PEG solutions led to reduction of the axial water content gradient due to the absence of an active endothelium layer thus improving utility of a half space; and To evaluate the results of a simplified model as compared to a more complicated, ostensibly more accurate model.

Figure 15:
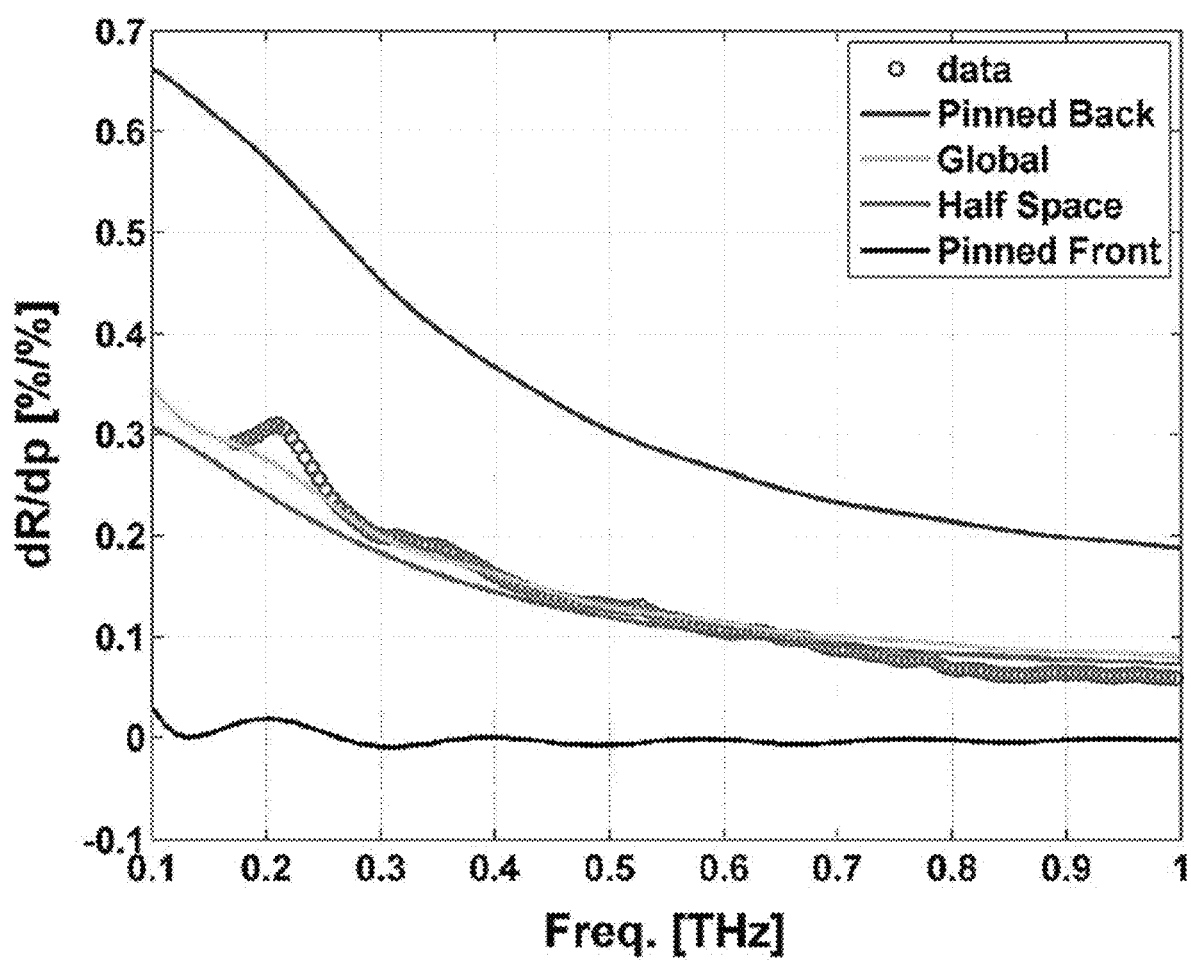
FIG. 15 provides a data graph of CTWC sensitivity fit to data confirming the validity of the Bruggeman Model, generated in accordance with various embodiments.

The results are displayed in FIG. 15. The exemplary data was acquired with a THz TDS system with spectral operating limits spanning ~180 GHz to 1000 GHz, which does not allow for investigation of 100 GHz properties but allows for analysis of trends dependent on illumination frequency. Because in vivo axial gradients are difficult to replicate ex vivo and impossible to verify non-destructively the hyperhydration/dehydration protocol was designed to modulate the CTWC globally and reduce the magnitude of the axial gradient.

The exemplary results support the intended setup. Accordingly, the pinned front gradient type demonstrates low sensitivity and a standing wave like behavior that continues throughout the entire computational domain. The pinned back gradient type demonstrates the largest sensitivity due to the largest changes in CTWC occurring in the top layer of the cornea. The global shift gradient type and half space produce similar results and demonstrate very good agreement with the experimental data. This agreement provides strong evidence that the Bruggeman, Debye, and stratified media theories are appropriate for corneal modeling and, more specifically, that the Bruggeman model enables an accurate, and straightforward method to calculate numerical derivatives in the reflectivity space, in accordance with several embodiments.

Exemplary Embodiment 2: THz Sensing of Corneal Tissue Water Content

In Exemplary Embodiment 1, a theoretical 1D wave model and simulation study of the THz frequency properties of the cornea was described, and its implications with respect to functional embodiments of THz corneal imaging/sensing methods and systems described. In particular, the simulations provide evidence concerning how the properties of the lossy etalon effect that arises from the cornea lying in between the aqueous humor and the cornea presents to external radiation, and elucidates the THz electromagnetic properties under simultaneous perturbations of corneal tissue water content (CTWC) and central corneal thickness (CCT). Three exemplary models of tissue water content (TWC) gradient types were explored: (1) pinned back where the CTWC changes occur primarily at the posterior surface, (2) pinned front where the TWC changes occur primarily at the anterior surface close to the aqueous humor, and (3) global where the CTWC modulation occurs evenly throughout the entire thickness of the cornea. The quantity $\overline{CTWC}$ was also introduced which represents the CTWC averaged over the entire thickness of the cornea to allow gradients types to be compared on a common axis, as generated in accordance with several embodiments.

The expected reflectivities of these gradient types were computed using various exemplary embodiments of system spectral transfer functions with center frequencies of 100 GHz and 525 GHz, and bandwidths of Q=5 and Q=50. The results discussed an anti-correlation between reflectivity and CTWC in the pinned front gradient type and identified an inherent ambiguity in CTWC sensing where numerous CCT-$\overline{CTWC}$ pairs resulted in the same reflectivity. These simulations confirm the thin-film like behavior of cornea when probed with millimeter wave and THz frequency illumination, demonstrating that simultaneous measurement of thickness and CTWC gradients through the acquisition of an ensemble of reflectivities at different frequencies may be achieved, in accordance with embodiments. Furthermore, due to the low physiologic variation of corneal structure, a strong set of a priori knowledge on corneal geometry precludes the need for phase sensitive measurements and allows for depth resolved measurements of the axial CTWC distribution in accordance with other embodiments.

In the current exemplary embodiment, THz imaging and millimeter wave reflectometry in accordance with embodiments are demonstrated for use in the generation of spatially and temporally resolved reflectivity maps of cornea. Contrast generation is provided in rabbit models and in vivo images of corneal tissue are presented. Statistically significant correlations are established between increasing millimeter wave reflectivities and increasing central corneal thickness (CCT) measurements. Conversely, correlations between CCT measurements and THz reflectivity were weak, as the THz data showed both increases and decreases in THz reflectivity as the corneal thickness increased. To further explore this effect an additional rabbit was prepared with the same protocol, euthanized, and the reflectivity was observed to increase as the corneal thickness increased, then decrease. Animal death is known to correlate with simultaneous increase in CTWC and CCT modeling of these changes predicted the nonmonotonic behavior. This data provides an in vivo demonstration of the inaccuracy of the CCT to TWC map employed by the state-of-the-art, such as, for example, CCT measurement methodology, and demonstrates the potential of THz CTWC imaging in overcoming these deficiencies.

Standoff Tissue Water Content Contrast Generation Systems

In accordance with exemplary embodiments, two CTWC sensing systems are provided for a rabbit trial; one narrow band system operating at 100 GHz (millimeter wave system) and one broad band system operating at a center frequency of ~525 GHz (THz system). Due to the size of the focused spot, the THz system was used to acquire images of a ~20 mm diameter area of the cornea while the 100 GHz system was utilized as a point measurement device confined to the corneal center.

Figure 16A:
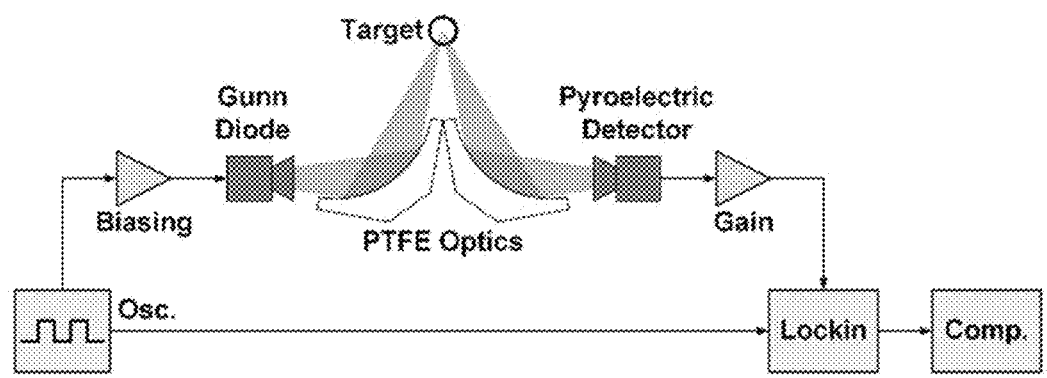
FIGS. 16A to 16C provide diagrams of a millimeter wave reflectometer, in accordance with embodiments, where: (A) is system block diagram, (B) is the illumination geometry, and (C) is a biasing scheme demonstrating low frequency chopping combined with high frequency FMCW.
Figure 16B:
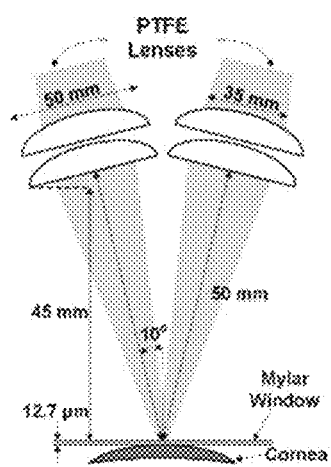

Millimeter wave (100 GHz) reflectometer: A block diagram of the millimeter wave reflectometer, in accordance with embodiments, is shown in FIG. 16A. In this embodiment, the source was a WR 10 waveguide-mounted Gunn diode from Spacek labs, which outputs a linearly polarized beam with a FWHM of ~10 deg and an average power of ~10 mW. The 100 GHz radiation was collimated and focused onto the target at a 20 deg incidence using a pair of 50 mm diameter, 100 mm focal length plano-convex Teflon (PTFE) lenses. Reflected illumination was collected by a second pair of plano-convex PTFE lenses and focused onto a pyroelectric detector with an NEP of ~1 $nW^2$ (FIG. 16B).

Figure 16C:
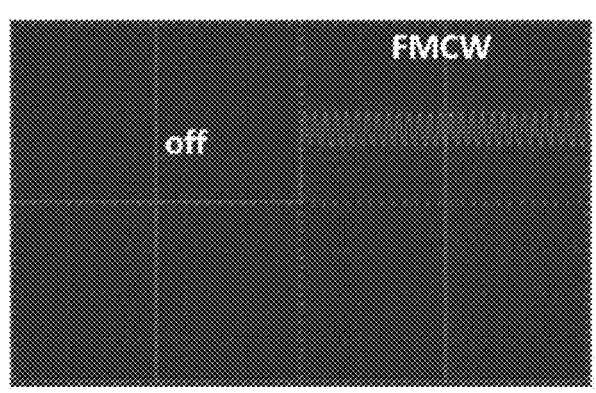

In many embodiments, the Gunn diode was frequency modulated at a rate of 1 kHz producing an RF bandwidth of ~3 GHz (FIG. 16C). Although the video bandwidth of the pyroelectric detector was 10 Hz, the device displayed significant 1/f noise up to ~25 Hz. As a result, amplitude modulation at 30 Hz was employed. The output of the pyroelectric detector was fed into a lock-in amplifier with a 1 ms time constant resulting in an effective data acquisition rate of ~10 Hz (limited by lock-in settling time and amplitude modulation period) and an effective noise equivalent power of ~100 $nW/Hz^{1/2}$. This arrangement produced ~66 sweeps through the RF spectrum in one on-cycle of the amplitude modulation, effectively providing a time averaged broadband signal to the detector and mitigating detrimental coherence effects that arise from the narrow instantaneous source line width and the non-zero Q of the optics train. The post detection signal to noise ratio (SNR) was ~30 dB. Knife edge measurements confirmed a 10%-90% spot size of ~4.5 mm, a diameter slightly smaller than the 5 mm diameter of the ultrasound pachymetry probe.

Figure 17A:
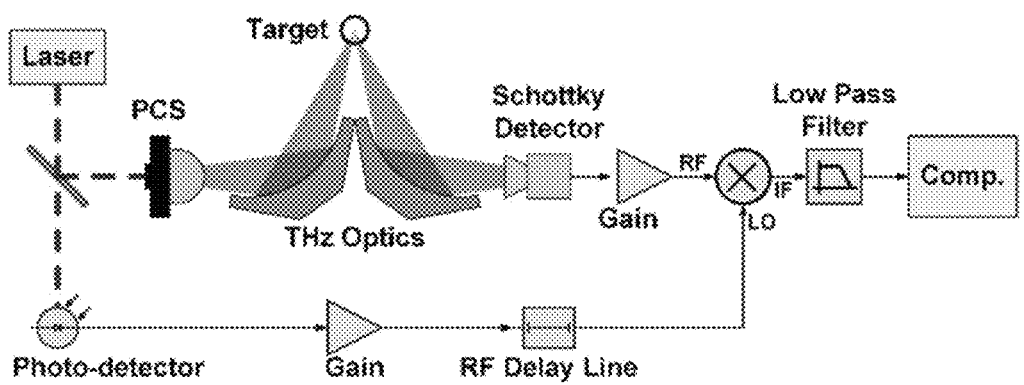
FIGS. 17A to 17C provide diagrams of a THz imaging system, in accordance with embodiments, where: (A) is a system block diagram, (B) is the illumination geometry, and (C) is a photoconductive switch power spectral density and detector spectral responsivity.
Figure 17B:
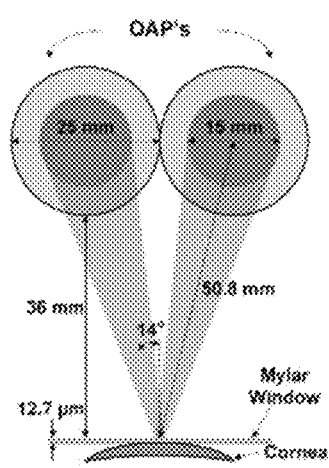
Figure 17C:
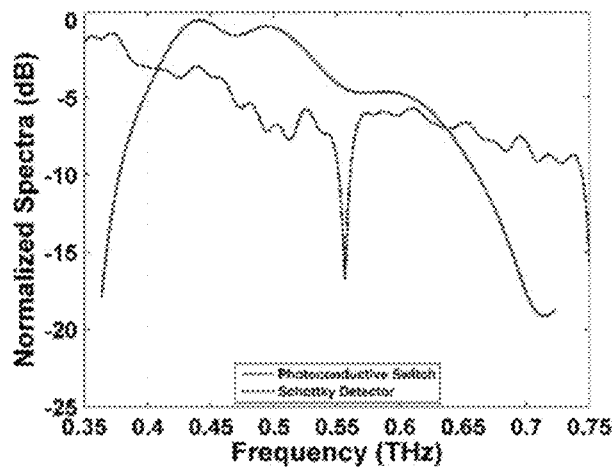

Reflective THz imaging system: A block diagram for the THz imaging system and its corresponding illumination geometry, in accordance with embodiments, is displayed in FIG. 17A and FIG. 17B, respectively. The THz source, receiver electronics, and system design, in accordance with embodiments, are summarized below. The photoconductive switch source was pumped by a 780-nm mode-locked laser with a ~230 fs pulse width, 20 MHz repetition frequency, and ~8 mW of average power. The chip was mounted on the backside of a silicon hyper-hemisphere and the free space output was collimated by a 76.2 mm effective focal length (EFL) off-axis parabolic (OAP) mirror. The beam is focused onto the target using a 50.8 mm EFL OAP mirror at a ~14 degree incidence angle (FIG. 17A). The reflected radiation was collimated by a second 50.8 mm EFL OAP and then focused with a 25.4 mm EFL OAP to the feedhorn of a WR1.5 waveguide mounted Schottky diode detector. The rectified THz pulses were amplified with 38 dB of gain and sent to a gated receiver driven with a reference RF pulse generated using a beam sampler, photodiode, and RF amplifier. This system architecture yields an effective operational band proportional to the photoconductive switch power spectral density weighted by the Schottky diode spectral responsivity (FIG. 17C). (See, Z. D. Taylor, et al., Terahertz Science and Technology, IEEE Transactions on, vol. 1, pp. 201-219, 2011, the disclosure of which is incorporated herein by reference.) Pixels were acquired with a 1 ms integration time and imagery was generated by raster scanning the animal model beneath the fixed, focused THz beam using x and y axis stepper motors. A diffraction limited spot size of 1 mm at a 36 mm standoff distance was measured with a knife edge target. A peak SNR of >40 dB was measured using a 1 ms.

System sensitivity analysis: In accordance with embodiments, the sensitivity of both the millimeter wave and THz imaging systems to changes in water content in a number of different calibration targets maybe determined. (See, S. Sung, et al., "Reflective measurement of water concentration using millimeter wave illumination," in SPIE Health Monitoring of Structural and Biological Systems 2011, San Diego, Calif., 2011, pp. 798434-798434; and Z. D. Taylor, et al., "THz imaging based on water-concentration contrast," in SPIE Terahertz for Military and Security Applications VI, Orlando, Fla., USA, 2008, pp. 69490D-8, the disclosures of which are incorporated herein by reference.) While these targets can be a good representation of thick, heterogeneous tissue such as skin, muscle, fat, etc. they are not optimal for cornea since it is difficult to create tissue water gradients and striated structures that accurately mimic in vivo cornea. However, drying targets provide a straightforward, application relevant method of measuring the millimeter wave and THz imaging systems sensitivities to changes in reflectivity by producing very small drops in the reflectivity in an observable manner.

Previously, a Noise Equivalent Delta Water Content (NEAWC) system, where the assumption was that the tissue of interest mimics a half space (no index discontinuities in the thickness dimension) and that changes in tissue water content distributed somewhat evenly throughout the probing depth of the millimeter wave or THz imaging system, has been suggested. Results from simulations in Exemplary Embodiment 1 indicate the nonmonotonic behavior of corneal reflectivity as a function of thickness and CTWC arising from etalon effects. The desire to resolve the etalon in measurements suggest that it would be more appropriate to look at the Noise Equivalent Reflectance Difference (NERD), which imposes a systematic limit on how small of a change in reflectance can be resolved.

In these experiments a 0.15 mm thick polypropylene towel was wetted with a volume of water and the reflectivity and weight of the target were probed until the target weight had dropped to its dry value. The polypropylene (PP) towel was chosen because of the tiny fibers and frequency independent index provide a low loss, nearly dispersion free target constituent across the frequency bands of interest. (See, J. W. Lamb, International Journal of Infrared and Millimeter Waves, vol. 17, pp. 1997-2034, 1996, the disclosure of which is incorporated herein by reference.) The thinness of the towel was desired as it limited the development of a water content gradient during the drying process, which was not desired for characterization as it complicates the modeling. The THz setup flattened the towel against a 13 mm thick PP slab while the millimeter wave setup suspended the towel across open air. The THz system utilized OAP mirrors and a detector with a wavelength sized aperture and thus is sensitive to changes in target height. To compensate the rigid, low reflectivity (index) PP slab was selected to ensure flatness and reduce the influence from standing waves at high water fill factors (this setup demonstrates significant etalon effects at lower water fill factors). (See, D. B. Bennett, et al., IEEE Sensors Journal, vol. 11, pp. 1530-437X, 2010, the disclosure of which is incorporated herein by reference.)

Figure 18:
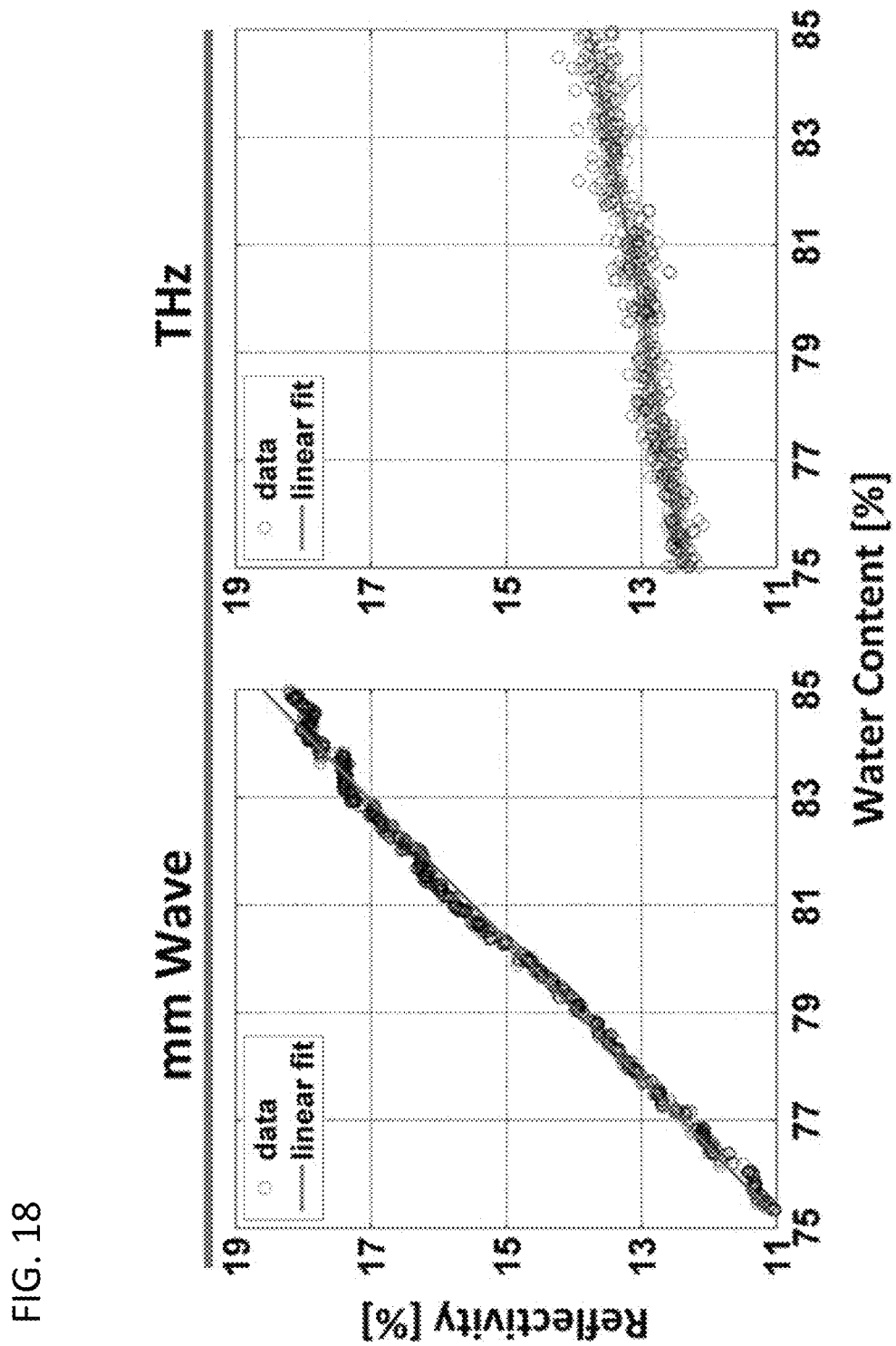
FIG. 18 provides sensitivity analysis of the millimeter wave sensing system (left) and THz imaging system (right), generated in accordance with various embodiments.

The millimeter wave system employed dielectric lenses and a large aperture (>5 mm) pyroelectric detector and thus was significantly less sensitive to target height. Additionally, the shorter optical path length (within the towel) and reduced loss presented by the wetted towel, as compared to the THz system, lends increased sensitivity to the presence of a backing. Thus, a suspended target mounting was desired. The results of the drying experiments over water content fractions relevant to the cornea are displayed in FIG. 18 for each system below each corresponding experimental setup. The difference in mount backing provides the added bonus that the measured reflectivities ranges overlap facilitating analysis of system performance on similar parts of the Fresnel coefficient curves due to transmission losses.

Two features are immediately apparent from these embodiments. First, the slopes of each system are significantly different with the millimeter wave system displaying 0.78%/% and the THz system displaying ~0.15%/% due to the large difference in water dielectric function between the operational bandwidths. Second, the measurement noise variance of the THz system is ~2.5× larger that the millimeter wave system. While receiver architectures, power levels, components, NEPs, etc. are starkly different between the two systems, and derivation of noise performance is beyond the scope of this paper, the superior performance of the millimeter wave system is attributed to differences in post detection bandwidth which is orders of magnitude lower (30 Hz vs ~10 GHz) than the THz system due the benefits of lock-in detection.

$$NERD = \sqrt{\frac{SSE}{N}} = \sqrt{\frac{1}{N}\sum_{i=1}^{N}[y_i - f_i]^2} \qquad \text{EQ. 22}$$

$$NE\Delta WC = NERD\left(\frac{dR_s}{dp_w}\right)^{-1} \qquad \text{EQ. 23}$$

In many embodiments, it is possible to ascertain system NERD through regression analysis. (See S. Sung, et al., "in SPIE Health Monitoring of Structural and Biological Systems 2011, San Diego, Calif., 2011, pp. 798434-798434, the disclosure of which is incorporated herein by reference.) In the above equations, $y_i$ are the reflectivity measurements at a particular water content percentage, $f_i$ is the least squares fitted line evaluated at the same water content percentage that yielded measurement $y_i$, SSE is the sum of squares errors between the measurement and fit, and N is the total number or points used to compute the fit.

EQ. 23 described the system NEΔWC for a particular NERD where $R_s$ is the measured sample reflectivity; $p_w$ is the water volume fraction. While the NEΔWC derived from the NERD from the PP towel target is not directly applicable to the cornea due to the diffusion air in the towel target and differences between the material stack that the layered structure of tissues pertinent to CTWC it is instructive to demonstrate inherent differences associated with the choice of center frequency. The sensitivity characterization results are displayed in Table 1, below. In embodiments, the millimeter wave system achieved a NERD of 0.0587% and the THz system achieved a NERD of 0.1204%

TABLE 1

Noise Equivalent Metrics

| System | Slope$\left(\frac{dR_S}{dp_W}\right)$ [%/%] | NERD [%] | NEΔWC [%] |
|---|---|---|---|
| mm Wave | 0.7765 | 0.0587 | 0.0763 |
| THz | 0.1459 | 0.1204 | 2.3761 |

Figure 19A:
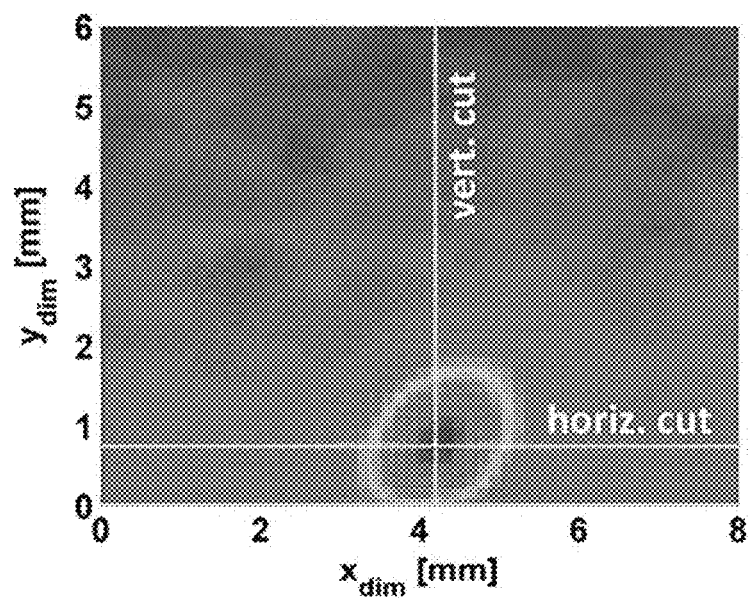
FIGS. 19A & 19B provide imaging results of corneal geometry phantom (PTFE sphere), generated in accordance with various embodiments, where: A) THz image of the sphere with the imaging axis parallel to the normal of the sphere apex, and B) horizontal and vertical cuts through the image superimposed with Gaussian fits.
Figure 19B:
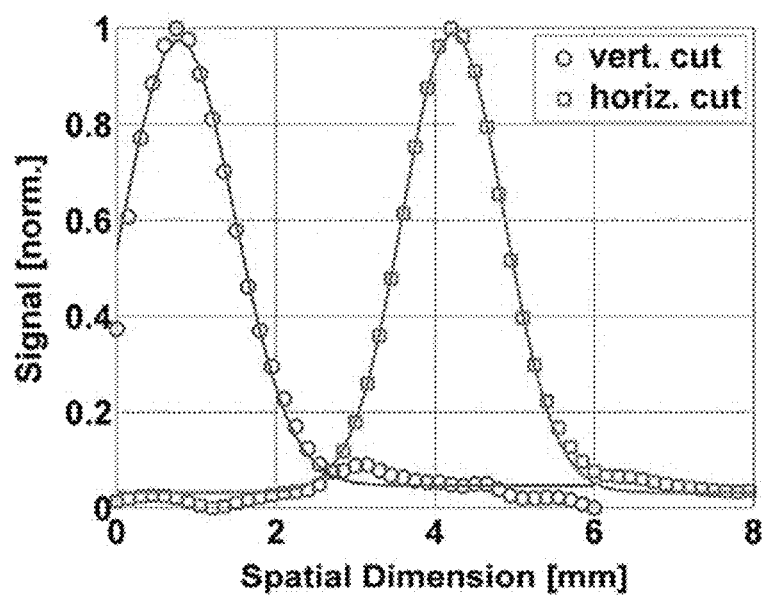

Dielectric Window: All THz imaging results of animal models reported in the literature were obtained with a dielectric window pressed firmly against the tissue of interest to flatten the field of view (FOV). Prior to implementing a window, the feasibility of imaging cornea using an off-axis imaging system as shown in FIGS. 16A and 17A without field flattening was explored through reflective imaging of a curved cornea phantom target (FIGS. 19A & 19B). The phantom target consisted of an 18 mm diameter PTFE sphere with the apex positioned in the imaging system focal plane. This diameter was chosen because it matches the average radius of curvature of human cornea. Note that there is no water in this phantom model as this experiment was intended to isolate the effect of geometry.

A THz image of the cornea phantom is displayed in FIG. 19A where a darker gray corresponds to increased reflectivity and a lighter gray corresponds to less. Horizontal and vertical cuts sampled from the paths denoted by the dotted lines on FIG. 19A are displayed in FIG. 19B. Superimposed on each cut are Gaussian fits. The fits' standard deviations (~0.896 mm) were corrected for the increased width due to the blurring kernel used for image denoising (Gaussian with σ=0.24 mm). This yielded a 1/e width of 2σ=1.73 mm, a FWHM of 2.03 mm and 10-90 width of ~1.42 mm. Note that the 10%-90% spot size of the system is 1.1 mm.

Inspection of FIGS. 19A & 19B illustrate the loss of signal as the beam focus leaves the center of the sphere. The most intense pixels at the center are aligned with the apex of the ball and produce a strong reflection. Within a few pixels of the apex, the pixel intensity falls far below the maximum. This effect is especially problematic in the context of imaging for corneal diseases, which requires a water content sensitivity of 1% and below, corresponding to a noise equivalent reflectivity difference (NERD) of ~0.1%. Reflectivity variations due to water concentration are nearly impossible to discern while signal variation is dominated by geometric variation. This precipitous signal drop can be attributed to the off axis parabolic mirrors used in THz imaging systems. These elements are well-known to behave poorly when the target surface normal is not correctly aligned with the focal axis. Preliminary ray tracing and physical optics work suggest that the significant drop in signal is due to the reflected energy not making it to the detector plane.

From these imaging results it is evident that in embodiments the performance of THz imaging systems when imaging significantly curved surfaces can be improved using a window to flatten the field. While contact is not ideal for clinical translation, its use is not unprecedented and there are many examples of ophthalmologic imaging systems that employ the use of rigid corneal flattening windows, such as confocal microscopy. (See, H. D. Cavanagh, et al., Ophthalmology, vol. 100, pp. 1444-1454, 1993 Oct. 1 1993; and R. A. Malik, et al., Diabetologia, vol. 46, pp. 683-688, 2003 May 1 2003, the disclosures of which are incorporated herein by reference.)

One final point regarding the dielectric window is it's interaction with the tear film. The low contact pressure provided by the window combined with the speculum used to keep the eye open may eliminate the tear film since the natural blink reflex could not replenish the film, but the window also acts as a barrier and constrains moisture loss from the epithelium.

In Vivo Trials

Figure 20:
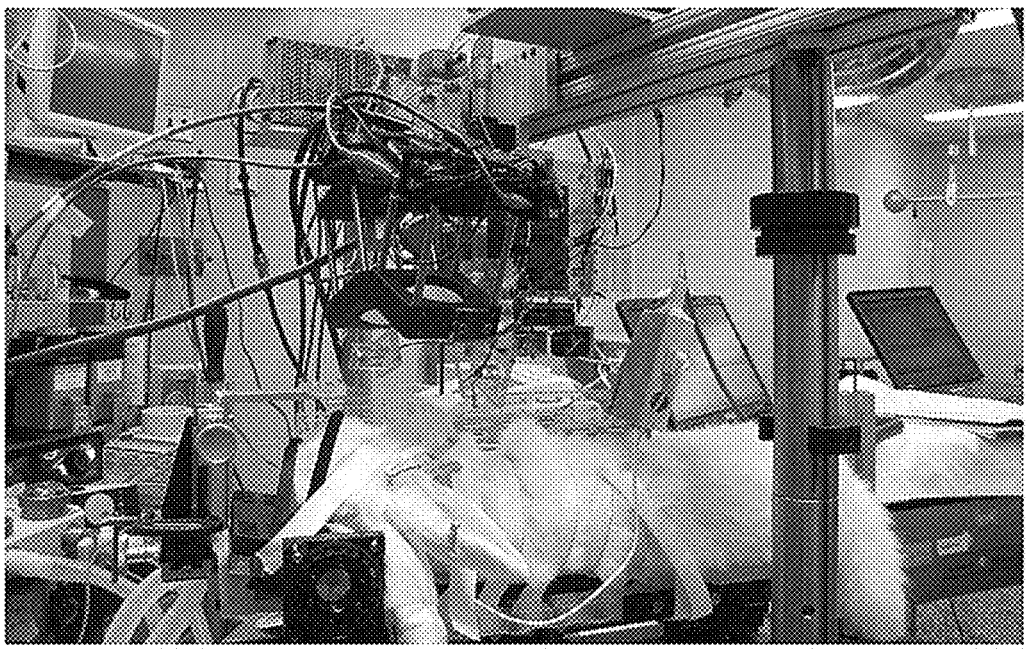
FIG. 20 provides photos of rabbit cornea imaging, in accordance with various embodiments, where (top) shows the rabbit model placed below the THz and millimeter wave imaging systems, and (bottom) is a close up of rabbit cornea and Mylar window.
Figure 20:
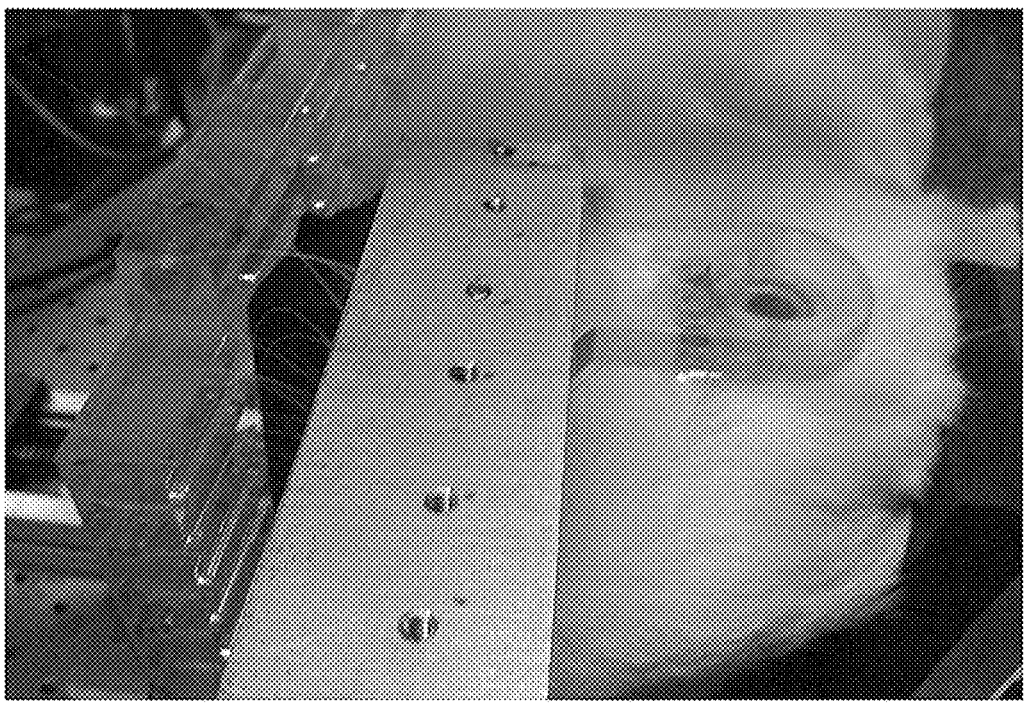

Five rabbits were anesthetized using 30 mg/kg and 5 mg/kg of Ketamine and Xylazine, respectively, followed by intubation with a 1.5 mg/ml flow of isofluorane. Each rabbit was placed in turn on an imaging cart with the head support panel adjusted to accommodate the rabbit's neck and head and secure the intubation tubes (as shown in FIG. 20).

Next, the right eye was held open and dehydration was attempted using a gentle air blower for 15 min. A Mylar window, of 12.7 µm, was lowered onto the cornea's surface to secure it in place and constrain it to a horizontal planar geometry with respect to the imaging optics. The following measurements were then obtained in the listed order every 10 to 20 minutes for the subsequent imaging period.

Thickness Measurement: An average of five readings were taken using the ultrasound pachymeter. These measurements were made through the Mylar window and the substrate thickness was subtracted out.

Millimeter Wave Point Reflectivity: An average of 100 millimeter wave reflectivity measurements obtained with the lock-in amplifier. A class I, 650 nm targeting laser was employed to ensure overlap between the probe and focused 100 GHz beam.

THz Reflectivity Maps: A THz image of a 20 mm×20 mm FOV was obtained with 0.5 mm pixels. The FOV was intentionally made larger than the cornea/window contact for the monitoring of system drift and noise through analysis of pixels along the periphery.

The thickness and 100 GHz point measurements each required ~1 minute acquisition time while the THz imaging required ~5 minutes. With the Mylar window separating the epithelium from the outside environment, the dehydrated cornea was assumed to increase in TWC to a slightly hyperhydrated state over the course of one to two hours.

CCT Calculations: While rabbit corneas are a very good physiologic model of human cornea in terms of their healthy TWC and radius of curvature, they are, on average, thinner than healthy human cornea, ranging from ~0.3 mm to ~0.5 mm as compared to the ~0.45 mm to ~0.7 mm spanned by human cornea. A modified CCT to $\overline{CTWC}$ equation taking this difference in thickness is given in EQ. 24 with the same functional form as the clinically employed human EQ. 25.

$$\overline{CTWC}_{rabbit} = \frac{CCT - 0.075}{CCT + 0.062} \qquad \text{EQ. 24}$$
$$CCT \sim \in [0.3, 0.5]$$

$$\overline{CTWC}_{human} = \frac{CCT - 0.091}{CCT + 0.051} \qquad \text{EQ. 25}$$
$$CCT \sim \in [0.45, 0.7]$$

Figure 21:
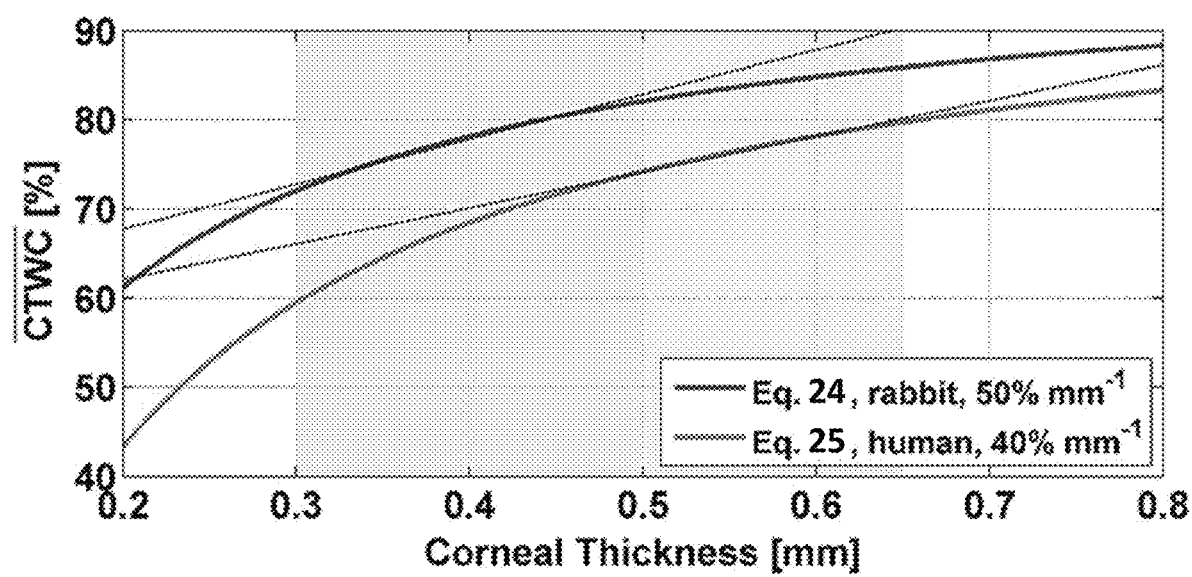
FIG. 21 provides a data graph comparing CCT to CTWC percentage relation for rabbit cornea and human cornea.

Limited data exists regarding the theoretical and/or practical domains for these equations. The ones denoted here are based on a rough survey of the literature and should not be interpreted as exact limits. A plot of both EQ. 24 and EQ. 25 are displayed in FIG. 21 with linear fits, calculated over the appropriate thickness ranges, superimposed on the curves. Additionally, both curves are plotted against shaded regions that cover the non-overlapping ranges of corneal thickness for rabbits and humans.

CCT Measurements: The CCT measurements for all five rabbits are displayed in FIG. 22 throughout the entire course of the CTWC monitoring experiments. The data points represent averages of five measurements for each time point, which was done to overcome variance intrinsic to contact probe measurements. Linear fits are superimposed on the data points. Each rabbit displayed an increase in CCT as a function of time with an average rate of ~25.6±4 microns per hour indicating protocol consistency.

Figure 22:
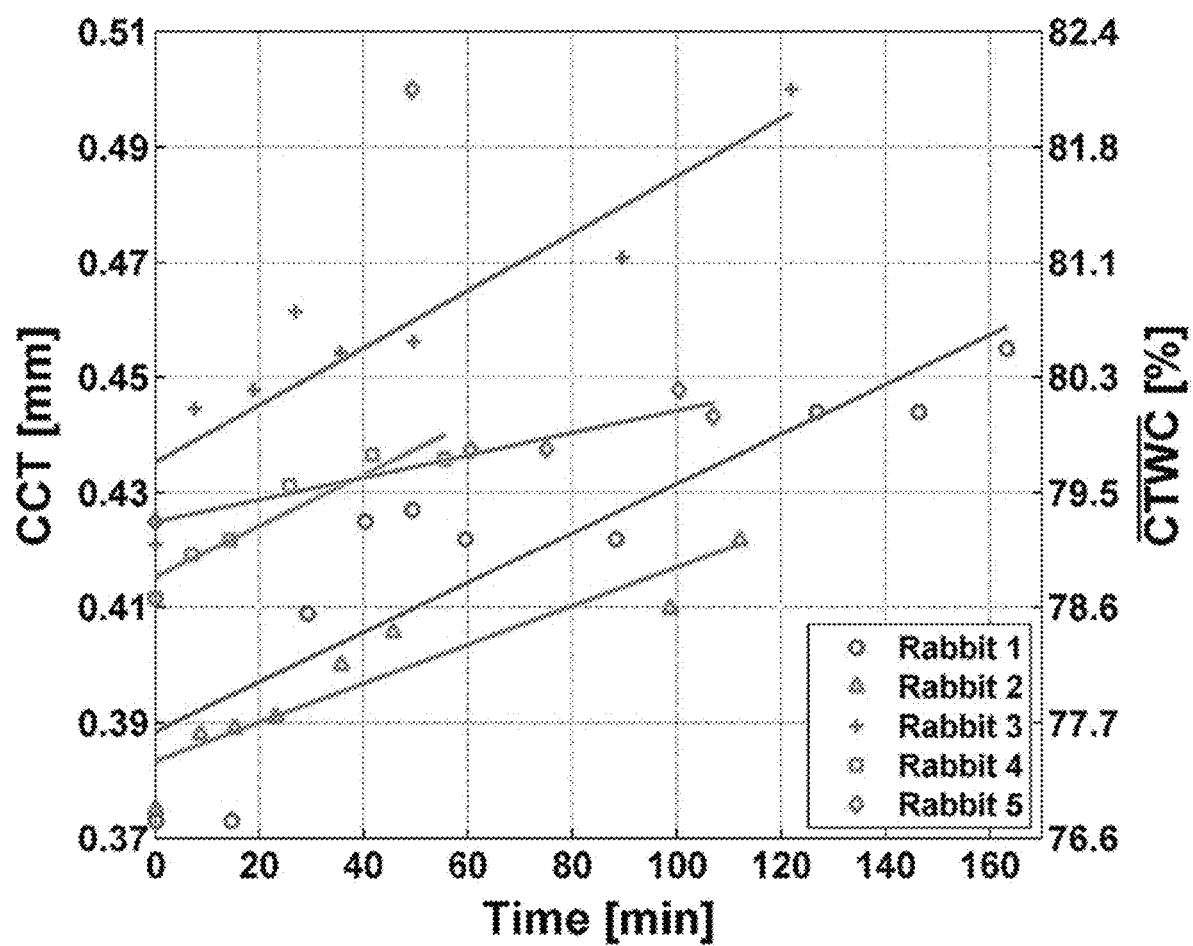
FIG. 22 provides a data graph measuring CCT for all rabbits in the trial and their associated CTWC levels.

The estimated mean TWC of the cornea $\overline{CTWC}$ is indicated by the y-axis on the right side of the figure and was computed with EQ. 24. Note that the mapping from CCT to $\overline{CTWC}$ is non-linear resulting in a shrinking TWC differential due to the negative concavity of EQ. 24. One important point apparent from inspection of FIG. 22 is the variance in CCT of the five different rabbit cornea at the start of the experiment reflecting the large physiologic variation of in vivo corneas. The thickness in the healthy corneas range from 0.373 mm to 0.425 mm (N=5 measurements per quoted healthy thickness value), which EQ. 24 predicts as a range of CTWCs from 76.8% to 79.4%. This was assumed to be entirely due to natural physiologic variation of healthy cornea as all animals were determined by the attending veterinarian to have healthy corneas just prior to anesthesia and the commencement of experiments. A $\overline{CTWC}$ value of 76.8% suggests compromised corneal health whose deteriorated state would be detected upon visual inspection. This is further illustration the limitation of the thickness to CTWC mapping on which all pachymetry is based.

100 GHz Results: The results of the millimeter wave point measurements are displayed in FIG. 23 where the reflectivity has been plotted against CCT measurements indicated on the bottom x-axis and estimated $\overline{CTWC}$ indicted on the top x-axis. Strong, positive correlation between increasing CCT and increasing millimeter wave reflectivity was observed. Linear fits were superimposed on the data corresponding to the hypothesized approximate linear increase in millimeter wave reflectivity to linear increase in $\overline{CTWC}$.

Figure 23:
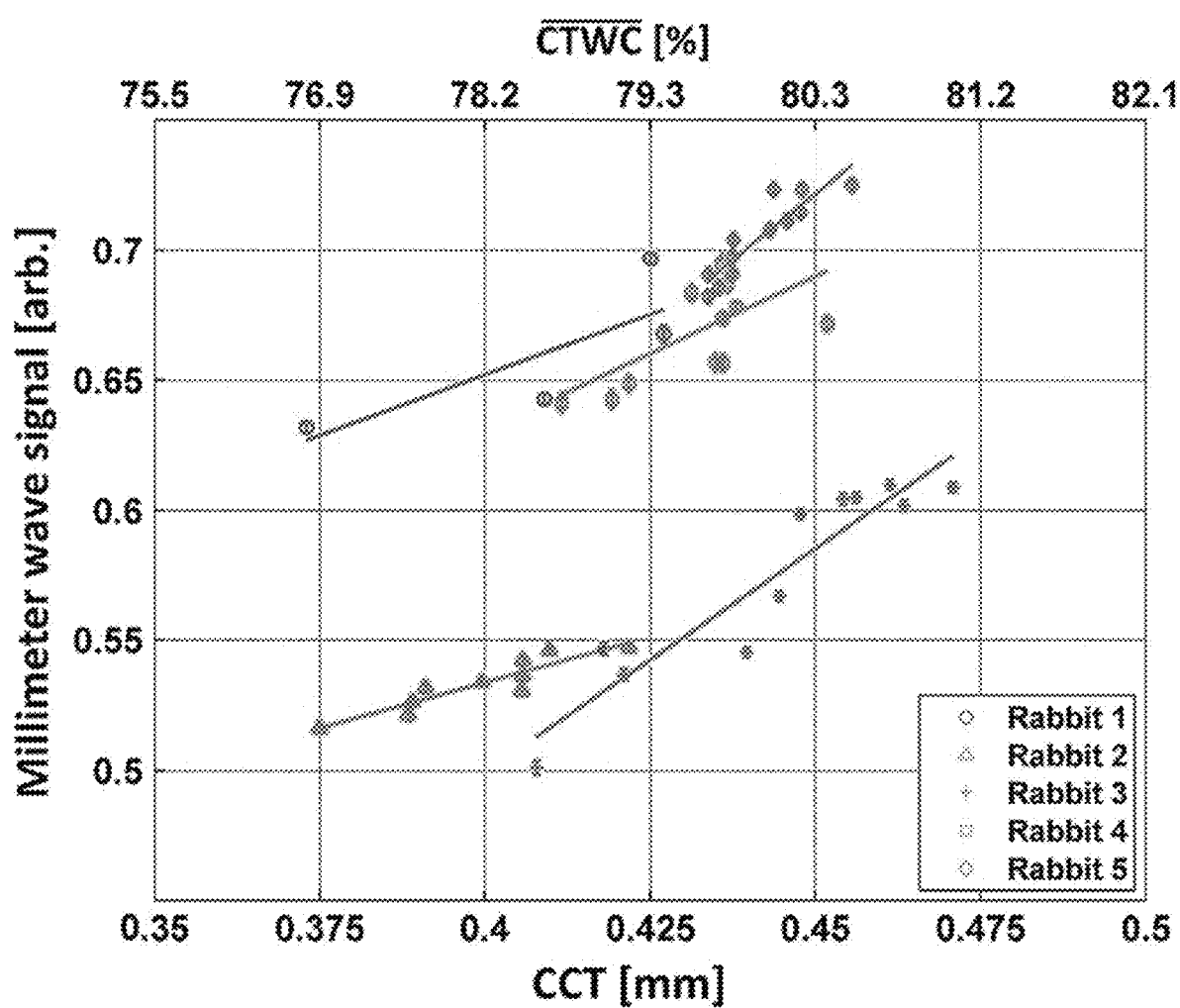
FIG. 23 provides a data graph measure 100 GHz wave signal plotted against the CCT measurements reflected in the lower x-axis, where the corresponding CTWC increases predicted by CCT theory are displayed on the top x-axis, generated in accordance with various embodiments.
Figure 24:
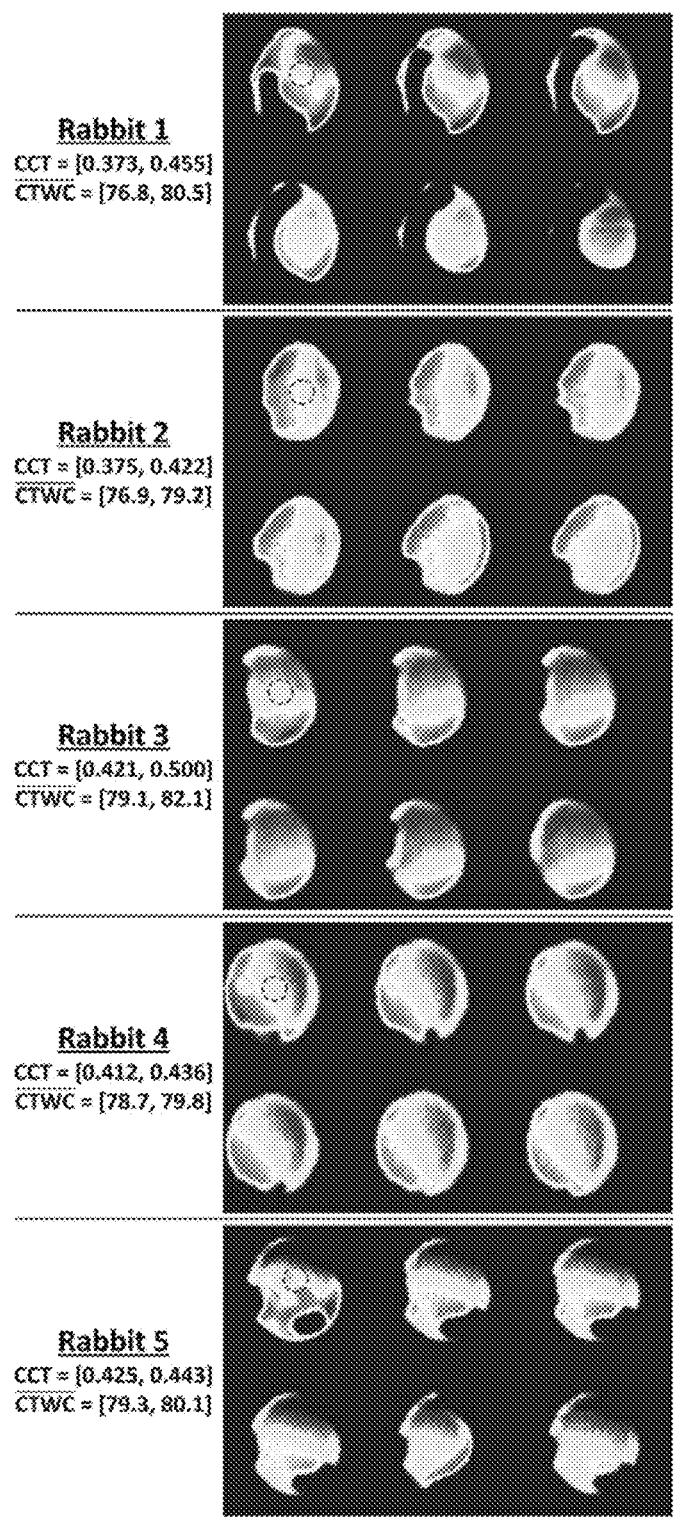
FIG. 24 provides selected THz reflectivity maps of CTWC for all five rabbit models, where each image series is accompanied by its CCT range and computed CTWC levels (time increases, from left to right and top to bottom for each image series, and the dotted circles overlaid on the top left cornea of each image denote the ultrasound probe region of interest location), generated in accordance with various embodiments.

Although the increases in FIGS. 22 and 23 display good correlation, the ensemble of millimeter wave reflectivity slope magnitudes appear to have more variation than the ensemble of CCT slope magnitudes. If this signal variation is due to real physiologic variation, the millimeter wave measurement may have significantly greater sensitivity and/or larger dynamic range than corneal pachymetry. Conversely, as mentioned previously, the mapping from CCT to $\overline{CTWC}$ is not well understood and this variance may be due entirely to the limitations inherent to the understanding described in EQ. 24.

Reflective THz Imaging: Six THz images from each of the five rabbit models acquired throughout the experiments are shown in FIG. 19 with a standard false color pallet (color online) where red areas correspond to increased reflectivity and blue less. Each set has been normalized to its' individual global maximum. The CCT measurement range and corresponding estimated CTWC range computed with EQ. 24 has been noted next to each image set. The top left image in each series was acquired at time 0 and the last image in each series is located in the bottom right where time is incremented from left to right, top to bottom. The images reveal noticeable, spatially varying shifts in contrast throughout the cornea for the duration of the experiment. The perimeter of the cornea is also changes with time suggesting that the corneal thickness is sufficiently perturbed to increase the total surface area of cornea touching the window as the cornea swells. As mentioned above, the corneal flattening window was applied with light contact pressure to minimize the effect of the window on corneal physiology.

Region of Interest Analysis: A region of interest is indicated by a dotted circle on the first image of each image series. The diameter matches that of the ultrasound probe employed in the pachymetry measurements and the location indicates the interrogated area. In addition to laser targeting, small fiducial markers (transparent to THz illumination) on the Mylar window helped ensure repeatable probing location. The FOV was intentionally larger than the rabbits' corneas, guaranteeing the absence of cornea in the periphery of the images and allowing for accurate monitoring of system drift and noise.

To confirm accurate placement of the ultrasound probe image processing techniques were utilized to verify that the ultrasound probe was placed at the apex of the cornea. The THz cornea images were converted to binary masks using a threshold four times larger than the standard deviation of the pixels located in the corners of each FOV. The resulting masks were morphologically closed using a disc-shaped structuring element. Then, the centroids of the cornea masks were computed, and a circular mask with a radius corresponding to the pachymeter's radius (5 mm) was placed at the centroid, creating the pachymeter test mask. This result was compared to registered visible images of the fiducials markers against the cornea under test. The mean reflectivities and standard deviations in the pachymeter mask and in the cornea mask were then computed and confirmed to be statistically insignificant.

Figure 25:
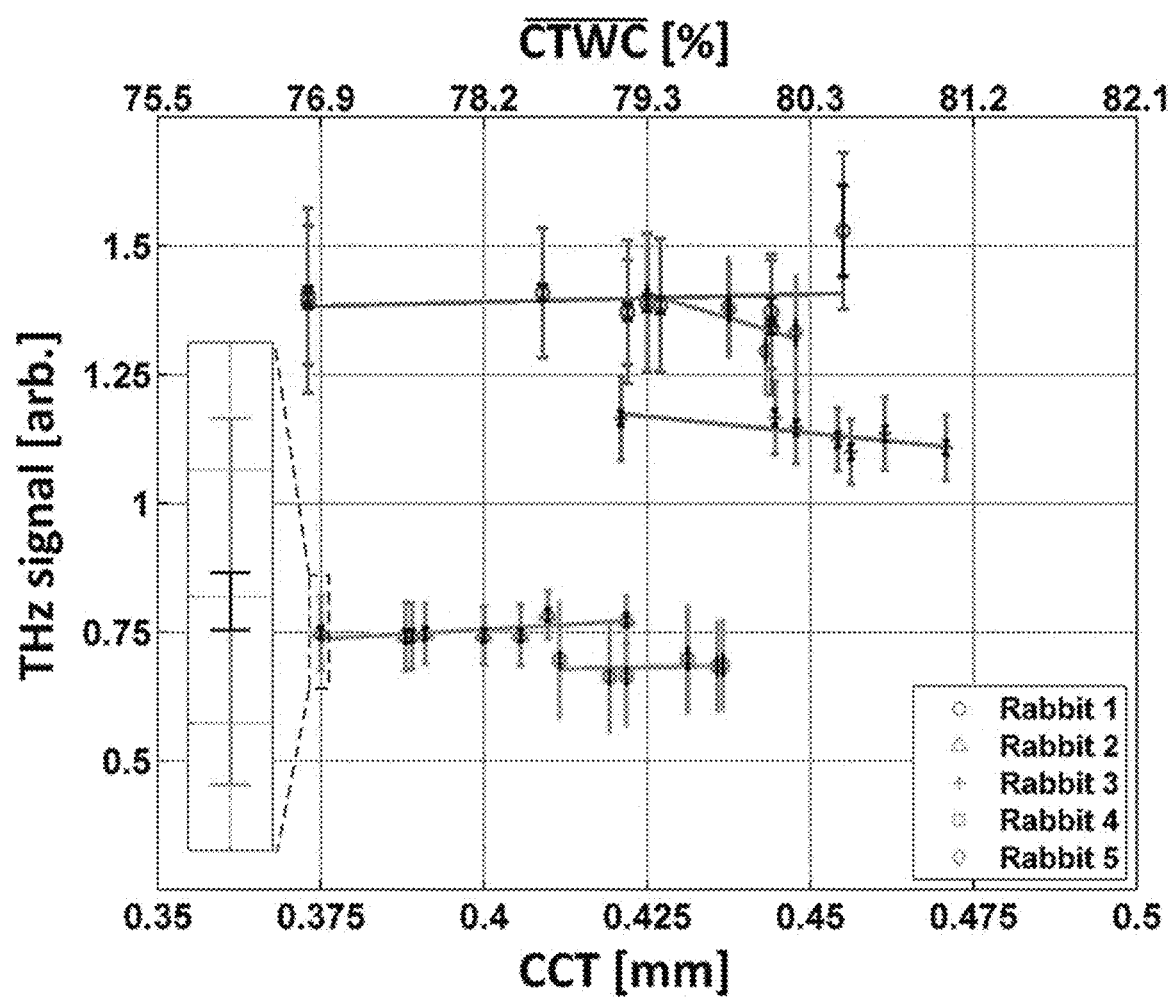
FIG. 25 provides a data graph of THz reflectivity signal computed within the indicated region of interest as a function of acquired CCT measurements reflected in the lower x-axis, where the corresponding CTWC increases predicted by CCT theory are displayed on the top x-axis, and where a zoom-in of the first point in the rabbit 4 series is displayed in the inset demonstrating the difference in variation between estimated system noise and contrast observed in the 5 mm diameter FOV, generated in accordance with various embodiments.

The average reflectivities of these regions of interest are displayed in FIG. 25 where the larger error bars correspond to the variation within the pachymeter mask and the smaller error bars are the variation due to system noise assuming negligible effects of shot noise at these power levels. (See, J. L. Hesler and T. W. Crowe, "NEP and responsivity of THz zero-bias Schottky diode detectors," in Infrared and Millimeter Waves, 2007 and the 2007 15th International Conference on Terahertz Electronics. IRMMW-THz. Joint 32nd International Conference on, 2007, pp. 844-845, the disclosure of which is incorporated herein by reference.) A zoom-in of one of the data points on the right side of FIG. 25 demonstrates the difference in magnitude between the variation within the cornea mask and the system noise.

A number of interesting features are observed in these companion plots. First, the error bars computed from data points within the region of interest are significantly larger than those plotted for the millimeter wave measurement in FIG. 23. However, the signal to noise ratio (SNR) of each system is comparable as evidenced by the similar noise error bars. This result indicates that the majority of the variance in signal amplitude within the region of interest arises from the spatial variation of the corneal reflectivity (i.e. real signal); even if the ultrasound probe could be scanned the contact area is too large to capture the spatial variation of cornea properties. However, the most surprising result of the ROI plots is the nearly zero correlation between THz reflectivity and CCT measurements. Rabbits 1 and 2 display slight increases in reflectivity while rabbits 3, 4, and 5 display slight decreases. In both cases the total change is, at maximum, nearly an order of magnitude less than the variance. This confirms the result from Exemplary Embodiment 1 that THz measurements in accordance with embodiments are capable of decoupling the measurement of CTWC from CCT.

Sensitivity Calculations: As a comparison of system performance, the thickness sensitivity of each system was computed using the slope of the regression line fit to each rabbit data set and the variance about each point. The CCT/$\overline{CTWC}$ relationship described in EQ. 24 and EQ. 25 is approximate so it is more appropriate to compute sensitivity in terms of CCT directly. As discussed in our previous publication, any path through the entire thickness/$\overline{CTWC}$ pace generally produces a nonlinear (nonmonotonic) profile. However, linear functions provide a high goodness of fit over the limited thickness range variation observed.

$$CCT_{sens.} = \frac{\max(\sigma_n)}{df_n/dCCT} \quad \text{EQ. 26}$$

Thickness sensitivity was computed using EQ. 26 where $\max(\sigma_n)$ is the maximum standard deviation observed in rabbit n and $df_n/dCCT$ is the slope of the regression line for rabbit n. The results are set forth in Table 2, below.

TABLE 2

Measured Sensitivities

| Rabbit (n) | Measured CCT slope μm/hr | Measured 100 GHz CCT sens. [μm] | Measured THz CCT sens. [μm] |
|---|---|---|---|
| 1 | 25.8 | 3.27 | 582.6 |
| 2 | 20.2 | 3.14 | 98.2 |
| 3 | 29.9 | 1.4 | −64.2 |
| 4 | 26.7 | 3.11 | 476.0 |
| 5 | 11.6 | 1.29 | −34.2 |

These results suggest that millimeter reflectometry based CTWC measurements are anywhere from one to two orders of magnitude more sensitive than those acquired with the 525 GHz system. Furthermore, the sensitivity of the THz imaging system was calculated to be negative in two out of the five rabbits. This statistically insignificant change in THz signal paired with a significant increase in millimeter wave signal suggests that signal variation cannot be attributed entirely to shifts in $\overline{CTWC}$.

Analysis

Figure 26:
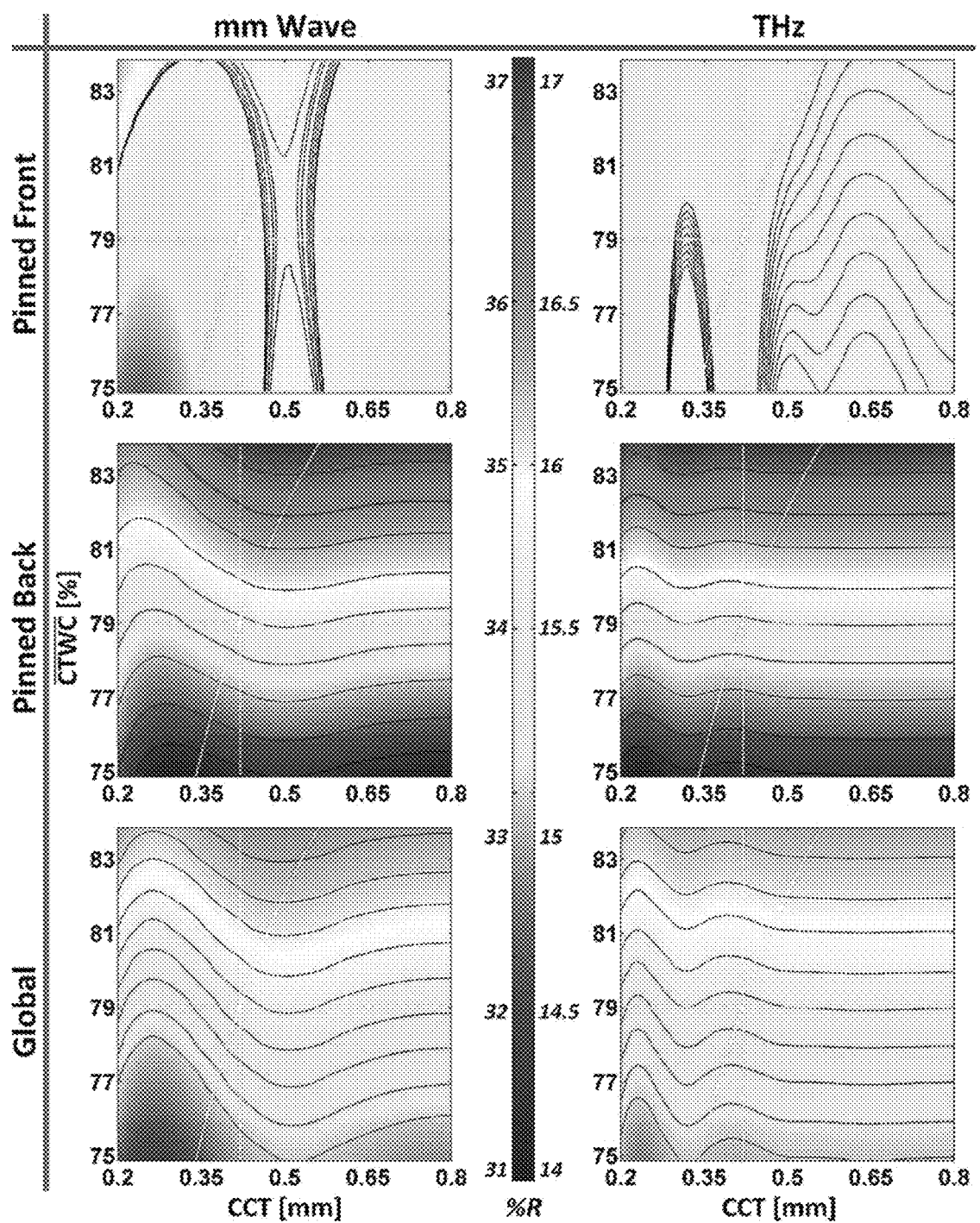
FIG. 26 provides the dependence of corneal reflectivity on TWC and thickness computed for the (left column) 100 GHz system and (right column) 525 GHz system for the gradient types (top row) pinned front, (middle row) pinned back, and (bottom row) global (the figures within each row are displayed with a common colormap, with pixel intensities representing reflectivity), in accordance of various embodiments.

To explore the source of variation in the data, the $\overline{CTWC}$-thickness reflectivity spaces presented in Exemplary Embodiment 1, described above, were recomputed for the operating spectra of both systems with the 12.7 μm thick Mylar window included in the stratified media model. The spaces are displayed in FIG. 26 with corresponding constant thickness, constant $\overline{CTWC}$, and CCT paths plotted using EQ. 24.

The millimeter wave spaces are very similar to those presented in Exemplary Embodiment 1 owing to a time averaged RF bandwidth that is roughly rectangular but still symmetric. The THz spaces are similar to the Q=5 system in Exemplary Embodiment 1 albeit with slightly larger maximum reflectivities and reflectivity ranges. This difference arises from the photoconductive switch PSD and Schottky diode spectral responsivity, which are heavily skewed towards the lower frequencies, thus accessing larger overall tissue reflectivities and TWC sensitivities.

Thickness Variations: The ultrasound pachymeter used in these studies relies on a pulse echo methodology with range gating to ascertain the axial location of the acoustic impedance discontinuity at the endothelium/aqueous humor interface. (See, N. Ehlers and J. Hjortdal, "Corneal thickness: measurement and implications," Experimental Eye Research, vol. 78, pp. 543-548, 3// 2004, the disclosure of which is incorporated herein by reference.) None of the steps in the protocol were thought to have compromised this discontinuity, so thickness values extracted by the ultrasound measurements may be assumed to be accurate. Therefore, only the constant $\overline{CTWC}$ paths and CCT projections were analyzed.

Figure 27:
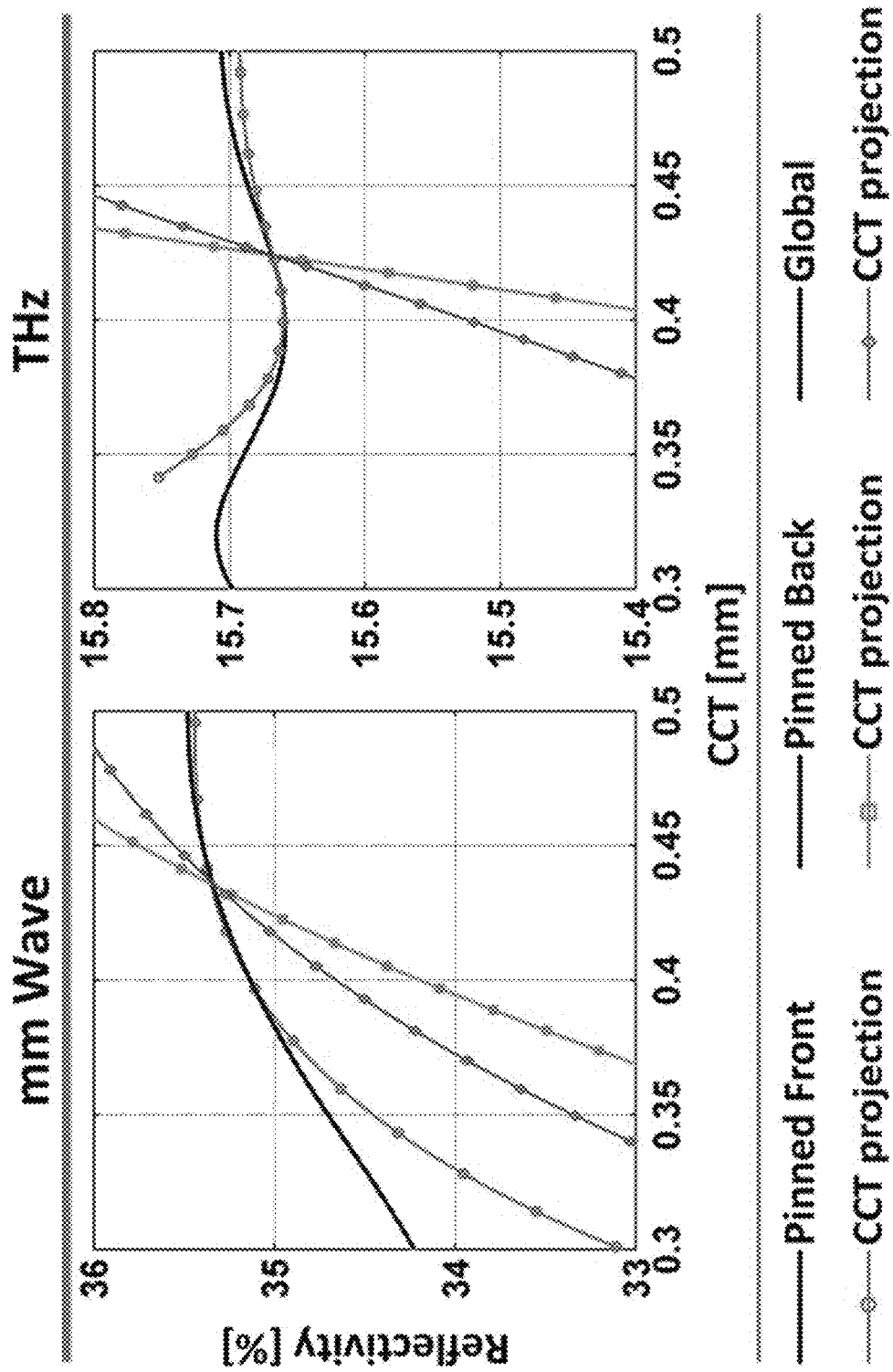
FIG. 27 provides a data graph of constant CTWC cuts at 79% water by weight with varying distance over the range measured by ultrasound pachymetry (note that in the case of constant CTWC-varying CCT the three gradient types yield the same behavior which is represented by the solid line), generated in accordance of various embodiments.

The expected reflectivity of cornea as a function of thickness, averaged over the operational band of both the millimeter wave and THz imaging systems are displayed on the left and right side respectively of FIG. 27 using a volumetric average CTWC of 79.4%. Comprehensive analysis requires one to analyze a family of curves at varying constant CTWC percentages. However, since experimental calibration to determine accurate absolute reflectivity is difficult, it is instructive to instead look at the trends of changes in relative CTWC. In this case, constant (CTWC)⁻ profiles at 77%, 78%, 79%, 80%, 81%, etc. produce nearly identical variation trends within a particular band. Thus fixing the analysis to 79.4% is sufficient.

Over the range of thicknesses measured experimentally (0.375 mm to 0.475 mm), if the $\overline{CTWC}$ remains constant, the millimeter wave system is predicted to measure an increase in reflectivity as corneal thickness increases. Similarly, if $\overline{CTWC}$, and thickness are increasing simultaneously all three candidate distributions yield monotonically increasing reflectivity. In contrast, the THz system is predicted to measure a minor decrease in reflectivity as the corneal thickness increases from 375 to 400 μm, followed by a minor increase in reflectivity as corneal thickness increases from 400 to 475 μm. However, the total variation is <0.05%, which is beyond the measured NERD (see above) of the THz imaging system. When simultaneous CTWC/thickness increases are considered the pinned front gradient type displays similar behavior with a total variation of <0.1% while the pinned back and global variation gradient types display significant increases over the range with a predicted gain of >0.5%; a factor of four larger than the measured NERD.

The protocol employed external means to perturb CTWC; namely blowing dry air and application of a dielectric window. Further, histologic analysis of the tissue post experiment confirmed that none of the protocol steps affected the deeper layers of the cornea. Thus, it can be concluded, with high confidence, that the outer layers of the cornea were most affected and that the pinned back gradient case is the most appropriate model of experimental parameters.

The millimeter wave data matches the pinned back case quite well with statistically significant, positive correlations between CCT and reflectivity. The THz system displayed a slight increase in reflectivity from ~0.375-0.400 mm, followed by a slight decrease in reflectivity from ~0.400-0.475 mm, which is inverted from what is predicted by FIG. 27. However, the variance of the results indicates statistically insignificant changes for all rabbit models, which is predicted by the FIG. 27 considering constant CTWC.

From this ensemble of curves, it is evident that the only explanation that fits the experimental observations is that the protocol was not perturbing the CTWC but appreciably modulating the thickness. While the difficulties associated with perturbing healthy CTWC without injuring corneal tissue are known, it is surprising that the CCT changed so significantly for an apparent lack in CTWC change. (See, J. W. Ruberti and S. D. Klyce, Exp Eye Res, vol. 76, pp.

349-59, March 2003, the disclosure of which is incorporated herein by reference.) This result leads to a number of interesting observations:

There is poor correlation between corneal thickness and CTWC in vivo. The lack of a one-to-one mapping between corneal thickness and CTWC and the inability of pachymetry to correct for physiologic variation is well known, yet this represents in vivo study with quantifies those inaccuracies.

While the center areas of each cornea display minimal changes in reflectivity (CTWC) the perimeters of some of the samples show marked changes throughout the duration of the experiment. Standard corneal physiology indicates that the perimeter of the cornea is anywhere from 9% to 52% thinner than the central corneal dimension. It is possible that the reflectivity changes at the edges of the cornea and/or decreases as predicted by modeling efforts correspond to thickness variations. Replacing ultrasonic pachymeter spot measurements with OCT based pachymetry, which can provide full 3D characterization the entire corneal geometry should help improve the accuracy of the measurements by allowing the resolution of spatially varying etalons.

As discussed previously, the refractive index of the non-water constituents of cornea at THz frequencies are not well characterized. Similarly, the ratios of bound to unbound water in vivo is also not known. Shifts in refractive index will change the free spectral range (FSR) of the lossy cornea cavity, thus shifting the range over which increases and decreases in THz corneal reflectivity occur in the fixed CTWC, varying thickness case.

Perturbations observed in corneal thickness was caused by the use of the Mylar window, which applies a very slight pressure to the cornea although care was taken to ensure the window applied the same pressure as a corneal probe. This observation indicates that THz or millimeter wave CTWC studies may be improved using non-contact, windowless system architecture.

Post Mortem Study: Previous embodiments identified the hypothesized dominant role of varying optical path length and the minimal role of CTWC in the reflectivity signals observed in healthy cornea experiments. To further elucidate the role of corneal tissue geometry on reflectivity signal a preliminary experiment on one additional rabbit using the millimeter wave reflectometer was performed.

The animal model was prepared with the same protocol discussed above. Following gas anesthesia an ensemble of healthy CCT measurements were acquired and yielded a mean of 0.42 mm. The animal was then euthanized. Once death was confirmed five pairs of CCT and millimeter wave reflectivity measurements were obtained over the course of 45 minutes.

The goal of the five animal experiments was to assess the performance of THz and millimeter wave reflectometers when presented with live healthy cornea. The aim of this experiment was to initiate a change in corneal thickness that was paired with a definite change in CTWC and whose change in CTWC resulted in the occurrence of an observable etalon. When the rabbit dies, the cornea begins to lose water through the top side of the cornea due to disappearance of the tear film while also experiencing a gain in CTWC from the backside due the death of the endothelium and subsequent diffusion. In this experimental setup the presence of the Mylar window prevents water from evaporating from the front side, ensuring that the CTWC changes only on the backside the cornea swells as CTWC increases. This protocol recreates the pinned front CTWC gradient type introduced and discussed above. Note that the CCT projection for the pinned front gradient type (FIG. 27) predicts a maximum reflectivity at ~0.483 mm assuming a baseline $\overline{CTWC}$ of 79.4%.

Figure 28:
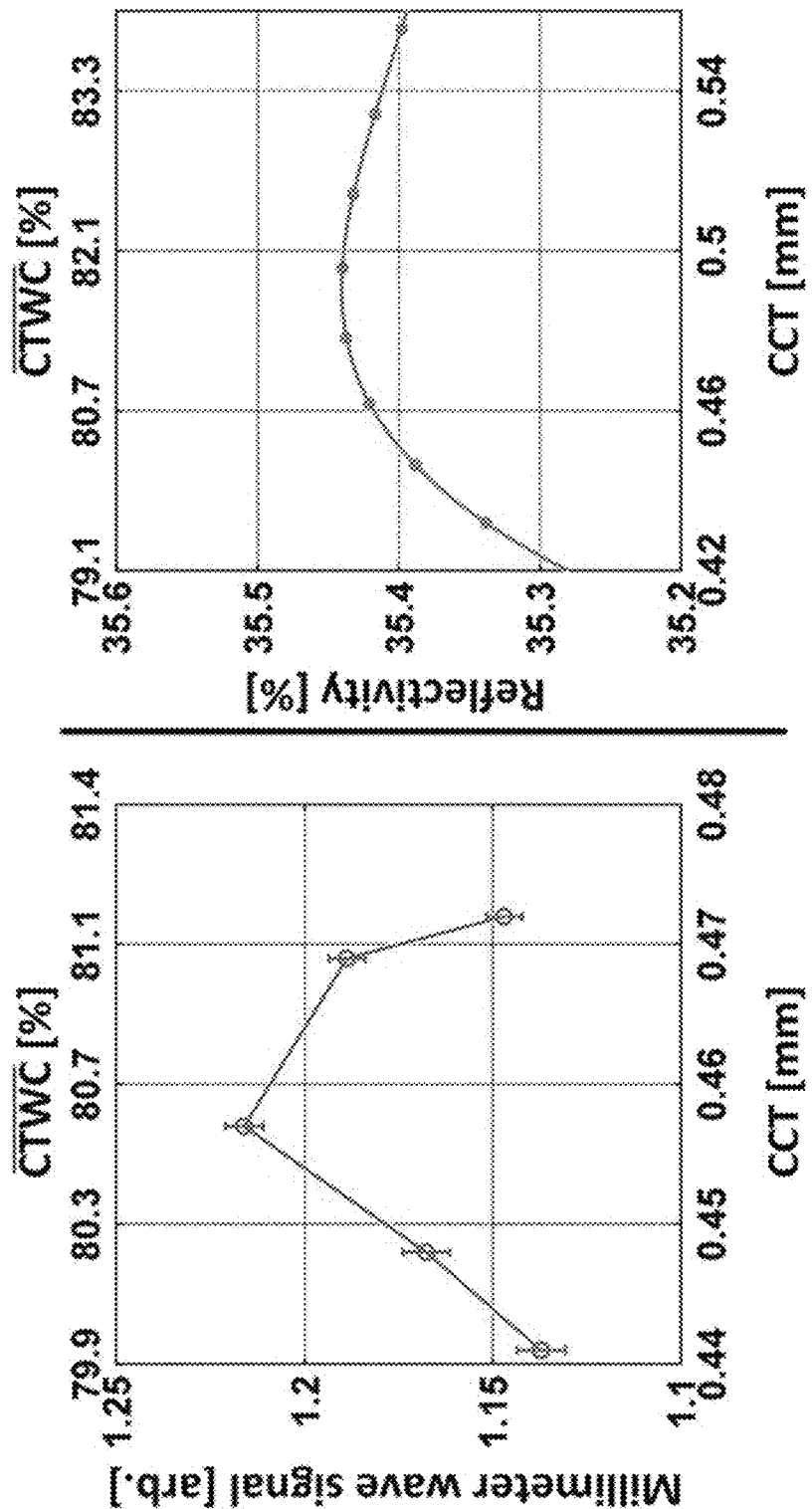
FIG. 28 provides a data graph of a post mortem study, where (left) Observed change in reflectivity at 100 GHz per change in CCT, and (right) predicted change in reflectivity for the pinned front gradient case, generated in accordance of various embodiments.

The millimeter wave system was chosen because NERD characterization suggested sufficient sensitivity to detect the expected variation in reflectivity and one system was desired to minimize the effects of movement when switching between imaging modalities. The results of the experiment are displayed in the left side of FIG. 28, and predicted pinned front behavior is plotted in the right side of FIG. 28 with a swing in reflectivity that is ~ a factor of 5 larger than our noise limited reflectivity difference (NERD). A significant increase in reflectivity was observed followed by a significant decreases as the CCT ranged from 0.441 mm to 0.475 mm. The data suggests that a maximum in reflectivity occurred somewhere between 0.457 mm and 0.469 mm which is 0.014 mm to 0.026 mm offset from the predicted maximum. In short, a large ensemble of CTWC gradient and CTWC/CCT pairs predict a thickness based standing wave when plugged into the effective media theory model and the observed results are compelling.

Summary

A study of the utility of THz imaging and millimeter wave reflectometry for the measurement of CTWC was performed with five rabbit models. These results provide that embodiments of methods and systems may be used to obtain THz images of cornea in viva.

During the study, a protocol was implemented to dehydrate and then hyperhydrate healthy cornea over the course of 1-3 hours during which clinically accepted ultrasound pachymetry measurements mapped thickness to CTWC. Companion millimeter wave reflectivity spot measurements and THz reflectivity maps, in accordance with embodiments were also obtained. Increases in millimeter wave reflectivity and thickness were noted with good correlation. THz CTWC maps, however displayed marked reflectivity increases in some areas, decreases in others, and a relative lack of CTWC change in the region probed with the pachymeter. The results indicate that the protocol changed the thickness of the cornea but not the CTWC, and that trends in corneal thickness do not correlate with changes in CTWC gradients or CTWC, indicating that current state of the art pachymeter measurements that relate CTWC and CCT are fundamentally flawed.

This result also confirms that operational parameters such as frequency, angle of incidence, CTWC etc. can markedly change the computed CTWC due to the structural similarity with optical thin films. For this reason, many embodiments of CTWC sensing system architectures involved one of the following:

Reflectivity maps at multiple frequencies are acquired and correlated with spatially resolved thickness maps obtained with OCT; and Reflectivity maps at multiple frequencies are acquired and modeling is used to obtain both CTWC and thickness maps simultaneously.

Regardless of the precise combination of reflectivity maps and thickness maps or modeling used, a single frequency or single band integrated measurement is not sufficient for decoupling CTWC based signal variation from CCT based signal variation, in accordance with embodiments. Further, contact between the imaging/sensing system and cornea may confound the aggregate RF properties. Accordingly, in many embodiments, non-contact, spectrally resolved measurements are used.

Exemplary Embodiment 3: THz Imaging System Designs

In this Exemplary Embodiment, terahertz (THz) imaging system designs incorporating a combination of plane and off axis parabolic (OAP) mirrors to scan a beam at normal incidence across the radial extent of the cornea while keeping the source, detector, and, most importantly, the patient stationary are described in accordance with various embodiments of the invention. In many embodiments, this method acquires an image of a spherical surface with an arbitrary radius of curvature by an orthographic projection of the spherical surface to Cartesian coordinates. The designs result in non-contact imaging of corneal reflectivity and result in the elimination of temporal thickness variations.

Described within this Exemplary Embodiment is a framework for providing THz imaging/sensing apparatus and methods for performing non-contact imaging of CTWC in human cornea. Imaging principles, quasioptical modeling, and physical optics modeling are also presented. In accordance with multiple embodiments, the quasioptical modeling treats the OAP mirror as an ensemble of thin lenses of varying effective focal lengths coupled with varying free space path lengths. The accuracy of this quasioptical technique embodiment is assessed with a physical optics simulation code. Many embodiments are also directed to an augmented design that improves image acquisition rate through the introduction of a second OAP mirror to the scanning subsystem. Physical optics verification of the relevant quasioptical modeling is also presented.

Anatomy of the Cornea and its Compatibility with THz Imaging

As previously discussed, in general, the corneal surface is aspherical where the deviation from an ideal sphere increases toward the periphery. Human cornea is also somewhat astigmatic, demonstrating different curvature and, hence, optical power as a function of cross-sectional meridian angles. Characterization of corneal topology is critically important in visual acuity interventions such as, for example, Laser-Assisted in situ Keratomileusis (LASIK) and Photorefractive Keratectomy (PRK) where photonic base ablation of the corneal stroma is performed to modulate the measured, non-ideal corneal topology to one that minimizes refractive wave front aberrations. Corneal topology mapping is a mature field, and corneal surface profiles can be obtained with the Videokeratography (S. J. Bogan, et al., "Classification of normal corneal topography based on computer-assisted videokeratography," Archives of Ophthalmology, 108:945-49, 1990, the disclosure of which is incorporated herein by reference) or Scheimpflug photography (O. Hockwin, et al., Ophthalmic Research, 15:102-08, 1983, the disclosure of which is incorporated herein by reference) techniques, which interpret the surface height measurements in refractive power at each local surface. In particular, Videokeratoscopy (R. A. Applegate and H. C. Howland, IEEE Engineering in Medicine and Biology Magazine, 14:30-42, 1995, the disclosure of which is incorporated herein by reference) can be used to construct dioptric power maps from corneal surface height data, which can be further fitted to a parametric surface to analyze higher-order surface features from disease or refractive surgery (J. Schwiegerling and J. E. Greivenkamp, Optometry & Vision Science, 74:906-916, 1997, the disclosure of which is incorporated herein by reference). However, despite the maturity of topology mapping technology, there is no standardized method for analyzing topographical information.

Figure 29:
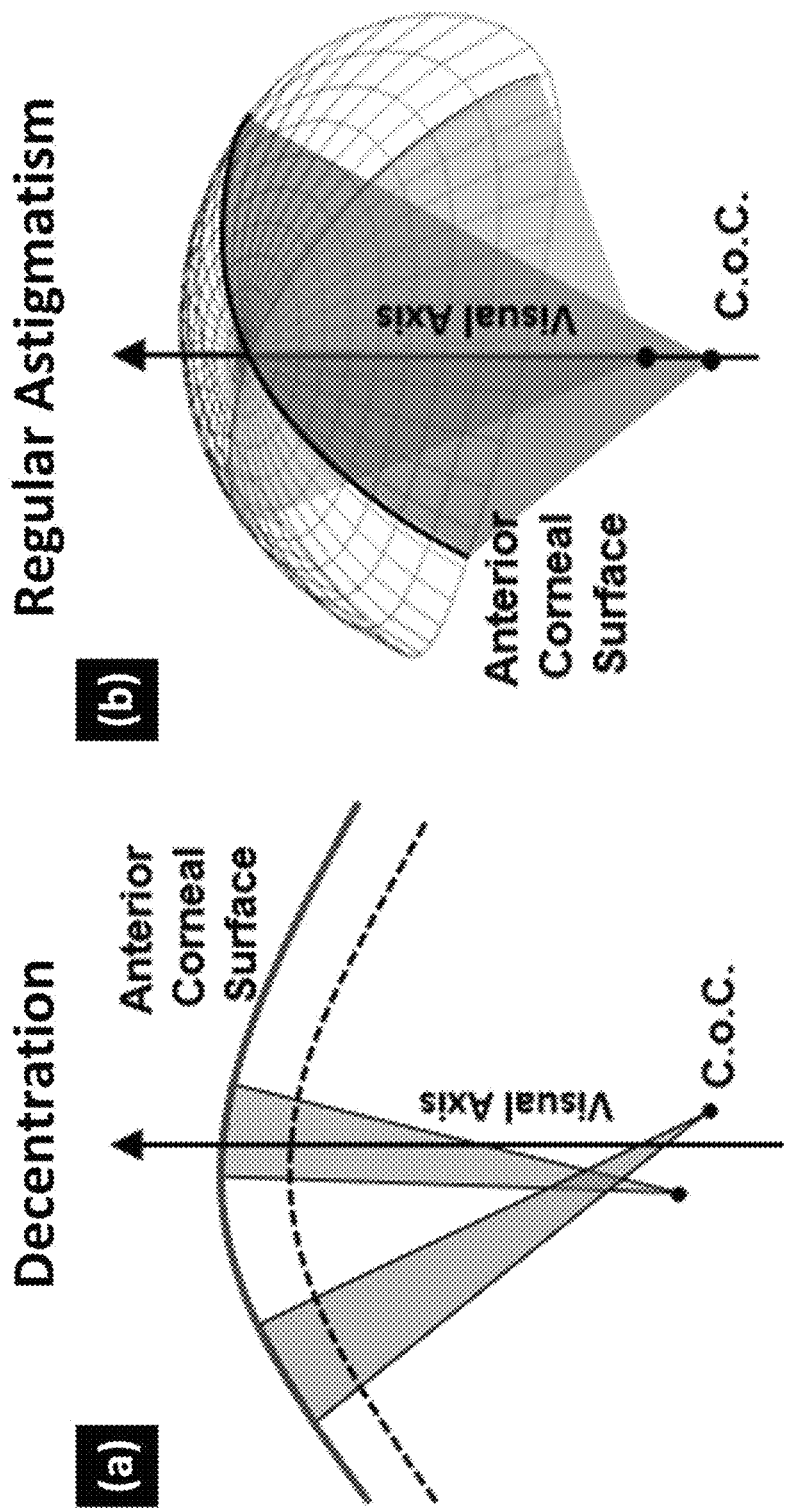
FIG. 29 provides a pictorial description of (left) decentration and (b) "regular" astigmatism in corneal anatomy.

The Fourier decomposition analysis of the corneal surface by Hjortdal et al. (J. Ø. Hjortdal, L. Erdmann, and T. Bek, Ophthalmic and Physiological Optics, 15:171-85, 1995; T. W. Raasch, Optometry & Vision Science, 72:809-15, 1995; the disclosures of which are incorporated herein by reference) was utilized to explore the deviations between average human cornea topology and an ideal sphere and hence assess the compatibility of the expected range of corneal curvatures with several embodiments of various THz imaging system designs. This spectral decomposition method characterizes the corneal surface's deviation from ideal spherical surface by Fourier components for healthy and diseased cornea eyes. The fundamental mode (first term in the Fourier series expansion) is attributed to decentration (pictorial representation in FIG. 29 (left panel)), and the second term is attributed to "regular" astigmatism (pictorial representation in FIG. 29 (right panel)). Higher order Fourier terms are typically grouped together as "higher order surface irregularities" and contribute less to the overall corneal shape than either decentration or astigmatism. In general, these parameters increase for equal height contour lines further from the corneal apex.

To compute the standard deviation in radius of curvature (RoC) expected in a sample of patients, the Fourier components available in Hjortdal et al. were utilized in accordance with numerous embodiments. These values were reported as diopters across the meridian cross-section as a function of radial distance from the center of the cornea and the meridian angle. The diopters were averaged and converted to an expected RoC deviation using EQ. 27 where $P_i$ is optical power in diopter, n is the refractive index of the cornea (taken to be $P_{typical}$=44, n=1.376), and $\Delta r$ is the resulting standard deviation in the RoC.

$$\Delta r = (n-1)\left(\frac{1}{P_2} - \frac{1}{P_1}\right) \quad \text{EQ. 27}$$

Figure 30:
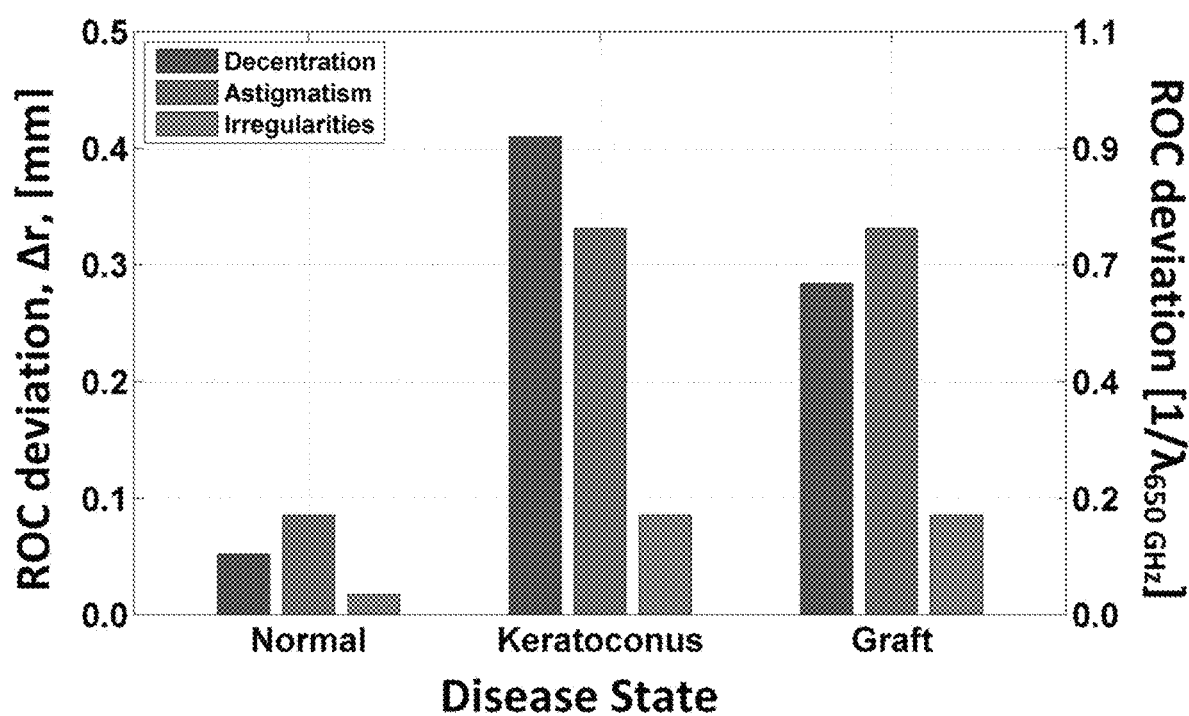
FIG. 30 provides a data chart of average radius curvature (RoC) variations in corona from Fourier decomposition (EQ. 27) applied to healthy cornea, Keratoconus, and grafted cornea.

The average RoC deviation from the first term in the series (decentration), the second term in the series (astigmatism) and the higher order terms are displayed in FIG. 30 for healthy eyes (N=25), Keratoconic eyes (N=13), and grafted cornea (N=20). It should be noted that the data that is derived in this example would also adequately describe all endothelial dystrophies such as Fuch's, because the expected deviation of corneal shape from ideal is anticipated to be the greatest in Keratoconus and corneal graft rejection; thus these pathologies serve as sufficient upper bounds on the spherical properties of endothelial diseased cornea.

For normal healthy eyes, decentration produces a mean RoC displacement deviation of ~0.05 mm, regular astigmatism is slightly higher at ~0.08 mm, and the sum total of higher modes contributes a negligible ~0.015 mm. Keratoconus is a condition where the cornea thickens and the CCT increases at a rate faster than the periphery. The mean RoC displacement deviation arising for decentration, astigmatism, and higher order irregularities are ~0.4 mm, ~0.35 mm, and ~0.08 mm respectively. Finally, for a grafted cornea, where a patient's diseased cornea has been removed and transplanted with a donor cornea, the mean RoC displacement deviation arising for decentration, astigmatism, and higher order irregularities, are ~0.3 mm, ~0.35 mm, and ~0.08 mm, respectively.

The RoC deviation data in FIG. 30 represents the expected geometric variation from an ideal sphere. It is instructive to view this variation in geometry with respect to the wavelength of the THz frequency illumination. For example, imaging systems operating at 650 GHz correspond to a free space wavelength of 0.462 mm (right vertical axis of FIG. 30). When normalized to wavelength, the corneal radius of curvature is ~8 mm/0.462 mm=17.32λ. To add bounds on the deviation, in accordance with multiple embodiments, one assumes that the variations described by the decentration, astigmatism, and higher order irregularities are uncorrelated and that total standard deviation can be computed as the square root of the sum of squares of each individual standard deviation. This assumption results in the following normalized geometry: Normal, healthy cornea=17.32λ±0.21λ, Keratoconus=17.32λ±1.16λ, and grafted cornea=17.32λ±1.01λ, corresponding to coefficients of variance (100*σ/μ) of 1.21%, 6.69% and 5.83%. Accordingly, with respect to the illumination wavelength, the corneal surface can be considered as in many embodiments, to first order, an ideal sphere with maximum expected deviations approximately one free space wavelength.

Spherical Surface Imaging

Spherical Surface Scanning Principle: Numerous embodiments are directed to active imaging of a spherical surface, which comprises positioning the CoC of the target coincident with the focal point of an OAP mirror and then transmitting a collimated illumination beam into the clear aperture of the mirror, parallel to the CA normal (FIGS. 31A & 31B). In such embodiments, the focused radiation is normal to the spherical surface and, in the limit of geometric optics, has a phase front curvature equal to the spherical surface RoC. The reflected, diverging beam is re-collimated by the OAP mirror and arrives coincident with the transmitted beam path. In such embodiments, moving the transverse location of the collimated beam while maintaining a path parallel to the mirror's clear normal sweeps the location of the illumination spot on the spherical surface, and thus a complete image can be constructed. The retrodirective nature of embodiments of such an arrangement is compatible with any transceiver design that can multiplex/demultiplex the input and output beams using, e.g., a wire grid, thin film, or polarizing beam splitter.

In several embodiments, imaging techniques accomplish spherical surface $(\theta,\varphi)$ imaging by the geometrical projection of the target's spherical surface into a planar coordinate system $(x,y)$. This is a restatement of the Fourier-Transform property of an optical focusing element as demonstrated with a 90° off-axis parabolic mirror (OAP) in FIGS. 31A and 31B. Unlike the Mercator projection, which transforms the surface from spherical coordinates via a cylindrical projection to rectilinear coordinates, embodiments of the current method perform mapping from spherical coordinates via projection by a paraboloid surface into a rectilinear coordinate system and represents a conformal mapping of a spherical surface to an orthogonal, rectilinear projection. This mapping operation is different from, but shares resemblance to the conic orthographic mapping projections in cartography, such as the Lambert Conformal Conic Projection (J. P. Snyder, USGS Numbered Series, 1532:101, 1982, the disclosure of which is incorporated herein by reference).

Figure 32:
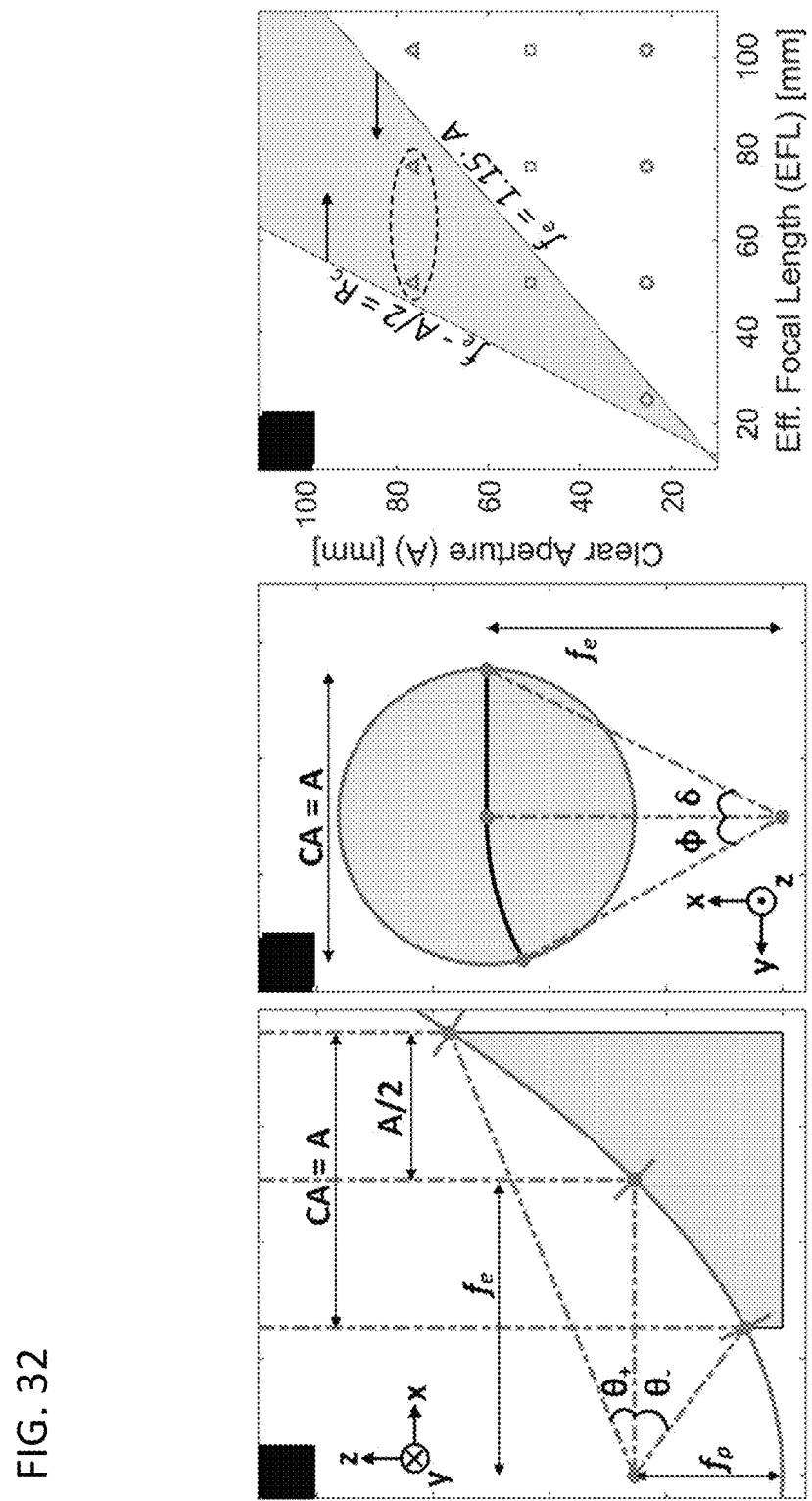
FIG. 32 provides a diagram of half of 90° OAP mirrors, where (left) is a side view, (middle) is a clear aperture view and (right) is design space bordered by offset $f_e$−A/2=$R_c$ and $f_e$=1.15A in accordance with various embodiments.

Effective Imaging Optic f/# and Offset: In embodiments, the maximum extent of target surface coverage is determined by the $f/\# = f_e/A = 2f_0/A$ of the mirror where $f_e$ is the effective focal length (EFL), $f_0$ is the parent focal length (PFL) and A is the clear aperture diameter (FIG. 32 (left panel)). A typical human cornea spans ~60° (±30°) about its apex, thus an imaging optic should approach $f_e/A$=2·tan(30°)~1.15 to span ±30° in both azimuthal and elevation from the corneal apex.

Table 3 lists the azimuthal and elevation angles subtended by a 90° off-axis parabolic reflector parameterized with commercially available f/#s. Note that because the focusing geometry (FIG. 32) is asymmetric, the azimuthal coverage angle $(\theta_-+\theta_+$ (FIG. 32 (left panel)) is not bisected by the 90° ray (i.e., $\theta_->\theta_+$, $\forall f_e$, A). The 90° geometry results in the relation $\theta_+<\delta<\varphi<\theta_-$ therefore the angle $\theta_+$ angle forms the lower bound on the OAP f/#. The results in Table 3 indicate that the angles subtended by an f/0.66 are sufficient to cover the entire angular extent of the cornea.

TABLE 3

| Spherical coverage angle (deg.) by imaging reflector f/# | | | | |
|---|---|---|---|---|
| f/# ($f_e$/A) | 0.66 | 1 | 2 | 3 |
| $\theta_-$ | 62.8 | 36.9 | 16.3 | 10.4 |
| $\theta_+$ | 30.7 | 22.6 | 12.7 | 8.8 |
| $\varphi$ | 44.5 | 29.0 | 14.4 | 9.6 |
| $\delta$ | 37.2 | 26.6 | 14.0 | 9.5 | f/# is scale invariant and does not consider the size of the target relative to the size of the focusing objective. Practical considerations suggest that the combination of focal length and clear aperture should avoid positioning the apex of the cornea inside the mirror. In other words, the "flange distance" should be greater than the corneal radius of curvature: $f_e-A/2>Rc$. The flange distance and f/# are displayed in FIG. 32 (right panel), where all combinations to the right of the $f_e-A/2=Rc$ line yield sufficiently large flange offsets and all combinations to the left of the $f_e=1.15A$ yield f/#s greater than 1.15. Markers representing standard, commercially available pairs of effective focal lengths and apertures are superimposed on this space with the 76.2 mm diameter mirrors indicated by the dotted contour. Examples described within utilized a 76.2 mm diameter f/0.66 OAP, but other measurements can be used, in accordance with various embodiments of the invention.

Quasioptical Analysis

Figure 31A:
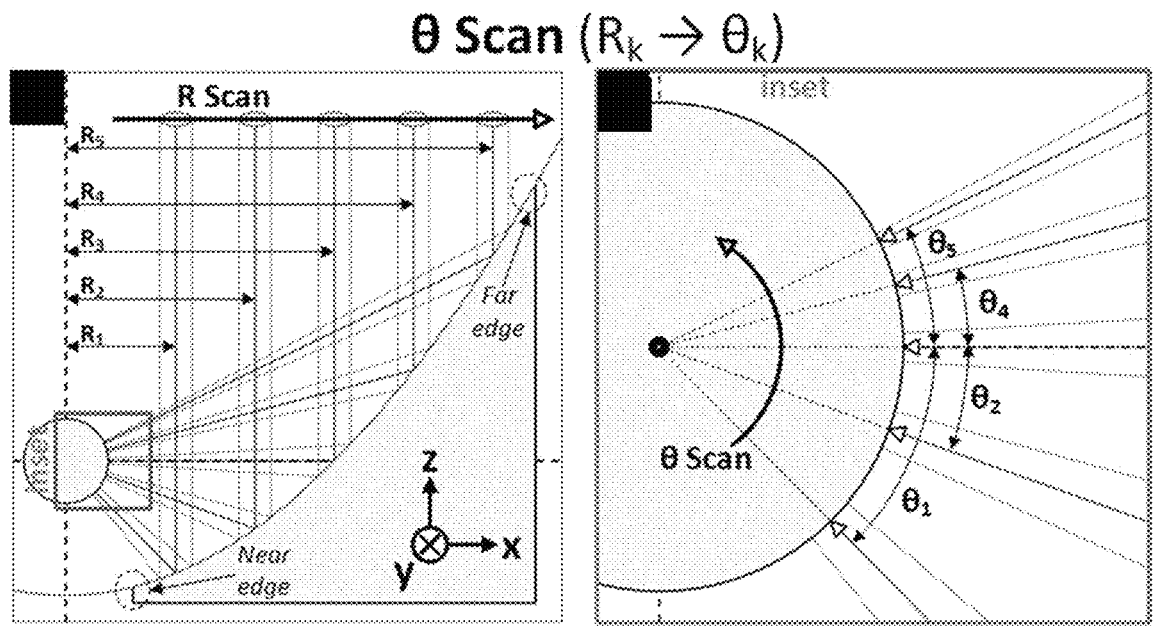
FIG. 31 provides a diagram of mapping transverse translation in the mirror CA plane to angular translation on the corneal surface, where (top) transverse scan locations $R_1R_S$ are mapped to angular scan location $\theta_1$-$\theta_S$ and (bottom) transverse scan locations $d_1$-$d_5$ are mapped to angular scan locations $\phi_1$-$\phi_5$, in accordance with various embodiments.
Figure 31B:
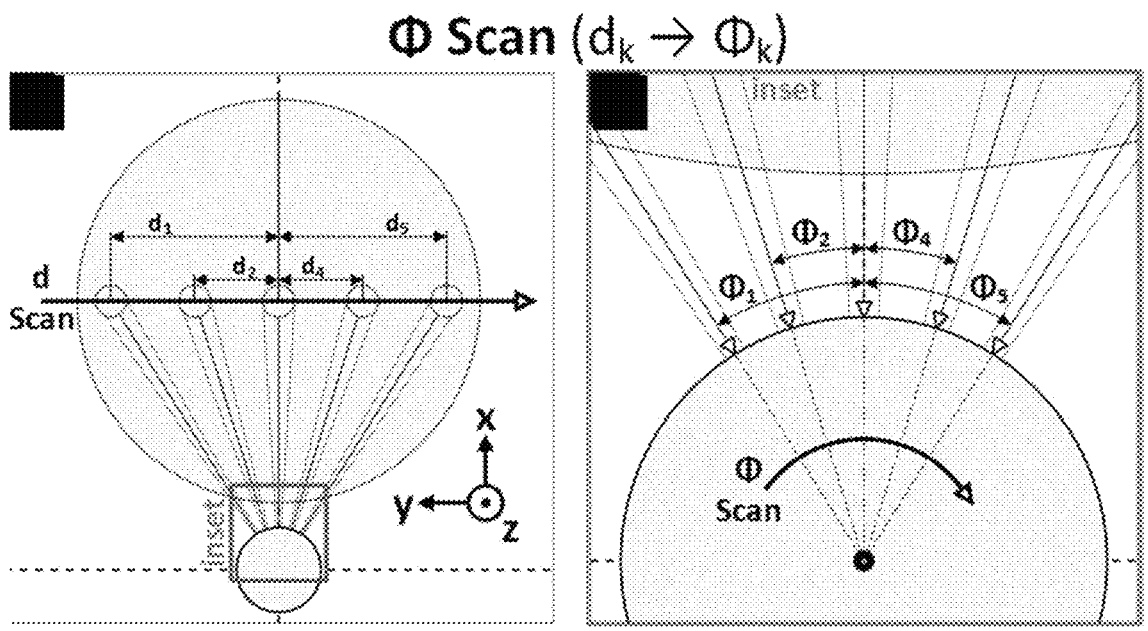

A straightforward exemplary method to implement the beam scanning described in FIGS. 31A & 31B utilizes a set of plane mirrors that scans the collimated input beam in two orthogonal directions parallel to the clear aperture plane of the OAP mirror. This concept is displayed in FIG. 33 where the input and output beams are multiplexed/demultiplexed by a beam splitter that optically collocates the THz emitter and detector. In accordance with various embodiments, imaging system designs are organized into three subsystems that are independent of each other, and are separately optimized for desired imaging operation performance: 1) transceiver subsystem, 2) scanning subsystem, and 3) imaging mirror.

Figure 33:
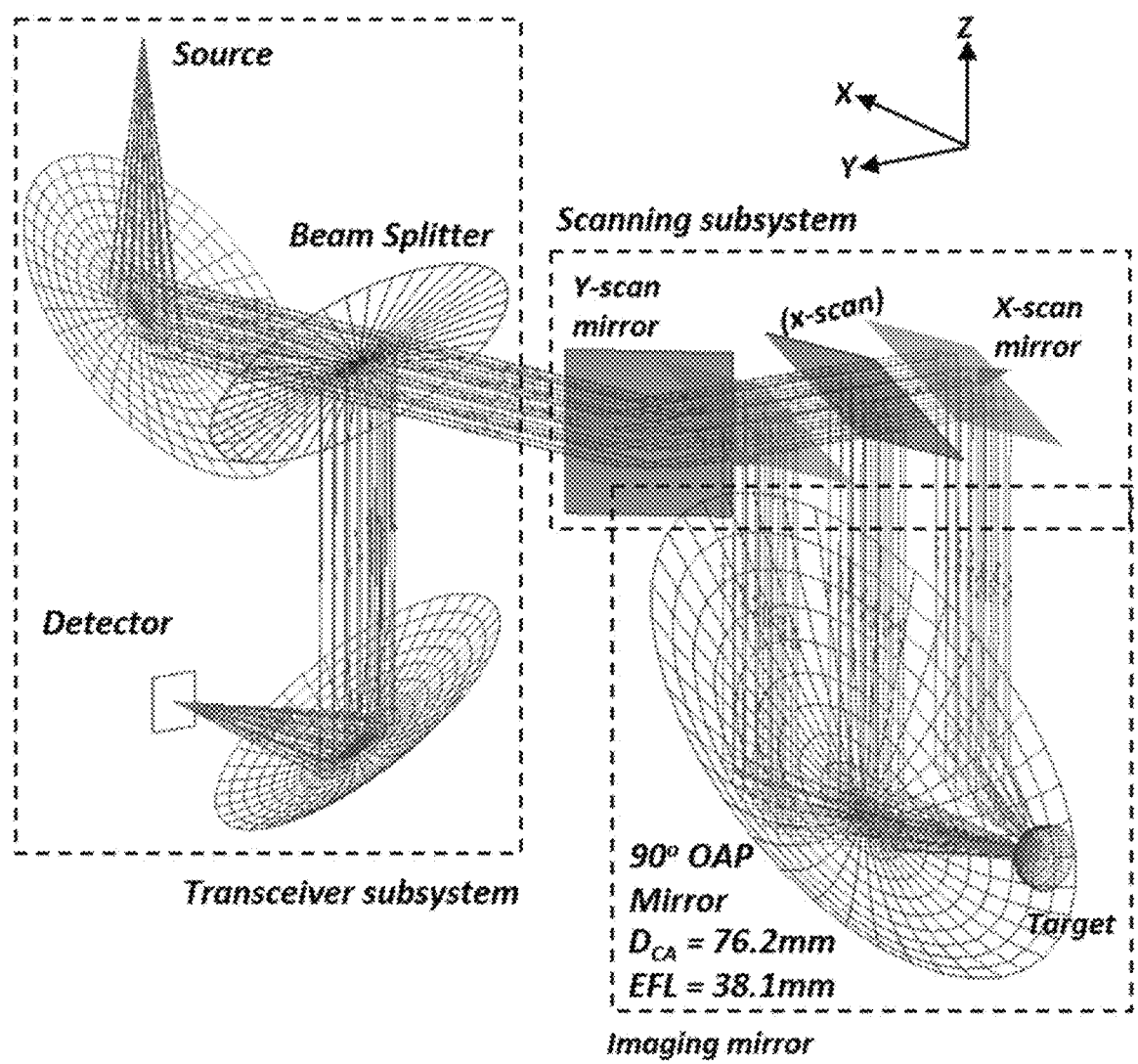
FIG. 33 provides a diagram of a single mirror, rectilinear scanning system design in accordance with various embodiments.

In several embodiments, the plane mirrors labeled "x-scan" and "y-scan" are mutually orthogonal, and linear translation of these optics enables transverse positioning of the collimated beam anywhere within the OAP CA. Since the OAP mirror is radially symmetric, several embodiments of the scanning methodology described in FIG. 33 are valid for any plane orthogonal to the x-y-plane and coincident with the OAP focal point.

As discussed previously, in embodiments the cornea CoC is positioned coincident with the OAP mirror's focal point and all rays of the focused beam are locally orthogonal to the spherical surface. Thus, in the limit of geometric optics, all reflected beams, independent of scan mirror position will arrive at the detector feedhorn with identical beam convergence angle and beam transverse location and extent. This concept is implemented in various embodiments of the invention and demonstrated with the three-superimposed beam paths in FIG. 33. In such embodiments, the y-scan mirror may be held stationary and a parallel bundle of rays were traced (ASAP, Breault Inc.) for three separated x-scan mirror locations oriented symmetric about the OAP CA centroid. The results of this ray tracing demonstrate that three separate illuminated areas on the corneal target all result in identical, received beam properties/profiles at the detector.

Quasioptical Setup and Modeling: In accordance with several embodiments, it is observed that the imaging mirror is over-dimensioned with respect to the cross section of the beam. At any scan location, the beam effectively sees only the local surface of the imaging OAP mirror. Therefore, the transformation of the THz beam as a function of scan location can be approximated to be transformation by a local segment of the imaging mirror surface. Given a reasonable input collimated beam size, such segment spans moderate changes in curvature and focal distance. Accordingly, many embodiments are directed to the mirror surface segment to be approximated as a thin lens whose focal length is equal to the central beam path length from the mirror surface to the focus.

These approximations allow for the use of quasioptical analysis with Gaussian optics and ABCD matrices to compute the resulting beam transformation relation as a function of scan location, thus the image transfer function by the imaging OAP mirror, in accordance with several embodiments of the invention. An embodiment of the analysis setup is displayed in FIG. 34 (top-left panel), where the shaded circle represents the cross section of cornea with an 8 mm radius of curvature and the mirror is a 76.2 mm clear aperture, 25.4 mm PFL, 90° OAP mirror.

Figure 34:
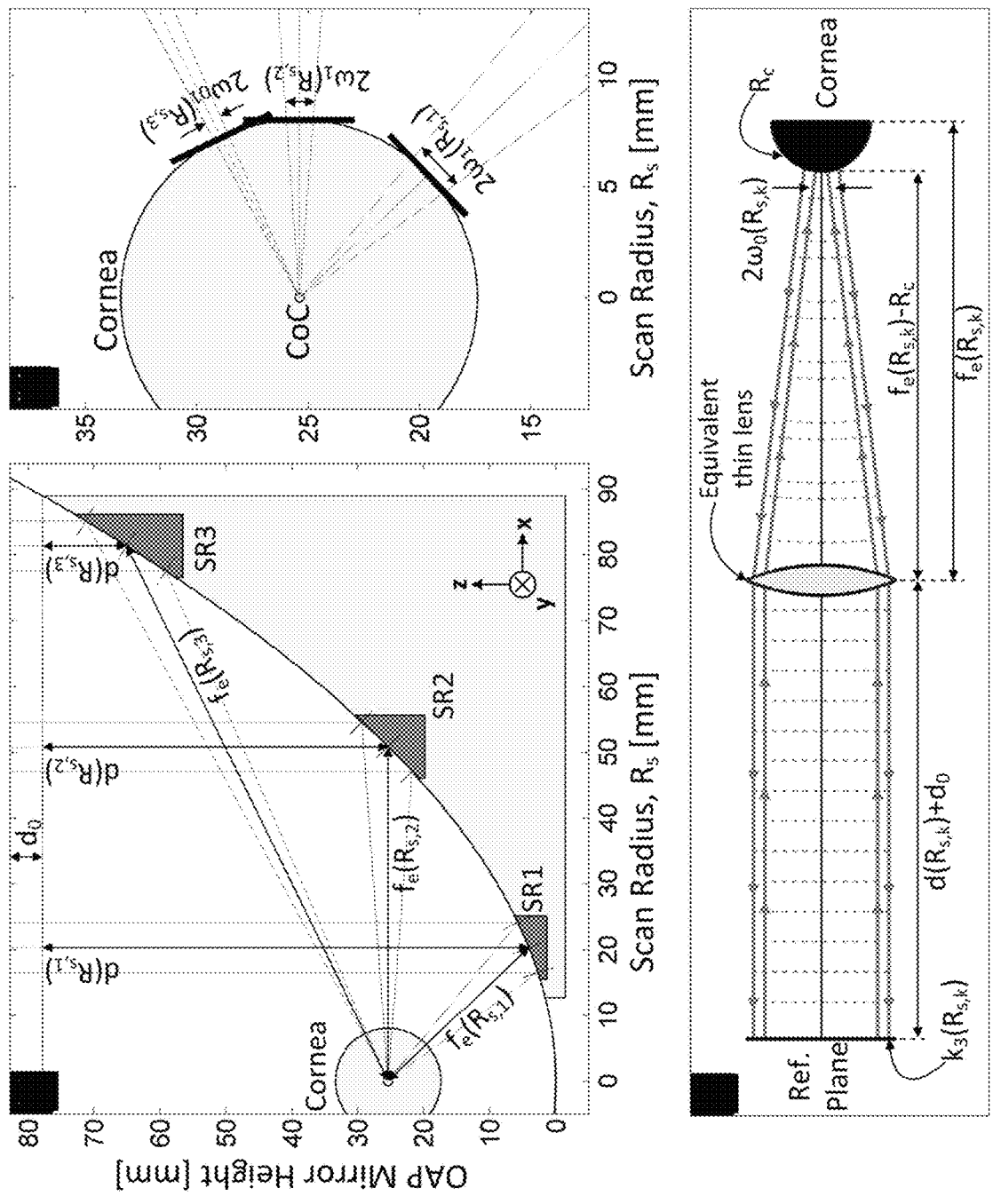
FIG. 34 provides a ray path diagram of the beam scanning showing (top-left) respective parabolic mirror segmentation location, (top-right) definition of spot size on the surface of the cornea, and (bottom) thin lens equivalent of the overall beam path, in accordance with various embodiments.

As shown in FIG. 34, three parallel ray bundles are parallel to the clear aperture and aligned with the center and 85% fill widths of the OAP. As mentioned above, if the incident beam is much smaller in diameter than the CA, the sub-reflector area defined by the beam transverse extent can be considered its own OAP mirror. In accordance with numerous embodiments, a Gaussian beam can then be traced using: 1) distance of free space travel between a reference plane and the mirror surface height defined by the intersection of the profile and collimated beam centroid, and 2) the effective focal length of the sub reflector defined by the line segment between the collimated beam centroid and parabolic intersection and the effective focal point of the entire OAP. In the limit of the paraxial approximation, this concept yields a collimated path length, focused path length, and effective focal length that are all dependent on distance between the mirror focal point and collimated beam centroid. The problem may then be recast to that described by FIG. 34 (bottom panel). The collimated beam travels a distance $d(R_s)$, is focused by a thin lens of $f_e(R_s)$ and then travels $f_e(R_s)-R_c$ to a convex reflector of radius $R_c$ (cornea). The mirror and cornea geometry ensures normal incidence for all Rs within the clear aperture of the mirror, resulting in the beam retracing its path back through the mirror collinear with the incidence path.

$$f_e(R_s) = (4f_p)^{-1} R_s^2 + f_p = f_e \quad \text{EQ. 28}$$

$$d(R_s) = (4f_p)^{-1}\left[\left(2f_p + \frac{A}{2}\right)^2 - R_s^2\right] = d \quad \text{EQ. 29}$$

Expressions for the radially dependent focal length and beam clear aperture path length are defined in EQ. 28 and EQ. 29. Note that these expressions are defined for the domain $R_m \in 2f_0 \pm A/2$, and are explicitly for a 90° OAP, $R_s$ is the horizontal distance from the mirror focal point to the centroid of the collimated input beam and $f_p$ is the parent focal length of the mirror.

$$M_{P \to C}(R_m) = \begin{bmatrix} 1 & f_e - R_C \\ 0 & 1 \end{bmatrix} \begin{bmatrix} 1 & 0 \\ f_e^{-1} & 1 \end{bmatrix} \begin{bmatrix} 1 & d + d_0 \\ 0 & 1 \end{bmatrix} \quad \text{EQ. 30}$$

$$M_{C \to P}(R_m) = \begin{bmatrix} 1 & d + d_0 \\ 0 & 1 \end{bmatrix} \begin{bmatrix} 1 & 0 \\ f_e^{-1} & 1 \end{bmatrix} \begin{bmatrix} 1 & f_e - R_C \\ 0 & 1 \end{bmatrix} \quad \text{EQ. 31}$$

$$M_C = \begin{bmatrix} 1 & 0 \\ 2/R_C & 1 \end{bmatrix} \quad \text{EQ. 32}$$

$$M_1 = M_{P \to C} \quad \text{EQ. 33}$$

$$M_2 = M_C M_{P \to C} = M_C M_1 \quad \text{EQ. 34}$$

$$M_3 = M_{C \to P} M_C M_{P \to C} = M_{C \to P} M_2 \quad \text{EQ. 35}$$

To summarize the problem description, in accordance with many various embodiments, a reference plane is defined at a distance do from the upper tip of the OAP. This reference plane is where the collimated beam (plane coincident with the beam waist) was launched and where the 2D coupling coefficient was computed. $M_1 = M_{P\text{-}C}$ (EQ. 30, EQ. 33) is the transfer matrix describing the propagation of the beam from the reference plane (P) to the cornea (C). The beam traverses a path length $d+d_0$, is focused by a thin lens of the $f_e$, and propagates a distance $f_e - R_c$ to the surface of the spherical reflector (cornea). $M_2 = M_C M_{P\text{-}C}$ (EQ. 32, EQ. 34) describes the propagation of the beam through $M_1$ and the subsequent reflection from the spherical reflector. The overall retrodirective transmission through the optical system is described by $M_3 = M_{C\text{-}P} M_C M_{P\text{-}C}$ (EQ. 32, EQ. 35), where the beam starts and stops at the reference plane.

$$\frac{1}{q_k} = \frac{1}{R_k} - j\frac{\lambda_0}{\pi n \omega_k} \to \frac{1}{q_0} = -j\frac{\lambda_0}{\pi n \omega_0} \quad \text{EQ. 36}$$

$$M_k = \begin{bmatrix} A_k & B_k \\ C_k & D_k \end{bmatrix} \quad \text{EQ. 37}$$

$$q_k = \frac{A_k q_0 + B_k}{C_k q_0 + D_k} \quad \text{EQ. 38}$$

In accordance with multiple embodiments, the standard complex beam parameter relations listed in equations EQ. 36-EQ. 38 may be used to compute the spot size on target ($M_1$), the beam radius of curvature immediately prior to ($M_1$) and following ($M_2$) reflection from the cornea, and the coupling coefficient between the input and output beams at the reference plane ($M_3$). These factors were calculated for all relevant $R_s$ with an input complex beam parameters q0 parameterized by $\omega_0$ and a constant $R_0 \to \infty$.

Results—Spot Size on Cornea Surface: The spot size on the target was assessed as a function of input beam waist size at the reference plane and radial distance from the effective focal point of the OAP mirror using equations EQ. 33 and EQ. 36-EQ. 38. ARCD matrix formulism and the complex beam parameter describe the properties of a beam at a defined distance along the optical axis, on a plane that is transverse to the optical axis at this defined distance. When applied to the analysis of the cornea, this results in the characterization of the spot size on a plane tangent to the corneal surface and normal to the beam centroid as depicted in FIG. 34 (top-right panel). Due the relatively small extent of the focused beam with respect to the corneal RoC, the spot size computed on a plane is considered an accurate estimate of the spot size computed by projecting the beam on to the corneal surface and assessing the extent of the intersection contour.

$$\omega_1 = \frac{\lambda}{\pi}\left[\mathbb{R}\left\{\frac{j}{q_1}\right\}\right]^{-1} \quad \text{EQ. 39}$$

In several embodiments, the input Gaussian beam radius (wo) at the reference plane was varied from 4 mm to 12 mm and the resulting output spot radius as a function of input radius and mirror position (Rm) are superimposed on the shaded outline profile of a 76.2 mm CA, 25.4 mm PFL, 90° OAP mirror length for reference. Note the dotted line style at the extreme ends of each curve. These represent a practical CA limitation imposed by beam clipping. The extreme points on each size of the curve represent the edge of the mirror CA. The second set of points located closer to the mirror CA axis represent one input beam radius from the edge of the mirror. In practice, the focusing performance described by the solid curves bordered by the interior points is feasible and diffractive effects must be considered for beam centroid locations outside the solid line intervals.

The 4 mm input spot size demonstrates a decreasing focused spot size for decreasing $R_s \rightarrow f_e(R_s)$. In this case the effective f/#, which is a combination of the focal length of the sub-reflector, the beam input diameter, and the center wavelength, results in a beam waist that occurs "outside" of the cornea for large $R_s$, and the beam is diverging prior to being incident on the corneal surface. As the effective f/# is decreased (decreasing $R_s$) and the focused path length decreases (decreasing $R_s$), the beam waist decreases and its location converges to the surface of the cornea. Further decreases in $R_s$ result in the beam waist locating to "inside" the cornea paired with an increasing convergence angle. While the focused waist continues to decrease in size, the corneal surface intercepts the beam at a distance that is increasing from the location of the waist. This leads to an increase in detected spot size. This interplay between spot size, waist location, and convergence angle produces a tradespace for a given spot size where the minimum beam diameter utilizes a beam centroid location that lies at $R_s \sim 37$ mm.

Accordingly, in many embodiments, this behavior is somewhat reversed for the 12 mm input radius. The focused spot reaches its maximum at the shortest effective focal length and its minimum with an $R_m$ that is nearly at the extreme edge of the OAP. Unlike the 4 mm radius beam, the 12 mm radius beam produces a waist that is "inside" the cornea for all $R_s$, and the offset between the sub-reflector focal point and waist location is small with respect to $R_c$ for nearly all $R_s$. Since the input beam is large, the effective beam f/# is small and leads to large convergence angles and thus large spot sizes on the corneal surface. The optimum tradeoff between competing factors occurs at $R_b \sim 82$ mm.

The intermediate input spot sizes demonstrate varying dependencies on the aforementioned factors, and it is clear by inspection that there exists some intermediary that balances the following three competing factors:

Decreasing Rs decreases the effective focal length of the sub-reflector and, thus, decreases the size of the focused beam waist (geometric).

Decreasing Rs increases the convergence angle of the beam and can increase the beam spot size on the corneal surface depending on beam input parameters (geometric).

Decreasing the input beam waist decreases the convergence angle while increasing the offset between sub-reflector focal point (corneal center of curvature) and focused beam waist. This can result in an increase or decrease in the spot size on the corneal surface depending on the f/# of the OAP, the input diameter of the beam, and the wavelength (quasioptics).

Figure 35:
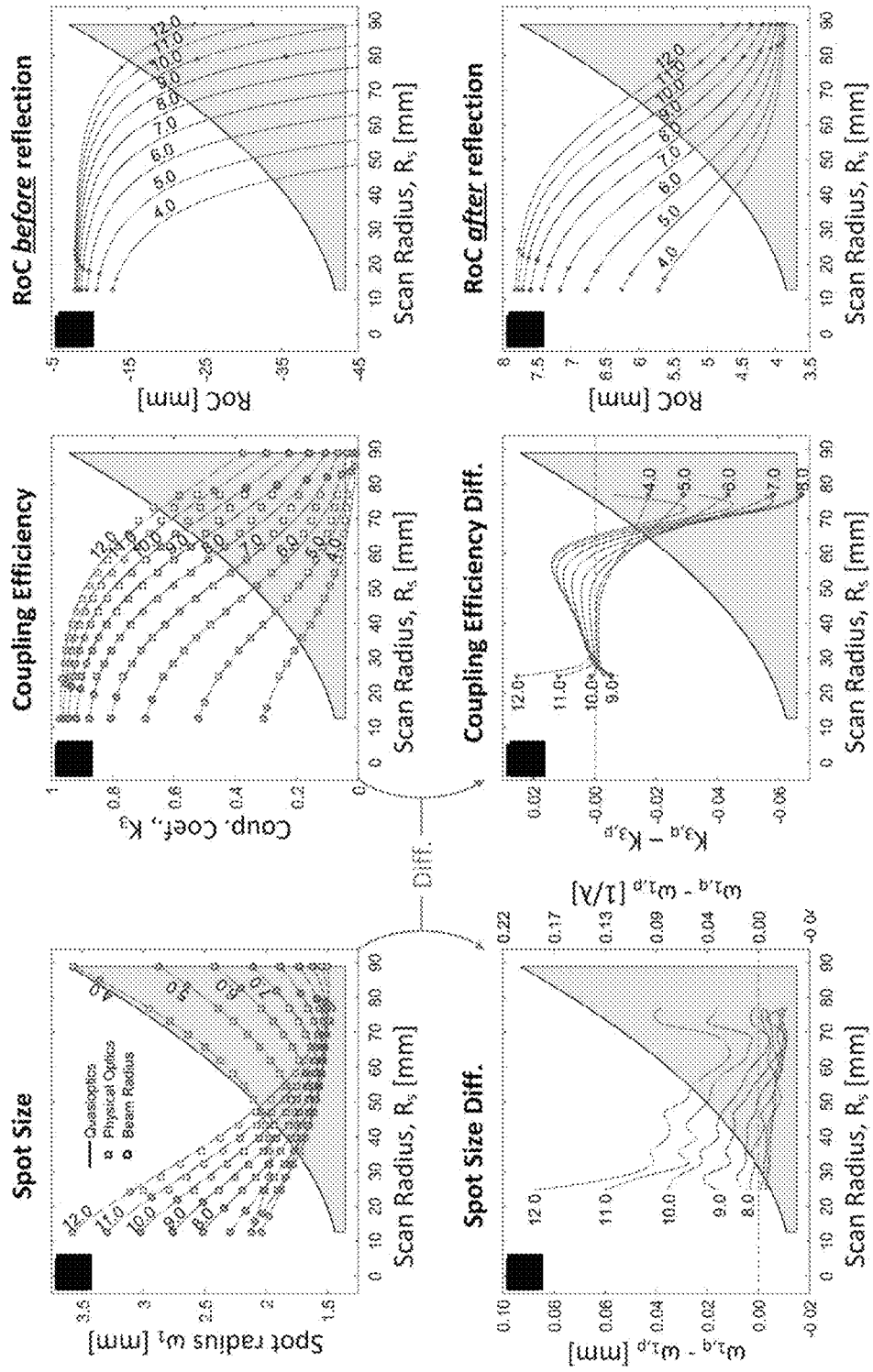
FIG. 35 provides a selection of data graphs relating scan radius to (left) spot size, (middle) coupling efficiency, and (right) RoC before and after reflection, in accordance with various embodiments.

The results in FIG. 35 demonstrate an interesting tradeoff between input and output spot size and mirror clear aperture location ($R_s$) which arises from the fact that the focused beam parameters are characterized at a distance $R_c > 0$ from the geometric focal point of the considered sub-reflector.

Coupling efficiency: The source mirror and detector mirror, encircled with the dotted lines in FIG. 33 were designed with identical CA and PFL and were oriented with respect to the beam splitter to maintain a "tip-to-tip" configuration (J. A. Murphy, International Journal of Infrared and Millimeter Waves, 8:1165-87, 1987; M. Malone, et al., 2006, pp. 62880Z-62880Z-9; the disclosures of which are incorporated herein by reference). In many embodiments, ideal operation is defined by the beam maintaining a high level of collimation in all paths between the OAP mirrors. Given the symmetry of the optical layout, the coupling efficiency between the source and detector can be accurately assessed as the similarity of the input and reflected output beams at the reference plane. To the coupling efficiency between input beam ($q_0$) and output beam ($q_3$) is given in EQ. 41:

$$q_3 = \frac{A_3 q_0 + B_3}{C_3 q_0 + D_3} \quad \text{EQ. 40}$$

$$K_3(q_0, q_3) = \frac{4}{\left(\frac{\omega_0}{\omega_3} + \frac{\omega_3}{\omega_0}\right)^2 + \left(\frac{\pi \omega_0 \omega_3}{\lambda}\right)^2 \left(\frac{1}{R_3} - \frac{1}{R_0}\right)^2} \quad \text{EQ. 41}$$

In several embodiments, the 2D beam coupling coefficient is defined in EQ 41 with the relationship between the input and output complex beam parameters ($q_{in}=q_0$, $q_{out}=q_3$) defined in EQ. 40. The coupling coefficient is calculated at the reference plane and is written explicitly in terms of the input and output spot sizes and radii of curvature, which together define their respective complex beam parameters. Note that EQ. 41 does not account for beam clipping and/or beam walk off due to finite aperture size and beam divergence.

The coupling coefficient as a function of mirror position and input beam diameter are displayed in FIG. 35 (top-middle panel), which confirms the expected relation between input and output beam matching. As the beam input radius increases and the sub-reflector effective focal length decreases (decreasing $R_m$) the RoC matching between the focused beam and cornea improves, resulting in a reduced perturbation of the illumination beam and increased matching at the reference plane. At 8 mm (nearest integer to the spot size optimized input beam of 7.6 mm) the coupling efficiency at the clipping threshold ranges from 0.17 to 0.87. The 12 mm beam ranges from 0.57-0.95 and the 4 mm beam ranges from 0.30-0.03. These results confirm a monotonically decreasing coupling efficiency for increasing input spot size independent of the input beam radius.

Results—Beam RoC and Coupling: As discussed in the previous sections, in the limit of geometric optics, the beam focused by any arbitrary sub-reflector creates a focus at the center of the corneal radius of curvature. Furthermore, and in accordance with multiple embodiments, the focused beam has a radius of curvature that is defined entirely by the distance between the corneal CoC and any plane of interest. As was observed in the spot size plot, this is not the case for Gaussian beams. Visualization of the beam RoC prior to reflection yields further insight to this behavior and inspection of the RoC following reflection gives an indication of overall beam coupling efficiency.

$$R_{1,2} = \left[\mathbb{R}\left\{\frac{1}{q_{1,2}}\right\}\right]^{-1} \qquad \text{EQ. 42}$$

The RoC for the pre and post corneal reflection are displayed in FIG. 34 (top-left panel) and (top middle) respectively. The pre-reflection RoC are consistent with what was observed with the spot size characterization in FIG. 35. The RoCs resulting from the smaller input spot sizes are asymptotic and rapidly diverge to negative infinity for larger mirror $R_s$. As the input spot size is increased the beam waist decreases and converges on the corneal CoC. This results in the effective phase center of the beam being located at the CoC and beam RoC converging towards the corneal RoC. The reflected beam RoC demonstrates significantly less variation than the pre-reflection RoC as a function of mirror radius $R_s$ and suggests that the post reflection RoC is the primary determinant of the coupling efficiency.

Observances: In accordance with several embodiments, the quasioptical design and analysis space for corneal imaging is unique because (1) the target is spherical, leading to increased divergence in reflection compared to the canonical flat target; (2) the target surface is NOT located at the focal point defined by the optics or beam calculations, leading to complex beam dynamics on target; and (3) in the limit of ray tracing, the beam is normally incident across the entire target surface, suggesting a minimal dependence on beam polarization.

The results indicate that for a fixed input beam radius, and optimal alignment, the signal from the lower region of the cornea will always be higher than the upper region of the cornea. These observations also suggest that the imaging field may be homogenized in terms of beam radius and coupling efficiency if the input beam radius is allowed to vary as a function of mirror position. In addition, methods in accordance with embodiments may be to remove thin lens approximation treatment of the mirror surface segment. In such embodiments, any propagated beam can be decomposed to include higher-order Hermite-Gaussian or Laguerre-Gaussian modes, and an augmented ray-transfer method can be applied to beam propagation, thereby accounting for the asymmetric geometry of the mirror segment.

Physical Optics Analysis

Spot size: Many embodiments leverage a physical optics code (GRASP, Ticra Inc., Copenhagen, Denmark) to evaluate the utility and accuracy of the quasioptical analysis. The electric field distribution of the focused beam was calculated in the E-plane, H-plane, and transverse plane at the intersection of the beam centroid and corneal surface using input beam parameters from FIG. 35. These planes are defined by the x', y', and z' axes in the FIG. 36 (top-left and top-right panels). Additionally, the input beam was TM polarized (E-field entirely in the x-z or x'-z' plane) to match various exemplary embodiments described in Exemplary Embodiment 5, below.

Figure 36:
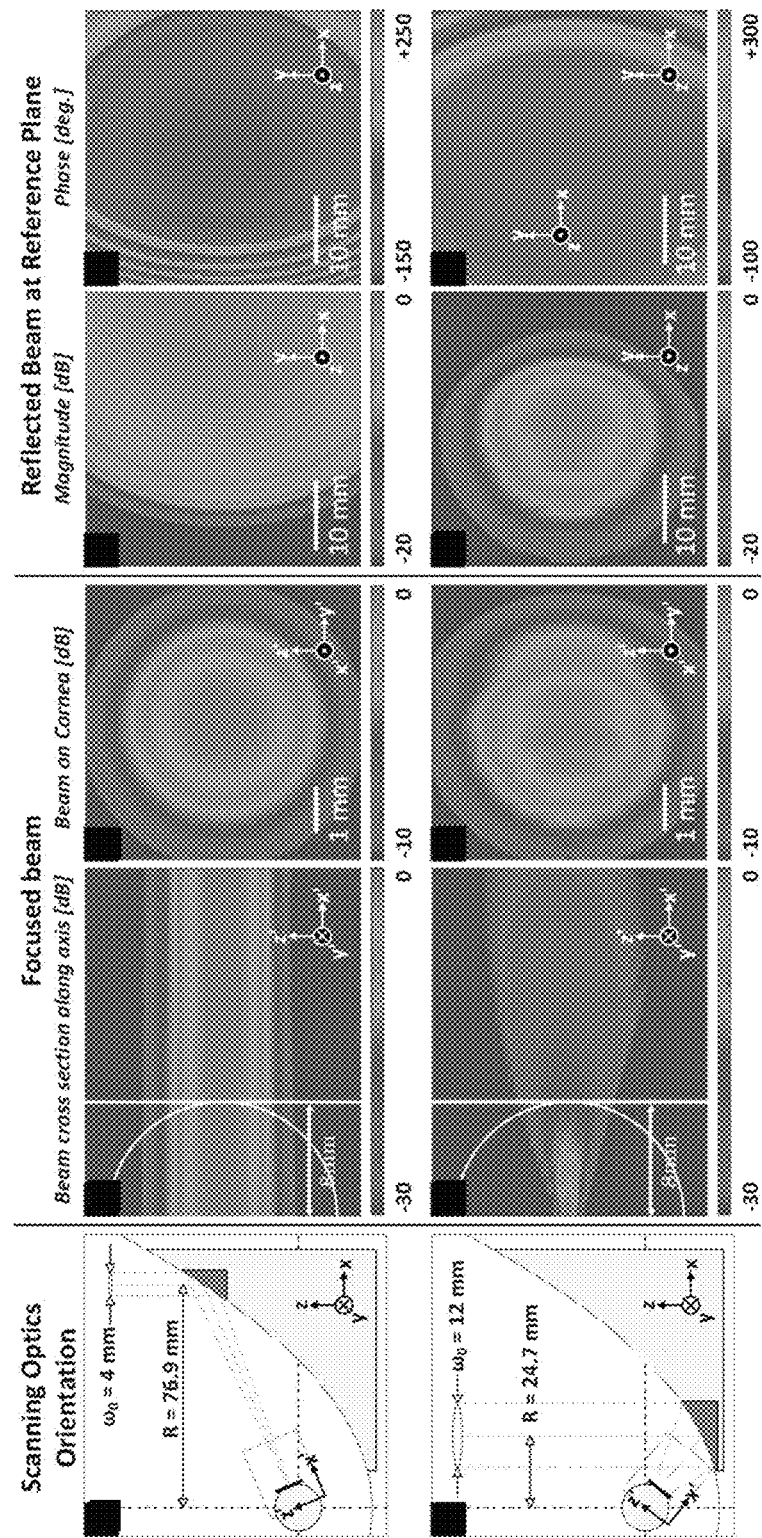
FIG. 36 provides a collection of (left) configuration diagrams and resultant images of the (middle) focused beam and (right) reflected beam at reference plane, in accordance with various embodiments.

An example of the focused beam for the input parameters $\omega_0$=4 mm, $R_s$=76.9 mm is displayed in FIG. 36 (top-row Focused beam panels) in dB scale with accompanying scale bars indicating FOV dimensions. The E-field distribution in the x'-z' plane confirms that the fields are nearly Gaussian. This was also observed on the target (y'-z') which demonstrates vanishingly small radially asymmetry (ellipticity ~1) and an apparent lack of cross polarization. The predicted short Rayleigh length at $\omega_0$=4 mm was also observed and inspection of FIG. 36 (Beam cross section along axis [dB], top panel) confirms the focused beam waist is located prior to the surface of the cornea. The nearly Gaussian field distribution was attributed to the negligible effect of reflector geometry, as the local curvature of the mirror surface was nearly symmetric about the beam centroid over the extent of the collimated beam.

A complementary example of a large input beam radius ($\omega_0$=12 mm) and short scan radius (Rs=24.7 mm) is also displayed in FIG. 36 (bottom-row Focused beam panels). The large collimated beam radius and increased mirror curvature result in the focused beam waist lying nearly coincident with the corneal CoC/OAP focal point which is visible in the x'-z' cut in FIG. 36 (Beam cross section along axis [dB], bottom panel). Increased diffraction and the effects of increased mirror asymmetry about the beam centroid are also apparent and manifest as multiple local extremum in the field distributions of FIG. 36 (bottom-row Focused beam panels) and significant radial asymmetry.

In accordance with a number of embodiments, the average spot size on target (x'-y' tangent plane) was computed numerically by obtaining the modulus of the E-field to suppress diffractive effects due to finite aperture size, finding the location of the peak amplitude, computing the lie closed contour of the modulus, and then computing the average radius of the 1/e contour. These results are superimposed with a square marker (□) in FIG. 35 (top-left panel) and demonstrate good agreement between quasioptical analysis and physical optics. The level of fit is further explored in FIG. 35 (top-middle panel) which reports the difference between quasioptical radius ($\omega_{1,q}$) and physical optics average radius ($\omega_{1,p}$): $\omega_{1,q}-\omega_{1,p}$. The spot size differential further substantiates the general correlation between decreasing spot size radius and improved goodness of fit. Additionally, the graph elucidates the increased effects of diffraction and offset reflector configuration for larger input diameters and smaller scan radii.

Coupling: In accordance with several embodiments, GRASP was also used to evaluate the coupling between the input beam and the reflected output beam at the reference plane. The magnitude of the reflected beam for the $\omega_0$=4 mm, R=76.9 mm pair demonstrates a significant increase in main lobe extent compared to the initial 4 mm. This corroborates with the results obtained with quasioptical analysis that indicate substantial beam divergence over the optical path, which manifests in a broad re-collimated beam radius (FIG. 36 (Beam on Cornea [dB]). Additionally, the multiple extremum in the unwrapped phase plot (FIG. 36 (Phase [deg.])) suggests that the reference plane is located approximately one Rayleigh length from the mirror surface furthering supporting significant beam divergence.

The converse is true for the $\omega_0$=12 mm, R=24.7 mm beam which demonstrates a transverse extent at the reference plane only slight larger than the initial beam. The phase plot is also more uniforms with extremum spaced farther apart. These plots indicate that the reference plane is likely well within one collimated beam Rayleigh length and strongly corroborate with the quasioptical analysis.

$$\overline{K_3} = \frac{\left|\int\int (\vec{E}_0 \cdot \vec{E}_3) dA\right|^2}{\int\int |\vec{E}_0|^2 dA \int\int |\vec{E}_3|^2 dA} \qquad \text{EQ. 43}$$

The coupling coefficient quantifying coupling between the input beam and reflected output beam was computed with EQ. 43, which references the square of the inner product of the vector fields with the product of the total energy in each field. The complex vector inner product accounts for mismatch between amplitude, phase, and polarization. The coupling coefficient computations were superimposed with a square marker (□) in FIG. 36 and again demonstrate good agreement between quasitopical methods and physical optics. The differential between the quasioptical coupling coefficient ($K_{3,p}$) and the physical optics coupling coefficient ($K_{3,q}$): $K_{3,p}$–$K_{3,q}$ is plotted in FIG. 36 (bottom-left panel) and reveals a maximum deviation of ~6.5% at $\omega_0$~8 mm, R~76.9 mm. The larger input spot radii are not monotonic across the scan range and this variation likely the result of edge diffraction.

Double Mirror (Angular) Scanning

Figure 37:
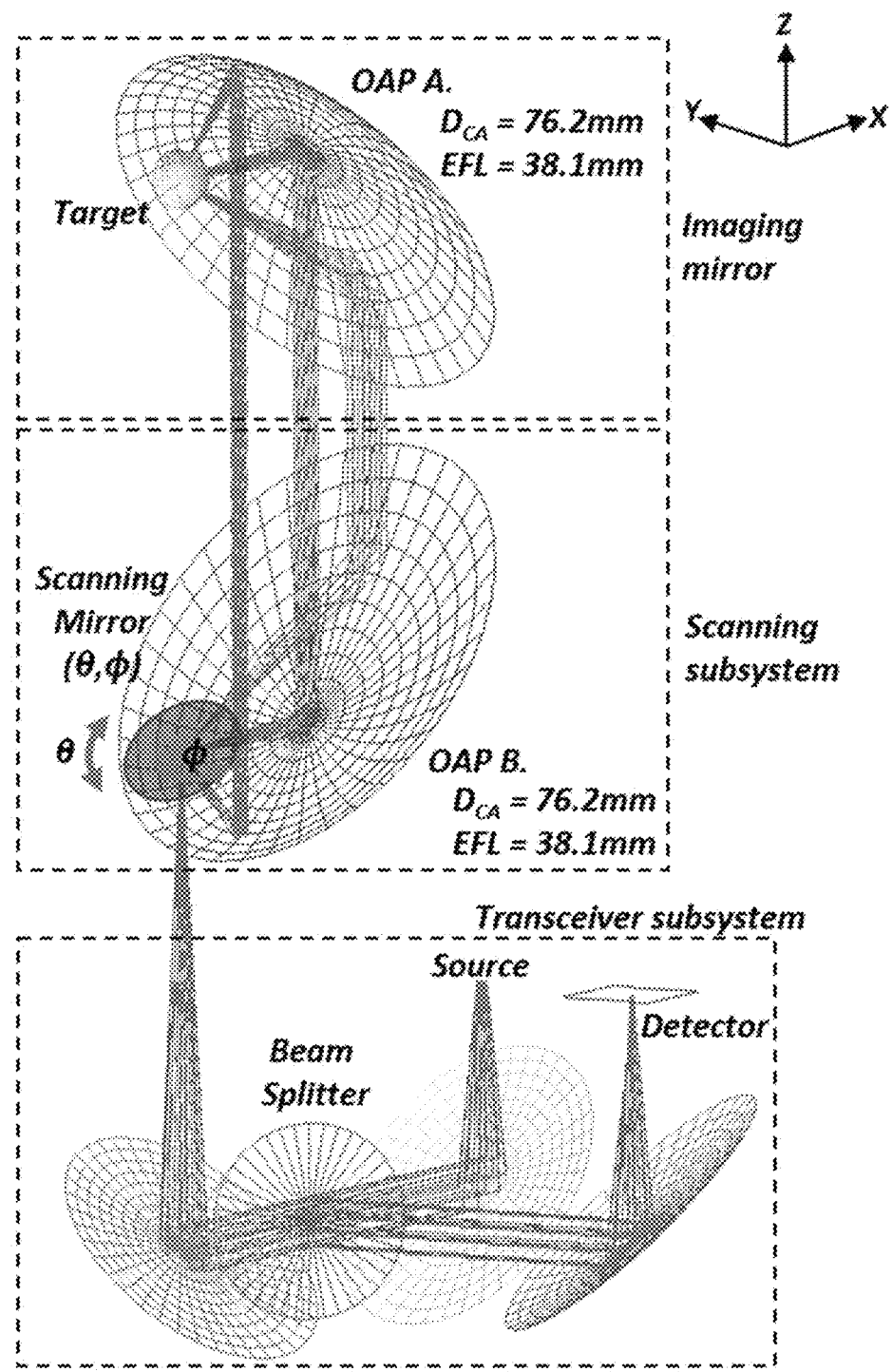
FIG. 37 provides a diagram of a double mirror, angular scanning image system design in accordance with various embodiments.

One potential weakness of the rectilinear scan design is the relatively large transverse displacement necessary to scan a comparatively small angular FOV on the cornea. This relationship creates a limitation on image acquisition rate that may hinder translational feasibility. A more efficient scanning mechanism in terms of the ratio of scanning optical translation vs beam location on target is displayed in FIG. 37, in accordance with embodiments.

Standard optical system design decouple the azimuthal and elevation scan directions to separate planar mirrors whose axes are mutually orthogonal. Due to the comparatively short Rayleigh lengths at the design wavelength, the angular scanning in accordance with embodiments was designed with a single gimbal-mirror-like optical translation where rotational motion is about the center point of the mirror surface, in accordance with many embodiments. This design allows for an overall shorter optical path compared to the rectilinear scanning design Transverse translation of a collimated beam results in the angular scanning of a focused beam at the target plane. In embodiments of this angular implementation, and in accordance with several embodiments, a second parabolic mirror, identical to the focusing objective, is added to the beam path in the symmetric "tip-to-tip" orientation. In such embodiments, the THz beam is focused onto the surface of the angular scanning mirror and then the diverging beam is directed to varying sub-segments of the added parabolic reflector. This angular scan results in the transverse translation of a collimated beam in the clear aperture plane of the focusing OAP.

There are many benefits to this orientation, including:
1) Angular scanning at moderate speeds can produce rapid transverse translation in the collimated beam path and the total image acquisition time can be greatly reduced; and
2) The collimated beam diameter is a function of scanning angle resulting in a partial optimization of beam parameters with respect to the spot size on target. Recall that in the rectilinear scanning (constant collimated beam diameter) case, larger beam diameters at the far edge of the OAP minimized the spot size while smaller beam diameters at the near edge of the OAP minimized the spot size. This behavior is intrinsic to the angular scanning design as evidence by the ray paths in FIG. 37 (left panel).

Quasioptical analysis setup: The quasioptical setup and problem definition are displayed in FIG. 38 left and right panels, respectively. The mirror front surface centroid is coincident with the focal point of t OAP 1 and the cornea CoC is coincident with the focal point of OAP 2. The beam angle theta is designed with respect to the z-axis (standard spherical coordinates). In this exemplary FIG. 38 (left panel), the beam is diverging from the scanning mirror at a divergence half angle of 5°. The beam centroids deflected towards sub-reflectors 1, 2 and 3 (SR1, SR2, and SR3) form angles of 125°, 90°, and 63°, respectively with the vertical axis. These beams result in collimated beam diameters (in the limit of geometric optics) of 5.54 mm, 8.89 mm, and 14.25 mm. In numerous embodiments, the equivalent quasioptical thin lens problem is displayed in FIG. 38 (left panel) and the representative ABCD matrices are given in equations EQ. 44-EQ. 49.

$$R_s = 2f_p\left[\tan\left(\frac{\pi}{2} - \theta\right) + \sec\left(\frac{\pi}{2} - \theta\right)\right] \qquad \text{EQ. 44}$$

$$M_{p \to C} = \begin{bmatrix} 2 - R_C f_e^{-1} & f_e - R_C \\ f_e^{-1} & 1 \end{bmatrix}\begin{bmatrix} 1 & 2d + d_0 \\ 0 & 1 \end{bmatrix}\begin{bmatrix} 1 & f_e \\ f_e^{-1} & 1 \end{bmatrix} \qquad \text{EQ. 45}$$

$$M_{C \to p} = \begin{bmatrix} 2 & f_e \\ f_e^{-1} & 1 \end{bmatrix}\begin{bmatrix} 1 & 2d + d_0 \\ 0 & 1 \end{bmatrix}\begin{bmatrix} 1 & f_e - R_C \\ f_e^{-1} & 2 - R_C f_e^{-1} \end{bmatrix} \qquad \text{EQ. 46}$$

$$M_1 = M_{p \to C} \qquad \text{EQ. 47}$$

$$M_2 = M_C M_{p \to C} = M_C M_1 \qquad \text{EQ. 48}$$

$$M_3 = M_{C \to p} M_C M_{p \to C} = M_{C \to p} M_2 \qquad \text{EQ. 49}$$

The notation and formulism in equations EQ. 44-EQ. 49 is the same as used in EQs. 30-EQ. 35 with the exception that some matrix multiplication has been carried out in the interest of space. The reference, angularly scanned plane located at the focal point of OAP1. The beam travels a free space path length of $f_e(R_s)$, is collimated by a thin lens of ($R_s$), travels a free space path length of $2d(R_s)+d_0$ where do is the tip-to-tip separation of the two OAPs, is focused by a thin lens of focal length $f_e(R_s)$, and then travels $f_e(R_s)-R_c$ to the corneal surface. This path is described in EQ. 45 and the reverse is described in EQ. 46. The complete path is $M_C$-$PM_C M_{P-C}$ where $M_C$ is defined in EQ. 32. The scan radius dependent focal length was computed with EQ. 28, and the angularly dependent scan radius is given in EQ. 44.

Figure 39:
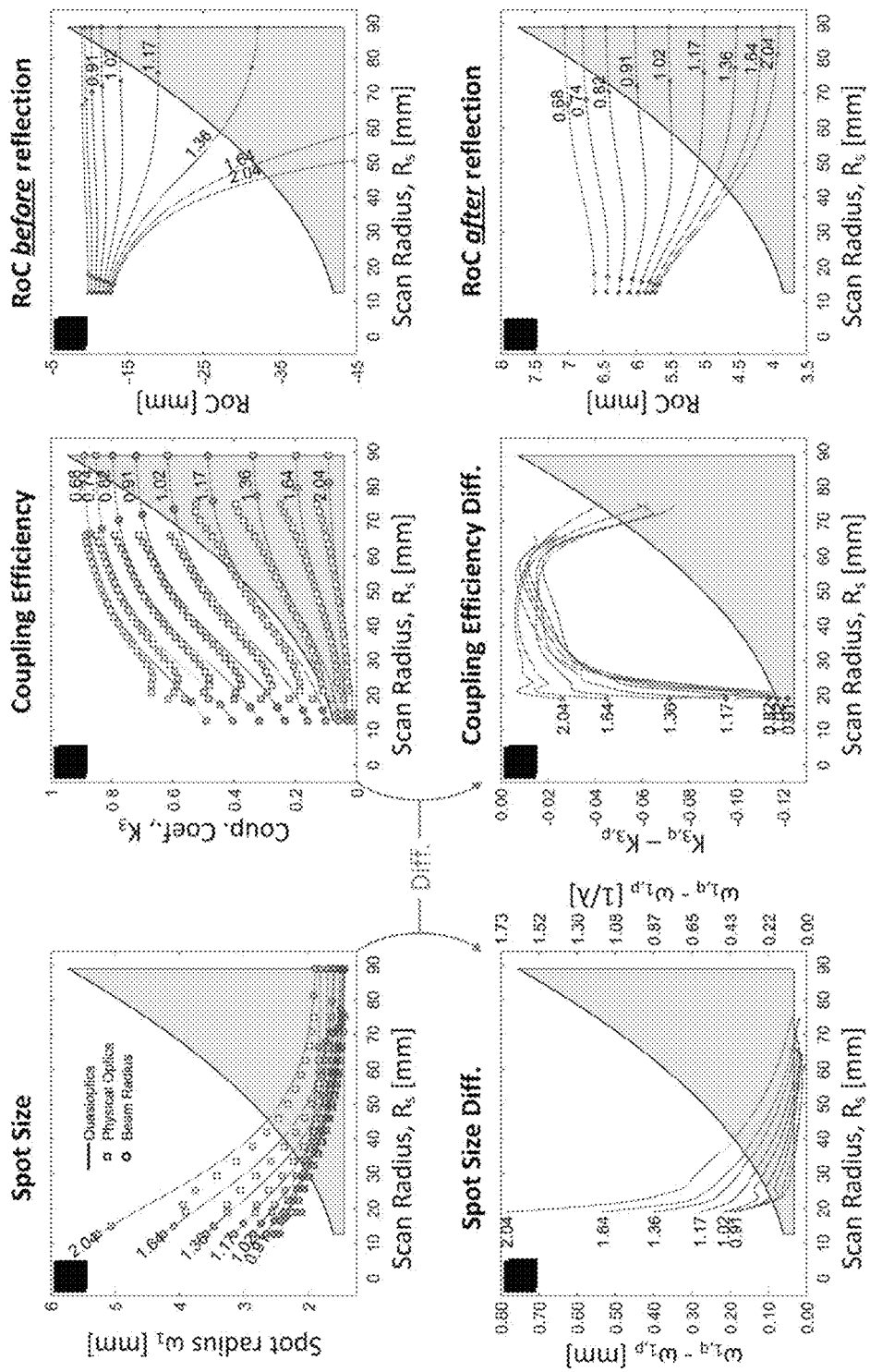
FIG. 39 provides a selection of data graphs relating scan radius to (left) spot size, (middle) coupling efficiency, and (right) RoC before and after reflection, in accordance with various embodiments.

Quasioptical Computation—Spot Size: The spot size computations as a function of radially dependent scanning position and spot size at the scanning mirror plane are shown in FIG. 39 (top-left panel), in accordance with many embodiments of the invention. The computed parameters are displayed as a function of collimated beam centroid location following collimation by OAP1 (EQ. 44). Additionally, the considered focused beam radii ($\omega_{02}$) were the collimated beam radii utilized in the rectilinear scanning simulations ($\omega_{01}$) focused by a 76.2 mm CA, 38.1 mm parent focal length mirror (EQ. 50).

$$\omega_{0,2} = \frac{2\lambda^2 \omega_{0,1} f_p (4f_p^2 + 1)^{1/2}}{4\lambda^2 f_p^2 + \omega_{0,1}^4 \pi^2}, \omega_{0,1} = 4 \ldots 12 \qquad \text{EQ. 50}$$

A key difference is the monotonic decreasing behavior the spot size as a function of mirror position of all considered scanned focused spot diameters. The interplay between Rayleigh length and beam effective f/#are apparent as evidenced by the varying crossover points between the larger and smaller spot size diameters however the effect is greatly reduced. Additionally, and in accordance with several embodiments, as the focused spot size becomes smaller, the overall slope of the spot size curve drops and the spot size on target becomes nearly uniform in its distribution.

Figure 38:
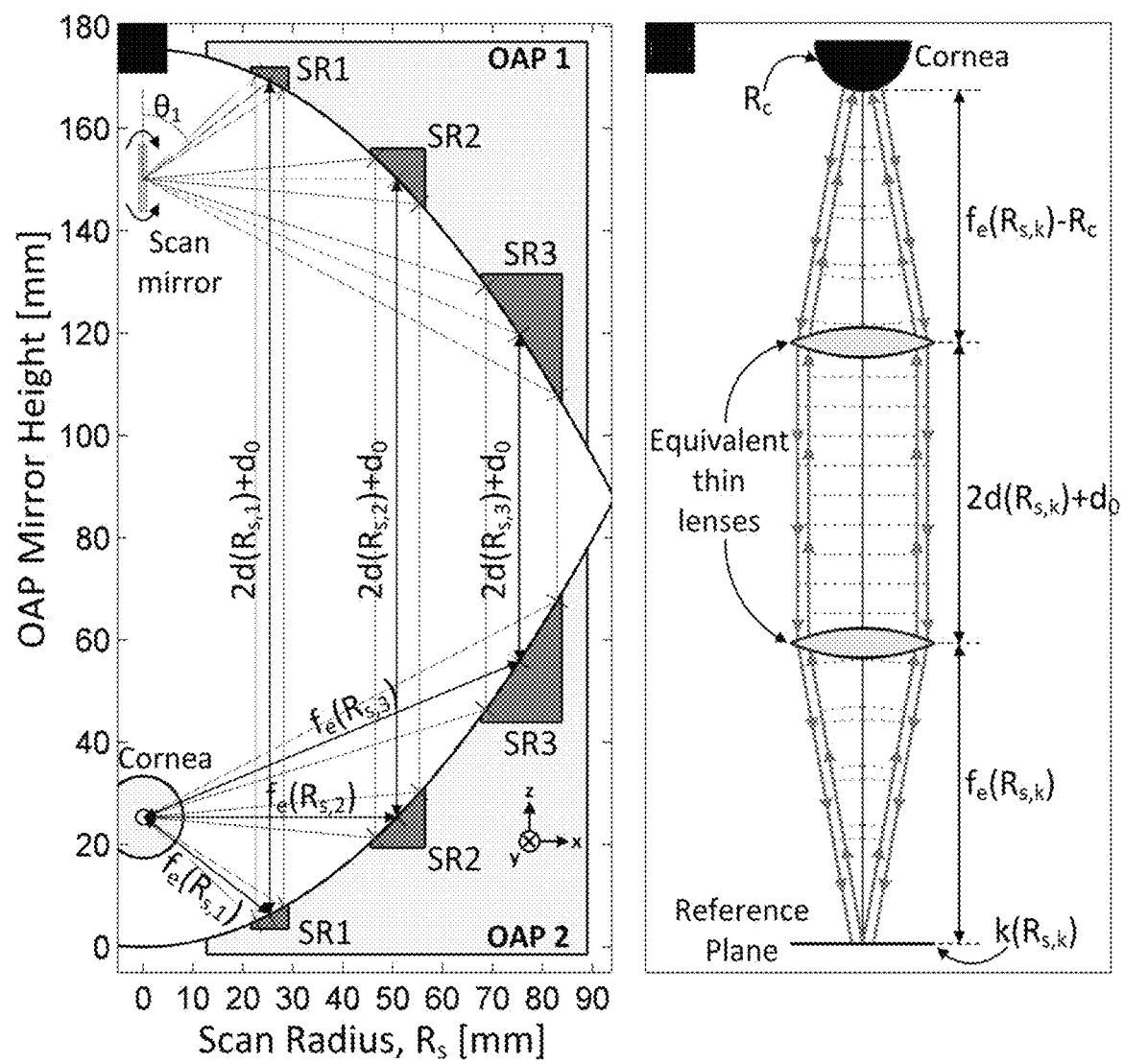
FIG. 38 provides a ray path diagram of the double mirror, angular scanning system where (left) is a parabolic mirror segmentation and (right) is thin lens equivalent of the overall beam path, in accordance with various embodiments.

Quasioptical Computation Coupling Coefficient: The beam coupling coefficients for the two-mirror scanning system were computed with EQ. 36 and EQ. 35 where the reference plane was defined as the scanning mirror plane (FIG. 38). The results (FIG. 38 (top-middle panel)) are all monotonically increasing as a function of mirror radius, which is in contrast to the rectilinear case where every curve is monotonically decreasing. This is due primarily to the collimated beam parameters of the mirror where larger R corresponds to increased collimated beam diameter and decreased collimated beam path length.

Of note is the decrease in peak and mirror radius integrated average coupling coefficient in the angular scanning system as compared to the rectilinear scanning case. In accordance with many embodiments, the angular scanning system produces a superior radius of curvature profile for nearly all the considered spot size diameters, which suggests that it should achieve superior coupling. This is likely due to the apparent sensitivity of the coupling coefficient to beam Rayleigh length. However, the denominator of EQ. 46 includes ratios of input and output spot sizes and input and output radii of curvature. These parameters did not change significantly in the collimated section of a beam path but can change rapidly over short distances in the converging/diverging parts of the beam path.

Quasioptical Computation—Radius of Curvature: The radii of curvature of the beam immediately prior and following reflection from the cornea are displayed in FIG. 39 bottom-middle and bottom-right panels, respectively. Two of the curves (2.04 mm and 1.64 mm) rapidly approach for increase R and confirm that the beam waist goes from inside the cornea to outside the cornea. However, the remaining curves reaming finite and negative for the entire mirror range indicating a beam waist inside the cornea. Additionally, as the beam gets smaller, the radius of curvature plot converges to a flat curve that is effectively invariant to mirror position. For example, 0.68 mm and 0.74 mm radius beams produce a radius of curvature, immediately prior to the cornea, of −10±0.3 mm and −11±0.3 mm respectively confirming that the variable beam diameter system produces geometric optics like performance at small input beam diameters (e.g. point source)

The output beam radius of curvature in FIG. 39 (bottom-middle panel) is consistent with what is expected from the radius matching in FIG. 35 (bottom-middle panel). The radii of curvature of the small input beam diameters are largely unperturbed. In contrast, the largest beam diameters with beam waists that traverse the corneal surface behave the same as those in the rectilinear scan system.

Physical Optics—Spot Size: Physical optics analysis was also applied to the 2-mirror scanning system and two specific configurations are demonstrated in FIG. 40: small input beam waist paired with a large scan radius (FIG. 40 (top-left panel)) and large input beam waist paired with a small scan radius (FIG. 40 (bottom-left panel)). These configurations resulted respectively in a large scan radius paired with a larger scan diameter and a small scan radius paired with smaller beam diameter. Both configurations are antipodal to those in FIG. 36.

Figure 40:
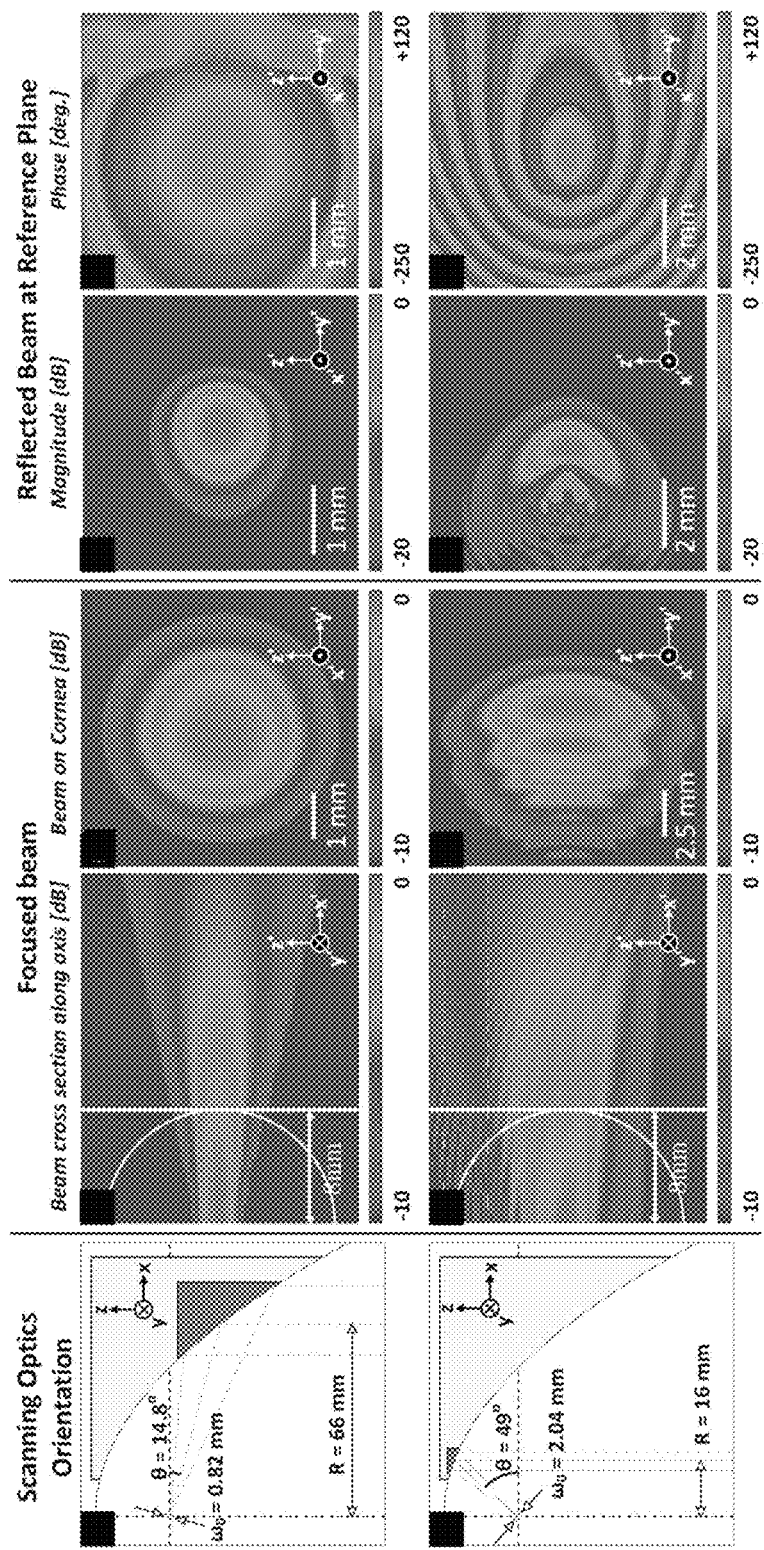
FIG. 40 provides a collection of (left) configuration diagrams and resultant images of the (middle) focused beam and (right) reflected beam at reference plane, in accordance with various embodiments.

The larger beam diameter and reduced reflector asymmetry about the beam centroid represented by the configuration in FIG. 40 (top-left panel) results in a focused beam with limited Gaussian mode content both in the x'-z' and y'-z' plane with good radial symmetry and a beam waist approximately coincident with the cornea CoC/OAP focal point. The configuration in FIG. 40 (bottom-left panel) resulted in substantial beam diffraction and significant beam asymmetry as a result of the short Rayleigh length of the collimated beam following reflection from the initial OAP.

The physical optics results are superimposed with a square marker (□) in FIG. 39 (top-left panel) and the differentials represented in FIG. 39 (top-right panel). One immediate difference from the rectilinear scanning system is the physical optics analysis predict a spot size smaller than that predicted by physical optics for any input pair. The analysis also indicates that the two analysis methods converge as the input beam radius decreases.

Physical Optics—Coupling Efficiency: The reflected beam magnitude and phase at the reference plane is displayed in FIG. 40 (Reflected Beam At Reference Plane panels). Quasioptical analysis predicts high coupling efficiency for the configuration in FIG. 40 (top-left panel) and this is confirmed with a high radial asymmetry in the magnitude and the relative uniformity of the phase across the majority of the beam. Similarly, the configuration in FIG. 40 (bottom-left panel) to result in poor coupling between input and output beams and this prediction is supported by the beam asymmetry, multiple beam extrema, and substantial field curvature indicated by the phase plot.

The physical optics results are superimposed with a square marker (□) in FIG. 39 (top-middle panel) and the differentials represented in FIG. 39 (bottom-left panel). Similar to the beam radius results, physical optics predicts a coupling efficiency that is higher than the quasioptical analysis for any input beam radius and angle. The comparison also exhibits peak agreement between quasioptics and physical optics in the center of the mirror and diverging predicted coupling at the edges of the mirror with the largest discrepancies occurring at the near edge. These beam paths feature the longest collimated beam path lengths in the system paired with the maximum mirror asymmetry about the beam centroid, generated in accordance with numerous embodiments of the invention. The magnitude of discrepancies between the two beam propagation techniques at these paths indicate the increased effects of beam asymmetry and diffraction on the performance of the angular scanning system as compared to the rectilinear scanning system.

Exemplary Embodiment 4: Scanning/Mapping Models

Exemplary Embodiment 3 introduced embodiments of a quasioptical theory that describes the expected spatial resolution and coupling efficiency of a single OAP mirror scanning mirror when a cornea (assumed to be an ideal sphere) is placed such that its center of curvature (CoC) is coincident with the OAP mirror focal point. The simulations revealed significant variation in optical performance across the OAP as a function of input diameter, which were corroborated with quasiphysical optics ray tracing codes. In this example, embodiments of optical system implementations are discussed that can achieve the scanning requirements presented in Exemplary Embodiment 3.

Quasioptical Alignment Sensitivity Analysis

Signal sensitivity as a function of target misalignment was explored for the rectilinear and angular scanning systems with non-sequential ray tracing (ASAP, Breault Inc.). In these exemplary embodiments, the systems were arranged as shown in FIG. 33 and FIG. 40, with the optical elements placed at the minimum allowable separation, thus reducing the free space path length for each optics train. A reference reflector with an 8 mm radius of curvature (RoC) was placed with its center of curvature (CoC) coincident with the focal point of the focusing/scanning mirror in each system. In many embodiments, the detector was modeled as a circular aperture measuring 2 mm on a side thus mimicking the zero bias Schottky diode package introduced in section XIV. In more embodiments, the source was modeled as a pencil beam with a 2 degree divergence angle corresponding to the 26 dB directivity output of a circular feedhorn. This exemplary combination of embodiments produced a ~10 mm collimated beam radius.

In both exemplary systems, the scanning mirrors were positioned such that the centroid of the focused beam was collinear with the optical axis of the reference reflector. Then the rays from the source were traced to the corneal surface, reflected, and traced back to the receiver. The total flux intercepted by the detector aperture in each system was quantified as the reference level of each perfectly aligned system. In many embodiments, the reference detector position was then displaced transversely in two dimensions in a plane defined by the surface normal to the mirror and corneal optical axes and coincident with the reference reflector apex. This concept is demonstrated pictorially in FIG. 41 (top panel), where the transverse plane is denoted by the axes X' and Y'. The plane was 1.2 mm×1.2 mm and discretized into a set of points with 0.2 mm center to center separation. At each transverse location, the source rays were retraced through the system and the total flux normalized by the reference flux to ascertain relative reductions in collected signal as a function of decentration.

Figure 41:
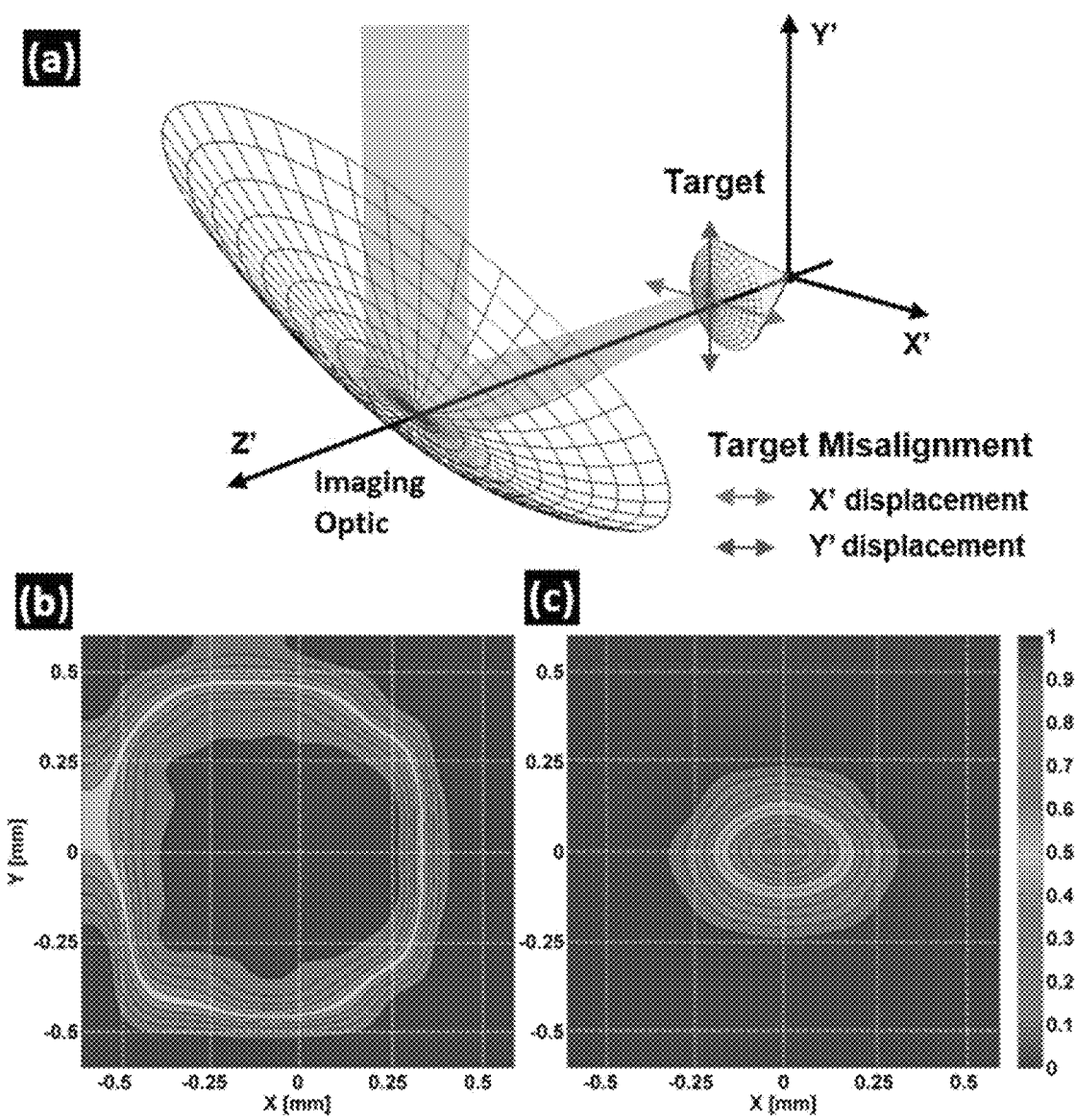
FIG. 41 provides target alignment sensitivity analysis, where (top) is a diagram of a cornea displaced from the ideal location in the transverse plane, (bottom-left) is collected signal for the rectilinear scanning system, as a function of corneal apex transverse location, and (bottom-right) is collected signal for the angular scanning system, as a function of corneal apex transverse location, in accordance with various embodiments.

The results of the simulation for the rectilinear scanning and double angular scanning systems are shown in FIG. 41 (bottom left and right panels), respectively, where the axes correspond to the deviation between the reference reflector optical axis and focused beam centroid. The color bar corresponds to the relative collected flux. The angular scanning system demonstrated a substantial increase in sensitivity to non-optimal alignment as compared to the rectilinear system characterized by a full width half max (FWHM) of 0.4 mm×0.25 mm and ~0.8 mm×0.8 mm for the angular and rectilinear systems, respectively. The apparent asymmetry in the rectilinear system is due to the overall asymmetry of the system using only one off-axis parabolic (OAP) mirror for the scanning function. This result contrasts with the mirror symmetry along both axes in the angular system because of the matched mirrored configuration of the OAP mirror pair.

With consideration of the two-pass path and in accordance with various embodiments, the rectilinear system beam path interfaces with four (×4) parabolic mirror surfaces, while the angular scanning system interfaces with eight (×8). When an OAP mirror focal point is misaligned with the target surface, the collected beam can be collimated on a path not parallel with the optical axis of the mirror, resulting in a transverse walk-off of the beam after focusing from a subsequent OAP and/or complete beam walk-off in the collimated beam path.

It was anticipated that the misalignment issues with patients could be caused by involuntary radial movements of the eyes known as Saccades while longitudinal movements could be constrained with the proper chin and head rests. Also, it is important to note that the ray tracing simulation does not take into consideration field and beam pattern matching and therefore serves as both an upper bound on alignment sensitivity. More importantly, a relative analysis between the systems that should give a good indication of trends computed with physical optics.

Beam Radius Optimization

Inspection of FIG. 35 and associated tradeoffs between competing factors on focused spot radius motivate the optimization of input spot size subject to a specific criterion. Two potential metrics were considered in the following equations where $\omega_0$ is the input collimated beam radius, w is the focused beam radius on the cornea, $R_{s,1}$ is the scan radius corresponding to the near edge of the OAP, $R_{s,2}$ is the scan radius corresponding to the far edge of the OAP. ("near" and "far" edge are defined with respect to the cornea, FIG. 31).

$$\omega_0 \text{ s.t.} \qquad \text{EQ. 51}$$
$$\omega_1(R_{s,1} + \omega_0, \omega_0) - \omega_1(R_{s,2} - \omega_0, \omega_0) = 0$$

$$\omega_0 \text{ s.t.} \qquad \text{EQ. 52}$$
$$\frac{\partial}{\partial \omega_0}\left(\frac{1}{R_{s,2} - R_{s,1}} \int_{R_{s,1}}^{R_{s,2}} \omega_1(r, \omega_0) dr\right) = 0$$

EQ. 51 is defined, in accordance in many embodiments, such that the spot sizes at the extremums of the scan range [$R_{s,1}$, $R_{s,2}$], limited by the collimated beam radius ($\omega_0$), are equal. This metric results in an approximate colocation of the smallest focused spot size with the apex of the cornea, while nearing a minimum in the asymmetry of the spot size about the corneal apex. EQ. 52 defines a collimated beam radius where the average focused spot size at the corneal surface is minimized, in accordance with various embodiments. The parameter space and solutions to these equations are displayed in FIG. 42. The cross over point of the two curves that satisfy EQ. 51 is denoted with the gray circle (o) marker and occurs at a collimated input waist of 6.25 mm. This result was computed with the quasioptical analysis of Example.

Figure 42:
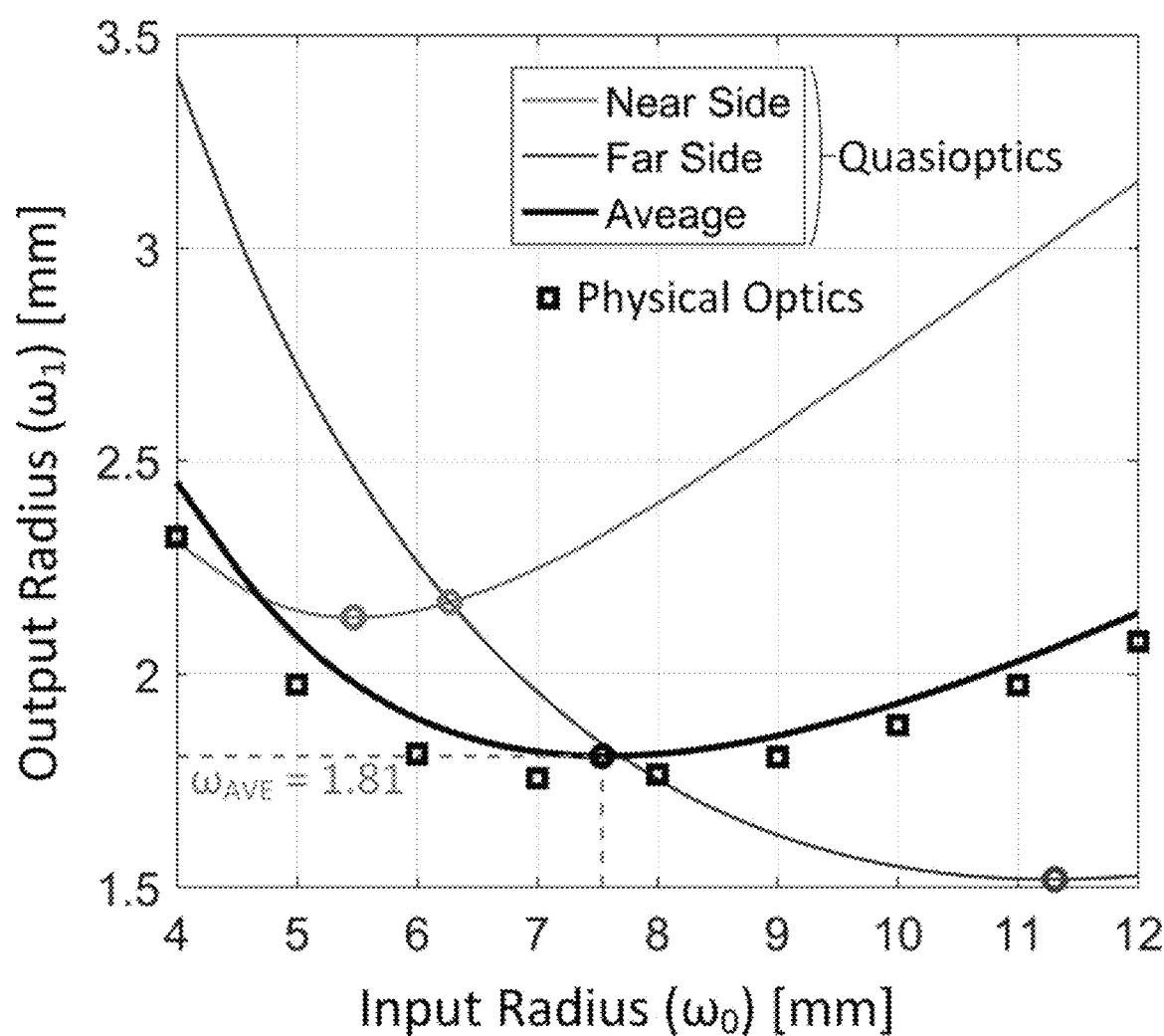
FIG. 42 provides a data graph of optimization space for EQ. 51 and EQ. 52, in accordance of various embodiments.

The input spot size dependent behavior of the solution of the differential in EQ. 52 is denoted with the solid black line in FIG. 42 and its minimum, which satisfies EQ. 52, is denoted by the circular marker (o) at $\omega_0$=7.6 mm. The solution space was also generated and analyzed with the physical optics analysis presented in FIG. 35 and plotted with the square (□) marker. The physical optics modeling demonstrated good agreement and identifies an optimal input radii of $\omega_0$~7.0 mm.

Current clinical practice prioritizes the status of the corneal center as providing the most utility when identifying disease processes, thus justifying the metric in EQ. 51 (B. Lackner, et al., *Optometry and Vision Science*, 82:892-99, 2005, the disclosure of which is incorporated herein by reference). However, certain corneal pathologies, e.g. corneal graft rejection, can create "edematous fronts" that migrate across the extent of the corneal surface. In many embodiments, detection of these features supports minimizing the spatial bias of imaging system, thus justifying the metric in EQ. 52. In accordance with several embodiments, the rectilinear system also exhibits increased coupling efficiencies as the input radius is increased therefore the optimal system parameter for this analysis were defined by $\omega_{in}$=7.6 mm.

Coordinate Transformation and Mapping

Mapping: The forward mapping from the transverse rectilinear coordinates of the parabolic mirror clear aperture (x, y) to the spherical coordinates of the cornea (θ, φ) are given in EQ. 53 and EQ. 54, in accordance with multiple embodiments of the invention. In addition, various embodiments of the reverse mapping from the spherical coordinates of the cornea (θ, φ) to the transverse rectilinear coordinates of the parabolic mirror clear aperture (x, y) are given in EQ. 55 and EQ. 56.

$$\theta = \frac{\pi}{2} - \tan^{-1}\left(\frac{\sqrt{x^2+y^2}}{4f_p} - \frac{f_p}{\sqrt{x^2+y^2}}\right) \quad \text{EQ. 53}$$

$$\phi = \tan^{-1}\left(\frac{y}{x}\right) \quad \text{EQ. 54}$$

$$x = 2f_p\cos(\phi)\left[\tan\left(\frac{\pi}{2}-\theta\right) + \sec\left(\frac{\pi}{2}-\theta\right)\right] \quad \text{EQ. 55}$$

$$y = x\tan(\phi) \quad \text{EQ. 56}$$

In accordance with some embodiments, these relations perform both conformal and orthogonal mapping from sampling coordinate to the target surface angular coordinate. $f_p$ is the parent focal length of the parabolic mirror, whose focal point is at (0, 0, $f_p$), and the parabolic vertex is coincident with the origin. The mapping assumes that the cornea is a spherical surface and that the input beam is perfectly collimated, thus there is no dependence on the height, z, above the mirror and no dependence on the corneal radius of curvature, Rc. All rays reaching the target surface are orthogonal to the local spherical surface. Therefore, each pixel position on the target can be fully described by the azimuthal (φ) and elevation (θ) angles corresponding to any pair of (x, y) coordinates.

Figure 43:
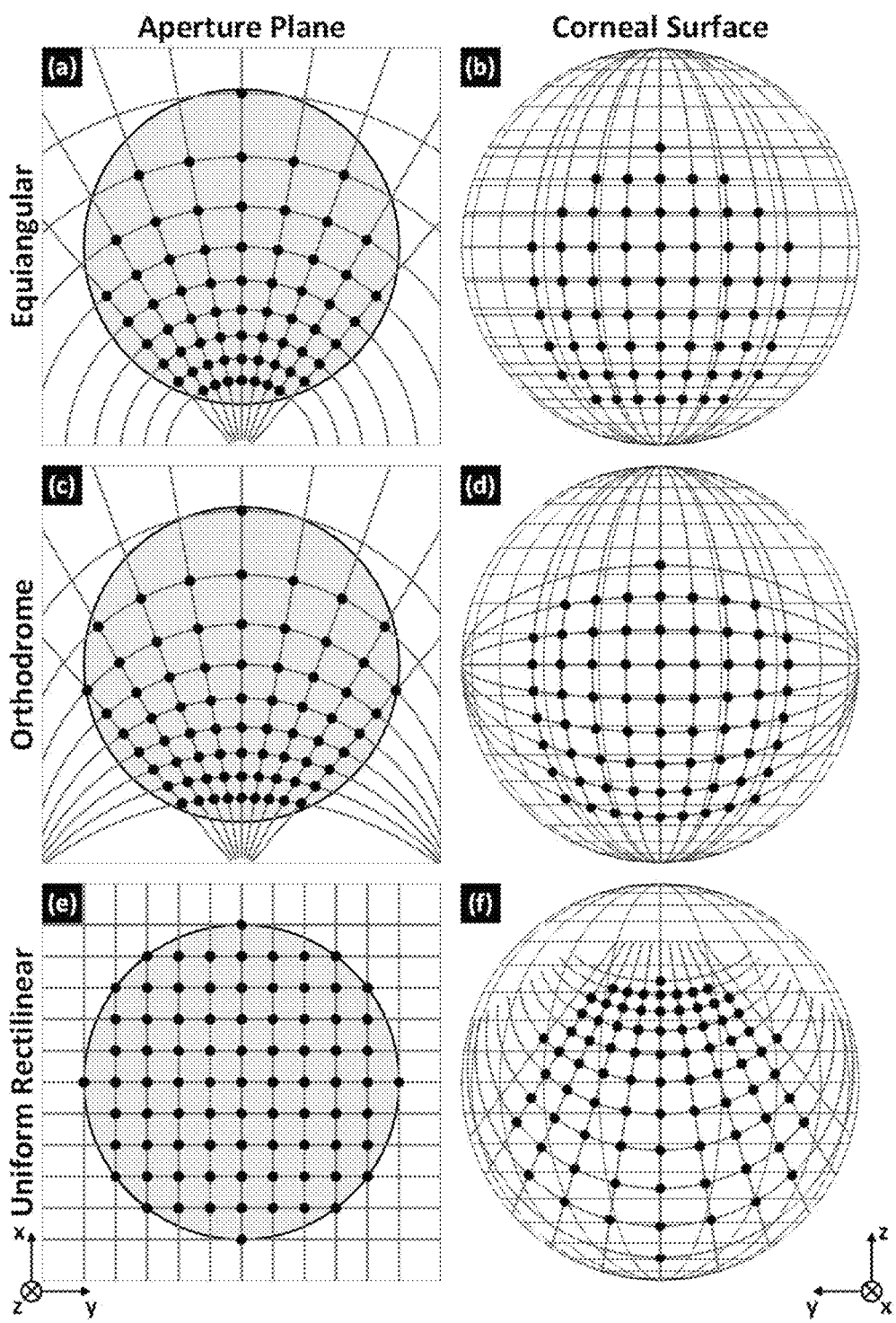
FIG. 43 provides a collection of mappings between a 90°, 76.2 mm CA, 25.4 PFL OAP mirror and an 8 mm RoC sphere (cornea) with three sampling types (equiangular, orthodrome, and uniform rectilinear) and two spaces (flat aperture plane and spherical corneal surface), in accordance with various embodiments.

Three different sampling grids were considered for the system and these are displayed in FIG. 43 for a 76.2 mm CA, 25.4 mm PFL, 90° OAP mirror. The grids and associated mappings adhere to standard spherical coordinate formulism, thus the vertical axis in the plots of the OAP clear aperture corresponds to the x-axis and the horizontal axis corresponds to the y-axis. The mirror clear aperture axis is parallel to the z-axis and pierces the x-y plane point (x, y)=(2fp, 0); its focal point is at (x, y, z)=(0, 0, 0), and its vertex is at (x, y, z)=(0, 0,-$f_p$). The apex (center) of the cornea is pierced by the x-axis and is located at (x, y, z)=(8 mm, 0, 0); (R, θ, φ)=(8 mm, +π/2, 0) in spherical coordinates.

The sampling grid displayed in FIG. 43 (top-left panel) is termed "Equiangular scanning" and is the implementation of equal increments (10o=π/18) in both the θ and φ directions, represented by the longitudinal (blue) latitude (red) traces, respectively. The corresponding mapping back to the mirror clear aperture x-y plane is displayed in FIG. 43. The black circular makers (●) represent the intersections of the θ-scan φ-scan lines, and thus sampling locations in the x-y plane. The fixed-φ-varying-θ curves (longitude) are mapped to straight lines, distributed radially, in the aperture space that intersect (x, y)=(0, 0). The fixed-θ, varying-φ curves (latitude) are mapped to circles in the x-y plane, where the radii were calculated with EQ 55 and φ=0.

The mapping of the equiangular scanning confirms that the beam scanning must be the densest towards the near edge of the OAP CA and then progressively less dense as the beam is moved radially outward from the corneal center of curvature, in accordance with many embodiments. This observation is consistent with the optical power of the OAP, which is inversely proportional to the distance from the parent focal point ($R_s$). FIG. 43 (Equiangular panels) also serve as a pictorial justification of orienting the mirror and the optic such that the mirror focal axis pierces the (θ, φ)=(π/2, 0) instead of the standard (θ, φ)=(0, 0). Equiangular scanning about the (0°, 0°) point results in a substantial decrease in sampling density as the beam is traversed from the corneal apex to the periphery. This sampling density variation is significantly higher than that achieved with the (π/2, 0) orientation, thus reducing the uniform sampling density necessary to sufficiently sample the equiangular space.

The sampling grid in FIG. 43 (middle-left and middle-right panels) are termed "orthodromic" and is a modification of the equiangular scanning. In this sampling distribution the circular paths described by scanning φ at a given θ (red latitude lines in FIG. 43 (Equiangular panels)) are replaced by orthodromes which are defined as curves on the surface of a sphere that are formed by the intersection of the sphere and a plane that is coincident with the sphere center point. In spherical coordinates, all longitude lines are orthodromes while only one of the latitude lines (equator) is an orthodrome. In many embodiments, the orthodrome-scanning grid replaces the latitude scan paths with orthodromes that are defined by a sphere of radius 8 mm (cornea) and the intersection of a plane defined by the following three points:

P1: (Rc, θ, φ)=(8, π/2,−π/2).
P2: (Rc, θ, φ)=(8, π/2,+π/2).
P3: (Rc, θ, φ)=(8, θ$_0$, 0).

where point P3 defines the angle the plane makes with the z-axis. In accordance with multiple embodiments, the spherical coordinates defining the orthodromic scanning path is:

$$\theta = \cot^{-1}\left(\tan\left(\frac{\pi}{2}-\theta_0\right)\cos(\phi)\right), \forall \phi \in [-\pi, \pi] \quad \text{EQ. 57}$$

The "latitude" orthodrome scan lines mapped to the OAP mirror CA plane are similar to the equiangular scan latitude lines with a comparative increased curvature closer to the mirror focal point decreased curvature at the extreme periphery of the mirror aperture.

The utility of the orthodromic scanning is most readily apparent for spot size characterization of spherical "knife-edge" targets. Consider the intersection of every "latitude" with the longitude curve at φ=0°. At any given intersection point the tangent lines of both curves are perpendicular and coplanar. Now consider a spherical knife-edge target constructed of one dielectric hemisphere and one metallic hemisphere. If the interface of the two hemispheres is coplanar with the φ=0° longitude curve, then all orthodrome beam paths will be perpendicular to the metal-dielectric interface, and the measured knife-edge response will be the true knife-edge response of the beam.

The final sampling grid considered is termed "Uniform-rectilinear" and is described in FIG. 43 (bottom panels with the uniform, rectilinear in the bottom-left panel mapped onto the corneal spherical surface in bottom-right panel). This sampling grid results in significant sparsity of sampling points towards the bottom section of the cornea. In accordance with some embodiments, this sampling grid is the most straightforward to implement for linear translation stages, and thus its sufficiency at resolving the equiangular and orthodromic scanning schemes was considered.

It will be understood that embodiments of each of these sampling grids may be used in association with THz imaging/sensing systems and methods to determine an optimal scanning strategy for producing an image of the cornea.

Sampling

Embodiments of the three mappings yield varying sampling density on target for a given input beam-scanning scheme. The system implementation described in the following sections, in accordance with several embodiments, utilized uniform rectilinear sampling to simplify automation and utilized equiangular and orthodromic sampling schemes in post processing to characterize coupling efficiency and spot size on target. Thus, it was necessary to identify a rectilinear sampling density sufficient to resolve critical equiangular and orthodromic sampling given a set of spatial resolution criteria. Analysis of FIG. 43 indicates that the curvature of equiangular scan paths towards the near side of the mirror is higher than that of the orthodromic scan paths, confirming discrepancy between the uniform rectilinear and equiangular sampling locations as compared to the discrepancy between uniform rectilinear and orthodromic sampling locations. Thus, the equiangular sampling scheme may be used as the reference for uniform rectilinear sample planning.

Many embodiments are directed to considering the spatial resolution on the corneal surface in the context of spherical chord length which, for spot radii less than the corneal radius of curvature, is nearly equivalent to the spherical chord length (the paraxial approximation holds to 1 part in 103 up to a focused spot radius of 5 mm; significantly larger than the maximum predicted 3.6 mm). Consider a minimum spot center-to-center distance of $\Delta d$ on the surface of a sphere with radius $R_c$. In several embodiments, the angular displacement required to achieve this step along the spherical dimensions $\theta$ and $\varphi$ are:

$$\Delta\theta(\phi) = \Delta\theta = \cos^{-1}\left(1 - \frac{\Delta d^2}{2R_C^2}\right) \qquad \text{EQ. 58}$$

$$\Delta\phi(\theta) = \cos^{-1}\left(1 - \frac{\Delta d^2}{2R_C^2 \sin^2(\theta)}\right) \qquad \text{EQ. 59}$$

$$\Delta\gamma = \Delta\phi\left(\theta = \frac{\pi}{2}\right) = \Delta\theta(\phi) \qquad \text{EQ. 60}$$

Note that $\Delta\varphi$ is a function of $\theta$ while $\Delta\theta$ is invariant to $\varphi$. To define an equiangular spherical sampling grid that sufficiently samples the expected spatial frequencies as defined by the chord length $\Delta d$, one can find the angular locations that maximize the change in $\Delta d$ for a given change in $\Delta\varphi$ and $\Delta\theta$. Inspection of EQ. 58 and EQ. 59 confirm that this occurs at the spherical equator ($\theta=\pi/2$) and is denoted ($\Delta\gamma$) (EQ. 60).

Next, the scan radii in the aperture plane, informed by the $\Delta\gamma$, that corresponds to the latitude scan lines on the corneal surface, were computed. The equiangular sampling and parabolic mapping described in FIG. 43 (equiangular panels) revealed that for a given chord length sample separation, the samples at the near edge of the mirror are more sparsely distributed on target than the far edge. Accordingly, in many embodiments as many samples should be packed into the near edge region of the mirror as possible with the following considerations: 1) how many samples positions should be oriented along the first radial scan line, and 2) what should the radius of the first scan line be given a collimated beam radius and desired number of sample positions on the first row. Through analysis of the relevant trigonometry, the following angles were defined in accordance with multiple embodiments:

$$\Delta\alpha = (N-1)\Delta\gamma \qquad \text{EQ. 61}$$

$$\Delta\beta = 2\sin^{-1}\left(\frac{2f_p \sin\left(\frac{\Delta\alpha}{2}\right)}{\frac{A}{2} - \delta\omega_0}\right) - \Delta\alpha \qquad \text{EQ. 62}$$

$\Delta\alpha$ is the angle subtended by the line segments from the corneal center of curvature to the centroids of the outer most beams aligned on the first scan line. $\Delta\beta$ is the angle subtended by the line segments from the mirror clear aperture center to the centroids of the outer most beams aligned on the first scan line. A is the mirror clear aperture diameter, $\omega_0$ is the beam waist radius, $f_p$ is the parent focal length of the mirror, and $\delta$ is the clipping multiplication factor. The equations are defined such that the beam centroid of the outer most beams are located at a distance $\Delta\omega_0$ from the mirror edge. The parameter $\delta$ can be adjusted to avoid diffraction due to beam clipping at the edges.

$$R_{s0} = \frac{\left(\frac{A}{2} - \delta\omega_0\right)\sin\left(\frac{\Delta\beta}{2}\right)}{\sin\left(\frac{\Delta\alpha}{2}\right)} \qquad \text{EQ. 63}$$

$$\theta_0 = \frac{\pi}{2} - \tan^{-1}\left(\frac{R_{s0}}{4f_p} - \frac{f_p}{R_{s0}}\right) \qquad \text{EQ. 64}$$

$$R_{sn} = 2f_p\left[\begin{array}{l}\tan\left(n\Delta\gamma + \frac{\pi}{2} - \theta_0\right) + \\ \sec\left(n\Delta\gamma + \frac{\pi}{2} - \theta_0\right)\end{array}\right], n = 1 \qquad \text{EQ. 65}$$

EQ. 63 gives the radius of the first scan line. This radius corresponds to $\theta 0$ in spherical coordinates (EQ. 64)) and the subsequent scan radii ($R_{sn}$) required to maintain equiangular scanning is given in EQ. 65. Examples of one beam and six beams on the initial radial scan path are displayed in FIG. 45 (top-left and top-right panels), respectively.

Figure 44:
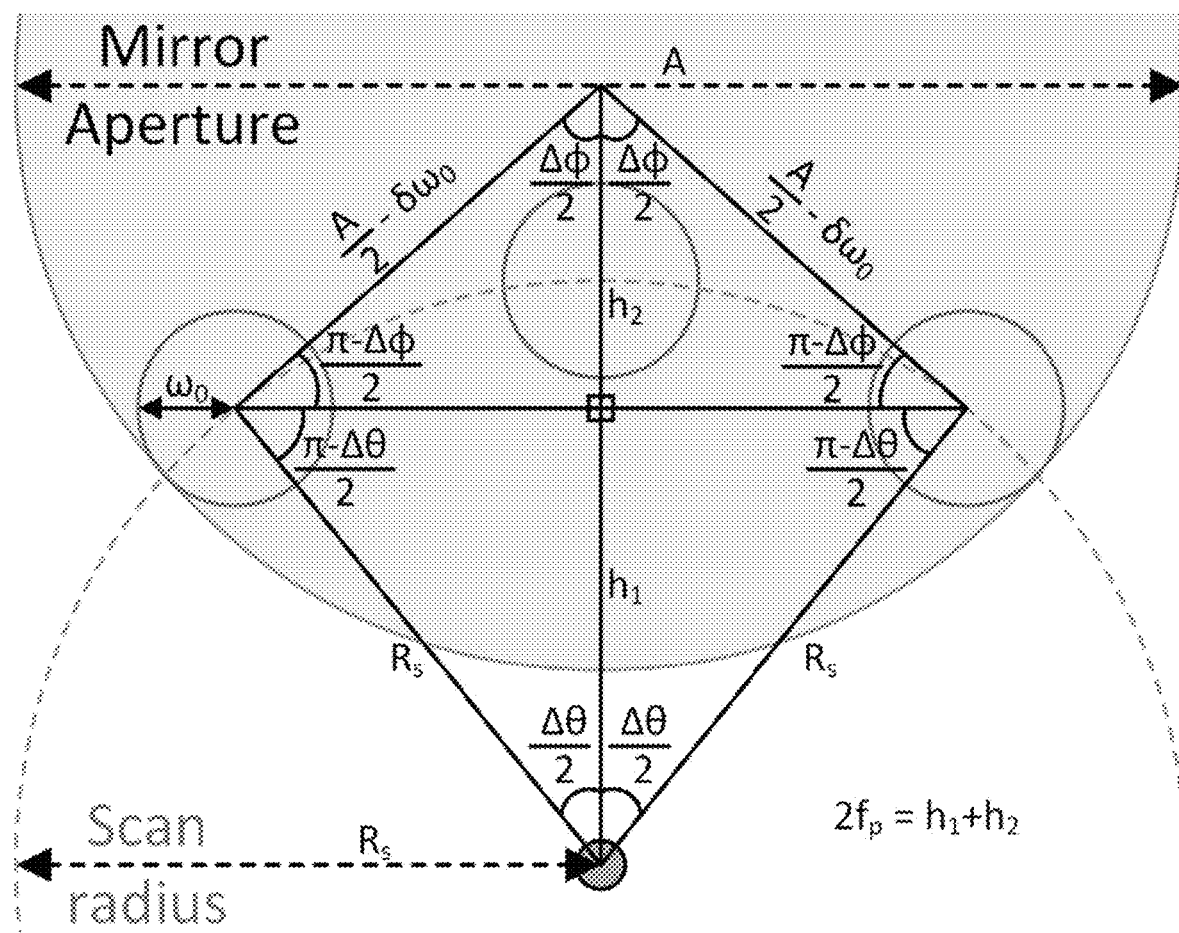
FIG. 44 provides a graphic of geometry to compute optimal beam packing, in accordance of various embodiments.

Beam packing and sampling: To explore the solution space, an optimization metric was defined as the equiangular sampling grid that yielded the maximum number of unclipped beams inside the mirror aperture using a mirror diameter of 76.2 mm and setting $\delta=1$. The space was parameterized as a function of input beam radius and desired minimum sample center to center spacing (chord length, EQ. 58 and EQ. 59), which was set equal to the focused beam radius on target, as shown in FIG. 44.

Figure 45:
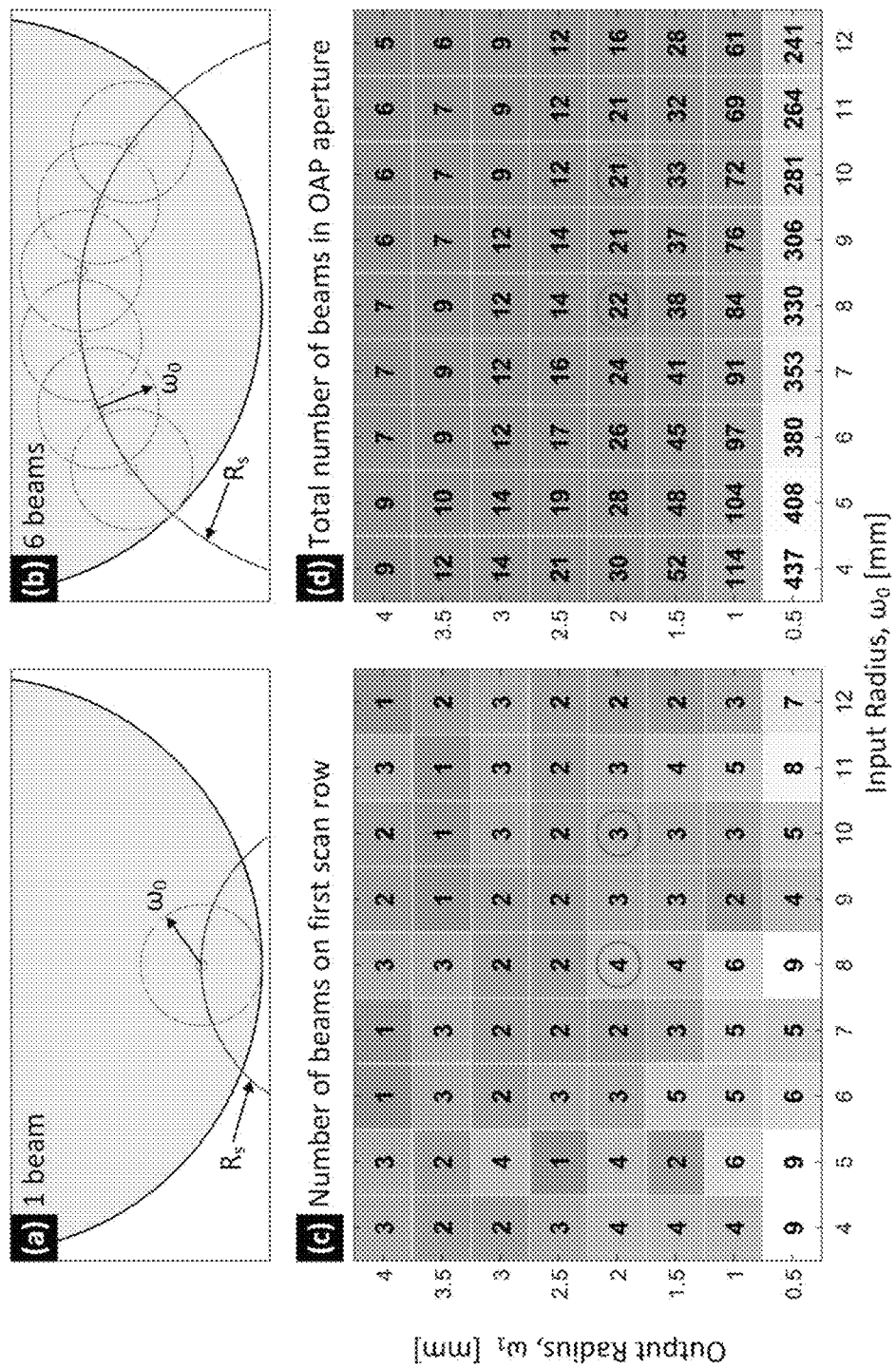
FIG. 45 provides a collection of (top) beam packing schematics and (bottom) the respective number of beams and sampling locations, in accordance with various embodiments.

The x-axis of the grid in FIG. 45 (bottom panels) is the input beam radius and the vertical axis is the desired minimal sample spacing. FIG. 45 (bottom-left panel) reports the number of beams on the first scan radius that yielded the maximum number of beams packed into the aperture and FIG. 45 (bottom-right panel) reports the corresponding maximum number of packed beams. The results reveal an interesting relationship between the explored parameters. While any linear path across the space of FIG. 45 (bottom-right panel) yields a monotonic curve, the space in FIG. 45 (bottom-left panel) does not exhibit a similar relationship and many local extrema are observed. This suggests that sampling grid planning is very specific to not only the target spatial frequencies but also the optics used to route the illumination beam prior to the objective.

Figure 46:
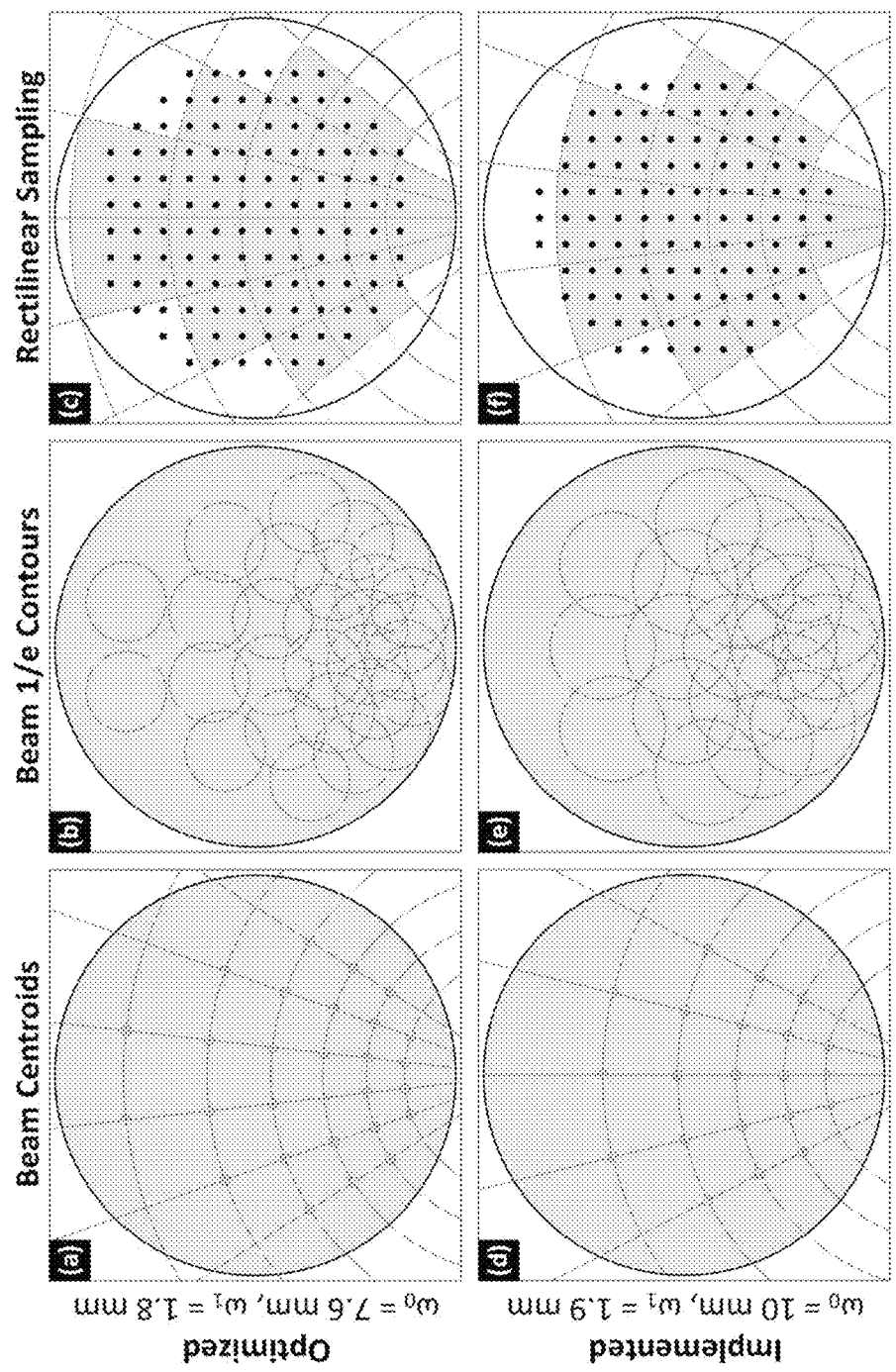
FIG. 46 provides a sampling scheme for an 8 mm input diameter and 1 mm center-to-center sampling spacing for (top) optimized beam packing and (bottom) implemented beam packing, in accordance with various embodiments.

The final computation was an empirical determination of the approximate uniform sampling grid such that each equiangular sampling location was intercepted by at least one uniform rectilinear scanning position. The optimal beam packing and uniform rectilinear sampling for an input radius of 7.6 mm and an output radius of 1.8 mm is shown in FIG. 46 (top panels). The 7.6 mm and 1.8 mm radii pair were computed to yield a minimum average spot size across the aperture. FIG. 46 (bottom panels) show the same optimal packing for an input radius of 10 mm and an output radius (from FIG. 41) of 1.9 mm. In accordance with multiple embodiments, the system described in subsequent sections produced a collimated beam radius of ~10 mm thus the FIG. 46 (bottom panels) represents the sampling planning space of the presented system implementation.

The sample locations indicated by the intersection of the equiangular longitude and latitude contours lines are denoted by the (○) marker in FIG. 46. Intersections that do not have markers correspond to locations whose minimum distance to the aperture is less than the collimated beam radius ($\omega_0$). FIG. 46 (middle panels) superimposes beam lie contour lines centered at the sampling locations from FIG. 46 (left panels) and demonstrate substantial beam overlap toward the near edge of the mirror. The beam overlap reduces as the scan radius increases and, in the case of the (7.6 mm, 1.8 mm beam pair) the larges scan radius positions beams with no critical overlap in the aperture plane.

The scan lines from FIG. 46 (left and middle panels) were redrawn for FIG. 46 (right panels) and subtend areas (shaded) that fall within the beam area covered by the beam contours FIG. 46 (middle panels). Uniform rectilinear sampling grids were superimposed on the shaded regions and the grid density and offset were modulated until the smallest integer center-to-center separation in millimeters was identified that places at least one sample in every shaded location. A minimum of 5 mm center-to-center separation was identified for both the optimal input beam radius (FIG. 46 (top panels)) and the realized input beam radius (FIG. 46 (bottom panels)). Note that there are an even number of sample positions on every latitude line in FIG. 46 and odd number in FIG. 46 and note that in both cases, none of the horizontal sampling grid lines lie coincident with the horizontally oriented diameter of the mirror aperture due to the modulation of the grid off set. Define $x_0=0$ and $y_0=2f_p$, and the center to center separation as $\Delta$. The baseline rectilinear sampling grid is defined as $(x_0 \pm k_x \Delta, y_0 \pm k_y \Delta)$ where $k_x$ and $k_y$ are integers and the grid is subject to the constraint that the 1/e beam contours do not spill over the mirror aperture. Thus the sampling grid for FIG. 46 (top panels) is $(x_0 \pm [k_x+\frac{1}{2}]\Delta, y_0 \pm [k_y \frac{1}{2}]\Delta)$ and $(x_0 \pm [k_x]\Delta, y_0 \pm [k_y+\frac{1}{2}]\Delta)$ for FIG. 46 (bottom panels).

Many embodiments are directed to scanning methodologies for use with Tl-Hz imaging/sensing systems that meet the necessary sampling conditions described in the scanning model.

Exemplary Embodiment 5: Non-Contact In Vivo THz Imaging

In Exemplary Embodiments 3 & 4, various embodiments of non-contact terahertz (THz) corneal imaging systems were presented. Human cornea exhibits limited interpatient variation in corneal topography with respect to a free space wavelength in the THz band. This, combined with the vanishingly small deviation between the wavelength normalized optical sag of an in vivo cornea and the sag of an ideal sphere, enable the utilization of a very constrained design space. In accordance with many embodiments, the field of view, field curvature, and target tissue thickness range can all be assumed a priori with a very high degree of confidence, and system implementations need only deal with a very limited number of possible use cases. This makes THz corneal imaging unique amongst all surface tissue diagnostics imaging research fields.

In this exemplary embodiment, a THz scanning/imaging system is constructed in accordance with several embodiments and the optical performance assessed in characterization targets. Experimental spatial resolution and coupling coefficient data was compared to the theory developed in Exemplary Embodiments 3 & 4 and goodness of fit quantified.

THz Corneal Hydration Imager Implementation

Figure 47:
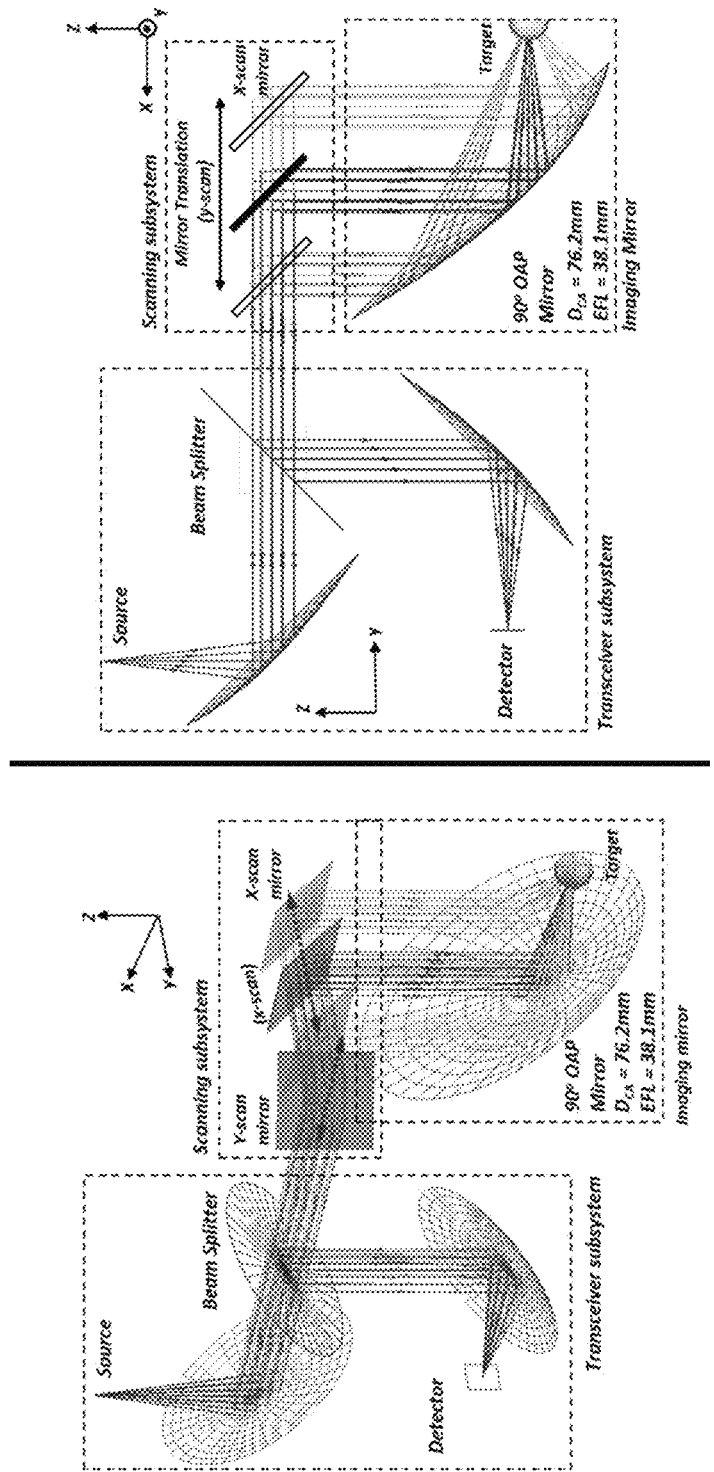
FIG. 47 provides a schematic of a single mirror, rectilinear scanning imaging system design comprised of three distinct subsystems, in accordance with various embodiments.
Figure 48:
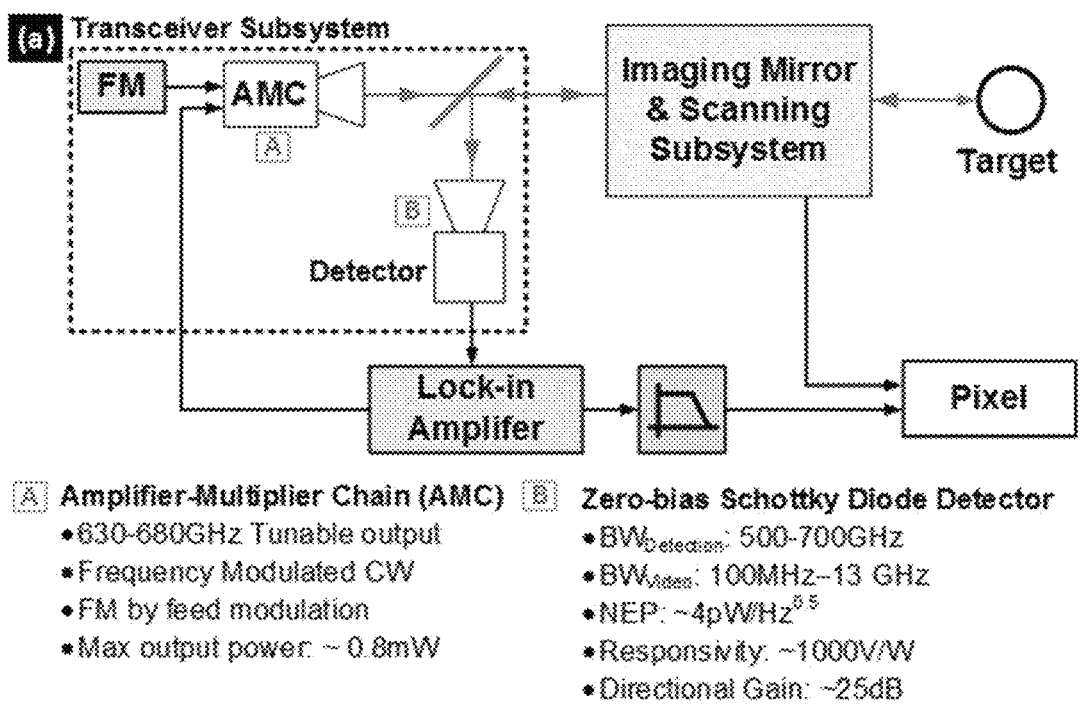
FIG. 48 provides a collection of images of a an imaging system where (top) is a block diagram of the imaging system employing frequency-modulated CW THz source, zero-bias Schottky diode detector, and lock-in detection scheme, (bottom-left) is a CAD rendering, and (bottom-right) is a photographic image of a scanning imaging system, in accordance with various embodiments.
Figure 48:
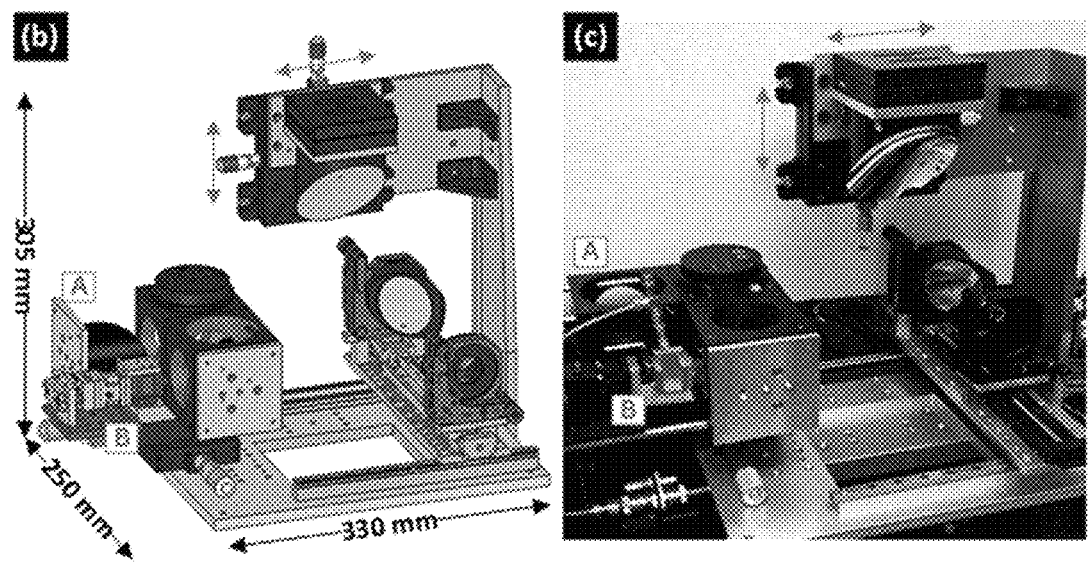

System: A prototype system, with the optical layout detailed in FIG. 47, was constructed with a solid-state frequency-modulated continuous wave THz source (Amplifier-multiplier chain, Virginia Diodes, Virginia) centered at 650 GHz, in accordance with an embodiment of the invention. The detector was a WR1.5 waveguide mounted Schottky diode detector (ZBD) (Virginia Diodes, Va.) with a 500 GHz-700 GHz detection bandwidth. Both the source and detector were coupled to diagonal feedhorn antennas with 26 dB of gain and aperture dimensions of 2.4 mm×2.4 mm. Because of the high coherence of the source and specularity of the cornea, a significant standing wave can be generated between the source, target, and detector and observed as large variations in return signal as the scanning mirror position changes the total optical path length. To mitigate standing waves, the output was frequency modulated over ~2 GHz at a rate of 100 kHz, providing a frequency bandwidth that exceeds the expected full etalon period of the optical path. The source was also amplitude modulated at ~900 Hz, and the rectified signal from the ZBD was detected with a Lock-in amplifier (Stanford Research Systems, CA) using an integration time of 3 milliseconds (ms). These parameters are summarized in the block diagram of FIG. 48 (top panel).

The optical layout of the system was the same as that described in Exemplary Embodiment 3, and used a 25.4 mm PFL, 76.2 mm CA, 90° OAP mirrors to collimate radiation from the multiplier chain and focus reflected radiation into the detector aperture. The combination of feedhorn directivity and OAP PFL yielded a collimated spot 1/e field radius of ~10 mm as measured with a knife-edge target. The focusing mirror was a 76.2 mm CA, 25.4 mm PFL OAP. Beam scanning was performed with two 50.8 mm diameter gold-coated plane mirrors. A CAD design of the system and an image of the constructed system are displayed in FIG. 48 (bottom-left and bottom-right panels, respectively).

Figure 49:
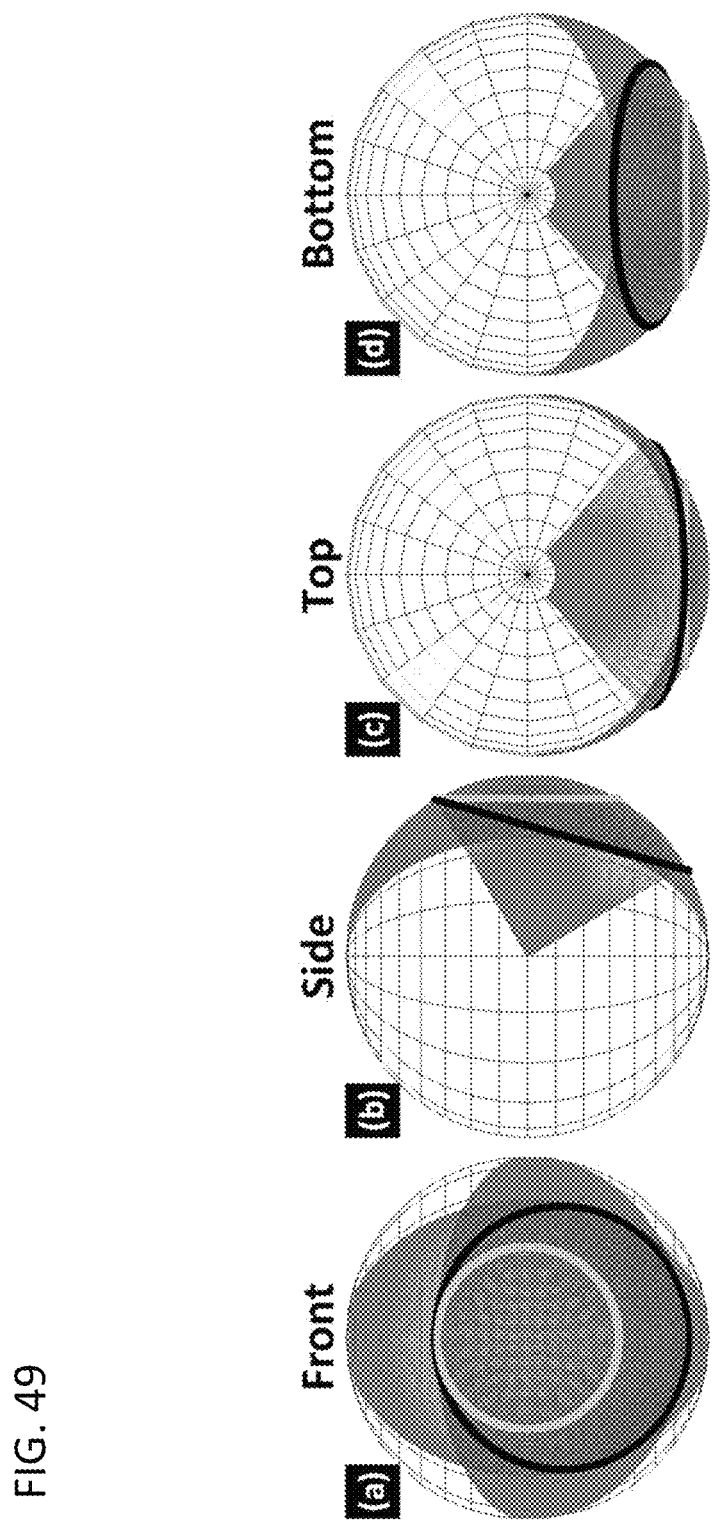
FIG. 49 provides corneal coverage data by a 76.2 mm CA, 25.4 PFL OAP, where the black circle on the surface denotes the mapped CA of the OAP, and the gray circle denotes the extent of the cornea, in accordance with various embodiments.

The total coverage of a spherical surface obtained with the 25.4 mm PFL, 76.2 mm CA, 90° OAP is detailed in FIG. 49 where the gray contour is the extent of the cornea and the black contour is the mapped CA of the scanning OAP and hence the coverage. These contour lines are superimposed on a set of mapped orthodrome scan lines that subtend the entire extent of the mirror.

Figure 50:
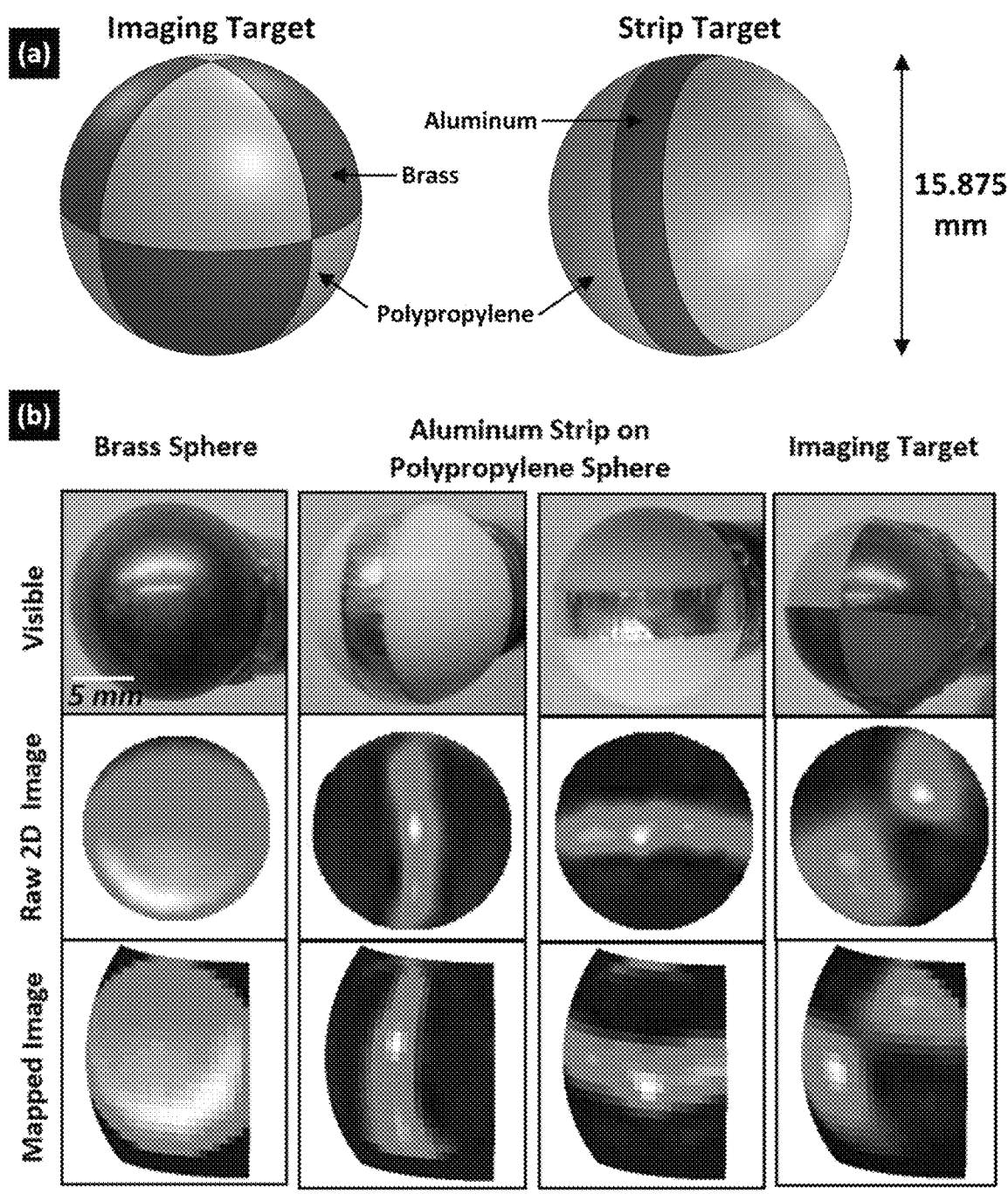
FIG. 50 provides a collection of images of characterization targets where (top) are CAD drawings and (bottom) are visible images of characterization targets, in accordance with various embodiments.

Imaging Results: Three spherical targets with 5/16"=7.93 mm radii of curvature were imaged in accordance with various embodiments:

1) A brass sphere to evaluate the uniformity of the FOV and its relation to the modeled coupling efficiency.
2) A polypropylene sphere with a 3 mm wide strip of Al Tape positioned such that the center of the strip was collinear with an orthodrome of the sphere. This target was rotated 90 degrees between image acquisitions to confirm that the mapping and sampling distributions behaved as expected.
3) A bespoke "checkerboard" target that consisted of quarter sphere sections of polypropylene and brass. This target was intended to provide knife-edge measurements in two orthogonal dimensions on one surface thus removing the need to realign/reposition for characterization along different axes. CAD drawings of the strip and checkerboard target are shown in FIG. 50 (top panel). The images were sampled using the uniform rectilinear grid pattern with a 5 mm step size. The translation of pixel data from aperture plane to sphere was performed by first up sampling the aperture space image and then performing the mapping described by EQ. 53-EQ. 56.

The characterization target imaging results are displayed in FIG. 50 (lower panel) where the top row is the visible image of the target and its orientation in the system, the middle row is the 2D image of the aperture plane, and the bottom row is the data mapped to a 7.93 mm radius sphere using EQ. 55 and EQ. 56.

In accordance with multiple embodiments, the image of the brass sphere displays an increase in signal from the top of the FOV to the bottom with a spatial gradient that is generally radially symmetric from target center of curvature. Assuming uniform reflectivity across the brass, this signal intensity is consistent with what was predicted by the coupling coefficient analysis in Exemplary Embodiment 3. There are some breaks in the radial symmetry of the reflected signal on the outer periphery of the mirror, which are likely due to diffraction arising from beam clipping and possible suboptimal alignment.

The vertically oriented aluminum strip displays similar behavior with the signal in the center of the strip generally increasing from the top of the FOV to the bottom with some local extrema in the signal. Additionally, the apparent strip width widens from top to bottom which is consistent with the expected increase in spot size (for a 10 mm input radius) as the radial distance from the target vertical axis and collimated beam centroid location is decreased.

In many embodiments, the mapped THz image of the horizontal strip maintains a fairly constant apparent thickness although there are also local extrema in the observed signal. Close inspection of the visible images reveals a slightly rough surface profile along both the center and the edges of the tape and we believe this is primarily responsible for the observed signal variation.

The checkerboard target serves as a clear demonstration of the asymmetry of the FOV about the OAP mirror optical axis. The intersection of the adjacent brass and polypropylene quarter spheres were aligned with the optical axis and this intersection is above the center of the FOV for the mapped image (bottom right of FIG. 50). The edges also appear to be somewhat less sharp that that acquired with the Al tape strip target suggesting that the variation in edge height between dielectric and metallic regions strongly contribute to the overall contrast.

Data Fits to Quasioptical and Physical Optics Analysis

In accordance with several embodiments, model fits to data were applied to pixel values in the aperture plan space. The desired sampling locations on the sphere were defined and then mapped to scan trajectories on the aperture plane space. These scan trajectories were then superimposed on the aperture plan imaging data and image profiles along these trajectories were analyzed to determine coupling efficiency and resolution. THz images in the mirror aperture plane space were masked to a circle with radius $A/2-\omega_0$ to mitigate aberrations due to beam clipping.

Coupling Coefficient Fits: The brass sphere data was sampled with equiangular scan lines where the longitude and latitude was spaced at ~5 degrees and positions selected such that the majority of the 'non-clipped' clear aperture was visited. The brass sphere was assumed to have negligible variation in THz reflectivity across the imaged area and thus variation in measured reflectivity was attributed primarily to the expected variation in coupling efficiency analyzed in Exemplary Embodiment 3. The coupling coefficient was expected to display radial symmetry thus equiangular scan lines were chosen for FOV sampling as described in Exemplary Embodiment 4. The profiles extracted from the scan paths were then compared to EQ. 67 [5] and the physical optics simulations for an input spot radius of 10 mm.

$$q_3 = \frac{A_3 q_0 + B_3}{C_3 q_0 + D_3} \quad \text{EQ. 66}$$

$$K(q_0, q_3) = \frac{4}{\left(\frac{\omega_0}{\omega_3} + \frac{\omega_3}{\omega_0}\right)^2 + \left(\frac{\pi \omega_0 \omega_3}{\lambda}\right)^2 \left(\frac{1}{R_3} - \frac{1}{R_0}\right)^2} \quad \text{EQ. 67}$$

Figure 51:
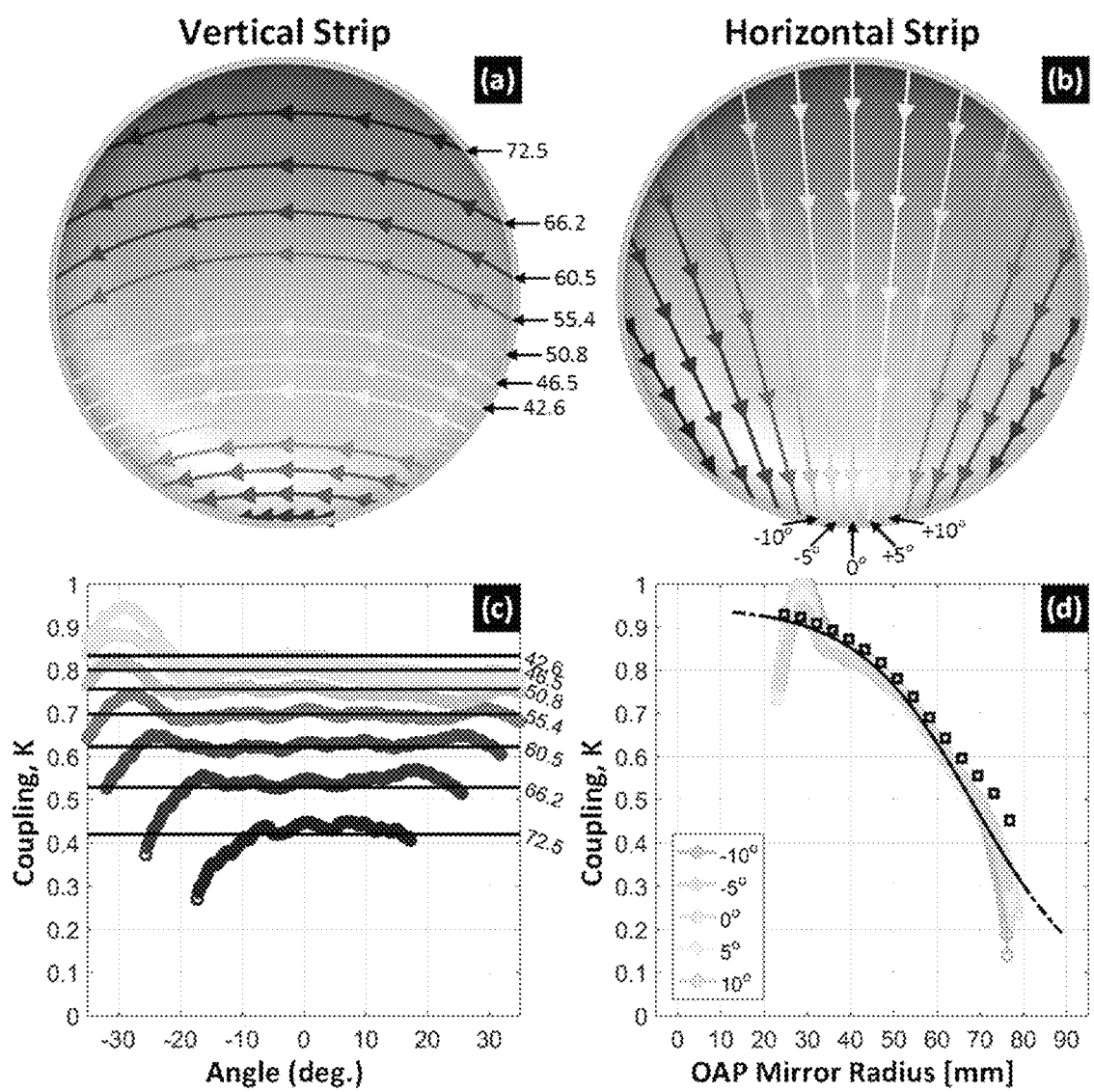
FIG. 51 provides a coupling calibration target, in accordance with various embodiments, where (top-left) provides latitude (equiangular) scan lines superimposed on the imaging data, (top-right) provided longitude (equiangular) scan lines on the imaging data, (bottom) provides latitude and longitude scan profiles.

The latitude scan lines and their associated profiles are displayed in FIG. 51 (top-left and top-right panels, respectively), where the coupling coefficient was assumed to be radially symmetric (independent of $\varphi$) and thus constant as a function of arc length, in accordance with multiple embodiments. The scan paths in FIG. 51 (top panels) corresponding to the image profiles in FIG. 51 (bottom panels) are color coded and the arrows in FIG. 51 (top panels) denote the direction of increasing arc length which corresponds to the horizontal axis of FIG. 51 (lower panels). Image profiles corresponding to the longitude scan lines in FIG. 51 (top-left panel) are displayed in FIG. 51 (lower-left panel) and include a superimposed fit to EQ. 67. The image profiles were normalized to data obtained from a flat Al target placed such that the surface was coincident with the center of curvature of the brass sphere, and 0 reflection obtained by removing all targets from the imaging system.

Several embodiments are directed to the coupling coefficient depending on four variable parameters: 1) input radius of curvature, 2) output radius of curvature, 3) input spot size, and 4) output spot size. The good agreement between theory and data between both the trends normalized return signal strongly the accuracy of the analysis developed in Exemplary Embodiment 3. The deviation from theory at the extrema of each profile suggest that beam clipping may contribute significantly to the measured signal even at $1 \cdot \omega_0$ from the mirror aperture edge and these effects may be considered in future design iterations.

Al strip fits: The rotated Al strip images were analyzed with the orthodromic scan lines. These lines ensure that the scan path is always orthogonal to the reflectivity discontinuities (edges) of the target features.

$$\gamma(d) = 2(d_0 - d) \qquad \text{EQ. 68}$$

$$C_b(d) = A\left[1 - \Phi\left(\frac{\gamma(d) - D}{\omega_1}\right) + Q\left(\frac{\gamma(d) + D}{\omega_1}\right)\right] + B \qquad \text{EQ. 69}$$

Figure 52:
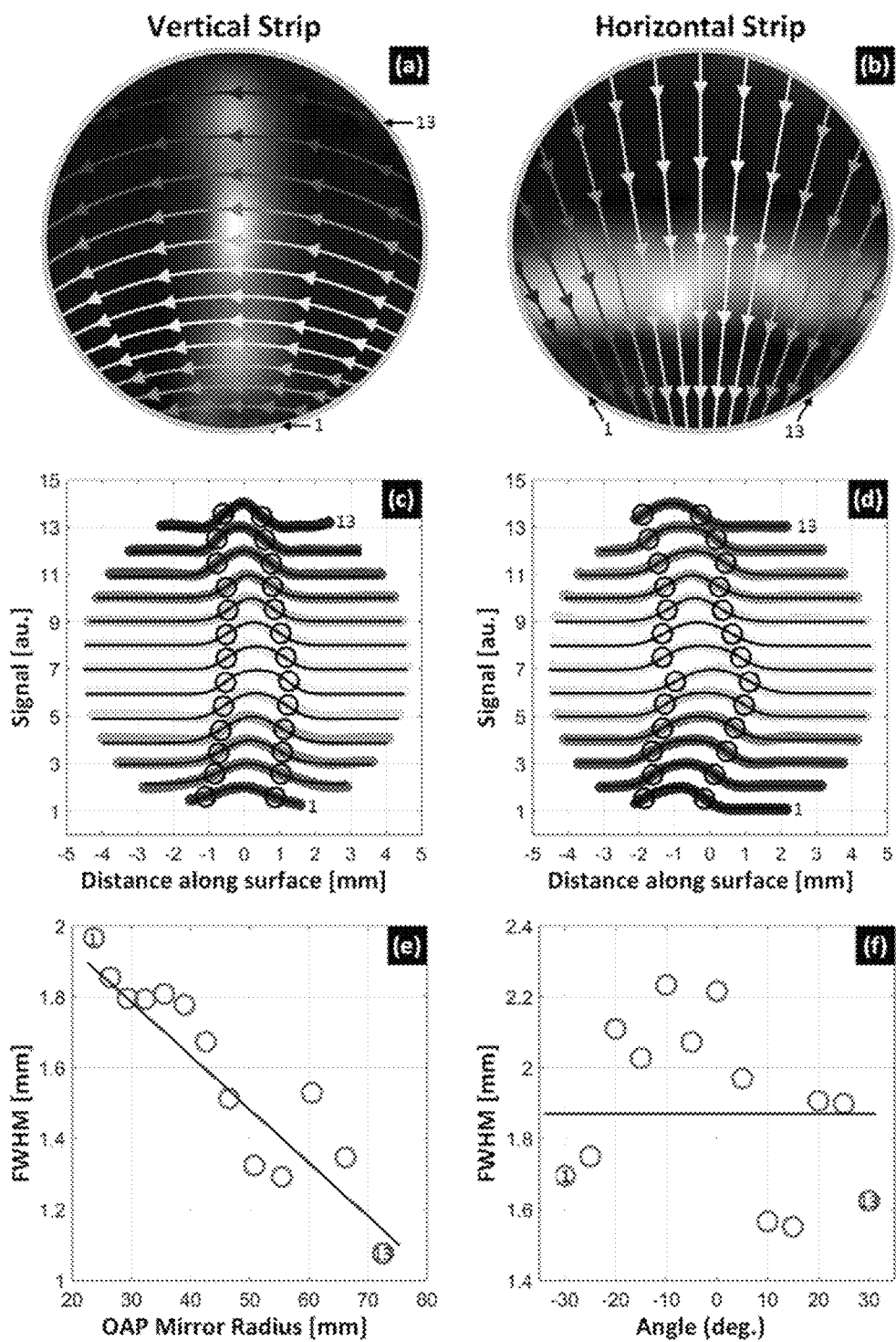
FIG. 52 provides an Al strip resolution target, in accordance with various embodiments, where (top-left) provides orthodrome scan lines orthogonal to the vertical strip orientation, (top-right) provides orthodrome scan lines orthogonal to the horizontal strip orientation, (middle) provides corresponding image profiles, (bottom) provides extracted FWHM.

Data from the Orthodromic profiles orthogonal to the center line of the bar in the vertical and horizontal positions (FIG. 52 (top-left) and FIG. 52 (top-right) respectively) were fit to EQ. 69, which describes the convolution of a 1D Gaussian distribution of spot size $\omega_0$ with a rect function of width D and center located at do. The function $\Phi(\cdot)$ is the left sided integral of standard normal and the function $Q(\cdot)$ is the right sided integral of the standard normal. The variable d is the spatial arc length along the surface of the cornea. Offset parameters A and B were included to improve the fit. The "long" direction of the bar was much larger than the transverse extent of the focused beam so it was sufficient to model the data with an integral along one dimension.

The profiles and superimposed fits are displayed in FIG. 52 (middle panels) for the vertical and horizontal orientations respectively. Additionally, the full width at half max (FWHM) as defined by the FWHM of EQ. 69 informed by the extracted fit parameters are demarcated (□). As evidenced by FIG. 52 (lower panels) the extracted FWHM is substantially less than 3 mm (the width of the Al bar and thus lower limit of the convolved width) with the vertical bar FWHM ranging from 1.1 mm-1.95 mm and the horizontal bar ranging from 1.55 mm-2.25 mm. This is likely due to the geometric surface discontinuities between the Al tape and polypropylene ball. Wrinkles in both the tape surface and tape edges are visible in FIG. 50. As a result of large optical path lengths, it is believed that when the tape surface normal is not parallel to the normal of the underlying spherical surface the beam walks away from the detector feedhorn.

The FWHM data from the fits to the vertical bar is plotted against mirror radius in FIG. 52 (bottom-left panel) with a least squares fit line superimposed on the data. While the FWHM are narrower than what was anticipated, the fits display a strong negative correlation between mirror scan radius ($R_s$) and measured apparent spot size; behavior consistent with that computed for in input field radius (wo) of ~10 mm. The extracted FWHM for the horizontal bar orientation are displayed in FIG. 52 (lower right) as a function of orthodrome angle with respect the central orthodrome with the average of the data superimposed. The data demonstrates some variation but the correlation between spot size and angle is $\rho \sim 0.05$ supporting the expected independence of focused spot size over a large angle for a given scan radius.

Step Response Fits: In accordance with several embodiments, the checkerboard images were also analyzed with orthodromic scan lines and the extracted image profiles were fit to EQ. 70 and EQ. 71 for rising edge and falling edge response respectively. EQ. 70 and EQ. 71 describe the convolution of a Gaussian beam (field radius too) with a unit step function centered at $d=d_0$. The amplitude factor A and offset B were included to maximize goodness of fit and EQ. 70 and EQ. 71 are related by the equivalence in Equation EQ. 72.

$$C_\Phi(d) = A \cdot \Phi\left(\frac{2(d - d_0)}{\omega_1}\right) + B \qquad \text{EQ. 70}$$

$$C_Q(d) = A \cdot Q\left(\frac{2(d - d_0)}{\omega_1}\right) + B \qquad \text{EQ. 71}$$

$$C_\Phi(d) = -C_Q(d) + A + 2B \qquad \text{EQ. 72}$$

Figure 53:
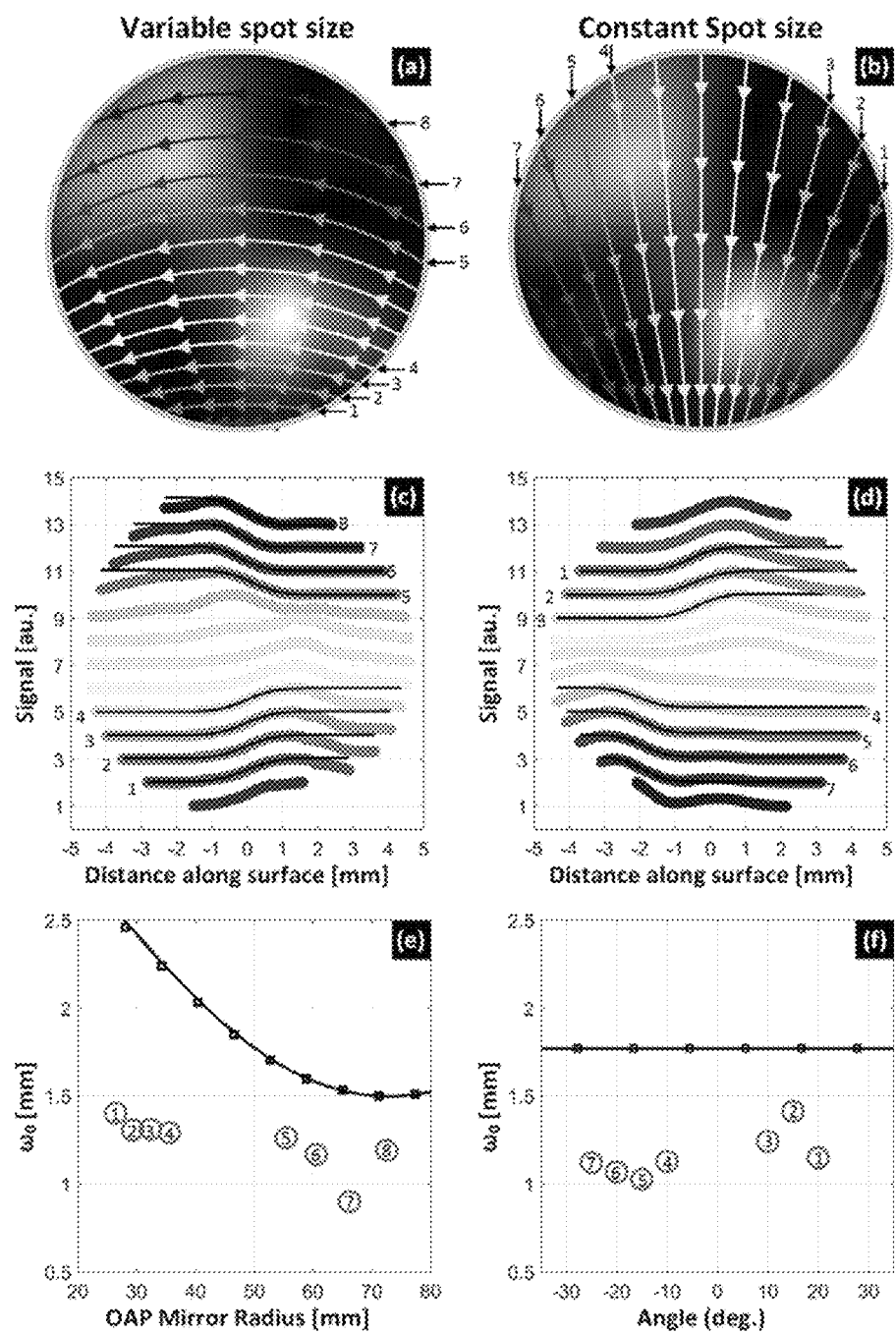
FIG. 53 provides a checkerboard target, in accordance with various embodiments, where (top-left) provides orthodromic scan lines orthogonal to the vertical edges, (top-right) provides orthodromic scan lines orthogonal to the horizontal edges, (middle) provides corresponding image profiles, (bottom) provides extracted lie field radii.

The horizontal orthodrome cuts and associated fits are displayed in FIG. 53 (left panels). In accordance with several embodiments, eight cuts were analyzed comprising of the bottom and top regions of the FOV (labeled 1-8 in FIG. 53 (top-left panel)). The center (~$2\omega_0$ width) area of the FOV was ignored to avoid artifacts due to the presence of the checkerboard corner.

The expected focused field radius for a collimated input beam of radius 10 mm is superimposed on the extracted spot field radii (FIG. 53 (bottom-left panel)). The results are consistent with theory and demonstrate a maximum deviation from the focused spot radius curve of 0.473 mm and a standard deviation of 0.233 mm.

Closer inspection of FIG. 53 (middle left) reveal that for the majority of the image profiles the signal gradually falls off after the peak of the step response. The optical properties of the beam on target are radially symmetric and the circular lines of constant spot size and coupling efficiency are not co-linear with the orthodrome lines used to ascertain the spot size. A deconvolution of coupling efficiency may be used to improve the fits.

Seven vertical orthodrome profiles and associated fits are displayed in FIG. 53 (right panels) and, as in the previous analysis on the horizontal profiles, the center region was not analyzed. The extracted focused field radius is plotted vs orthodrome angle and the expected spot size at the mirror radius corresponding to the mapped target edge location is superimposed. There is a good agreement in fit between the measured data and the field radius computed with both quasioptical and physical optics analysis and the results support the relative invariance of the spot size to edges at the spherical target equator. The measured peak deviation was 0.175 mm and the standard deviation was 0.105 mm.

Characterization Target Limitations: In accordance with many embodiments, the combination of path length of the optics train, low f/# of the OAPs, and high directivity of the source and detector resulted in a system that is sensitive to misalignment between the mirror focal point and corneal radius of curvature. This manifests as a sensitivity to surface discontinuities (geometric), which was observed in the characterization target data. The tape strip targets and, to a lesser extent, the checkerboard target both exhibited raised edges and uncontrollable surface roughness which confounded the acquisition of uncluttered resolution data. While these efforts reveal difficulties in characterizing the beam profile on target, there is limited concern for these issues affecting in vivo corneal imaging as human cornea does not have discontinuities the surface height profile and the surface roughness (~15 um) is minimal.

Corneal Phantom

Figure 54:
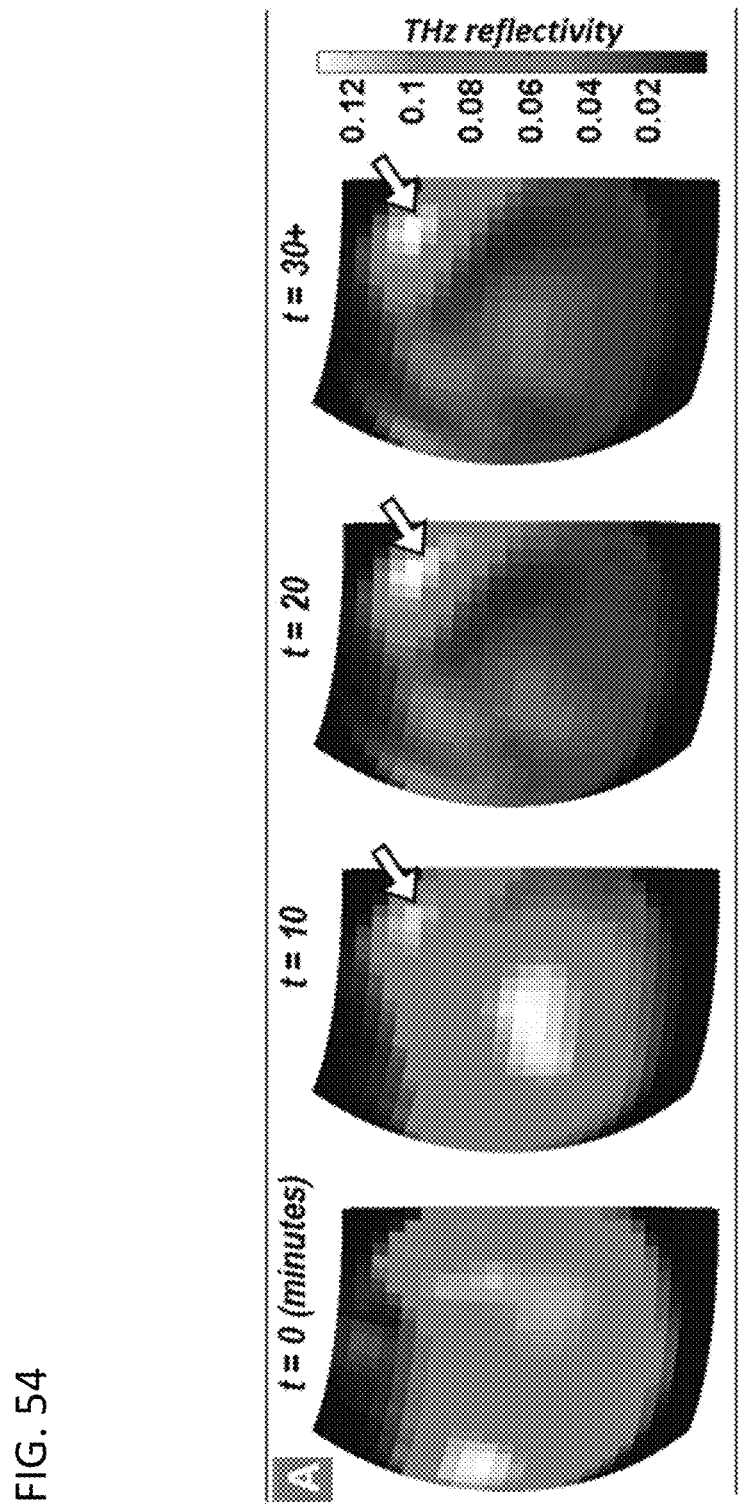
FIG. 54 provides time-lapse images of a drying contact lens mapped to a spherical surface, generated in accordance of various embodiments.

Several embodiments demonstrate the ability of THz to image corneal phantoms. In this example, the water content imaging capabilities of this system were explored by acquiring time-lapse images of a corneal phantom (soft contact lens) undergoing desiccation. A contact lens was immersed in water for 5 minutes prior to imaging and then placed on a polypropylene ball identical in size to the calibration brass ball target. Then it was left to dry while THz images were consecutively acquired over a 30-minute period (FIG. 54). The THz images were normalized to the brass sphere data and visualized the drying process of the contact lens from the thinner and exposed outer rim toward the center. This result is consistent with the behavior predicted by evaporation and diffusion, and correlates to the dynamics observed in the drying of flattened ex vivo cornea.

A high reflectivity spot persisted in the upper right corner of the field of view throughout the drying process. This may be a thin film etalon effect due to the coherence of the source and narrow, time averaged line width. We suspect this etalon was created by the warping and rolling of the edges of lens as it is dried, creating a small air gap in between the contact lens layers and the polypropylene ball. The net effect is a larger effective wave impedance. The behavior is repeatable but does not occupy the same location in the field of view further supporting the role of uncontrollable air gaps and the resulting etalon.

The results demonstrate THz reflectivity changes by hydration change are successfully captured by the imaging system. Overall, good signal return from the entire extent of the contact lens surface suggests the imaging system can effectively perform imaging of a corneal target. Further, standing waves appear to be further suppressed as compared to the brass ball data due to the relatively low reflection coefficient of the target (~12%) and thus reduced quality factor (Q) of the optical path.

Exemplary Embodiment 6: Traumatic Brain Injury & Other Conditions Having Abnormal Intraocular Pressure Traumatic Brain Injury (TBI) is a physical injury to brain tissue that temporarily or permanently impairs brain function, is one of the leading causes of death and disability in adolescents and adults. 1.6 million people sustain traumatic brain injuries, of whom 800,000 receive early outpatient care and 270,000 require hospital admission in the United States alone. Economic costs per case are estimated to be between $33,284 to $35,954 for mild and $25,174 to $81,153 for moderate TBI, resulting in an annual direct cost burden of TBI (mild, moderate, and severe) to be $302 million. TBI is graded as mild, moderate, or severe based on the level of consciousness or Glasgow coma scale (GCS) score after resuscitation. Mild TBI (GCS 13-15) is in most cases a concussion where full neurological recovery is expected, in moderate TBI (GCS 9-13) the patient is lethargic or stuporous, and in severe injury (GCS 3-8) the patient is usually comatose. Patients diagnosed with severe TBI have a significant risk of intracranial hypertension, hypotension, hypoxemia, and brain edema. Of these secondary injuries, intracranial hypertension, or increased intracranial pressure (ICP), is of particular significance. ICP is closely related to cerebral perfusion, or blood flow in the brain. The potential benefits of ICP monitoring include earlier detection of intracranial mass lesion, avoidance of indiscriminate use of therapies to control ICP, drainage of cerebrospinal fluid with reduction of ICP and improvement of CPP, and determination of prognosis.

Identification of TBI in the acute stages may lower the risk of secondary injury and subsequent long-term care costs. A set of prognostic indicators for classification of TBI has been established by The U.S. Department of Education, National Institute on Disability and Rehabilitation Research in conjunction with 17 TBI research hospitals around the U.S that include: 1) amnesia for the event, 2) a GCS score of less than 15 during the first 24 hours, and 3) ICP monitoring. Although amnesia is a good indicator of TBI severity and a reasonable predictor of long-term outcomes, this slow evaluation method (one month of amnesia indicates severe TBI) cannot be implemented in the acute response to patient diagnosis.

The GCS is a TBI severity assessment system that relies on subjective observations of eye opening, best motor response, and verbal response. TBI patients with a GCS score that is mild or moderate usually require a CT scan; however, this data acquisition process is slow and expensive. The cost is compounded given CTs do not furnish a direct assessment of ICP (two or more scans are required to assess trends), and in 9-13% of patients, the CT image will appear normal even with elevated ICP. The current gold standards for ICP monitoring are the ventriculostomy tube, which requires a specialist for accurate insertion and is more suitable for the intensive care unit, and Lumbar puncture (LP). Although LP does allow transient manipulation or sampling of the intracranial fluid system, it is invasive, often painful, and may result in after affects. Given the time sensitive need for more direct data, advances in non-invasive ICP monitoring techniques are required.

In comparison with other noninvasive alternatives of ICP measurement (transcranial Doppler, measurement of tympanic membrane displacement, and oculodynamometry), measuring intraocular pressure (IOP) is less expensive, time efficient, more available, and less dependent on expert technicians. Recent publications suggest a strong correlation between IOP and ICP (p 0.001; r 0.955; n 50). However, the physiologic mechanism responsible for elevations of IOP remains unclear. One study suggests that the cerebrospinal fluid (CSF) surrounding the optic nerve sheath transmits elevations of ICP through the eyeball, raising the IOP level. Other potential mechanisms suggest that the rise in the ophthalmic venous pressure (as the result of ICP elevation) could be transmitted directly to the ocular fluid raising IOP or increased venous pressure in the cavernous sinus (also the direct effect of ICP rise) is transmitted to episcleral veins by the superior ophthalmic vein and causes an increase in IOP. Stromal edema is a well-known clinical feature of increased IOP, which in turn causes an abnormal hydration of the cornea. Based on this rationale, changes in ICP may manifest as changes in corneal hydration following TBI.

Figure 55:
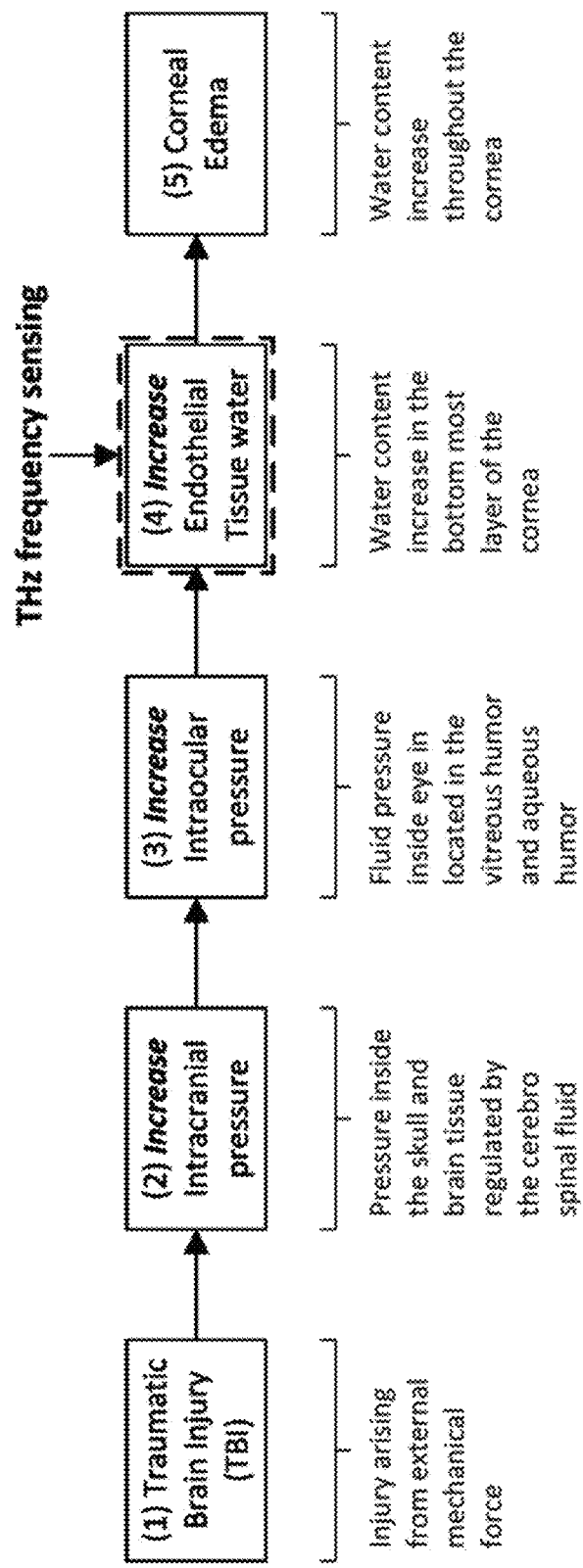
FIG. 55 provides a flowchart of a method for detecting traumatic brain energy in accordance with embodiments.

Embodiments are directed to methods whereby the traumatic brain injury (TBI) and other diseases that have abnormal intraocular pressure can be detected and classified with a simultaneous measurement of cornea thickness and a spatial map of corneal water content in the thickness dimension. (See, FIGS. 55 to 57) Traumatic brain injury occurs when the head of an individual experiences blunt force trauma. This leads to following physiologic response of interest (FIG. 55):

TBI→increase in intracranial pressure;
increase in intracranial pressure→increase in intraoccular pressure;
increase in intraoccular pressure→increase in the water content of the corneal endothelium; and
increase in corneal endothelium water→increase in corneal stroma water content (corneal edema).

Figure 56:
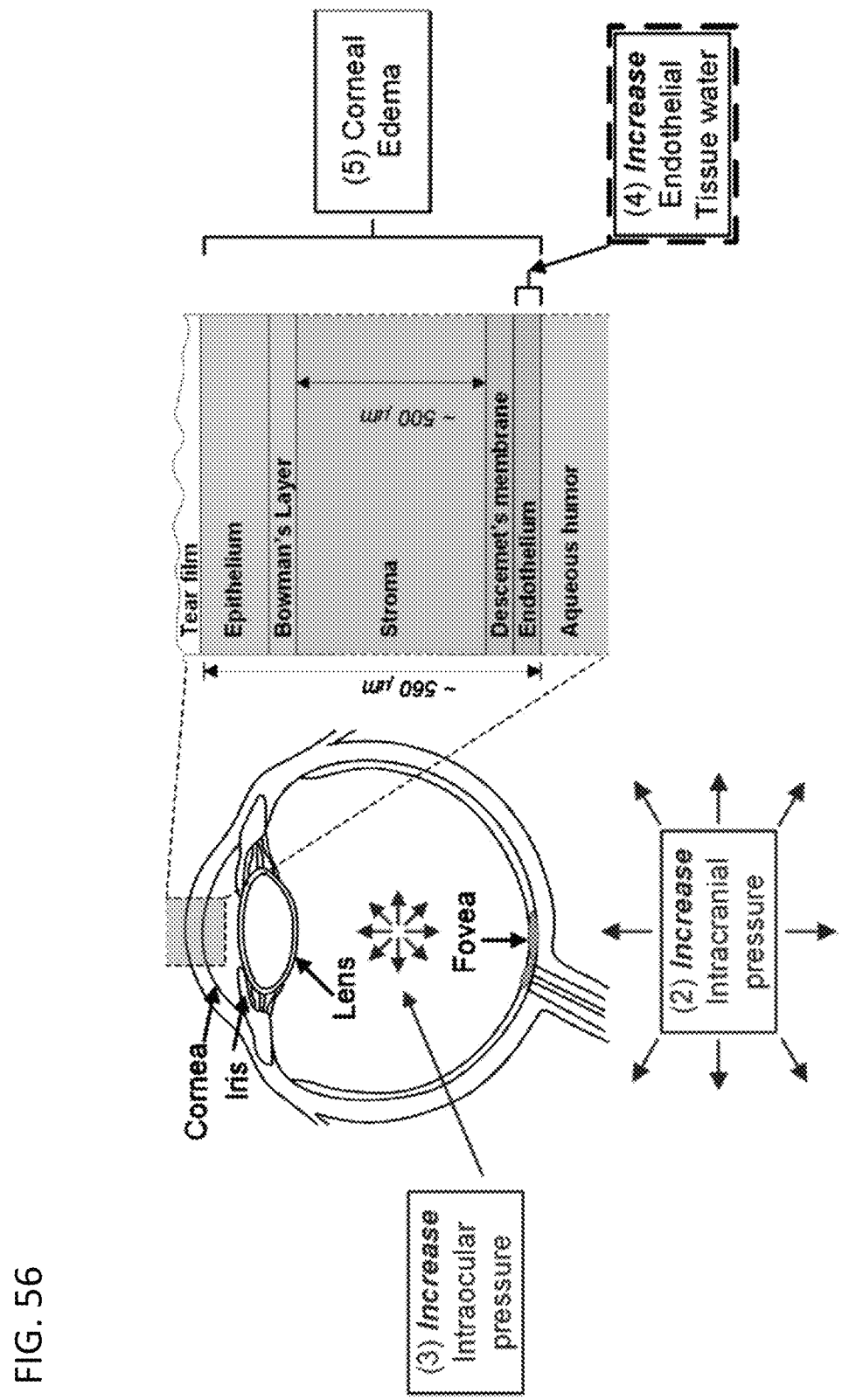
FIG. 56 provides a schematic of the physiology of the eye.
Figure 57:
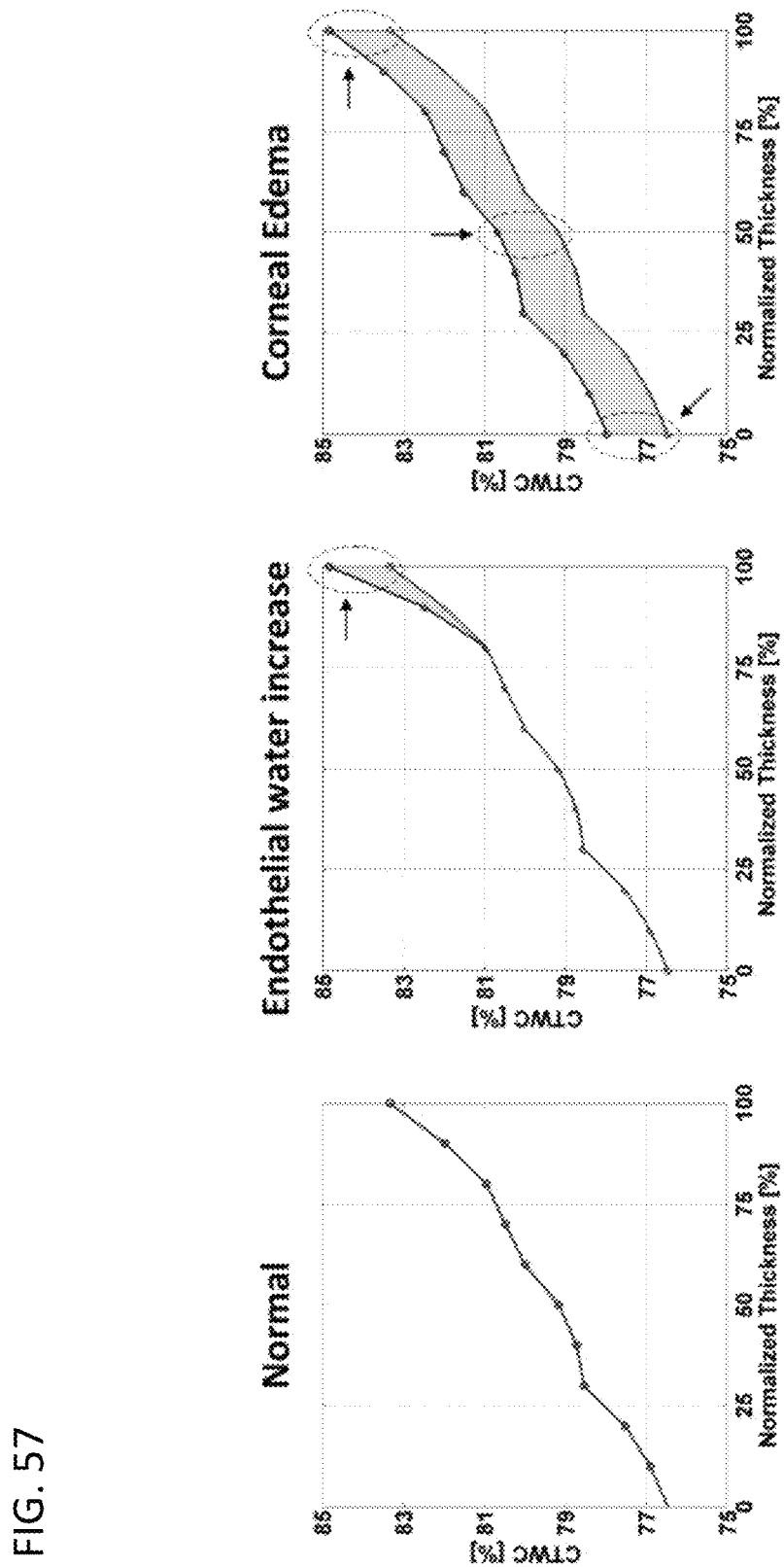
FIG. 57 provides data concerning the water content of the cornea under normal and edema conditions in accordance with embodiments.

As the pressure inside the cranium of a patient with a TBI increases it imparts an increase in intraocular pressure, which manifests as an increase in pressure in the vitreous humor and then aqueous humor. Increased pressure in the aqueous humor is coupled directly to the endothelium, disrupting the barrier function and corneal water content maintenance functions of the layer (FIG. 56). This results in and increase in the water content of the corneal endothelium. Depending on the severity of the TBI the increase in intracranial and intraocular pressure may lead to increases in stromal water content and hence corneal edema (FIG. 57).

Embodiments of the technique utilize measurements of the water content gradient in the thickness (axial) dimension of the cornea to perform early and accurate detection and assessment of TBI. Three methodologies are proposed:

Detection of an increase in endothelial water content over what is known to be a normal gradient value indicates the presence of a TBI. This method is calibration free as it relies on the spatial derivative of the axial water content.

Measurement of general corneal edema, which may be present due to significant lapsed time between injury and measurement or may be due to a severe TBI.

Measurement of the axial water content gradient as it changes through a period of time. This metrology can also be calibration free.

The above three methodologies can be combined, in accordance with embodiments, to identify a trajectory through the injury space spanned by the physiologic parameters affected by TBI. When combined with spatially resolved axial gradients (imaging) and spatially resolved thickness measurements this technique provide an early and accurate detection and classification of TBI. In various embodiments corneal thickness measurements and axially resolved corneal tissue water content measurements can be performed with OCT, ultrasound, visible light, infrared light, or RF illumination; or some combination of the listed modalities.

It should be understood that the systems and methods employed to detect CTWC for TBI can also be applied, in accordance with various embodiments, to other diseases or medical complications having abnormal intraocular pressure, as understood in the various medical fields. For example, these diseases can include glaucoma, iritis, retinal detachment, hypertension, or physical obstruction. Accordingly, embodiments are directed to quick assessment of these diseases by measuring CTWC.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method for the THz imaging a cornea comprising:
generating an illumination beam having a frequency that is variable about at least one central wavelength greater than 0.1 THz;
illuminating a cornea with the illumination beam at multiple frequencies to produce a plurality of reflected signals therefrom, wherein the multiple frequencies are accomplished by frequency sweeping, using multiple bandwidths at a single frequency, or using multiple frequencies at a single bandwidth;
detecting the plurality of reflected signals across a spectrum of frequencies; and
combining the plurality of reflected signals to obtain a plurality of reflectivity maps of the cornea, said reflectivity maps having a combined signal variation indicative of at least the corneal total water content and central corneal thickness.

2. The method of claim 1, wherein the illumination beam has a variable bandwidth configured such that both narrowband and broadband illumination beams may be generated.

3. The method of claim 2, wherein one or both the frequency and bandwidth of the illumination beam may be varied during the illumination.

4. The method of claim 3, wherein the frequency is swept between about 0.1 and about 1 THz, and wherein the bandwidth of the illumination beam may have a Q of between about 5 and 50.

5. The method of claim 1, wherein at least two illumination beams are generated, at least one millimeter wave illumination beam having a central frequency less 0.5 THz and at least one THz illumination beam having a central frequency greater than 0.5 THz, and wherein the at least one millimeter wave illumination beam generates a measurement of the central corneal thickness, and wherein the at least one THz illumination beam generates a reflectivity map of the corneal total water content.

6. The method of claim 1, wherein the reflectivity maps are further correlated with a separately obtained spatially resolved thickness map.

7. The method of claim 1, wherein the reflectivity map elucidates the nature of the tissue water content gradient of the cornea, and wherein the tissue water content gradient corresponds to a model tissue water content gradient selected from the group of pinned back, pinned front and global.

8. The method of claim 7, wherein determining the tissue water content gradient is further used to diagnose at least one corneal disorder.

9. The method of claim 8, wherein the disorder is selected from the group consisting of Fuchs' endothelial dystrophy, keratoconus, pseudophakic bullous keratopathy, graft rejection, and brain trauma.

10. The method of claim 1, wherein the method generates simultaneous corneal total water content and central corneal thickness using parameters of the cornea determined a priori.

11. The method of claim 1, wherein the cornea is field-flattened prior to illumination.

12. A THz cornea sensing apparatus comprising:
an emission source configured to generate an illumination beam having a frequency that is variable about at least one central wavelength greater than 0.1 THz;
a detector configured to receive and record a THz signal across a spectrum of frequencies;
one or more transmission optics disposed in optical alignment between the emission source and a target cornea, and configured such that the transmission optics directs the illumination beam to impinge upon a target area on the surface of the cornea, and gathers a reflected THz signal from the target cornea and transmits the reflected THz signal to the detector; and
an analyzer for using a plurality of reflected THz signals obtained at a plurality of illumination beam frequencies to produce a plurality of reflectivity maps of the cornea, said plurality of illumination beam frequencies being accomplished by frequency sweeping, using multiple bandwidths at a single frequency, or using multiple frequencies at a single bandwidth, and said reflectivity maps having a combined signal variation indicative of at least the corneal total water content and central corneal thickness.

13. The apparatus of claim 12, wherein the apparatus is configured to generate an illumination beam having a variable bandwidth configured such that both narrowband and broadband illumination beams may be generated.

14. The apparatus of claim 13, wherein one or both the frequency and bandwidth of the illumination beam may be varied.

15. The apparatus of claim 14, wherein the frequency may be varied between about 0.1 and about 1 THz, and wherein the bandwidth of the illumination beam may have a Q of between about 5 and 50.

16. The apparatus of claim 12, wherein the apparatus is configured to generate at least two illumination beams, at least one millimeter wave illumination beam having a central frequency less 0.5 THz and at least one THz illumination beam having a central frequency greater than 0.5 THz, and wherein the at least one millimeter wave illumination beam generates a measurement of the central corneal thickness, and wherein the at least one THz illumination beam generates a reflectivity map of the corneal total water content.

17. The apparatus of claim 12, wherein the analyzer is configured to correlate the reflectivity maps with a separately obtained spatially resolved thickness map.

18. The apparatus of claim 12, wherein the cornea is field-flattened prior to illumination using a dielectric window transparent to the illumination beam.

19. The apparatus of claim 12, wherein the transmission optics at least comprise at least two 90° off-axis parabolic mirrors arranged in an angled tip-to-tip geometry.

20. The apparatus of claim 12, wherein:
the illumination beam is collimated;
the transmission optics includes at least one off-axis parabolic mirror, and at least one scanning mirror;
wherein the center of curvature of the cornea is approximately coincident with the focal point of the off-axis parabolic mirror, and wherein the collimated illumination beam is reflected from off-axis parabolic mirror onto the cornea;
wherein the reflected signal is recollimated by the off-axis parabolic mirror; and
wherein the collimated illumination beam is reflected off the scanning mirror and onto the off-axis parabolic mirror, and wherein the scanning mirror is configured to alter the transverse location of the collimated illumination beam on the off-axis parabolic mirror, such that the target area of the surface of the cornea illuminated by the collimated illumination beam is concomitantly altered, and the reflectivity map of the cornea is obtained without field-flattening.

21. The apparatus of claim 20, wherein the scanning mirror maintains a parallel path of the collimated illumination beam relative to the clear normal of the off-axis parabolic mirror during alteration of the transverse location.

22. The apparatus of claim 20, further comprising at least two scanning mirrors having axes that are mutually orthogonal, wherein a first scanning mirror controls the azimuthal location of the collimated illumination beam, and a second scanning mirror alters the elevation location of the collimated illumination beam.

23. The apparatus of claim 20, wherein the radius of the collimated illumination beam is varied dependent of the incident location of the beam on the off-axis parabolic mirror.

24. The apparatus of claim 20, further comprising:
a second off-axis parabolic mirror disposed within a beam path of the collimated illumination beam in a symmetric tip to tip orientation;
wherein the scanning mirror is configured to gimbal about a center point thereof; and
wherein the scanning mirror directs the collimated illumination beam onto the second off-axis mirror, such that angular deflection of the scanning mirror causes transvers translation of the collimated illumination beam in the clear aperture plane of the first off-axis parabolic mirror.

25. The apparatus of claim 20, wherein the off-axis parabolic mirror is a low f/#off-axis parabolic mirror.

* * * * *